United States Patent
Mayer et al.

(10) Patent No.: US 6,541,423 B1
(45) Date of Patent: Apr. 1, 2003

(54) 4-(3′,4′-HETEROCYCLYL BENZOYL) PYRAZOLES AS HERBICIDAL AGENTS

(75) Inventors: Guido Mayer, Neustadt (DE); Ernst Baumann, Dudenhofen (DE); Wolfgang von Deyn, Neustadt (DE); Steffen Kudis, Mannheim (DE); Klaus Langemann, Worms (DE); Ulf Misslitz, Neustadt (DE); Ulf Neidlein, Mannheim (DE); Matthias Witschel, Ludwigshafen (DE); Michael Rack, Heidelberg (DE); Thorsten Volk, Mannheim (DE); Martina Otten, Ludwigshafen (DE); Karl-Otto Westphalen, Speyer (DE); Helmut Walter, Obrigheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/959,636
(22) PCT Filed: May 5, 2000
(86) PCT No.: PCT/EP00/04040
§ 371 (c)(1), (2), (4) Date: Nov. 1, 2001
(87) PCT Pub. No.: WO00/68228
PCT Pub. Date: Nov. 16, 2000

(30) Foreign Application Priority Data

May 7, 1999 (DE) ......... 199 21 240

(51) Int. Cl.⁷ ............ C07D 417/06; C07D 403/06; A01N 43/76
(52) U.S. Cl. .......... 504/139; 504/140; 548/127; 548/222; 548/261; 548/364.4
(58) Field of Search ............ 548/217, 364.4, 548/127, 222, 261; 504/139, 140

(56) References Cited

FOREIGN PATENT DOCUMENTS

| WO | WO-A-97/08164 | * | 3/1997 |
| WO | WO-A-97/09327 | * | 3/1997 |
| WO | WO-A-96/05197 | * | 2/1998 |

* cited by examiner

Primary Examiner—Jospeh K. McKane
Assistant Examiner—Kamal Saeed
(74) Attorney, Agent, or Firm—Keil & Weinkauf

(57) ABSTRACT

The invention relates to pyrazolyl derivatives of benzo-condensated, unsaturated 5-membered nitrogen heterocycles of the general formula (I), wherein X represents N or a group C—$R^3$; Y is O, S, SO, $SO_2$ or $NR^4$ or X—Y is S=N, and wherein X means sulfur, and the variables $R^1$, $R^2$ and Pz have the meanings indicated in claim 1. The invention, further relates to a method of producing said compounds, to agents that contain them and to their use as herbicidal agents.

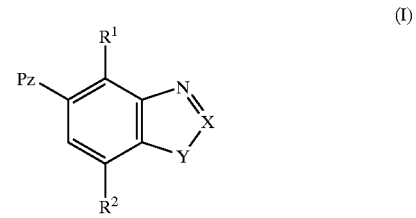

(I)

16 Claims, No Drawings

4-(3',4'-HETEROCYCLYL BENZOYL) PYRAZOLES AS HERBICIDAL AGENTS

This is a 371 of International application PCT/EP00/04040 filed May 5, 2000. The present invention relates to pyrazolyl derivatives of benzo-fused unsaturated 5-membered nitrogen heterocycles, to processes for preparing such pyrazolyl derivatives, to compositions comprising such compounds, and to the use of the pyrazoyl derivatives or of the compositions comprising them for controlling harmful plants.

WO 96/05197 discloses saccharin derivatives having herbicidal action which are substituted on the benzene ring of the saccharin skeleton by a (5-hydroxypyrazol-4-yl)carbonyl radical. WO 97/30993 and WO 97/09327 disclose dioxothiochromane derivatives and dihydrobenzothiophene derivatives having herbicidal action which likewise have a (5-hydroxypyrazol-4-yl)carbonyl radical on the benzene ring of the sulfur heterocycles.

WO 97/08164 discloses, inter alia, benzo-fused derivatives of γ-butyrolactam having herbicidal action which likewise have a (5-hydroxypyrazol-4-yl)carbonyl radical.

However, the herbicidal properties of the compounds known from the publications mentioned and their compatibility with crop plants do not meet all of the criteria required from herbicides.

EP-A-822 187 discloses herbicides based on aryl-substituted pyrazoles of the formula

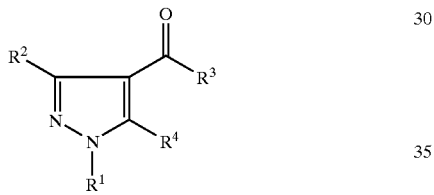

where $R^1$ is hydrogen or a protective group suitable for a pesticide, $R^4$ is preferably hydrogen and $R^2$ and $R^3$ are phenyl, naphthyl or heterocyclic groups which are unsubstituted or substituted. $R^3$ is preferably a 5- or 6-membered heterocyclic ring and in particular a thiophene group. The herbicidal action of the compounds described in this publication and their crop plant compatibility are likewise not satisfactory.

It is an object of the present invention to provide novel compounds having herbicidal action which preferably have greater activity than the herbicidal substances of the prior art and/or better selectivity with respect to harmful plants.

We have found that this object is achieved by pyrazolyl derivatives of benzo-fused unsaturated 5-membered nitrogen heterocycles of the formula I defined below.

Consequently, the present invention relates to pyrazolyl derivatives of benzo-fused unsaturated 5-membered nitrogen heterocycles of the formla I,

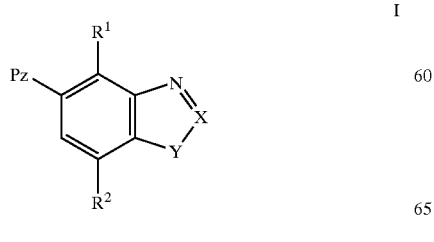

I where

X is N or a group C—$R^3$;

Y is O, S, SO, $SO_2$ or $NR^4$; or

X—Y is S=N, and X is sulfur;

$R^1$ is hydrogen, nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, $C_1$–$C_6$-alkoxy-$C_1$–$C_6$-alkyl, $C_1$–$C_6$-alkylthio-$C_1$–$C_6$-alkyl, $C_1$–$C_6$-alkylsulfinyl-$C_1$–$C_6$-alkyl, $C_1$–$C_6$-alkylsulfonyl-$C_1$–$C_6$-alkyl, $C_1$–$C_6$-alkylamino-$C_1$–$C_6$-alkyl, or di($C_1$–$C_6$-alkyl)amino-$C_1$–$C_6$-alkyl;

$R^2$ is hydrogen, halogen or $C_1$–$C_6$-alkyl;

$R^3$ is hydrogen, halogen, nitro, cyano, hydroxyl, amino, mercapto, thiocyanato, hydrazide, $C_1$–$C_6$-alkyl, $C_1$–$C_6$-haloalkyl, $C_1$–$C_6$-hydroxyalkyl, $C_1$–$C_6$-aminoalkyl, $C_1$–$C_6$-alkoxy-$C_1$–$C_6$-alkyl, $C_1$–$C_6$-alkylcarbonyl-$C_1$–$C_6$-alkyl, $C_1$–$C_6$-alkoxy, $C_1$–$C_6$-haloalkoxy, $C_1$–$C_6$-hydroxyalkoxy, $C_1$–$C_6$-alkoxy-$C_1$–$C_6$-alkoxy, $C_3$–$C_6$-cycloalkyl, is $C_1$–$C_6$-alkylamino, di-$C_1$–$C_6$-alkylamino, $C_3$–$C_6$-cycloalkylamino, where the alkyl and cycloalkyl groups of the three last-mentioned radicals may be partially or fully halogenated and/or may carry one, two or three substituents selected from the group consisting of $C_1$–$C_4$-alkoxy and hydroxyl, is $C_1$–$C_6$-alkylthio, $C_1$–$C_6$-haloalkylthio, $C_1$–$C_6$-hydroxyalkylthio, $C_1$–$C_6$-alkoxy-$C_1$–$C_6$-alkylthio, $C_1$–$C_6$-alkylsulfinyl, $C_1$–$C_6$-alkylsulfonyl, is phenyl, naphthyl, heterocyclyl, phenylamino, phenoxy, diphenylamino, where the phenyl and heterocyclyl groups of the six last-mentioned radicals for their part may be partially or fully halogenated and/or may carry one, two or three substituents selected from the group consisting of nitro, cyano, hydroxyl, $C_1$–$C_4$-alkyl, $C_1$–$C_4$-haloalkyl, $C_1$–$C_4$-alkoxy and $C_1$–$C_4$-haloalkoxy, is $C(O)OR^5$, or $C(O)N(R^6)R^7$;

$R^4$ is hydrogen, $C_1$–$C_6$-alkyl, $C_1$–$C_6$-haloalkyl, $C_1$–$C_6$-hydroxyalkyl, $C_1$–$C_6$-alkoxy-$C_1$–$C_6$-alkyl, is phenyl, naphthyl, where the two last-mentioned radicals for their part may be partially or fully halogenated and/or may carry one, two or three substituents selected from the group consisting of nitro, cyano, hydroxyl, $C_1$–$C_4$-alkyl, $C_1$–$C_4$-haloalkyl, $C_1$–$C_4$-alkoxy and $C_1$–$C_4$-haloalkoxy;

where $R^5$ is hydrogen, $C_1$–$C_6$-alkyl, $C_1$–$C_6$-haloalkyl, $C_1$–$C_6$-hydroxyalkyl, $C_1$–$C_6$-alkoxy-$C_1$–$C_6$-alkyl, is phenyl, naphthyl or heterocyclyl, where the three last-mentioned radicals for their part may be partially or fully halogenated and/or may carry one, two or three substituents selected from the group consisting of nitro cyano, hydroxyl, $C_1$–$C_4$-alkyl, $C_1$–$C_4$-haloalkyl, $C_1$–$C_4$-alkoxy and $C_1$–$C_4$-haloalkoxy; and $R^6$, $R^7$ independently of one another are hydrogen, $C_1$–$C_6$-alkyl, $C_1$–$C_6$-haloalkyl, $C_1$–$C_6$-hydroxyalkyl, $C_1$–$C_6$-alkoxy-$C_1$–$C_6$-alkyl, are phenyl or naphthyl, where the two last-mentioned radicals for their part may be partially or fully halogenated and/or may carry one, two or three substituents selected from the group consisting of nitro, cyano, hydroxyl, $C_1$–$C_4$-alkyl, $C_1$–$C_4$-haloalkyl, $C_1$–$C_4$-alkoxy and $C_1$–$C_4$-haloalkoxy;

and Pz is a radical of the formula IIa or IIb,

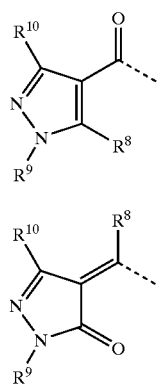

where the variables $R^8$, $R^9$ and $R^{10}$ are as defined below:

$R^8$ is hydroxyl, mercapto, halogen, $OR^{11}$, $SR^{11}$, $SOR^{12}$, $SO_2R^{12}$, $OSO_2R^{12}$, $P(O)R^{13}R^{14}$, $OP(O)R^{13}R^{14}$, $P(S)R^{13}R^{14}$, $OP(S)R^{13}R^{14}$, $NR^{15}R^{16}$, $ONR^{15}R^{16}$ or N-bonded heterocyclyl, which may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^9$ is hydrogen, $C_1$–$C_6$-alkyl, $C_3$–$C_6$-cycloalkyl, $C_1$–$C_6$-haloalkyl, hydroxyl, $C_1$–$C_6$-alkoxy or $C_1$–$C_6$-haloalkoxy;

$R^{10}$ is hydrogen, halogen, $C_1$–$C_6$-alkyl, $C_1$–$C_6$-haloalkyl, hydroxyl, $C_1$–$C_6$-alkoxy, $C_1$–$C_6$-haloalkoxy, $C_1$–$C_6$-alkylthio or $C_1$–$C_6$-haloalkylthio;

$R^{11}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkylcarbonyl, $C_2$–$C_6$-alkenylcarbonyl, $C_2$–$C_6$-alkynylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl)aminocarbonyl, N—($C_3$–$C_6$-alkenyl)—N—($C_1$–$C_6$-alkyl)aminocarbonyl, N—($C_3$–$C_6$-alkynyl)—N—($C_1$–$C_6$-alkyl)aminocarbonyl, N—($C_1$–$C_6$-alkoxy)—N—($C_1$–$C_6$-alkyl)aminocarbonyl, N—($C_3$–$C_6$-alkenyl)—N—($C_1$–$C_6$-alkoxy)aminocarbonyl, N—($C_3$–$C_6$-alkynyl)—N—($C_1$–$C_6$-alkoxy)aminocarbonyl, di($C_1$–$C_6$-alkyl)aminothiocarbonyl or $C_1$–$C_6$-alkoxyimino-$C_1$–$C_6$-alkyl, where the alkyl, cycloalkyl and alkoxy radicals mentioned may be partially or fully halogenated and/or may carry one, two or three of the following groups: cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, $C_1$–$C_4$-alkylaminocarbonyl, di($C_1$–$C_4$-alkyl)aminocarbonyl, aminocarbonyl, $C_1$–$C_4$-alkylcarbonyloxy or $C_3$–$C_6$-cycloalkyl;

is phenyl, phenyl-$C_1$–$C_6$-alkyl, phenylcarbonyl-$C_1$–$C_6$-alkyl, phenylcarbonyl, phenoxycarbonyl, phenyloxythiocarbonyl, phenylaminocarbonyl, N—($C_1$–$C_6$-alkyl)—N-(phenyl)aminocarbonyl, phenyl-$C_2$–$C_6$-alkenylcarbonyl, heterocyclyl, heterocyclyl-$C_1$–$C_6$-alkyl, heterdcyclylcarbonyl-$C_1$–$C_6$-alkyl, heterocyclylcarbonyl, heterocyclyloxycarbonyl, heterocyclyloxythiocarbonyl, heterocyclylaminocarbonyl, N—($C_1$–$C_6$-alkyl)—N-(heterocyclyl)aminocarbonyl, or heterocyclyl-$C_2$–$C_6$-alkenylcarbonyl, where the phenyl and the heterocyclyl radical of the 18 last-mentioned substituents may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{12}$ is $C_1$–$C_6$-alkyl, $C_3$–$C_6$-alkenyl, $C_3$–$C_6$-alkynyl or $C_3$–$C_6$-cycloalkyl, where the four radicals mentioned may be partially or fully halogenated and/or may carry one, two or three of the following groups: cyano, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylcarbonyl, $C_1$–$C_4$-alkoxycarbonyl or $C_1$–$C_4$-haloalkoxycarbonyl;

is phenyl, phenyl-$C_1$–$C_6$-alkyl, heterocyclyl or heterocyclyl-$C_1$–$C_6$-alkyl, where the phenyl and the heterocyclyl radical of the last-mentioned substituents may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{13}$, $R^{14}$ independently of one another are hydrogen, hydroxyl, $C_1$–$C_6$-alkyl, $C_1$–$C_6$-alkoxy, $C_1$–$C_6$-alkylthio, phenyl, phenyl-$C_1$–$C_4$-alkyl or phenoxy, where the three last-mentioned substituents may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{15}$ is hydrogen, $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkylcarbonyl, hydroxyl, $C_1$–$C_6$-alkoxy, $C_3$–$C_6$-alkenyloxy, $C_3$–$C_6$-alkynyloxy, amino, $C_1$–$C_6$-alkylamino, di($C_1$–$C_6$-alkyl)amino or $C_1$–$C_6$-alkylcarbonylamino, where the alkyl, cycloalkyl and alkoxy radicals mentioned may be partially or fully halogenated and/or may carry one, two or three radicals selected from the following group: cyano, $C_1$–$C_4$-alkoxycarbonyl, $C_1$–$C_4$-alkylaminocarbonyl, di($C_1$–$C_4$-alkyl)aminocarbonyl or $C_3$–$C_6$-cycloalkyl;

is phenyl, phenyl-$C_1$–$C_4$-alkyl, phenylcarbonyl, heterocyclyl, heterocyclyl-$C_1$–$C_4$-alkyl or heterocyclylcarbonyl, where the phenyl or heterocyclyl radical of the six last-mentioned substituents may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy or $C_1$–$C_4$-haloalkoxy; and $R^{16}$ is hydrogen, $C_1$–$C_6$-alkyl or $C_3$–$C_6$-alkenyl, $C_3$–$C_6$-alkynyl;

and their agriculturally useful salts.

Furthermore we have found herbicidal compositions which comprise the pyrazolyl derivatives of the formula I and have very good herbicidal action. Moreover, we have found processes for preparing these compositions and methods for controlling undesirable vegetation using the pyrazolyl derivatives of the formula I.

Depending on the substitution pattern, the compounds of the formula I may contain one or more chiral centers, in which case they are present as enantiomers or diasteromer mixtures. The invention provides both the pure enantiomers or diastereomers and their mixtures.

The compounds of the formula I may also be present in the form of their agriculturally useful salts, the type of salt generally being immaterial. In general, the salts of those cations and the acid addition salts of those acids are suitable whose cations and anions, respectively, do not negatively affect the herbicidal action of the compounds I.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, where, if desired, one to four hydrogen atoms may be replaced by $C_1$–$C_4$-alkyl, hydroxy-$C_1$–$C_4$-alkyl, $C_1$–$C_4$-alkoxy-$C_1$–$C_4$-alkyl, hydroxy-$C_1$–$C_4$-alkoxy-$C_1$–$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium, furthermore phosphonium ions, sulfonium ions, preferably tri($C_1$–$C_4$-alkyl)sulfonium, and sulfoxonium ions, preferably tri($C_1$–$C_4$-alkyl)sulfoxonium.

Anions of useful acid addition salts are primarily chloride, bromide, fluoride, hydrogen sulfate, sulfate, dihydrogen phosphate, hydrogen phosphate, nitrate, bicarbonate, carbonate, hexafluorosilicate, hexafluorophosphate, benzoate and the anions of $C_1$–$C_4$-alkanoic acids, preferably formate, acetate, propionate and butyrate.

For $R^8$=hydroxyl or mercapto {Z=O,S}, IIa also represents the tautomeric forms IIa' and IIa"

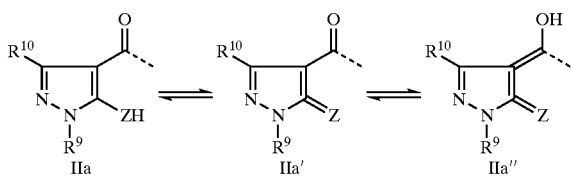

and IIb also represents the tautomeric forms IIb' and IIb"

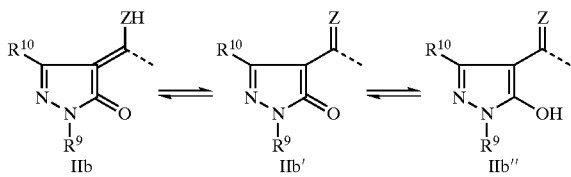

The organic molecular moieties mentioned for the substituents $R^1$ to $R^{16}$ or as radicals on phenyl and heterocyclyl radicals are collective terms for individual enumerations of the particular group members. All hydrocarbon chains, i.e. all alkyl, haloalkyl, alkoxy, haloalkoxy, alkylthio, haloalkylthio, alkylsulfinyl, haloalkylsulfinyl, alkylsulfonyl, haloalkylsulfonyl, N-alkylamino, N,N-dialkylamino, N-haloalkylamino, N-alkoxyamino, N-alkoxy-N-alkylamino, N-alkylcarbonylamino, alkylcarbonyl, haloalkylcarbonyl, alkoxycarbonyl, haloalkoxycarbonyl, alkylthiocarbonyl, alkylcarbonyloxy, alkylaminocarbonyl, dialkylaminocarbonyl, dialkylaminothiocarbonyl, alkoxyalkyl, alkoxyiminoalkyl, phenylalkylcarbonyl, heterocyclylalkylcarbonyl, phenylalkenylcarbonyl, heterocyclylalkenylcarbonyl, N-alkoxy-N-alkylaminocarbonyl, N-alkyl-N-phenylaminocarbonyl, N-alkyl-N-heterocyclylaminocarbonyl, phenylalkyl, heterocyclylalkyl, phenylcarbonylalkyl, heterocyclylcarbonylalkyl, alkoxyalkoxycarbonyl, alkenylcarbonyl, alkenyloxycarbonyl, alkenylaminocarbonyl, N-alkenyl-N-alkylaminocarbonyl, N-alkenyl-N-alkoxyaminocarbonyl, alkynylcarbonyl, alkynyloxycarbonyl, alkynylaminocarbonyl, N-alkynyl-N-alkylaminocarbonyl, N-alkynyl-N-alkoxyaminocarbonyl, alkenyl, alkynyl, haloalkenyl, haloalkynyl, alkenyloxy, alkynyloxy, alkanediyl, alkenediyl, alkadienediyl or alkynediyl moieties can be straight-chain or branched. Unless indicated otherwise, halogenated substituents preferably carry one to five identical or different halogen atoms. The expression halogen represents in each case fluorine, chlorine, bromine or iodine.

Examples of other meanings are:

$C_1$–$C_4$-alkyl: for example methyl, ethyl, propyl, 1-methylethyl, butyl, 1-methylpropyl, 2-methylpropyl or 1,1-dimethylethyl;

$C_1$–$C_6$-alkyl, and the alkyl moieties of $C_1$–$C_6$-alkylamino, di($C_1$–$C_6$-alkyl)amino, N—($C_1$–$C_6$-alkoxy)—N—($C_1$–$C_6$-alkyl)amino, N—($C_1$–$C_6$-alkoxy)—N—($C_1$–$C_6$-alkyl)aminocarbonyl, N—($C_3$–$C_6$-alkenyl)—N—($C_1$–$C_6$-alkyl)aminocarbonyl, ($C_3$–$C_6$-alkynyl)—N—($C_1$–$C_6$-alkyl)aminocarbonyl, N—($C_1$–$C_6$-alkyl)—N-phenylaminocarbonyl, N—($C_1$–$C_6$-alkyl)—N-heterocyclylaminocarbonyl: $C_1$–$C_4$-alkyl as mentioned above, and also, for example, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl or 1-ethyl-3-methylpropyl;

$C_1$–$C_4$-haloalkyl: a $C_1$–$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$–$C_6$-haloalkyl, and the haloalkyl moieties of N—$C_1$–$C_6$-haloalkylamino: $C_1$–$C_4$-haloalkyl, as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

$C_1$–$C_4$-alkoxy: for example methoxy, ethoxy, propoxy, 1-methylethoxy, butoxy, 1-methylpropoxy, 2-methylpropoxy or 1,1-dimethylethoxy;

$C_1$–$C_6$-alkoxy, and the alkoxy moieties of N—$C_1$–$C_6$-alkoxyamino, N—($C_1$–$C_6$-alkoxy)—N—($C_1$–$C_6$-alkyl)amino, $C_1$–$C_6$-alkoxyimino-$C_1$–$C_6$-alkyl, N—($C_1$–$C_6$-alkoxy)—N—($C_1$–$C_6$-alkyl)aminocarbonyl, N—($C_3$–$C_6$-alkenyl)—N—($C_1$–$C_6$-alkoxy) aminocarbonyl and N—($C_3$–$C_6$-alkynyl)—N—($C_1$–$C_6$-alkoxy) aminocarbonyl: $C_1$–$C_4$-alkoxy as mentioned above, and also, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy;

$C_1$–$C_6$-haloalkoxy: $C_1$–$C_4$-haloalkoxy as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy;

$C_1$–$C_4$-alkylthio ($C_1$–$C_4$-alkylsulfanyl: $C_1$–$C_4$-alkyl-S—): for example methylthio, ethylthio, propylthio, 1-methylethylthio, butylthio 1-methylpropylthio, 2-methylpropylthio or 1,1-dimethylethylthio;

$C_1$–$C_6$-alkylthio, and the alkylthio moieties of $C_1$–$C_6$-alkylthiocarbonyl: $C_1$–$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio;

$C_1$–$C_4$-haloalkylthio: a $C_1$–$C_4$-alkylthio radical as mentioned above which is partially or fully substituted by fluorine, chlorine, bromine and/or iodine, i.e., for example, fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trichloroethylthio, 2,2,2-trifluoroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio or nonafluorobutylthio;

$C_1$–$C_6$-haloalkylthio: $C_1$–$C_4$-haloalkylthio as mentioned above, and also 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio or dodecafluorohexylthio;

$C_1$–$C_4$-alkylsulfinyl ($C_1$–$C_4$-alkyl-S(=O)—): for example, methylsulfinyl, ethylsulfinyl, propylsulfinyl, 1-methylethylsulfinyl, butylsulfinyl, 1-methylpropylsulfinyl, 2-methylpropylsulfinyl or 1,1-dimethylethylsulfinyl;

$C_1$–$C_6$-alkylsulfinyl: $C_1$–$C_4$-alkylsulfinyl as mentioned above, and also pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl;

$C_1$–$C_4$-haloalkylsulfinyl: a $C_1$–$C_4$-alkylsulfinyl radical as mentioned above which is partially or fully substituted by fluorine, chlorine, bromine and/or iodine, i.e., for example, fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl or nonafluorobutylsulfinyl;

$C_1$–$C_6$-haloalkylsulfinyl: $C_1$–$C_4$-haloalkylsulfinyl as mentioned above, and also 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl;

$C_1$–$C_4$-alkylsulfonyl ($C_1$–$C_4$-alkyl-S(=O)$_2$—): for example methylsulfonyl, ethylsulfonyl, propylsulfonyl, 1-methylethylsulfonyl, butylsulfonyl, 1-methylpropylsulfonyl, 2-methylpropylsulfonyl or 1,1-dimethylethylsulfonyl;

$C_1$–$C_6$-alkylsulfonyl: $C_1$–$C_4$-alkylsulfonyl, as mentioned above, and also pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl;

$C_1$–$C_4$-haloalkylsulfonyl: a $C_1$–$C_4$-alkylsulfonyl radical as mentioned above which is partially or fully substituted by fluorine, chlorine, bromine and/or iodine, i.e., for example, fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl or nonafluorobutylsulfonyl;

$C_1$–$C_6$-haloalkylsulfonyl: $C_1$–$C_4$-haloalkylsulfonyl as mentioned above, and also 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl or dodecafluorohexylsulfonyl;

$C_1$–$C_6$-alkylamino: methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino;

di($C_1$–$C_4$-alkyl)amino: for example N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-methyl-N-(1,1-dimethylethyl)amino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di($C_1$–$C_6$-alkyl)amino: di($C_1$–$C_4$-alkyl)amino as mentioned above, and also N,N-dipentylamino, N,N-dihexylamino, N-methyl-N-pentylamino, N-ethyl-N-pentylamino, N-methyl-N-hexylamino or N-ethyl-N-hexylamino;

$C_1$–$C_4$-alkylcarbonyl: for example methylcarbonyl, ethylcarbonyl, propylcarbonyl, 1-methylethylcarbonyl, butylcarbonyl, 1-methylpropylcarbonyl, 2-methylpropylcarbonyl or 1,1-dimethylethylcarbonyl;

$C_1$–$C_6$-alkylcarbonyl, and the alkylcarbonyl radicals of $C_1$–$C_6$-alkylcarbonyl-$C_1$–$C_6$-alkyl, $C_1$–$C_6$-alkylcarbonylamino: $C_1$–$C_4$-alkylcarbonyl as mentioned above, and also, for example, pentylcarbonyl, 1-methylbutylcarbonyl, 2-methylbutylcarbonyl, 3-methylbutylcarbonyl, 2,2-dimethylpropylcarbonyl, 1-ethylpropylcarbonyl, hexylcarbonyl, 1,1-dimethylpropylcarbonyl, 1,2-dimethylpropylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl;

$C_1$–$C_4$-haloalkylcarbonyl: a $C_1$–$C_4$-alkylcarbonyl radical as mentioned above which is partially or fully substituted by fluorine, chlorine, bromine and/or iodine, i.e. for example, chloroacetyl, dichloroacetyl, trichloroacetyl, fluoroacetyl, difluoroacetyl, trifluoroacetyl, chlorofluoroacetyl, dichlorofluoroacetyl, chlorodifluoroacetyl, 2-fluoroethylcarbonyl, 2-chloroethylcarbonyl, 2-bromoethylcarbonyl, 2-iodoethylcarbonyl, 2,2-difluoroethylcarbonyl, 2,2,2-trifluoroethylcarbonyl, 2-chloro-2-fluoroethylcarbonyl, 2-chloro-2,2-difluoroethylcarbonyl, 2,2-dichloro-2-fluoroethylcarbonyl, 2,2,2-trichloroethylcarbonyl, pentafluoroethylcarbonyl, 2-fluoropropylcarbonyl, 3-fluoropropylcarbonyl, 2,2-diflubropropylcarbonyl, 2,3-difluoropropylcarbonyl, 2-chloropropylcarbonyl, 3-chloropropylcarbonyl, 2,3-dichloropropylcarbonyl, 2-bromopropylcarbonyl, 3-bromopropylcarbonyl, 3,3,3-trifluoropropylcarbonyl, 3,3,3-trichloropropylcarbonyl, 2,2,3,3,3-pentafluoropropylcarbonyl, heptafluoropropylcarbonyl, 1-(fluoromethyl)-2-fluoroethylcarbonyl, 1-(chloromethyl)-2-chloroethylcarbonyl, 1-(bromomethyl)-2-bromoethylcarbonyl, 4-fluorobutylcarbonyl, 4-chlorobutylcarbonyl, 4-bromobutylcarbonyl or nonafluorobutylcarbonyl;

$C_1$–$C_6$-haloalkylcarbonyl: a $C_1$–$C_4$-haloalkylcarbonyl radical as mentioned above, and also 5-fluoropentylcarbonyl, 5-chloropentylcarbonyl, 5-bromopentylcarbonyl, perfluoropentylcarbonyl, 6-fluorohexylcarbonyl, 6-chlorohexylcarbonyl, 6-bromohexylcarbonyl or perfluorohexylcarbonyl;

$C_1$–$C_4$-alkoxycarbonyl: for example methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl;

$C_1$–$C_6$-alkoxycarbonyl: $C_1$–$C_4$-alkoxydcarbonyl as mentioned above, and also, for example, pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl;

$C_1$–$C_4$-haloalkoxycarbonyl: a $C_1$–$C_4$-alkoxycarbonyl radical as mentioned above which is partially or fully substituted by fluorine, chlorine, bromine and/or iodine, i.e., for example fluoromethoxycarbonyl, difluoromethoxycarbonyl, trifluoromethoxycarbonyl, chlorodifluoromethoxycarbonyl, bromodifluoromethoxycarbonyl, 2-fluoroethoxycarbonyl, 2-chloroethoxycarbonyl, 2-bromoethoxycarbonyl, 2-iodoethoxycarbonyl, 2,2-difluoroethoxycarbonyl, 2,2,2-trifluoroethoxycarbonyl, 2-chloro-2-fluoroethoxycarbonyl, 2-chloro-2,2-difluoroethoxycarbonyl, 2,2-dichloro-2-fluoroethoxycarbonyl, 2,2,2-trichloroethoxycarbonyl, pentafluoroethoxycarbonyl, 2-fluoropropoxycarbonyl, 3-fluoropropoxycarbonyl, 2-chloropropoxycarbonyl, 3-chloropropoxycarbonyl, 2-bromopropoxycarbonyl, 3-bromopropoxycarbonyl, 2,2-difluoropropoxycarbonyl, 2,3-difluoropropoxycarbnyl, 2,3-dichloropropoxycarbonyl, 3,3,3-trifluoropropoxycarbonyl, 3,3,3-trichloropropoxycarbonyl, 2,2,3,3,3-pentafluoropropoxycarbonyl, heptafluoropropoxycarbonyl, 1-(fluoromethyl)-2-fluoroethoxycarbonyl, 1-(chloromethyl)-2-chloroethoxycarbonyl, 1-(bromomethyl)-2-bromoethoxycarbonyl, 4-fluorobutoxycarbonyl, 4-chlorobutoxycarbonyl, 4-bromobutoxycarbonyl or 4-iodobutoxycarbonyl;

$C_1$–$C_6$-halooxycarbonyl: a $C_1$–$C_4$-halooxycarbonyl radical as mentioned above, and also 5-fluoropentoxycarbonyl, 5-chloropentoxycarbonyl, 5-bromopentoxycarbonyl, 6-fluorohexoxycarbonyl, 6-chlorohexoxycarbonyl or 6-bromohexoxycarbonyl;

($C_1$–$C_4$-alkyl)carbonyloxy: acetyloxy, ethylcarbonyloxy, propylcarbonyloxy, 1-methylethylcarbonyloxy, butylcarbonyloxy, 1-methylpropylcarbonyloxy, 2-methylpropylcarbonyloxy or 1,1-dimethylethylcarbonyloxy;

($C_1$–$C_4$-alkylamino)carbonyl: for example methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl or 1,1-dimethylethylaminocarbonyl;

($C_1$–$C_6$-alkylamino)carbonyl: ($C_1$–$C_4$-alkylamino)carbonyl as mentioned above, and also, for example, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl or 1-ethyl-2-methylpropylaminocarbonyl;

di($C_1$–$C_4$-alkyl)aminocarbonyl: for example N,N-dimethylaminocarbonyl, N,N-diethylaminocarbonyl, N,N-di(1-methylethyl)aminocarbonyl, N,N-dipropylaminocarbonyl, N,N-dibutylaminocarbonyl, N,N-di(1-methylpropyl)aminocarbonyl, N,N-di(2-methylpropyl)aminocarbonyl, N,N-di(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl or N-(1,1-dimethylethyl)-N-(2-methylpropyl)aminocarbonyl;

di($C_1$–$C_6$-alkyl)aminocarbonyl: di($C_1$–$C_4$-alkyl)aminocarbonyl as mentioned above, and also, for example, N-methyl-N-pentylaminocarbonyl, N-methyl-N-(1-methylbutyl)aminocarbonyl, N-methyl-N-(2-methylbutyl)aminocarbonyl, N-methyl-N-(3-methylbutyl)aminocarbonyl, N-methyl-N-(2,2-dimethylpropyl)aminocarbonyl, N-methyl-N-(1-ethylpropyl)aminocarbonyl, N-methyl-N- hexylaminocarbonyl, N-methyl-N-(1,1-dimethylpropyl) aminocarbonyl, N-methyl-N-(1,2-dimethylpropyl) aminocarbonyl, N-methyl-N-(1-methylpentyl) aminocarbonyl, N-methyl-N-(2-methylpentyl) aminocarbonyl, N-methyl-N-(3-methylpentyl) aminocarbonyl, N-methyl-N-(4-methylpentyl) aminocarbonyl, N-methyl-N-(1,1-dimethylbutyl) aminocarbonyl, N-methyl-N-(1,2-dimethylbutyl) aminocarbonyl, N-methyl-N-(1,3-dimethylbutyl) aminocarbonyl, N-methyl-N-(2,2-dimethylbutyl) aminocarbonyl, N-methyl-N-(2,3-dimethylbutyl) aminocarbonyl, N-methyl-N-(3,3-dimethylbutyl) aminocarbonyl, N-methyl-N-(1-ethylbutyl) aminocarbonyl, N-methyl-N-(2-ethylbutyl) aminocarbonyl, N-methyl-N-(1,1,2-trimethylpropyl) aminocarbonyl, N-methyl-N-(1,2,2-trimethylpropyl) aminocarbonyl, N-methyl-N-(1-ethyl-1-methylpropyl) aminocarbonyl, N-methyl-N-(1-ethyl-2-methylpropyl) aminocarbonyl, N-ethyl-N-pentylaminocarbonyl, N-ethyl-N-(1-methylbutyl)aminocarbonyl, N-ethyl-N-(2-methylbutyl)aminocarbonyl, N-ethyl-N-(3-methylbutyl) aminocarbonyl, N-ethyl-N-(2,2-dimethylpropyl) aminocarbonyl, N-ethyl-N-(1-ethylpropyl) aminocarbonyl, N-ethyl-N-hexylaminocarbonyl, N-ethyl-N-(1,1-dimethylpropyl)aminocarbonyl, N-ethyl-N-(1,2-dimethylpropyl)aminocarbonyl, N-ethyl-N-(1-methylpentyl)aminocarbonyl, N-ethyl-N-(2-methylpentyl)aminocarbonyl, N-ethyl-N-(3-methylpentyl)aminocarbonyl, N-ethyl-N-(4-methylpentyl)aminocarbonyl, N-ethyl-N-(1,1-dimethylbutyl)aminocarbonyl, N-ethyl-N-(1,2-dimethylbutyl)aminocarbonyl, N-ethyl-N-(1,3-dimethylbutyl)aminocarbonyl, N-ethyl-N-(2,2-dimethylbutyl)aminocarbonyl, N-ethyl-N-(2,3-dimethylbutyl)aminocarbonyl, N-ethyl-N-(3,3-dimethylbutyl)aminocarbonyl, N-ethyl-N-(1-ethylbutyl) aminocarbonyl, N-ethyl-N-(2-ethylbutyl)aminocarbonyl, N-ethyl-N-(1,1,2-trimethylpropyl)aminocarbonyl, N-ethyl-N-(1,2,2-trimethylpropyl)aminocarbonyl, N-ethyl-N-(1-ethyl-1-methylpropyl)aminocarbonyl, N-ethyl-N-(1-ethyl-2-methylpropyl)aminocarbonyl, N-propyl-N-pentylaminocarbonyl, N-butyl-N-pentylaminocarbonyl, N,N-dipentylaminocarbonyl, N-propyl-N-hexylaminocarbonyl, N-butyl-N-hexylaminocarbonyl, N-pentyl-N-hexylaminocarbonyl or N,N-dihexylaminocarbonyl;

di($C_1$–$C_6$-alkyl)aminothiocarbonyl: for example N,N-dimethylaminothiocarbonyl, N,N-diethylaminothiocarbonyl, N,N-di(1-methylethyl) aminothiocarbonyl, N,N-dipropylaminothiocarbonyl, N,N-dibutylaminothiocarbonyl, N,N-di(1-methylpropyl) aminothiocarbonyl, N,N-di(2-methylpropyl) aminothiocarbonyl, N,N-di(1,1-dimethylethyl) aminothiocarbonyl, N-ethyl-N-methylaminothiocarbonyl, N-methyl-N-propylaminothiocarbonyl, N-methyl-N-(1-methylethyl) aminothiocarbonyl, N-butyl-N-methylaminothiocarbonyl, N-methyl-N-(1-methylpropyl) aminothiocarbonyl, N-methyl-N-(2-methylpropyl) aminothiocarbonyl, N-(1,1-dimethylethyl)-N-methylaminothiocarbonyl, N-ethyl-N-propylaminothiocarbonyl, N-ethyl-N-(1-methylethyl) aminothiocarbonyl, N-butyl-N-ethylaminothiocarbonyl, N-ethyl-N-(1-methylpropyl)aminothiocarbonyl, N-ethyl-N-(2-methyl-propyl)aminothiocarbonyl, N-ethyl-N-(1,1-dimethylethyl)aminothiocarbonyl, N-(1-methylethyl)-N-propylaminothiocarbonyl, N-butyl-N-propylaminothiocarbonyl, N-(1-methylpropyl)-N-propylaminothiocarbonyl, N-(2-methylpropyl)-N-propylaminothiocarbonyl, N-(1,1-dimethylethyl)-N-propylaminothiocarbonyl, N-butyl-N-(1-methylethyl) aminothiocarbonyl, N-(1-methylethyl)-N-(1-methylpropyl)aminothiocarbonyl, N-(1-methylethyl)-N-(2-methylpropyl)aminothiocarbonyl, N-(1,1-dimethylethyl)-N-(1-methylethyl)aminothiocarbonyl, N-butyl-N-(1-methylpropyl)aminothiocarbonyl, N-butyl-N-(2-methylpropyl)aminothiocarbonyl, N-butyl-N-(1,1-dimethylethyl)aminothiocarbonyl, N-(1-methylpropyl)-N-(2-methylpropyl)aminothiocarbonyl, N-(1,1-dimethylethyl)-N-(1-methylpropyl)aminothiocarbonyl, N-(1,1-dimethylethyl)-N-(2-methylpropyl) aminothiocarbonyl, N-methyl-N-pentylaminothiocarbonyl, N-methyl-N-(1-methylbutyl) amino-thiocarbonyl, N-methyl-N-(2-methylbutyl) aminothiocarbonyl, N-methyl-N-(3-methylbutyl) aminothiocarbonyl, N-methyl-N-(2,2-dimethylpropyl) aminothiocarbonyl, N-methyl-N-(1-ethylpropyl) aminothiocarbonyl, N-methyl-N-hexylaminothiocarbonyl, N-methyl-N-(1,1-dimethylpropyl)aminothiocarbonyl, N-methyl-N-(1,2-dimethylpropyl)aminothiocarbonyl, N-methyl-N-(1-methylpentyl)aminothiocarbonyl, N-methyl-N-(2-methylpentyl)aminothiocarbonyl, N-methyl-N-(3-methylpentyl)aminothiocarbonyl, N-methyl-N-(4-methylpentyl)aminothiocarbonyl, N-methyl-N-(1,1-dimethylbutyl)aminothiocarbonyl, N-methyl-N-(1,2-dimethylbutyl)aminothiocarbonyl, N-methyl-N-(1,3-dimethylbutyl)aminothiocarbonyl, N-methyl-N-(2,2-dimethylbutyl)aminothiocarbonyl, N-methyl-N-(2,3-dimethylbutyl)aminothiocarbonyl, N-methyl-N-(3,3-dimethylbutyl)aminothiocarbonyl, N-methyl-N-(1-ethylbutyl)aminothiocarbonyl, N-methyl-N-(2-ethylbutyl)aminothiocarbonyl, N-methyl-N-ethyl-N-(1,1,2-trimethylpropyl)aminothiocarbonyl, N-methyl-N-(1,2,2-trimethylpropyl)aminothiocarbonyl, N-methyl-N-(1-ethyl-1-methylpropyl)aminothiocarbonyl, N-methyl-N-(1-ethyl-2-methylpropyl)aminothiocarbonyl, N-ethyl-N-pentylaminothiocarbonyl, N-ethyl-N-(1-methylbutyl) aminothiocarbonyl, N-ethyl-N-(2-methylbutyl) aminothiocarbonyl, N-ethyl-N-(3-methylbutyl) aminothiocarbonyl, N-Ethyl-N-(2,2-dimethylpropyl) aminothiocarbonyl, N-ethyl-N-(1-ethylpropyl) aminothiocarbonyl, N-ethyl-N-hexylaminothiocarbonyl, N-ethyl-N-(1,1-dimethylpropyl)aminothiocarbonyl, N-ethyl-N-(1,2-dimethylpropyl)aminothiocarbonyl, N-ethyl-N-(1-methylpentyl)aminothiocarbonyl, N-ethyl-N-(2-methylpentyl)aminothiocarbonyl, N-ethyl-N-(3-methylpentyl)aminothiocarbonyl, N-ethyl-N-(4-methylpentyl)aminothiocarbonyl, N-ethyl-N-(1,1-dimethylbutyl)aminothiocarbonyl, N-ethyl-N-(1,2-dimethyl-butyl)aminothiocarbonyl, N-ethyl-N-(1,3-dimethylbutyl)aminothiocarbonyl, N-ethyl-N-(2,2-dimethylbutyl)aminothiocarbonyl, N-ethyl-N-(2,3-dimethylbutyl)aminothiocarbonyl, N-ethyl-N-(3,3-dimethylbutyl)aminothiocarbonyl, N-ethyl-N-(1-ethylbutyl)aminothiocarbonyl, N-ethyl-N-(2-ethylbutyl) aminothiocarbonyl, N-ethyl-N-(1,1,2-trimethylpropyl) aminothiocarbonyl, N-ethyl-N-(1,2,2-trimethylpropyl) aminothiocarbonyl, N-ethyl-N-(1-ethyl-1-methylpropyl) aminothiocarbonyl, N-ethyl-N-(1-ethyl-2-methylpropyl) aminothiocarbonyl, N-propyl-N-pentylaminothiocarbonyl, N-butyl-N-pentylaminothiocarbonyl, N,N-dipentylaminothiocarbonyl, N-propyl-N- hexylaminothiocarbonyl, N-butyl-N-hexylaminothiocarbonyl, N-pentyl-N-hexylaminothiocarbonyl or N,N-dihexylaminothiocarbonyl;

$C_1$–$C_6$-hydroxyalkyl: $C_1$–$C_6$-alkyl which is substituted by one to three OH groups, for example hydroxymethyl, 1-hydroxyethyl, 2-hydroxyethyl, 1,2-bishydroxyethyl, 1-hydroxypropyl, 2-hydroxypropyl, 3-hydroxypropyl, 4-hydroxybutyl, 2,2-dimethyl-3-hydroxypropyl;

phenyl-$C_1$–$C_6$-alkyl: $C_1$–$C_6$-alkyl which is substituted by a phenyl radical, for example benzyl, 1-phenylethyl and 2-phenylethyl, where the phenyl radical may, in the manner mentioned, be partially or fully halogenated or may carry one to three of the substituents mentioned above for phenyl; correspondingly, heterocyclyl-$C_1$–$C_6$-alkyl is a $C_1$–$C_6$-alkyl which is substituted by a heterocyclyl radical;

$C_1$–$C_6$-alkoxy-$C_1$–$C_6$-alkyl: $C_1$–$C_6$-alkyl which is substituted by $C_1$–$C_6$-alkoxy as mentioned above, i.e., for example, methoxymethyl, ethoxymethyl, propoxymethyl, (1-methylethoxy)methyl, butoxymethyl, (1-methylpropoxy)methyl, (2-methylpropoxy)methyl, (1,1-dimethylethoxy)methyl, 2-(methoxy)ethyl, 2-(ethoxy)ethyl, 2-(propoxy)ethyl, 2-(1-methylethoxy)ethyl, 2-(butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(propoxy)propyl, 2-(1-methylethoxy)propyl, 2-(butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(propoxy)propyl, 3-(1-methylethoxy)propyl, 3-(butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(propoxy)butyl, 2-(1-methylethoxy)butyl, 2-(butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(propoxy)butyl, 3-(1-methylethoxy)butyl, 3-(butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(propoxy)butyl, 4-(1-methylethoxy)butyl, 4-(butoxy)butyl, 4-(1-methylpropoxy)butyl, 4-(2-methylpropoxy)butyl or 4-(1,1-dimethylethoxy)butyl;

$C_1$–$C_6$-alkoxy-$C_1$–$C_6$-alkoxy, and the alkoxyalkoxy moieties of $C_1$–$C_6$-alkoxy-$C_1$–$C_6$-alkoxycarbonyl: $C_1$–$C_6$-alkoxy which is substituted by $C_1$–$C_6$-alkoxy as mentioned above, i.e, for example, methoxymethoxy, ethoxymethoxy, propoxymethoxy, (1-methylethoxy)methoxy, butoxymethoxy, (1-methylpropoxy)methoxy, (2-methylpropoxy)methoxy, (1,1-dimethylethoxy)methoxy, 2-(methoxy)ethoxy, 2-(ethoxy)ethoxy, 2-(propoxy)ethoxy, 2-(1-methylethoxy)ethoxy, 2-(butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(propoxy)propoxy, 2-(1-methylethoxy)propoxy, 2-(butoxy)propoxy, 2-(1-methylpropoxy)propoxy, 2-(2-methylpropoxy)propoxy, 2-(1,1-dimethylethoxy)propoxy, 3-(methoxy)propoxy, 3-(ethoxy)propoxy, 3-(propoxy)propoxy, 3-(1-methylethoxy)propoxy, 3-(butoxy)propoxy, 3-(1-methylpropoxy)propoxy, 3-(2-methylpropoxy)propoxy, 3-(1,1-dimethylethoxy)propoxy, 2-(methoxy)butoxy, 2-(ethoxy)butoxy, 2-(propoxy)butoxy, 2-(1-methylethoxy)butoxy, 2-(butoxy)butoxy, 2-(1-methylpropoxy)butoxy, 2-(2-methylpropoxy)butoxy, 2-(1,1-dimethylethoxy)butoxy, 3-(methoxy)butoxy, 3-(ethoxy)butoxy, 3-(propoxy)butoxy, 3-(1-methylethoxy)butoxy, 3-(butoxy)butoxy, 3-(1-methylpropoxy)butoxy, 3-(2-methylpropoxy)butoxy, 3-(1,1-dimethylethoxy)butoxy, 4-(methoxy)butoxy, 4-(ethoxy)butoxy, 4-(propoxy)butoxy, 4-(1-methylethoxy)butoxy, 4-(butoxy)butoxy, 4-(1-methylpropoxy)butoxy, 4-(2-methylpropoxy)butoxy or 4-(1,1-dimethylethoxy)butoxy;

$C_1$–$C_6$-alkylcarbonyl-$C_1$–$C_6$-alkyl: $C_1$–$C_6$-alkyl which is substituted by a $C_1$–$C_6$-alkylcarbonyl group, where both of the $C_1$–$C_6$-alkyl groups may carry one or more substituents selected from $C_1$–$C_4$-alkoxy and/or hydroxyl: for example acetylmethyl (=2-oxopropyl), 2-(acetyl)ethyl (=3-oxo-n-butyl), 3-oxo-n-pentyl, 1,1-dimethyl-2-oxopropyl, 3-hydroxy-2-oxopropyl or 3-hydroxy-2-oxobutyl;

$C_3$–$C_6$-alkenyl, and the alkenyl moieties of $C_3$–$C_6$-alkenylcarbonyl, $C_3$–$C_6$-alkenyloxy, $C_3$–$C_6$-alkenyloxycarbonyl, $C_3$–$C_6$-alkenylaminocarbonyl, N—($C_3$–$C_6$-alkenyl)—N—($C_1$–$C_6$-alkyl)aminocarbonyl, N—($C_3$–$C_6$-alkenyl)—N—($C_1$–$C_6$-alkoxy)aminocarbonyl: for example prop-2-en-1-yl, but-1-en-4-yl, 1-methylprop-2-en-1-yl, 2-methylprop-2-en-1-yl, 2-buten-1-yl, 1-penten-3-yl, 1-penten-4-yl, 2-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methyl-but-3-en-1-yl, 1,1-dimethylprop-2-en-1-yl, 1,2-dimethylprop-2-en-1-yl, 1-ethylprop-2-en-1-yl, hex-3-en-1-yl, hex-4-en-1-yl, hex-5-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl or 1-ethyl-2-methylprop-2-en-1-yl;

$C_2$–$C_6$-alkenyl, and the alkenyl moieties of $C_2$–$C_6$-alkenylcarbonyl, phenyl-$C_2$–$C_6$-alkenylcarbonyl and heterocyclyl-$C_2$–$C_6$-alkenylcarbonyl: $C_3$–$C_6$-alkenyl as mentioned above, and also ethenyl;

$C_3$–$C_6$-haloalkenyl: a $C_3$–$C_6$-alkenyl radical as mentioned above which is partially or fully substituted by fluorine, chlorine, bromine and/or iodine, i.e., for example, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl;

$C_3$–$C_6$-alkynyl, and the alkynyl moieties of $C_3$–$C_6$-alkynylcarbonyl, $C_3$–$C_6$-alkynyloxy, $C_3$–$C_6$-alkynyloxycarbonyl, $C_3$–$C_6$-alkynylaminocarbonyl, N—($C_3$–$C_6$-alkynyl)—N—($C_1$–$C_6$-alkyl)aminocarbonyl, N—($C_3$–$C_6$-alkynyl)—N—($C_1$–$C_6$-alkoxy)aminocarbonyl: for example propargyl, but-1-yn-3-yl, but-1-yn-4-yl, but-2-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl;

$C_2$–$C_6$-alkynyl, and the alkynyl moieties of $C_2$–$C_6$-alkynylcarbonyl: $C_3$–$C_6$-alkynyl as mentioned above, and also ethynyl;

$C_3$–$C_6$-haloalkynyl: a $C_3$–$C_6$-alkynyl radical as mentioned above which is partially or fully substituted by fluorine, chlorine, bromine and/or iodine, i.e., for example, 1,1-difluoroprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$–$C_6$-alkanediyl: methanediyl, ethane-1,1-diyl, ethane-1,2-diyl, propane-1,1-diyl, propane-1,2-diyl, propane-1,3-diyl, propane-2,2-diyl, butane-1,1-diyl, butane-1,2-diyl, butane-1,3-diyl, butane-1,4-diyl, 2-methylpropane-1,3-diyl, 2-methylpropane-1,2-diyl, 2-methylpropane-1,1-diyl, 1-methylpropane-1,2-diyl, 1-methylpropane-2,2-diyl, 1-methylpropane-1,1-diyl, pentane-1,1-diyl, pentane-1,2-diyl, pentane-1,3-diyl, pentane-1,5-diyl, pentane-2,3-diyl, pentane-2,2-diyl, 1-methylbutane-1,1-diyl, 1-methylbutane-1,2-diyl, 1-methylbutane-1,3-diyl, 1-methylbutane-1,4-diyl, 2-methylbutane-1,1-diyl, 2-methylbutane-1,2-diyl, 2-methylbutane-1,3-diyl, 2-methylbutane-1,4-diyl, 2,2-dimethylpropane-1,1-diyl, 2,2-dimethylpropane-1,3-diyl, 1,1-dimethylpropane-1,3-diyl, 1,1-dimethylpropane-1,2-diyl, 2,3-dimethylpropane-1,3-diyl, 2,3-dimethylpropane-1,2-diyl, 1,3-dimethylpropane-1,3-diyl, hexane-1,1-diyl, hexane-1,2-diyl, hexane-1,3-diyl, hexane-1,4-diyl, hexane-1,5-diyl, hexane-1,6-diyl, hexane-2,5-diyl, 2-methylpentane-1,1-diyl, 1-methylpentane-1,2-diyl, 1-methylpentane-1,3-diyl, 1-methylpentane-1,4-diyl, 1-methylpentane-1,5-diyl, 2-methylpentane-1,1-diyl, 2-methylpentane-1,2-diyl, 2-methylpentane-1,3-diyl, 2-methylpentane-1,4-diyl, 2-methylpentane-1,5-diyl, 3-methylpentane-1,1-diyl, 3-methylpentane-1,2-diyl, 3-methylpentane-1,3-diyl, 3-methylpentane-1,4-diyl, 3-methylpentane-1,5-diyl, 1,1-dimethylbutane-1,2-diyl, 1,1-dimethylbutane-1,3-diyl, 1,1-dimethylbutane-1,4-diyl, 1,2-dimethylbutane-1,1-diyl, 1,2-dimethylbutane-1,2-diyl, 1,2-dimethylbutane-1,3-diyl, 1,2-dimethylbutane-1,4-diyl, 1,3-dimethylbutane-1,1-diyl, 1,3-dimethylbutane-1,2-diyl, 1,3-dimethylbutane-1,3-diyl, 1,3-dimethylbutane-1,4-diyl, 1-ethylbutane-1,1-diyl, 1-ethylbutane-1,2-diyl, 1-ethylbutane-1,3-diyl, 1-ethylbutane-1,4-diyl, 2-ethylbutane-1,1-diyl, 2-ethylbutane-1,2-diyl, 2-ethylbutane-1,3-diyl, 2-ethylbutane-1,4-diyl, 2-ethylbutane-2,3-diyl, 2,2-dimethylbutane-1,1-diyl, 2,2-dimethylbutane-1,3-diyl, 2,2-dimethylbutane-1,4-diyl, 1-isopropylpropane-1,1-diyl, 1-isopropylpropane-1,2-diyl, 1-isopropylpropane-1,3-diyl, 2-isopropylpropane-1,1-diyl, 2-isopropylpropane-1,2-diyl, 2-isopropylpropane-1,3-diyl, 1,2,3-trimethylpropane-1,1-diyl, 1,2,3-trimethylpropane-1,2-diyl or 1,2,3-trimethylpropane-1,3-diyl;

$C_2$–$C_6$-alkenediyl: ethene-1,1-diyl, ethene-1,2-diyl, 1-propene-1,1-diyl, 1-propene-1,2-diyl, 1-propene-1,3-diyl, 2-propene-1,1-diyl, 2-propene-1,2-diyl, 2-propene-1,3-diyl, 1-butene-1,1-diyl, 1-butene-1,2-diyl, 1-butene-1,3-diyl, 1-butene-1,4-diyl, 2-butene-1,1-diyl, 2-butene-1,2-diyl, 2-butene-1,3-diyl, 2-butene-1,4-diyl, 3-butene-1,1-diyl, 3-butene-1,2-diyl, 3-butene-1,3-diyl, 3-butene-1,4-diyl, 1-methyl-1-propene-1,2-diyl, 1-methyl-1-propene-1,3-diyl, 1-methyl-2-propene-1,1-diyl, 1-methyl-2-propene-1,2-diyl, 1-methyl-2-propene-1,3-diyl, 2-methyl-1,1-propene-1,1-diyl, 2-methyl-1-propene-1,3-diyl, 3-butene-1,1-diyl, 3-butene-1,2-diyl, 3-butene-1,3-diyl, 3-butene-1,4-diyl, 1-pentene-1,1-diyl, 1-pentene-1,2-diyl, 1-pentene-1,3-diyl, 1-pentene-1,4-diyl, 1-pentene-1,5-diyl, 1-hexene-1,1-diyl, 1-hexene-1,2-diyl, 1-hexene-1,3-diyl, 1-hexene-1,4-diyl, 1-hexene-1,5-diyl or 1-hexene-1,6-diyl;

$C_2$–$C_6$-alkadienediyl: 1,3-butadiene-1,1-diyl, 1,3-butadiene-1,2-diyl, 1,3-butadiene-1,3-diyl, 1,3-butadiene-1,4-diyl, 1,3-pentadiene-1,1-diyl, 1,3-pentadiene-1,2-diyl, 1,3-pentadiene-1,3-diyl, 1,3-pentadiene-1,4-diyl, 1,3-pentadiene-1,5-diyl, 2,4-pentadiene-1,1-diyl, 2,4-pentadiene-1,2-diyl, 2,4-pentadiene-1,3-diyl, 2,4-pentadiene-1,4-diyl, 2,4-pentadiene-1,5-diyl, 1-methyl-1,3-butadiene-1,4-diyl, 1,3-hexadiene-1,1-diyl, 1,3-hexadiene-1,2-diyl, 1,3-hexadiene-1,3-diyl, 1,3-hexadiene-1,4-diyl, 1,3-hexadiene-1,5-diyl, 1,3-hexadiene-1,6-diyl, 1-methyl-1,3-pentadiene-1,2-diyl, 1-methyl-1,3-pentadiene-1,3-diyl, 1-methyl-1,3-pentadiene-1,4-diyl or 1-methyl-1,3-pentadiene-1,5-diyl;

$C_2$–$C_6$-alkynediyl: ethyne-1,2-diyl, 1-propyne-1,3-diyl, 2-propyne-1,1-diyl, 2-propyne-1,3-diyl, 1-butyne-1,3-diyl, 1-butyne-1,4-diyl, 2-butyne-1,1-diyl, 2-butyne-1,4-diyl, 1-methyl-2-propyne-1,1-diyl, 1-methyl-2-propyne-1,3-diyl, 1-pentyne-1,3-diyl, 1-pentyne-1,4-diyl, 1-pentyne-1,5-diyl, 2-pentyne-1,1-diyl, 2-pentyne-1,4-diyl, 2-pentyne-1,5-diyl, 3-pentyne-1,1-diyl, 3-pentyne-1,2-diyl, 3-pentyne-1,5-diyl, 4-pentyne-1,1-diyl, 4-pentyne-1,2-diyl, 4-pentyne-1,3-diyl, 4-pentyne-1,5-diyl, 1-hexyne-1,3-diyl, 1-hexyne-1,4-diyl, 1-hexyne-1,5-diyl, 1-hexyne-1,6-diyl, 2-hexyne-1,1-diyl, 2-hexyne-1,4-diyl, 2-hexyne-1,5-diyl, 2-hexyne-1,6-diyl, 3-hexyne-1,1-diyl, 3-hexyne-1,2-diyl, 3-hexyne-1,5-diyl, 3-hexyne-1,6-diyl, 4-hexyne-1,1-diyl, 4-hexyne-1,2-diyl, 4-hexyne-1,3-diyl, 4-hexyne-1,6-diyl, 5-hexyne-1,1-diyl, 5-hexyne-1,2-diyl, 5-hexyne-1,3-diyl, 5-hexyne-1,4-diyl or 5-hexyne-1,6-diyl;

$C_3$–$C_6$-cycloalkyl, and the cycloalkyl moieties of $C_3$–$C_6$-cycloalkylamino and $C_3$–$C_6$-cycloalkylcarbonyl: for example cyclopropyl, cyclobutyl, cyclopentyl or cyclohexyl;

heterocyclyl, and the heterocyclyl moieties of heterocyclyloxy, heterocyclylcarbonyl, heterocyclyl-$C_1$–$C_4$-alkyl, heterocyclyl-$C_1$–$C_6$-alkyl, heterocyclylsulfonyl or heterocyclyloxysulfonyl, heterocyclyloxycarbonyl, heterocyclyloxythiocarbonyl, heterocyclyl-$C_2$–$C_6$-alkenylcarbonyl, heterocyclylcarbonyl-$C_1$–$C_6$-alkyl, N—($C_1$–$C_6$-alkyl)—N-(heterocyclyl)aminocarbonyl, heterocyclylaminocarbonyl: a saturated, partially saturated or unsaturated 5- or 6-membered heterocyclic ring which contains one, two, there or four identical or different heteroatoms selected from the following group: oxygen, sulfur or nitrogen, i.e., for example, C-bonded 5-membered rings such as: tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, 2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 2-furyl, 3-furyl, 2-thienyl, 3-thienyl, pyrrol-2-yl, pyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-diokolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, $\Delta^3$-1,2-dithiol-3-yl, $\Delta^3$-1,2-dithiol-4-yl, $\Delta^3$-1,2-dithiol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-$\Delta^2$-oxadiazolin-4-yl, 1,2,3-$\Delta^2$-oxadiazolin-5-yl, 1,2,4-$\Delta^4$-oxadiazolin-3-yl, 1,2,4-$\Delta^4$-oxadiazolin-5-yl, 1,2,4-$\Delta^2$-oxadiazolin-3-yl, 1,2,4-$\Delta^2$-oxadiazolin-5-yl, 1,2,4-$\Delta^3$-oxadiazolin-3-yl, 1,2,4-$\Delta^3$-oxadiazolin-5-yl, 1,3,4-$\Delta^2$-oxadiazolin-2-yl, 1,3,4-$\Delta^2$-oxadiazolin-5-yl, 1,3,4-$\Delta^3$-oxadiazolin-2-yl, 1,3,4-oxadiazolin-2-yl, 1,2,4-$\Delta^4$-thiadiazolin-3-yl, 1,2,4-$\Delta^4$-thiadiazolin-5-yl, 1,2,4-$\Delta^3$-thiadiazolin-3-yl, 1,2,4-$\Delta^3$-thiadiazolin-5-yl, 1,2,4-$\Delta^2$-thiadiazolin-3-yl, 1,2,4-$\Delta^2$-thiadiazolin-5-yl, 1,3,4-$\Delta^2$-thiadiazolin-2-yl, 1,3,4-$\Delta^2$-thiadiazolin-5-yl, 1,3,4-$\Delta^3$-thiadiazolin-2-yl, 1,3,4-thiadiazolin-2-yl, 1,3,2-dioxathiolan-4-yl, 1,2,3-$\Delta^2$-triazolin-4-yl, 1,2,3-$\Delta^2$-triazolin-5-yl, 1,2,4-$\Delta^2$-triazolin-3-yl, 1,2,4-$\Delta^2$-triazolin-5-yl, 1,2,4-$\Delta^3$-triazolin-3-yl, 1,2,4-$\Delta^3$-triazolin-5-yl, 1,2,4-$\Delta^1$-triazolin-2-yl, 1,2,4-triazolin-3-yl, 3H-1,2,4-dithiazol-5-yl, 2H-1,3,4-dithiazol-5-yl, 2H-1,3,4-oxathiazol-5-yl, 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazol-2-yl, 1,2,3-triazol-4-yl, 1,2,4-triazol-3-yl, tetrazol-5-yl;

C-bonded 6-membered rings such as:

tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydropyran-6-yl, 2H-3,4-dihydrothiopyran-5-yl, 2H-3,4-dihydrothiopyran-4-yl, 2H-3,4-dihydropyran-3-yl, 2H-3,4-dihydropyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, pyridin-2-yl, pyridin-3-yl, pyridin-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5,6-tetrahydropyrimidin-2-yl, 3,4,5,6-tetrahydropyrimidin-4-yl, 3,4,5,6-tetrahydropyrimidin-5-yl, 3,4,5 6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,2-oxazin-3-yl, 2H-1,2-oxazin-4-yl, 2H-1,2-oxazin-5-yl, 2H-1,2-oxazin-6-yl, 2H-1,2-thiazin-3-yl, 2H-1,2-thiazin-4-yl, 2H-1,2-thiazin-5-yl, 2H-1,2-thiazin-6-yl, 4H-1,2-oxazin-3-yl, 4H-1,2-oxazin-4-yl, 4H-1,2-oxazin-5-yl, 4H-1,2-oxazin-6-yl, 4H-1,2-thiazin-3-yl, 4H-1,2-thiazin-4-yl, 4H-1,2-thiazin-5-yl, 4H-1,2-thiazin-6-yl, 6H-1,2-oxazin-3-yl, 6H-1,2-oxazin-4-yl, 6H-1,2-oxazin-5-yl, 6H-1,2-oxazin-6-yl, 6H-1,2-thiazin-3-yl, 6H-1,2-thiazin-4-yl, 6H-1,2-thiazin-5-yl, 6H-1,2-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl, 3,4-dihydropyrimidin-6-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl or 1,2,4,5-tetrazin-3-yl;

N-bonded 5-membered rings such as:

tetrahydropyrrol-1-yl, 2,3-dihydro-1H-pyrrol-1-yl, 2,5-dihydro-1H-pyrrol-1-yl, pyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl, pyrazol-1-yl, imidazol-1-yl, 1,2,4-$\Delta^4$-oxadiazolin-2-yl, 1,2,4-$\Delta^2$-oxadiazolin-4-yl, 1,2,4-$\Delta^3$-oxadiazolin-2-yl, 1,3,4-$\Delta^2$-oxadiazolin-4-yl, 1,2,4-$\Delta^5$-thiadiazolin-2-yl, 1,2,4-$\Delta^3$-thiadiazolin-2-yl, 1,2,4-$\Delta^2$-thiadiazolin-4-yl, 1,3,4-$\Delta^2$-thiadiazolin-4-yl, 1,2,3-$\Delta^2$-triazolin-1-yl, 1,2,4-$\Delta^2$-triazolin-4-yl, 1,2,4-$\Delta^2$-triazolin-4-yl, 1,2,4-$\Delta^3$-triazolin-1-yl, 1,2,4-$\Delta^1$-triazolin-4-yl, 1,2,3-triazol-1-yl, 1,2,4-triazol-1-yl, tetrazol-1-yl;

N-bonded 6-membered rings such as:

piperidin-1-yl, 1,2,3,4-tetrahydropyridin-1-yl, 1,2,5,6-tetrahydropyridin-1-yl, 1,4-dihydropyridin-1-yl, 1,2-dihydropyridin-1-yl, hexahydropyrimidin-1-yl, hexahydropyrazin-1-yl, hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl(morpholinyl), tetrahydro-1,2-oxazin-2-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl;

and also N-bonded cyclic imides such as:

phthalimide, tetrahydrophthalimide, succinimide, maleimide, glutarimide, 5-oxotriazolin-1-yl, 5-oxo-1,3,4-oxadiazolin-4-yl or 2,4-dioxo(1H,3H)pyrimidin-3-yl;

where, if appropriate, the sulfur of the heterocycles mentioned may be oxidized to S=O or S(=O)$_2$ and where a bicyclic ring system may be formed with a fused-on phenyl ring or with a $C_3$–$C_6$-carbocycle or with a further 5- to 6-membered heterocycle.

All phenyl rings or heterocyclyl radicals and all phenyl components in phenoxy, phenylalkyl, phenylcarbonylalkyl, phenylcarbonyl, phenylalkenylcarbonyl, phenoxycarbonyl, phenyloxythiocarbonyl, phenylaminocarbonyl and N-alkyl-N-phenylaminocarbonyl, phenylsulfonyl or phenoxysulfonyl or heterocyclyl components in heterocyclyloxy, heterocyclylalkyl, heterocyclylcarbonylalkyl, heterocyclylcarbonyl, heterocyclyloxythiocarbonyl, heterocyclylalkenylcarbonyl, heterocyclyloxycarbonyl, heterocyclylaminocarbonyl, N-alkyl-N-heterocyclylaminocarbonyl, heterocyclylsulfonyl or heterocyclyloxysulfonyl are, unless stated otherwise, preferably unsubstituted, or they carry one, two or three halogen atoms and/or a nitro group, a cyano radical and/or one or two methyl, trifluoromethyl, methoxy or trifluoromethoxy substituents.

With respect to the use of the compounds of the formula I according to the invention as herbicides, the variables X, Y, $R^1$ to $R^{16}$ preferably have the following meanings, in each case on their own or in combination:

$R^1$ is hydrogen, halogen, $C_1$–$C_6$-alkyl, $C_1$–$C_6$-alkyloxy, $C_1$–$C_6$-alkylthio, $C_1$–$C_6$-alkylsulfinyl, $C_1$–$C_6$-alkylsulfonyl, $C_1$–$C_6$-haloalkyl, $C_1$–$C_6$-alkoxyalkyl, $C_1$–$C_6$-alkylsulfonyl-$C_1$–$C_6$-alkyl, particularly preferably methyl, chloro, methoxy, methylthio, methylsulfinyl, methylsulfonyl, bromomethyl, methoxymethyl, methylsulfonylmethyl;

$R^2$ is hydrogen, halogen, for example chlorine or bromine, $C_1$–$C_6$-alkyl, for example methyl;

X is C—$R^3$ where $R^3$ is as defined above, or is N;

Y is S, $SO_2$ or $NR^4$ where $R^4$ is as defined above;

Pz is a radical of the formula IIa, where $R^8$, $R^9$ and $R^{10}$ are as defined above.

Preference is given, in particular, to compounds of the formula I where Y is O, S, $SO_2$ or N—$R^4$ and X is C—$R^3$. Preference is also given to compounds of the formula I where X is N and Y is S or N—$R^4$.

$R^8$, $R^9$ and $R^{10}$ independently of one another are preferably as defined below:

$R^8$ is hydroxyl, halogen, $OR^{11}$, $SR^{11}$, $SO_2R^{12}$, $OSO_2R^{12}$, $NR^{15}R^{16}$, $ONR^{15}R^{16}$ or N-bonded heterocyclyl which may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy or $C_1$–$C_4$-haloalkoxy; in particular hydroxyl, $OR^{11}$ or $OSO_2R^{12}$, specifically hydroxyl, $C_1$–$C_4$-alkyloxy, O—$CH_2$-phenyl, phenylcarbonyloxy, 2-, 3- or 4-fluorophenylcarbonyloxy, cyclopropylcarbonyloxy, $C_1$–$C_4$-sulfonyloxy, phenylsulfonyloxy and 2-, 3- or 4-methylphenylsulfonyloxy;

$R^9$ is $C_1$–$C_6$-alkyl, in particular $C_1$–$C_4$-alkyl, and $R^{10}$ is hydrogen or $C_1$–$C_4$-alkyl, in particular hydrogen or $C_1$–$C_4$-alkyl.

Preference is also given to compounds where $R^9$ is $C_3$–$C_6$-cycloalkyl, in particular cyclopropyl.

Particular preference is given to compounds of the formula I where X is C—$R^3$ and $R^3$ is hydrogen, halogen, cyano, thiocyanato, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkoxy-$C_1$–$C_6$-alkyl, is phenyl or pyridyl, where the two last-mentioned radicals may be partially or fully halogenated and/or may carry one, two or three, in particular one, of the following radicals: halogen, $C_1$–$C_4$-alkoxy, $C_1$–$C_4$-haloalkyl, and $C_1$–$C_4$-haloalkoxy; or is $COOR^5$ where $R^5$ is as defined above. Here, $R^5$ is in particular hydrogen or $C_1$–$C_6$-alkyl and particularly preferably hydrogen, methyl, ethyl, n-propyl, isopropyl, n-butyl, 2-butyl, isobutyl and tert-butyl.

Preference is also given to compounds I where $R^3$ is $C_3$–$C_6$-cycloalkyl or phenoxy which may be substituted as stated for phenyl.

Examples of preferred radicals $R^3$ are hydrogen, fluorine, chlorine, bromine, cyano, thiocyanato, methyl, ethyl, n-propyl, isopropyl, n-butyl, 2-butyl, isobutyl, tert-butyl, chloromethyl, dichloromethyl, trichloromethyl, fluoromethyl, difluoromethyl, trifluoromethyl, 2,2,2-trifluoroethyl, methoxymethyl, ethoxymethyl, methoxy, ethoxy, 1-propoxy, 2-propoxy, 1-butoxy, 2-butoxy, 2-methylprop-1-oxy, tert-butyloxy, difluoromethyloxy, trifluoromethyloxy, 2,2,2-trifluoroethyl-1-oxy, (methoxy) methyloxy, methylsulfanyl, ethylsulfanyl, n-propylsulfanyl, isopropylsulfanyl, 1-butylsulfanyl, 2-butylsulfanyl, 2-methylprop-1-ylsulfanyl, tert-butylsulfanyl, fluoromethylsulfanyl, trifluoromethylsulfanyl, 2,2,2-trifluoroethyl-1-sulfanyl, 2-(methylcarbonyl)ethyl, phenyl, 2-, 3- or 4-fluorophenyl, 2-, 3- or 4-chlorophenyl, 2-, 3- or 4-hydroxyphenyl, 2-, 3- or 4-methoxyphenyl, 2-, 3- or 4-(trifluoromethoxy)phenyl, 2-, 3- or 4-(difluoromethoxy) phenyl, 2-, 3- or 4-(trifluoromethyl)phenyl, 2-, 3- or 4-tolyl, 2-, 3- or 4-pyridinyl, 2-, 3- or 4-fluorophenoxy, 2-, 3- or 4-methoxyphenoxy, 2-, 3- or 4-trifluoromethylphenoxy, 2-, 3- or 4-chlorophenoxy, methoxycarbonyl, ethoxycarbonyl, trifluoromethoxycarbonyl, isopropoxycarbonyl, tert-butoxycarbonyl and phenoxycarbonyl.

Very particularly preferred compounds of the formula I where X=C—$R^3$ are those compounds where $R^3$ is hydrogen, halogen, in particular fluorine or chlorine, $C_1$–$C_4$-alkyl, $C_1$–$C_4$-haloalkyl, in particular fluoromethyl, difluoromethyl, trifluoromethyl and 2,2,2-trifluoroethyl, or phenyl or phenoxy where the phenyl or phenoxy radical may carry one, two or three, in particular one, substituent(s), selected from the group consisting of $C_1$–$C_4$-alkyl, in particular methyl, halogen, in particular fluorine or chlorine, $C_1$–$C_4$-alkoxy, in particular methoxy, or haloalkoxy, in particular trifluoromethoxy.

Among the pyrazole derivatives of the formula I mentioned above, particular preference is given to those compounds which are derived from benzothiazole-5-carboxylic acid, i.e. compounds of the formula I where X is a radical C—$R^3$ and Y is selected from the group consisting of S, SO and $SO_2$. In turn, among the pyrazole derivatives of benzothiazole preference is given to those where $R^3$ has one of the meanings mentioned above as being preferred. In particular, Y is S or $SO_2$.

Preference according to the invention is also given to those pyrazolyl derivatives which are derived from benzoxazole-5-carboxylic acid, i.e. compounds of the formula I where X is a group C—$R^3$ where $R^3$ is as defined above and Y is an oxygen atom. Among these, in turn, preference is given to those compounds where $R^3$ has the meanings given above as being preferred.

Preference is also given to pyrazole derivatives of the formula I which are derived from benzimidazole-5-carboxylic acid, i.e. compounds of the formula I where X is C—$R^3$, where $R^3$ is as defined above, and Y is a group N—$R^4$, where $R^4$ is as defined above. Among these, preference is given to those benzimidazole derivatives of the formula I where $R^3$ has the meanings given above as being preferred for $R^3$. Furthermore, preference is given to benzimidazole derivatives of the formula I where $R^4$ is hydrogen, $C_1$–$C_6$-alkyl or $C_1$–$C_6$-haloalkyl, in particular hydrogen, methyl, ethyl, n-propyl or isopropyl.

Preference according to the invention is also given to pyrazolyl derivatives of benzotriazole-5-carboxylic acid, i.e. compounds of the formula I where X is nitrogen and Y is a group N—$R^4$, where $R^4$ is as defined above. Among these, in turn, preference is given to those compounds where $R^4$ has the meanings given above as being preferred.

Preference according to the invention is also given to pyrazolyl derivatives of benzothiadiazole-5-carboxylic acid, i.e. compounds of the formula I where X is N and Y is S. Preference is also given to pyrazole derivatives of benzoisothiadiazolecarboxylic acid, i.e. compounds of the formula I where X—Y is S=N and X is S.

Among the pyrazolyl derivatives of the formula I mentioned as being preferred, preference is, in turn, given to those compounds where Pz in the formula I is a group of the formula IIa. Among these, in turn, particular preference is given to compounds of the formula I where the variables $R^8$, $R^9$ and $R^{10}$ in the formula IIa on their own, and particularly preferably in combination with one another, are as defined below:

$R^8$ is hydroxyl, halogen, $OR^{11}$, $SR^{11}$, $SO_2R^{12}$, $OSO_2R^{12}$, $NR^{15}R^{16}$, $ONR^{15}R^{16}$ or N-bonded heterocyclyl which may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy or $C_1$–$C_4$-haloalkoxy, in particular hydroxyl, $OR^{11}$ and $OSO_2R^{12}$;

$R^9$ is $C_1$–$C_4$-alkyl or cyclopropyl;

$R^{10}$ is hydrogen or $C_1$–$C_4$-alkyl.

Among the compounds of the formula I where Pz is a pyrazolyl radical of the formula IIa, very particular preference is given to those compounds where the variables $R^8$, $R^9$ and $R^{10}$ together have the following meanings:

$R^8$ is hydroxyl, $C_1$–$C_4$-alkyloxy, O—$CH_2$-phenyl, phenylcarbonyloxy, 2-, 3- or 4-fluorophenylcarbonyloxy, cyclopropylcarbonyloxy, $C_1$–$C_4$-sulfonyloxy, phenylsulfonyloxy and 2-, 3- or 4-methylphenylsulfonyloxy;

$R^9$ is $C_1$–$C_4$-alkyl or cyclopropyl and $R^{10}$ is hydrogen or $C_1$–$C_4$-alkyl.

Very particularly preferred radicals of the formula IIa are the radicals IIa1 to IIa90 given in Table 1.

TABLE 1

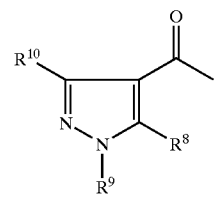

IIa

| IIa | $R^8$ | $R^9$ | $R^{10}$ |
|---|---|---|---|
| IIa1 | OH | $CH_3$ | H |
| IIa2 | $OCH_3$ | $CH_3$ | H |
| IIa3 | $OCH_2$—$C_6H_5$ | $CH_3$ | H |
| IIa4 | $OC(O)CH_3$ | $CH_3$ | H |
| IIa5 | $OC(O)C_6H_5$ | $CH_3$ | H |
| IIa6 | $OC(O)$—(3-$C_6H_4F$) | $CH_3$ | H |
| IIa7 | $OS(O)_2CH_3$ | $CH_3$ | H |
| IIa8 | $OS(O)_2$—(4-$C_6H_4CH_3$) | $CH_3$ | H |
| IIa9 | OH | $C_2H_5$ | H |
| IIa10 | $OCH_3$ | $C_2H_5$ | H |
| IIa11 | $OCH_2$—$C_6H_5$ | $C_2H_5$ | H |
| IIa12 | $OC(O)CH_3$ | $C_2H_5$ | H |
| IIa13 | $OC(O)C_6H_5$ | $C_2H_5$ | H |
| IIa14 | $OC(O)$—(3-$C_6H_4F$) | $C_2H_5$ | H |
| IIa15 | $OS(O)_2CH_3$ | $C_2H_5$ | H |
| IIa16 | $OS(O)_2$—(4-$C_6H_4CH_3$) | $C_2H_5$ | H |
| IIa17 | OH | i-$C_3H_7$ | H |
| IIa18 | $OCH_3$ | i-$C_3H_7$ | H |
| IIa19 | $OCH_2$—$C_6H_5$ | i-$C_3H_7$ | H |
| IIa20 | $OC(O)CH_3$ | i-$C_3H_7$ | H |
| IIa21 | $OC(O)C_6H_5$ | i-$C_3H_7$ | H |
| IIa22 | $OC(O)$—(3-$C_6H_4F$) | i-$C_3H_7$ | H |
| IIa23 | $OS(O)_2CH_3$ | i-$C_3H_7$ | H |
| IIa24 | $OS(O)_2$—(4-$C_6H_4CH_3$) | i-$C_3H_7$ | H |
| IIa25 | OH | t-$C_4H_9$ | H |
| IIa26 | $OCH_3$ | t-$C_4H_9$ | H |
| IIa27 | $OCH_2$—$C_6H_5$ | t-$C_4H_9$ | H |
| IIa28 | $OC(O)CH_3$ | t-$C_4H_9$ | H |
| IIa29 | $OC(O)C_6H_5$ | t-$C_4H_9$ | H |
| IIa30 | $OC(O)$—(3-$C_6H_4F$) | t-$C_4H_9$ | H |
| IIa31 | $OS(O)_2CH_3$ | t-$C_4H_9$ | H |
| IIa32 | $OS(O)_2$—(4-$C_6H_4CH_3$) | t-$C_4H_9$ | H |
| IIa33 | OH | $CH_3$ | $CH_3$ |
| IIa34 | $OCH_3$ | $CH_3$ | $CH_3$ |
| IIa35 | $OCH_2$—$C_6H_5$ | $CH_3$ | $CH_3$ |
| IIa36 | $OC(O)CH_3$ | $CH_3$ | $CH_3$ |
| IIa37 | $OC(O)C_6H_5$ | $CH_3$ | $CH_3$ |
| IIa38 | $OC(O)$—(3-$C_6H_4F$) | $CH_3$ | $CH_3$ |
| IIa39 | $OS(O)_2CH_3$ | $CH_3$ | $CH_3$ |
| IIa40 | $OS(O)_2$—(4-$C_6H_4CH_3$) | $CH_3$ | $CH_3$ |
| IIa41 | OH | $C_2H_5$ | $CH_3$ |
| IIa42 | $OCH_3$ | $C_2H_5$ | $CH_3$ |
| IIa43 | $OCH_2$—$C_6H_5$ | $C_2H_5$ | $CH_3$ |
| IIa44 | $OC(O)CH_3$ | $C_2H_5$ | $CH_3$ |
| IIa45 | $OC(O)C_6H_5$ | $C_2H_5$ | $CH_3$ |
| IIa46 | $OC(O)$—(3-$C_6H_4F$) | $C_2H_5$ | $CH_3$ |
| IIa47 | $OS(O)_2CH_3$ | $C_2H_5$ | $CH_3$ |
| IIa48 | $OS(O)_2$—(4-$C_6H_4CH_3$) | $C_2H_5$ | $CH_3$ |
| IIa49 | OH | i-$C_3H_7$ | $CH_3$ |
| IIa50 | $OCH_3$ | i-$C_3H_7$ | $CH_3$ |
| IIa51 | $OCH_2$—$C_6H_5$ | i-$C_3H_7$ | $CH_3$ |
| IIa52 | $OC(O)CH_3$ | i-$C_3H_7$ | $CH_3$ |
| IIa53 | $OC(O)C_6H_5$ | i-$C_3H_7$ | $CH_3$ |
| IIa54 | $OC(O)$—(3-$C_6H_4F$) | i-$C_3H_7$ | $CH_3$ |
| IIa55 | $OS(O)_2CH_3$ | i-$C_3H_7$ | $CH_3$ |
| IIa56 | $OS(O)_2$—(4-$C_6H_4CH_3$) | i-$C_3H_7$ | $CH_3$ |
| IIa57 | OH | t-$C_4H_9$ | $CH_3$ |
| IIa58 | $OCH_3$ | t-$C_4H_9$ | $CH_3$ |
| IIa59 | $OCH_2$—$C_6H_5$ | t-$C_4H_9$ | $CH_3$ |
| IIa60 | $OC(O)CH_3$ | t-$C_4H_9$ | $CH_3$ |
| IIa61 | $OC(O)C_6H_5$ | t-$C_4H_9$ | $CH_3$ |
| IIa62 | $OC(O)$—(3-$C_6H_4F$) | t-$C_4H_9$ | $CH_3$ |
| IIa63 | $OS(O)_2CH_3$ | t-$C_4H_9$ | $CH_3$ |
| IIa64 | $OS(O)_2$—(4-$C_6H_4CH_3$) | t-$C_4H_9$ | $CH_3$ |
| IIa65 | OH | c-$C_3H_5$ | $CH_3$ |
| IIa66 | $OCH_3$ | c-$C_3H_5$ | $CH_3$ |
| IIa67 | $OCH_2$—$C_6H_5$ | c-$C_3H_5$ | $CH_3$ |
| IIa68 | $OC(O)CH_3$ | c-$C_3H_5$ | $CH_3$ |
| IIa69 | $OC(O)C_6H_5$ | c-$C_3H_5$ | $CH_3$ |
| IIa70 | $OC(O)$—(3-$C_6H_4F$) | c-$C_3H_5$ | $CH_3$ |
| IIa71 | $OS(O)_2CH_3$ | c-$C_3H_5$ | $CH_3$ |
| IIa72 | $OS(O)_2$—(4-$C_6H_4CH_3$) | c-$C_3H_5$ | $CH_3$ |
| IIa73 | OH | c-$C_3H_5$ | H |
| IIa74 | $OCH_3$ | c-$C_3H_5$ | H |
| IIa75 | $OCH_2$—$C_6H_5$ | c-$C_3H_5$ | H |
| IIa76 | $OC(O)CH_3$ | c-$C_3H_5$ | H |
| IIa77 | $OC(O)C_6H_5$ | c-$C_3H_5$ | H |
| IIa78 | $OC(O)$—(3-$C_6H_4F$) | c-$C_3H_5$ | H |
| IIa79 | $OS(O)_2CH_3$ | c-$C_3H_5$ | H |
| IIa80 | $OS(O)_2$—(4-$C_6H_4CH_3$) | c-$C_3H_5$ | H |
| IIa81 | $OC(O)$c-$C_3H_5$ | $CH_3$ | H |
| IIa82 | $OC(O)$-c-$C_3H_5$ | $C_2H_5$ | H |
| IIa83 | $OC(O)$-c-$C_3H_5$ | i-$C_3H_7$ | H |
| IIa84 | $OC(O)$-c-$C_3H_5$ | t-$C_4H_9$ | H |

TABLE 1-continued

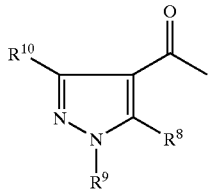

IIa

| IIa | R⁸ | R⁹ | R¹⁰ |
|---|---|---|---|
| IIa85 | OC(O)-c-$C_3H_5$ | c-$C_3H_5$ | H |
| IIa86 | OC(O)-c-$C_3H_5$ | $CH_3$ | $CH_3$ |
| IIa87 | OC(O)-c-$C_3H_5$ | $C_2H_5$ | $CH_3$ |
| IIa88 | OC(O)-c-$C_3H_5$ | i-$C_3H_7$ | $CH_3$ |
| IIa89 | OC(O)-c-$C_3H_5$ | t-$C_4H_9$ | $CH_3$ |
| IIa90 | OC(O)-c-$C_3H_5$ | c-$C_3H_5$ | $CH_3$ | i-$C_3H_7$: isopropyl
c-$C_3H_5$: cyclopropyl
t-$C_4H_9$: tertiary butyl
$C_6H_5$: phenyl
3-$C_6H_4F$: 3-fluorophenyl
4-$C_6H_4CH_3$: 4-methylphenyl

TABLE A

Particularly preferred combinations of $R^1$, $R^2$ and $R^3$

| | $R^3$ | $R^1$ | $R^2$ |
|---|---|---|---|
| 1 | H | $CH_3$ | $CH_3$ |
| 2 | F | $CH_3$ | $CH_3$ |
| 3 | Cl | $CH_3$ | $CH_3$ |
| 4 | Br | $CH_3$ | $CH_3$ |
| 5 | OH | $CH_3$ | $CH_3$ |
| 6 | SH | $CH_3$ | $CH_3$ |
| 7 | $NH_2$ | $CH_3$ | $CH_3$ |
| 8 | CN | $CH_3$ | $CH_3$ |
| 9 | $NO_2$ | $CH_3$ | $CH_3$ |
| 10 | SCN | $CH_3$ | $CH_3$ |
| 11 | NH—$NH_2$ | $CH_3$ | $CH_3$ |
| 12 | $CH_3$ | $CH_3$ | $CH_3$ |
| 13 | $C_2H_5$ | $CH_3$ | $CH_3$ |
| 14 | n-$C_3H_7$ | $CH_3$ | $CH_3$ |
| 15 | i-$C_3H_7$ | $CH_3$ | $CH_3$ |
| 16 | n-$C_4H_9$ | $CH_3$ | $CH_3$ |
| 17 | s-$C_4H_9$ | $CH_3$ | $CH_3$ |
| 18 | i-$C_4H_9$ | $CH_3$ | $CH_3$ |
| 19 | t-$C_4H_9$ | $CH_3$ | $CH_3$ |
| 20 | $CH_2Cl$ | $CH_3$ | $CH_3$ |
| 21 | $CHCl_2$ | $CH_3$ | $CH_3$ |
| 22 | $CCl_3$ | $CH_3$ | $CH_3$ |
| 23 | $CH_2F$ | $CH_3$ | $CH_3$ |
| 24 | $CHF_2$ | $CH_3$ | $CH_3$ |
| 25 | $CF_3$ | $CH_3$ | $CH_3$ |
| 26 | $CH_2CF_3$ | $CH_3$ | $CH_3$ |
| 27 | $CH_2OCH_3$ | $CH_3$ | $CH_3$ |
| 28 | $CH_2OCH_2CH_3$ | $CH_3$ | $CH_3$ |
| 29 | $CH_2NH_2$ | $CH_3$ | $CH_3$ |
| 30 | $OCH_3$ | $CH_3$ | $CH_3$ |
| 31 | $OC_2H_5$ | $CH_3$ | $CH_3$ |
| 32 | O-n-$C_3H_7$ | $CH_3$ | $CH_3$ |
| 33 | O-i-$C_3H_7$ | $CH_3$ | $CH_3$ |
| 34 | O-n-$C_4H_9$ | $CH_3$ | $CH_3$ |
| 35 | O-s-$C_4H_9$ | $CH_3$ | $CH_3$ |
| 36 | O-i-$C_4H_9$ | $CH_3$ | $CH_3$ |
| 37 | O-t-$C_4H_9$ | $CH_3$ | $CH_3$ |
| 38 | $OCHF_2$ | $CH_3$ | $CH_3$ |
| 39 | $OCF_3$ | $CH_3$ | $CH_3$ |
| 40 | $OCH_2CF_3$ | $CH_3$ | $CH_3$ |
| 41 | $OCH_2OCH_3$ | $CH_3$ | $CH_3$ |
| 42 | $SCH_3$ | $CH_3$ | $CH_3$ |
| 43 | $SC_2H_5$ | $CH_3$ | $CH_3$ |
| 44 | S-n-$C_3H_7$ | $CH_3$ | $CH_3$ |
| 45 | S-i-$C_3H_7$ | $CH_3$ | $CH_3$ |
| 46 | S-n-$C_4H_9$ | $CH_3$ | $CH_3$ |
| 47 | S-s-$C_4H_9$ | $CH_3$ | $CH_3$ |
| 48 | S-i-$C_4H_9$ | $CH_3$ | $CH_3$ |
| 49 | S-t-$C_4H_9$ | $CH_3$ | $CH_3$ |
| 50 | $SCHF_2$ | $CH_3$ | $CH_3$ |
| 51 | $SCF_3$ | $CH_3$ | $CH_3$ |
| 52 | $SCH_2CF_3$ | $CH_3$ | $CH_3$ |
| 53 | $SCH_2OCH_3$ | $CH_3$ | $CH_3$ |
| 54 | $NHCH_3$ | $CH_3$ | $CH_3$ |
| 55 | $NHC_2H_5$ | $CH_3$ | $CH_3$ |
| 56 | NH-phenyl | $CH_3$ | $CH_3$ |
| 57 | $N(CH_3)_2$ | $CH_3$ | $CH_3$ |
| 58 | $N(CH_2CH_3)_2$ | $CH_3$ | $CH_3$ |
| 59 | $N(phenyl)_2$ | $CH_3$ | $CH_3$ |
| 60 | $(CH_2)_2COCH_3$ | $CH_3$ | $CH_3$ |
| 61 | phenyl | $CH_3$ | $CH_3$ |
| 62 | 2-F-phenyl | $CH_3$ | $CH_3$ |
| 63 | 3-F-phenyl | $CH_3$ | $CH_3$ |
| 64 | 4-F-phenyl | $CH_3$ | $CH_3$ |
| 65 | 2-Cl-phenyl | $CH_3$ | $CH_3$ |
| 66 | 3-Cl-phenyl | $CH_3$ | $CH_3$ |
| 67 | 4-Cl-phenyl | $CH_3$ | $CH_3$ |
| 68 | 2-OH-phenyl | $CH_3$ | $CH_3$ |
| 69 | 3-OH-phenyl | $CH_3$ | $CH_3$ |
| 70 | 4-OH-phenyl | $CH_3$ | $CH_3$ |
| 71 | 2-$OCH_3$-phenyl | $CH_3$ | $CH_3$ |
| 72 | 3-$OCH_3$-phenyl | $CH_3$ | $CH_3$ |
| 73 | 4-$OCH_3$-phenyl | $CH_3$ | $CH_3$ |
| 74 | 2-$OCH_3$-phenyl | $CH_3$ | $CH_3$ |
| 75 | 3-$OCF_3$-phenyl | $CH_3$ | $CH_3$ |
| 76 | 4-$OCF_3$-phenyl | $CH_3$ | $CH_3$ |
| 77 | 2-$OCHF_2$-phenyl | $CH_3$ | $CH_3$ |
| 78 | 3-$OCHF_2$-phenyl | $CH_3$ | $CH_3$ |
| 79 | 4-$OCHF_2$-phenyl | $CH_3$ | $CH_3$ |
| 80 | 2-$CF_3$-phenyl | $CH_3$ | $CH_3$ |
| 81 | 3-$CF_3$-phenyl | $CH_3$ | $CH_3$ |
| 82 | 4-$CF_3$-phenyl | $CH_3$ | $CH_3$ |
| 83 | 2-$CH_3$-phenyl | $CH_3$ | $CH_3$ |
| 84 | 3-$CH_3$-phenyl | $CH_3$ | $CH_3$ |
| 85 | 4-$CH_3$-phenyl | $CH_3$ | $CH_3$ |
| 86 | 2-$NO_2$-phenyl | $CH_3$ | $CH_3$ |
| 87 | 3-$NO_2$-phenyl | $CH_3$ | $CH_3$ |
| 88 | 4-$NO_2$-phenyl | $CH_3$ | $CH_3$ |
| 89 | 2-pyridyl | $CH_3$ | $CH_3$ |
| 90 | 3-pyridyl | $CH_3$ | $CH_3$ |
| 91 | 4-pyridyl | $CH_3$ | $CH_3$ |
| 92 | 3'-$CH_3$-2-pyridyl | $CH_3$ | $CH_3$ |
| 93 | 4'-$CH_3$-2-pyridyl | $CH_3$ | $CH_3$ |
| 94 | 5'-$CH_3$-2-pyridyl | $CH_3$ | $CH_3$ |
| 95 | 6'-$CH_3$-2-pyridyl | $CH_3$ | $CH_3$ |
| 96 | 2'-$CH_3$-3-pyridyl | $CH_3$ | $CH_3$ |
| 97 | 4'-$CH_3$-3-pyridyl | $CH_3$ | $CH_3$ |
| 98 | 5'-$CH_3$-3-pyridyl | $CH_3$ | $CH_3$ |
| 99 | 6'-$CH_3$-3-pyridyl | $CH_3$ | $CH_3$ |
| 100 | 2'-$CH_3$-4-pyridyl | $CH_3$ | $CH_3$ |
| 101 | 3'-$CH_3$-4-pyridyl | $CH_3$ | $CH_3$ |
| 102 | 3'-Cl-2-pyridyl | $CH_3$ | $CH_3$ |
| 103 | 4'-Cl-2-pyridyl | $CH_3$ | $CH_3$ |
| 104 | 5'-Cl-2-pyridyl | $CH_3$ | $CH_3$ |
| 105 | 6'-Cl-2-pyridyl | $CH_3$ | $CH_3$ |
| 106 | 2'-Cl-3-pyridyl | $CH_3$ | $CH_3$ |
| 107 | 4'-Cl-3-pyridyl | $CH_3$ | $CH_3$ |
| 108 | 5'-Cl-3-pyridyl | $CH_3$ | $CH_3$ |
| 109 | 6'-Cl-3-pyridyl | $CH_3$ | $CH_3$ |
| 110 | 2'-Cl-4-pyridyl | $CH_3$ | $CH_3$ |
| 111 | 3'-Cl-4-pyridyl | $CH_3$ | $CH_3$ |
| 112 | cyclohexylamino | $CH_3$ | $CH_3$ |
| 113 | cyclopentylamino | $CH_3$ | $CH_3$ |
| 114 | morpholino | $CH_3$ | $CH_3$ |
| 115 | $CO_2H$ | $CH_3$ | $CH_3$ |
| 116 | $CO_2CH_3$ | $CH_3$ | $CH_3$ |
| 117 | $CO_2C_2H_5$ | $CH_3$ | $CH_3$ |
| 118 | $CO_2$-n-$C_3H_7$ | $CH_3$ | $CH_3$ |
| 119 | $CO_2$-i-$C_3H_7$ | $CH_3$ | $CH_3$ |

TABLE A-continued

Particularly preferred combinations of R¹, R² and R³

| | R³ | R¹ | R² |
|---|---|---|---|
| 120 | CO₂-n-C₄H₉ | CH₃ | CH₃ |
| 121 | CO₂-s-C₄H₉ | CH₃ | CH₃ |
| 122 | CO₂-i-C₄H₉ | CH₃ | CH₃ |
| 123 | CO₂-t-C₄H₉ | CH₃ | CH₃ |
| 124 | CO₂-Ph | CH₃ | CH₃ |
| 125 | CO₂-3-pyridyl | CH₃ | CH₃ |
| 126 | CONHCH₃ | CH₃ | CH₃ |
| 127 | CONHC₂H₅ | CH₃ | CH₃ |
| 128 | CONHPh | CH₃ | CH₃ |
| 129 | CON(CH₃)₂ | CH₃ | CH₃ |
| 130 | CON(CH₂CH₃)₂ | CH₃ | CH₃ |
| 131 | CON(phenyl)₂ | CH₃ | CH₃ |
| 132 | H | OCH₃ | CH₃ |
| 133 | F | OCH₃ | CH₃ |
| 134 | Cl | OCH₃ | CH₃ |
| 135 | Br | OCH₃ | CH₃ |
| 136 | OH | OCH₃ | CH₃ |
| 137 | SH | OCH₃ | CH₃ |
| 138 | NH₂ | OCH₃ | CH₃ |
| 139 | CN | OCH₃ | CH₃ |
| 140 | NO₂ | OCH₃ | CH₃ |
| 141 | SCN | OCH₃ | CH₃ |
| 142 | NH—NH₂ | OCH₃ | CH₃ |
| 143 | CH₃ | OCH₃ | CH₃ |
| 144 | C₂H₅ | OCH₃ | CH₃ |
| 145 | n-C₃H₇ | OCH₃ | CH₃ |
| 146 | i-C₃H₇ | OCH₃ | CH₃ |
| 147 | n-C₄H₉ | OCH₃ | CH₃ |
| 148 | s-C₄H₉ | OCH₃ | CH₃ |
| 149 | i-C₄H₉ | OCH₃ | CH₃ |
| 150 | t-C₄H₉ | OCH₃ | CH₃ |
| 151 | CH₂Cl | OCH₃ | CH₃ |
| 152 | CHCl₂ | OCH₃ | CH₃ |
| 153 | CCl₃ | OCH₃ | CH₃ |
| 154 | CH₂F | OCH₃ | CH₃ |
| 155 | CHF₂ | OCH₃ | CH₃ |
| 156 | CF₃ | OCH₃ | CH₃ |
| 157 | CH₂CF₃ | OCH₃ | CH₃ |
| 158 | CH₂OCH₃ | OCH₃ | CH₃ |
| 159 | CH₂OCH₂CH₃ | OCH₃ | CH₃ |
| 160 | CH₂NH₂ | OCH₃ | CH₃ |
| 161 | OCH₃ | OCH₃ | CH₃ |
| 162 | OC₂H₅ | OCH₃ | CH₃ |
| 163 | O-n-C₃H₇ | OCH₃ | CH₃ |
| 164 | O-i-C₃H₇ | OCH₃ | CH₃ |
| 165 | O-n-C₄H₉ | OCH₃ | CH₃ |
| 166 | O-s-C₄H₉ | OCH₃ | CH₃ |
| 167 | O-i-C₄H₉ | OCH₃ | CH₃ |
| 168 | O-t-C₄H₉ | OCH₃ | CH₃ |
| 169 | OCHF₂ | OCH₃ | CH₃ |
| 170 | OCF₃ | OCH₃ | CH₃ |
| 171 | OCH₂CF₃ | OCH₃ | CH₃ |
| 172 | OCH₂OCH₃ | OCH₃ | CH₃ |
| 173 | SCH₃ | OCH₃ | CH₃ |
| 174 | SC₂H₅ | OCH₃ | CH₃ |
| 175 | S-n-C₃H₇ | OCH₃ | CH₃ |
| 176 | S-i-C₃H₇ | OCH₃ | CH₃ |
| 177 | S-n-C₄H₉ | OCH₃ | CH₃ |
| 178 | S-s-C₄H₉ | OCH₃ | CH₃ |
| 179 | S-i-C₄H₉ | OCH₃ | CH₃ |
| 180 | S-t-C₄H₉ | OCH₃ | CH₃ |
| 181 | SCHF₂ | OCH₃ | CH₃ |
| 182 | SCF₃ | OCH₃ | CH₃ |
| 183 | SCH₂CF₃ | OCH₃ | CH₃ |
| 184 | SCH₂OCH₃ | OCH₃ | CH₃ |
| 185 | NHCH₃ | OCH₃ | CH₃ |
| 186 | NHC₂H₅ | OCH₃ | CH₃ |
| 187 | NHphenyl | OCH₃ | CH₃ |
| 188 | N(CH₃)₂ | OCH₃ | CH₃ |
| 189 | N(CH₂CH₃)₂ | OCH₃ | CH₃ |
| 190 | N(phenyl)₂ | OCH₃ | CH₃ |
| 191 | (CH₂)₂COCH₃ | OCH₃ | CH₃ |
| 192 | phenyl | OCH₃ | CH₃ |
| 193 | 2-F-phenyl | OCH₃ | CH₃ |
| 194 | 3-F-phenyl | OCH₃ | CH₃ |
| 195 | 4-F-phenyl | OCH₃ | CH₃ |
| 196 | 2-Cl-phenyl | OCH₃ | CH₃ |
| 197 | 3-Cl-phenyl | OCH₃ | CH₃ |
| 198 | 4-Cl-phenyl | OCH₃ | CH₃ |
| 199 | 2-OH-phenyl | OCH₃ | CH₃ |
| 200 | 3-OH-phenyl | OCH₃ | CH₃ |
| 201 | 4-OH-phenyl | OCH₃ | CH₃ |
| 202 | 2-OCH₃-phenyl | OCH₃ | CH₃ |
| 203 | 3-OCH₃-phenyl | OCH₃ | CH₃ |
| 204 | 4-OCH₃-phenyl | OCH₃ | CH₃ |
| 205 | 2-OCF₃-phenyl | OCH₃ | CH₃ |
| 206 | 3-OCF₃-phenyl | OCH₃ | CH₃ |
| 207 | 4-OCF₃-phenyl | OCH₃ | CH₃ |
| 208 | 2-OCHF₂-phenyl | OCH₃ | CH₃ |
| 209 | 3-OCHF₂-phenyl | OCH₃ | CH₃ |
| 210 | 4-OCHF₂-phenyl | OCH₃ | CH₃ |
| 211 | 2-CF₃-phenyl | OCH₃ | CH₃ |
| 212 | 3-CF₃-phenyl | OCH₃ | CH₃ |
| 213 | 4-CF₃-phenyl | OCH₃ | CH₃ |
| 214 | 2-CH₃-phenyl | OCH₃ | CH₃ |
| 215 | 3-CH₃-phenyl | OCH₃ | CH₃ |
| 216 | 4-CH₃-phenyl | OCH₃ | CH₃ |
| 217 | 2-NO₂-phenyl | OCH₃ | CH₃ |
| 218 | 3-NO₂-phenyl | OCH₃ | CH₃ |
| 219 | 4-NO₂-phenyl | OCH₃ | CH₃ |
| 220 | 2-pyridyl | OCH₃ | CH₃ |
| 221 | 3-pyridyl | OCH₃ | CH₃ |
| 222 | 4-pyridyl | OCH₃ | CH₃ |
| 223 | 3'-CH₃-2-pyridyl | OCH₃ | CH₃ |
| 224 | 4'-CH₃-2-pyridyl | OCH₃ | CH₃ |
| 225 | 5'-CH₃-2-pyridyl | OCH₃ | CH₃ |
| 226 | 6'-CH₃-2-pyridyl | OCH₃ | CH₃ |
| 227 | 2'-CH₃-3-pyridyl | OCH₃ | CH₃ |
| 228 | 4'-CH₃-3-pyridyl | OCH₃ | CH₃ |
| 229 | 5'-CH₃-3-pyridyl | OCH₃ | CH₃ |
| 230 | 6'-CH₃-3-pyridyl | OCH₃ | CH₃ |
| 231 | 2'-CH₃-4-pyridyl | OCH₃ | CH₃ |
| 232 | 3'-CH₃-4-pyridyl | OCH₃ | CH₃ |
| 233 | 3'-Cl-2-pyridyl | OCH₃ | CH₃ |
| 234 | 4'-Cl-2-pyridyl | OCH₃ | CH₃ |
| 235 | 5'-Cl-2-pyridyl | OCH₃ | CH₃ |
| 236 | 6'-Cl-2-pyridyl | OCH₃ | CH₃ |
| 237 | 2'-Cl-3-pyridyl | OCH₃ | CH₃ |
| 238 | 4'-Cl-3-pyridyl | OCH₃ | CH₃ |
| 239 | 5'-Cl-3-pyridyl | OCH₃ | CH₃ |
| 240 | 6'-Cl-3-pyridyl | OCH₃ | CH₃ |
| 241 | 2'-Cl-4-pyridyl | OCH₃ | CH₃ |
| 242 | 3'-Cl-4-pyridyl | OCH₃ | CH₃ |
| 243 | cyclohexylamino | OCH₃ | CH₃ |
| 244 | cyclopentylamino | OCH₃ | CH₃ |
| 245 | morpholino | OCH₃ | CH₃ |
| 246 | CO₂H | OCH₃ | CH₃ |
| 247 | CO₂CH₃ | OCH₃ | CH₃ |
| 248 | CO₂C₂H₅ | OCH₃ | CH₃ |
| 249 | CO₂-n-C₃H₇ | OCH₃ | CH₃ |
| 250 | CO₂-i-C₃H₇ | OCH₃ | CH₃ |
| 251 | CO₂-n-C₄H₉ | OCH₃ | CH₃ |
| 252 | CO₂-s-C₄H₉ | OCH₃ | CH₃ |
| 253 | CO₂-i-C₄H₉ | OCH₃ | CH₃ |
| 254 | CO₂-t-C₄H₉ | OCH₃ | CH₃ |
| 255 | CO₂-Ph | OCH₃ | CH₃ |
| 256 | CO₂-3-pyridyl | OCH₃ | CH₃ |
| 257 | CONHCH₃ | OCH₃ | CH₃ |
| 258 | CONHC₂H₅ | OCH₃ | CH₃ |
| 259 | CONHphenyl | OCH₃ | CH₃ |
| 260 | CON(CH₃)₂ | OCH₃ | CH₃ |
| 261 | CON(CH₂CH₃)₂ | OCH₃ | CH₃ |
| 262 | CON(phenyl)₂ | OCH₃ | CH₃ |
| 263 | H | Cl | CH₃ |
| 264 | F | Cl | CH₃ |
| 265 | Cl | Cl | CH₃ |
| 266 | Br | Cl | CH₃ |
| 267 | OH | Cl | CH₃ |
| 268 | SH | Cl | CH₃ |
| 269 | NH₂ | Cl | CH₃ |

TABLE A-continued

Particularly preferred combinations of $R^1$, $R^2$ and $R^3$

| | $R^3$ | $R^1$ | $R^2$ |
|---|---|---|---|
| 270 | CN | Cl | $CH_3$ |
| 271 | $NO_2$ | Cl | $CH_3$ |
| 272 | SCN | Cl | $CH_3$ |
| 273 | $NH-NH_2$ | Cl | $CH_3$ |
| 274 | $CH_3$ | Cl | $CH_3$ |
| 275 | $C_2H_5$ | Cl | $CH_3$ |
| 276 | $n-C_3H_7$ | Cl | $CH_3$ |
| 277 | $i-C_3H_7$ | Cl | $CH_3$ |
| 278 | $n-C_4H_9$ | Cl | $CH_3$ |
| 279 | $s-C_4H_9$ | Cl | $CH_3$ |
| 280 | $i-C_4H_9$ | Cl | $CH_3$ |
| 281 | $t-C_4H_9$ | Cl | $CH_3$ |
| 282 | $CH_2Cl$ | Cl | $CH_3$ |
| 283 | $CHCl_2$ | Cl | $CH_3$ |
| 284 | $CCl_3$ | Cl | $CH_3$ |
| 285 | $CH_2F$ | Cl | $CH_3$ |
| 286 | $CHF_2$ | Cl | $CH_3$ |
| 287 | $CF_3$ | Cl | $CH_3$ |
| 288 | $CH_2CF_3$ | Cl | $CH_3$ |
| 289 | $CH_2OCH_3$ | Cl | $CH_3$ |
| 290 | $CH_2OCH_2CH_3$ | Cl | $CH_3$ |
| 291 | $CH_2NH_2$ | Cl | $CH_3$ |
| 292 | $OCH_3$ | Cl | $CH_3$ |
| 293 | $OC_2H_5$ | Cl | $CH_3$ |
| 294 | $O-n-C_3H_7$ | Cl | $CH_3$ |
| 295 | $O-i-C_3H_7$ | Cl | $CH_3$ |
| 296 | $O-n-C_4H_9$ | Cl | $CH_3$ |
| 297 | $O-s-C_4H_9$ | Cl | $CH_3$ |
| 298 | $O-i-C_4H_9$ | Cl | $CH_3$ |
| 299 | $O-t-C_4H_9$ | Cl | $CH_3$ |
| 300 | $OCHF_2$ | Cl | $CH_3$ |
| 301 | $OCF_3$ | Cl | $CH_3$ |
| 302 | $OCH_2CF_3$ | Cl | $CH_3$ |
| 303 | $OCH_2OCH_3$ | Cl | $CH_3$ |
| 304 | $SCH_3$ | Cl | $CH_3$ |
| 305 | $SC_2H_5$ | Cl | $CH_3$ |
| 306 | $S-n-C_3H_7$ | Cl | $CH_3$ |
| 307 | $S-i-C_3H_7$ | Cl | $CH_3$ |
| 308 | $S-n-C_4H_9$ | Cl | $CH_3$ |
| 309 | $S-s-C_4H_9$ | Cl | $CH_3$ |
| 310 | $S-i-C_4H_9$ | Cl | $CH_3$ |
| 311 | $S-t-C_4H_9$ | Cl | $CH_3$ |
| 312 | $SCHF_2$ | Cl | $CH_3$ |
| 313 | $SCF_3$ | Cl | $CH_3$ |
| 314 | $SCH_2CF_3$ | Cl | $CH_3$ |
| 315 | $SCH_2OCH_3$ | Cl | $CH_3$ |
| 316 | $NHCH_3$ | Cl | $CH_3$ |
| 317 | $NHC_2H_5$ | Cl | $CH_3$ |
| 318 | NH-phenyl | Cl | $CH_3$ |
| 319 | $N(CH_3)_2$ | Cl | $CH_3$ |
| 320 | $N(CH_2CH_3)_2$ | Cl | $CH_3$ |
| 321 | $N(phenyl)_2$ | Cl | $CH_3$ |
| 322 | $(CH_2)_2COCH_3$ | Cl | $CH_3$ |
| 323 | phenyl | Cl | $CH_3$ |
| 324 | 2-F-phenyl | Cl | $CH_3$ |
| 325 | 3-F-phenyl | Cl | $CH_3$ |
| 326 | 4-F-phenyl | Cl | $CH_3$ |
| 327 | 2-Cl-phenyl | Cl | $CH_3$ |
| 328 | 3-Cl-phenyl | Cl | $CH_3$ |
| 329 | 4-Cl-phenyl | Cl | $CH_3$ |
| 330 | 2-OH-phenyl | Cl | $CH_3$ |
| 331 | 3-OH-phenyl | Cl | $CH_3$ |
| 332 | 4-OH-phenyl | Cl | $CH_3$ |
| 333 | $2-OCH_3$-phenyl | Cl | $CH_3$ |
| 334 | $3-OCH_3$-phenyl | Cl | $CH_3$ |
| 335 | $4-OCH_3$-phenyl | Cl | $CH_3$ |
| 336 | $2-OCF_3$-phenyl | Cl | $CH_3$ |
| 337 | $3-OCF_3$-phenyl | Cl | $CH_3$ |
| 338 | $4-OCF_3$-phenyl | Cl | $CH_3$ |
| 339 | $2-OCHF_2$-phenyl | Cl | $CH_3$ |
| 340 | $3-OCHF_2$-phenyl | Cl | $CH_3$ |
| 341 | $4-OCHF_2$-phenyl | Cl | $CH_3$ |
| 342 | $2-CF_3$-phenyl | Cl | $CH_3$ |
| 343 | $3-CF_3$-phenyl | Cl | $CH_3$ |
| 344 | $4-CF_3$-phenyl | Cl | $CH_3$ |
| 345 | $2-CH_3$-phenyl | Cl | $CH_3$ |
| 346 | $3-CH_3$-phenyl | Cl | $CH_3$ |
| 347 | $4-CH_3$-phenyl | Cl | $CH_3$ |
| 348 | $2-NO_2$-phenyl | Cl | $CH_3$ |
| 349 | $3-NO_2$-phenyl | Cl | $CH_3$ |
| 350 | $4-NO_2$-phenyl | Cl | $CH_3$ |
| 351 | 2-pyridyl | Cl | $CH_3$ |
| 352 | 3-pyridyl | Cl | $CH_3$ |
| 353 | 4-pyridyl | Cl | $CH_3$ |
| 354 | $3'-CH_3$-2-pyridyl | Cl | $CH_3$ |
| 355 | $4'-CH_3$-2-pyridyl | Cl | $CH_3$ |
| 356 | $5'-CH_3$-2-pyridyl | Cl | $CH_3$ |
| 357 | $6'-CH_3$-2-pyridyl | Cl | $CH_3$ |
| 358 | $2'-CH_3$-3-pyridyl | Cl | $CH_3$ |
| 359 | $4'-CH_3$-3-pyridyl | Cl | $CH_3$ |
| 360 | $5'-CH_3$-3-pyridyl | Cl | $CH_3$ |
| 361 | $6'-CH_3$-3-pyridyl | Cl | $CH_3$ |
| 362 | $2'-CH_3$-4-pyridyl | Cl | $CH_3$ |
| 363 | $3'-CH_3$-4-pyridyl | Cl | $CH_3$ |
| 364 | 3'-Cl-2-pyridyl | Cl | $CH_3$ |
| 365 | 4'-Cl-2-pyridyl | Cl | $CH_3$ |
| 366 | 5'-Cl-2-pyridyl | Cl | $CH_3$ |
| 367 | 6'-Cl-2-pyridyl | Cl | $CH_3$ |
| 368 | 2'-Cl-3-pyridyl | Cl | $CH_3$ |
| 369 | 4'-Cl-3-pyridyl | Cl | $CH_3$ |
| 370 | 5'-Cl-3-pyridyl | Cl | $CH_3$ |
| 371 | 6'-Cl-3-pyridyl | Cl | $CH_3$ |
| 372 | 2'-Cl-4-pyridyl | Cl | $CH_3$ |
| 373 | 3'-Cl-4-pyridyl | Cl | $CH_3$ |
| 374 | cyclohexylamino | Cl | $CH_3$ |
| 375 | cyclopentylamino | Cl | $CH_3$ |
| 376 | morpholino | Cl | $CH_3$ |
| 377 | $CO_2H$ | Cl | $CH_3$ |
| 378 | $CO_2CH_3$ | Cl | $CH_3$ |
| 379 | $CO_2C_2H_5$ | Cl | $CH_3$ |
| 380 | $CO_2-n-C_3H_7$ | Cl | $CH_3$ |
| 381 | $CO_2-i-C_3H_7$ | Cl | $CH_3$ |
| 382 | $CO_2-n-C_4H_9$ | Cl | $CH_3$ |
| 383 | $CO_2-s-C_4H_9$ | Cl | $CH_3$ |
| 384 | $CO_2-i-C_4H_9$ | Cl | $CH_3$ |
| 385 | $CO_2-t-C_4H_9$ | Cl | $CH_3$ |
| 386 | $CO_2$-phenyl | Cl | $CH_3$ |
| 387 | $CO_2$-3-pyridyl | Cl | $CH_3$ |
| 388 | $CONHCH_3$ | Cl | $CH_3$ |
| 389 | $CONHC_2H_5$ | Cl | $CH_3$ |
| 390 | CONH-phenyl | Cl | $CH_3$ |
| 391 | $CON(CH_3)_2$ | Cl | $CH_3$ |
| 392 | $CON(CH_2CH_3)_2$ | Cl | $CH_3$ |
| 393 | $CON(phenyl)_2$ | Cl | $CH_3$ |
| 394 | H | $CH_3$ | H |
| 395 | F | $CH_3$ | H |
| 396 | Cl | $CH_3$ | H |
| 397 | Br | $CH_3$ | H |
| 398 | OH | $CH_3$ | H |
| 399 | SH | $CH_3$ | H |
| 400 | $NH_2$ | $CH_3$ | H |
| 401 | CN | $CH_3$ | H |
| 402 | $NO_2$ | $CH_3$ | H |
| 403 | SCN | $CH_3$ | H |
| 404 | $NH-NH_2$ | $CH_3$ | H |
| 405 | $CH_3$ | $CH_3$ | H |
| 406 | $C_2H_5$ | $CH_3$ | H |
| 407 | $n-C_3H_7$ | $CH_3$ | H |
| 408 | $i-C_3H_7$ | $CH_3$ | H |
| 409 | $n-C_4H_9$ | $CH_3$ | H |
| 410 | $s-C_4H_9$ | $CH_3$ | H |
| 411 | $i-C_4H_9$ | $CH_3$ | H |
| 412 | $t-C_4H_9$ | $CH_3$ | H |
| 413 | $CH_2Cl$ | $CH_3$ | H |
| 414 | $CHCl_2$ | $CH_3$ | H |
| 415 | $CCl_3$ | $CH_3$ | H |
| 416 | $CH_2F$ | $CH_3$ | H |
| 417 | $CHF_2$ | $CH_3$ | H |
| 418 | $CF_3$ | $CH_3$ | H |
| 419 | $CH_2CF_3$ | $CH_3$ | H |

TABLE A-continued

Particularly preferred combinations of $R^1$, $R^2$ and $R^3$

| | $R^3$ | $R^1$ | $R^2$ |
|---|---|---|---|
| 420 | CH$_2$OCH$_3$ | CH$_3$ | H |
| 421 | CH$_2$OCH$_2$CH$_3$ | CH$_3$ | H |
| 422 | CH$_2$NH$_2$ | CH$_3$ | H |
| 423 | OCH$_3$ | CH$_3$ | H |
| 424 | OC$_2$H$_5$ | CH$_3$ | H |
| 425 | O-n-C$_3$H$_7$ | CH$_3$ | H |
| 426 | O-i-C$_3$H$_7$ | CH$_3$ | H |
| 427 | O-n-C$_4$H$_9$ | CH$_3$ | H |
| 428 | O-s-C$_4$H$_9$ | CH$_3$ | H |
| 429 | O-i-C$_4$H$_9$ | CH$_3$ | H |
| 430 | O-t-C$_4$H$_9$ | CH$_3$ | H |
| 431 | OCHF$_2$ | CH$_3$ | H |
| 432 | OCF$_3$ | CH$_3$ | H |
| 433 | OCH$_2$CF$_3$ | CH$_3$ | H |
| 434 | OCH$_2$OCH$_3$ | CH$_3$ | H |
| 435 | SCH$_3$ | CH$_3$ | H |
| 436 | SC$_2$H$_5$ | CH$_3$ | H |
| 437 | S-n-C$_3$H$_7$ | CH$_3$ | H |
| 438 | S-i-C$_3$H$_7$ | CH$_3$ | H |
| 439 | S-n-C$_4$H$_9$ | CH$_3$ | H |
| 440 | S-s-C$_4$H$_9$ | CH$_3$ | H |
| 441 | S-i-C$_4$H$_9$ | CH$_3$ | H |
| 442 | S-t-C$_4$H$_9$ | CH$_3$ | H |
| 443 | SCHF$_2$ | CH$_3$ | H |
| 444 | SCF$_3$ | CH$_3$ | H |
| 445 | SCH$_2$CF$_3$ | CH$_3$ | H |
| 446 | SCH$_2$OCH$_3$ | CH$_3$ | H |
| 447 | NHCH$_3$ | CH$_3$ | H |
| 448 | NHC$_2$H$_5$ | CH$_3$ | H |
| 449 | NH-phenyl | CH$_3$ | H |
| 450 | N(CH$_3$)$_2$ | CH$_3$ | H |
| 451 | N(CH$_2$CH$_3$)$_2$ | CH$_3$ | H |
| 452 | N(phenyl)$_2$ | CH$_3$ | H |
| 453 | (CH$_2$)$_2$COCH$_3$ | CH$_3$ | H |
| 454 | phenyl | CH$_3$ | H |
| 455 | 2-F-phenyl | CH$_3$ | H |
| 456 | 3-F-phenyl | CH$_3$ | H |
| 457 | 4-F-phenyl | CH$_3$ | H |
| 458 | 2-Cl-phenyl | CH$_3$ | H |
| 459 | 3-Cl-phenyl | CH$_3$ | H |
| 460 | 4-Cl-phenyl | CH$_3$ | H |
| 461 | 2-OH-phenyl | CH$_3$ | H |
| 462 | 3-OH-phenyl | CH$_3$ | H |
| 463 | 4-OH-phenyl | CH$_3$ | H |
| 464 | 2-OCH$_3$-phenyl | CH$_3$ | H |
| 465 | 3-OCH$_3$-phenyl | CH$_3$ | H |
| 466 | 4-OCH$_3$-phenyl | CH$_3$ | H |
| 467 | 2-OCF$_3$-phenyl | CH$_3$ | H |
| 468 | 3-OCF$_3$-phenyl | CH$_3$ | H |
| 469 | 4-OCF$_3$-phenyl | CH$_3$ | H |
| 470 | 2-OCHF$_2$-phenyl | CH$_3$ | H |
| 471 | 3-OCHF$_2$-phenyl | CH$_3$ | H |
| 472 | 4-OCHF$_2$-phenyl | CH$_3$ | H |
| 473 | 2-CF$_3$-phenyl | CH$_3$ | H |
| 474 | 3-CF$_3$-phenyl | CH$_3$ | H |
| 475 | 4-CF$_3$-phenyl | CH$_3$ | H |
| 476 | 2-CH$_3$-phenyl | CH$_3$ | H |
| 477 | 3-CH$_3$-phenyl | CH$_3$ | H |
| 478 | 4-CH$_3$-phenyl | CH$_3$ | H |
| 479 | 2-NO$_2$-phenyl | CH$_3$ | H |
| 480 | 3-NO$_2$-phenyl | CH$_3$ | H |
| 481 | 4-NO$_2$-phenyl | CH$_3$ | H |
| 482 | 2-pyridyl | CH$_3$ | H |
| 483 | 3-pyridyl | CH$_3$ | H |
| 484 | 4-pyridyl | CH$_3$ | H |
| 485 | 3'-CH$_3$-2-pyridyl | CH$_3$ | H |
| 486 | 4'-CH$_3$-2-pyridyl | CH$_3$ | H |
| 487 | 5'-CH$_3$-2-pyridyl | CH$_3$ | H |
| 488 | 6'-CH$_3$-2-pyridyl | CH$_3$ | H |
| 489 | 2'-CH$_3$-3-pyridyl | CH$_3$ | H |
| 490 | 4'-CH$_3$-3-pyridyl | CH$_3$ | H |
| 491 | 5'-CH$_3$-3-pyridyl | CH$_3$ | H |
| 492 | 6'-CH$_3$-3-pyridyl | CH$_3$ | H |
| 493 | 2'-CH$_3$-4-pyridyl | CH$_3$ | H |
| 494 | 3'-CH$_3$-4-pyridyl | CH$_3$ | H |
| 495 | 3'-Cl-2-pyridyl | CH$_3$ | H |
| 496 | 4'-Cl-2-pyridyl | CH$_3$ | H |
| 497 | 5'-Cl-2-pyridyl | CH$_3$ | H |
| 498 | 6'-Cl-2-pyridyl | CH$_3$ | H |
| 499 | 2'-Cl-3-pyridyl | CH$_3$ | H |
| 500 | 4'-Cl-3-pyridyl | CH$_3$ | H |
| 501 | 5'-Cl-3-pyridyl | CH$_3$ | H |
| 502 | 6'-Cl-3-pyridyl | CH$_3$ | H |
| 503 | 2'-Cl-4-pyridyl | CH$_3$ | H |
| 504 | 3'-Cl-4-pyridyl | CH$_3$ | H |
| 505 | cyclohexylamino | CH$_3$ | H |
| 506 | cyclopentylamino | CH$_3$ | H |
| 507 | morpholino | CH$_3$ | H |
| 508 | CO$_2$H | CH$_3$ | H |
| 509 | CO$_2$CH$_3$ | CH$_3$ | H |
| 510 | CO$_2$C$_2$H$_5$ | CH$_3$ | H |
| 511 | CO$_2$-n-C$_3$H$_7$ | CH$_3$ | H |
| 512 | CO$_2$-i-C$_3$H$_7$ | CH$_3$ | H |
| 513 | CO$_2$-n-C$_4$H$_9$ | CH$_3$ | H |
| 514 | CO$_2$-s-C$_4$H$_9$ | CH$_3$ | H |
| 515 | CO$_2$-i-C$_4$H$_9$ | CH$_3$ | H |
| 516 | CO$_2$-t-C$_4$H$_9$ | CH$_3$ | H |
| 517 | CO$_2$-Ph | CH$_3$ | H |
| 518 | CO$_2$-3-pyridyl | CH$_3$ | H |
| 519 | CONHCH$_3$ | CH$_3$ | H |
| 520 | CONHC$_2$H$_5$ | CH$_3$ | H |
| 521 | CONH-phenyl | CH$_3$ | H |
| 522 | CON(CH$_3$)$_2$ | CH$_3$ | H |
| 523 | CON(CH$_2$CH$_3$)$_2$ | CH$_3$ | H |
| 524 | CON(phenyl)$_2$ | CH$_3$ | H |
| 525 | H | OCH$_3$ | H |
| 526 | F | OCH$_3$ | H |
| 527 | Cl | OCH$_3$ | H |
| 528 | Br | OCH$_3$ | H |
| 529 | OH | OCH$_3$ | H |
| 530 | SH | OCH$_3$ | H |
| 531 | NH$_2$ | OCH$_3$ | H |
| 532 | CN | OCH$_3$ | H |
| 533 | NO$_2$ | OCH$_3$ | H |
| 534 | SCN | OCH$_3$ | H |
| 535 | NH—NH$_2$ | OCH$_3$ | H |
| 536 | CH$_3$ | OCH$_3$ | H |
| 537 | C$_2$H$_5$ | OCH$_3$ | H |
| 538 | n-C$_3$H$_7$ | OCH$_3$ | H |
| 539 | i-C$_3$H$_7$ | OCH$_3$ | H |
| 540 | n-C$_4$H$_9$ | OCH$_3$ | H |
| 541 | s-C$_4$H$_9$ | OCH$_3$ | H |
| 542 | i-C$_4$H$_9$ | OCH$_3$ | H |
| 543 | t-C$_4$H$_9$ | OCH$_3$ | H |
| 544 | CH$_2$Cl | OCH$_3$ | H |
| 545 | CHCl$_2$ | OCH$_3$ | H |
| 546 | CCl$_3$ | OCH$_3$ | H |
| 547 | CH$_2$F | OCH$_3$ | H |
| 548 | CHF$_2$ | OCH$_3$ | H |
| 549 | CF$_3$ | OCH$_3$ | H |
| 550 | CH$_2$CF$_3$ | OCH$_3$ | H |
| 551 | CH$_2$OCH$_3$ | OCH$_3$ | H |
| 552 | CH$_2$OCH$_2$CH$_3$ | OCH$_3$ | H |
| 553 | CH$_2$NH$_2$ | OCH$_3$ | H |
| 554 | OCH$_3$ | OCH$_3$ | H |
| 555 | OC$_2$H$_5$ | OCH$_3$ | H |
| 556 | O-n-C$_3$H$_7$ | OCH$_3$ | H |
| 557 | O-i-C$_3$H$_7$ | OCH$_3$ | H |
| 558 | O-n-C$_4$H$_9$ | OCH$_3$ | H |
| 559 | O-s-C$_4$H$_9$ | OCH$_3$ | H |
| 560 | O-i-C$_4$H$_9$ | OCH$_3$ | H |
| 561 | O-t-C$_4$H$_9$ | OCH$_3$ | H |
| 562 | OCHF$_2$ | OCH$_3$ | H |
| 563 | OCF$_3$ | OCH$_3$ | H |
| 564 | OCH$_2$CF$_3$ | OCH$_3$ | H |
| 565 | OCH$_2$OCH$_3$ | OCH$_3$ | H |
| 566 | SCH$_3$ | OCH$_3$ | H |
| 567 | SC$_2$H$_5$ | OCH$_3$ | H |
| 568 | S-n-C$_3$H$_7$ | OCH$_3$ | H |
| 569 | S-i-C$_3$H$_7$ | OCH$_3$ | H |

TABLE A-continued

Particularly preferred combinations of $R^1$, $R^2$ and $R^3$

| | $R^3$ | $R^1$ | $R^2$ |
|---|---|---|---|
| 570 | S-n-$C_4H_9$ | $OCH_3$ | H |
| 571 | S-s-$C_4H_9$ | $OCH_3$ | H |
| 572 | S-i-$C_4H_9$ | $OCH_3$ | H |
| 573 | S-t-$C_4H_9$ | $OCH_3$ | H |
| 574 | $SCHF_2$ | $OCH_3$ | H |
| 575 | $SCF_3$ | $OCH_3$ | H |
| 576 | $SCH_2CF_3$ | $OCH_3$ | H |
| 577 | $SCH_2OCH_3$ | $OCH_3$ | H |
| 578 | $NHCH_3$ | $OCH_3$ | H |
| 579 | $NHC_2H_5$ | $OCH_3$ | H |
| 580 | NHPh | $OCH_3$ | H |
| 581 | $N(CH_3)_2$ | $OCH_3$ | H |
| 582 | $N(CH_2CH_3)_2$ | $OCH_3$ | H |
| 583 | $N(phenyl)_2$ | $OCH_3$ | H |
| 584 | $(CH_2)_2COCH_3$ | $OCH_3$ | H |
| 585 | phenyl | $OCH_3$ | H |
| 586 | 2-F-phenyl | $OCH_3$ | H |
| 587 | 3-F-phenyl | $OCH_3$ | H |
| 588 | 4-F-phenyl | $OCH_3$ | H |
| 589 | 2-Cl-phenyl | $OCH_3$ | H |
| 590 | 3-Cl-phenyl | $OCH_3$ | H |
| 591 | 4-Cl-phenyl | $OCH_3$ | H |
| 592 | 2-OH-phenyl | $OCH_3$ | H |
| 593 | 3-OH-phenyl | $OCH_3$ | H |
| 594 | 4-OH-phenyl | $OCH_3$ | H |
| 595 | 2-$OCH_3$-phenyl | $OCH_3$ | H |
| 596 | 3-$OCH_3$-phenyl | $OCH_3$ | H |
| 597 | 4-$OCH_3$-phenyl | $OCH_3$ | H |
| 598 | 2-$OCF_3$-phenyl | $OCH_3$ | H |
| 599 | 3-$OCF_3$-phenyl | $OCH_3$ | H |
| 600 | 4-$OCF_3$-phenyl | $OCH_3$ | H |
| 601 | 2-$OCHF_2$-phenyl | $OCH_3$ | H |
| 602 | 3-$OCHF_2$-phenyl | $OCH_3$ | H |
| 603 | 4-$OCHF_2$-phenyl | $OCH_3$ | H |
| 604 | 2-$CF_3$-phenyl | $OCH_3$ | H |
| 605 | 3-$CF_3$-phenyl | $OCH_3$ | H |
| 606 | 4-$CF_3$-phenyl | $OCH_3$ | H |
| 607 | 2-$CH_3$-phenyl | $OCH_3$ | H |
| 608 | 3-$CH_3$-phenyl | $OCH_3$ | H |
| 609 | 4-$CH_3$-phenyl | $OCH_3$ | H |
| 610 | 2-$NO_2$-phenyl | $OCH_3$ | H |
| 611 | 3-$NO_2$-phenyl | $OCH_3$ | H |
| 612 | 4-$NO_2$-phenyl | $OCH_3$ | H |
| 613 | 2-pyridyl | $OCH_3$ | H |
| 614 | 3-pyridyl | $OCH_3$ | H |
| 615 | 4-pyridyl | $OCH_3$ | H |
| 616 | 3'-$CH_3$-2-pyridyl | $OCH_3$ | H |
| 617 | 4'-$CH_3$-2-pyridyl | $OCH_3$ | H |
| 618 | 5'-$CH_3$-2-pyridyl | $OCH_3$ | H |
| 619 | 6'-$CH_3$-2-pyridyl | $OCH_3$ | H |
| 620 | 2'-$CH_3$-3-pyridyl | $OCH_3$ | H |
| 621 | 4'-$CH_3$-3-pyridyl | $OCH_3$ | H |
| 622 | 5'-$CH_3$-3-pyridyl | $OCH_3$ | H |
| 623 | 6'-$CH_3$-3-pyridyl | $OCH_3$ | H |
| 624 | 2'-$CH_3$-4-pyridyl | $OCH_3$ | H |
| 625 | 3'-$CH_3$-4-pyridyl | $OCH_3$ | H |
| 626 | 3'-Cl-2-pyridyl | $OCH_3$ | H |
| 627 | 4'-Cl-2-pyridyl | $OCH_3$ | H |
| 628 | 5'-Cl-2-pyridyl | $OCH_3$ | H |
| 629 | 6'-Cl-2-pyridyl | $OCH_3$ | H |
| 630 | 2'-Cl-3-pyridyl | $OCH_3$ | H |
| 631 | 4'-Cl-3-pyridyl | $OCH_3$ | H |
| 632 | 5'-Cl-3-pyridyl | $OCH_3$ | H |
| 633 | 6'-Cl-3-pyridyl | $OCH_3$ | H |
| 634 | 2'-Cl-4-pyridyl | $OCH_3$ | H |
| 635 | 3'-Cl-4-pyridyl | $OCH_3$ | H |
| 636 | cyclohexylamino | $OCH_3$ | H |
| 637 | cyclopentylamino | $OCH_3$ | H |
| 638 | morpholino | $OCH_3$ | H |
| 639 | $CO_2H$ | $OCH_3$ | H |
| 640 | $CO_2CH_3$ | $OCH_3$ | H |
| 641 | $CO_2C_2H_5$ | $OCH_3$ | H |
| 642 | $CO_2$-n-$C_3H_7$ | $OCH_3$ | H |
| 643 | $CO_2$-i-$C_3H_7$ | $OCH_3$ | H |
| 644 | $CO_2$-n-$C_4H_9$ | $OCH_3$ | H |
| 645 | $CO_2$-s-$C_4H_9$ | $OCH_3$ | H |
| 646 | $CO_2$-i-$C_4H_9$ | $OCH_3$ | H |
| 647 | $CO_2$-t-$C_4H_9$ | $OCH_3$ | H |
| 648 | $CO_2$-Ph | $OCH_3$ | H |
| 649 | $CO_2$-3-pyridyl | $OCH_3$ | H |
| 650 | $CONHCH_3$ | $OCH_3$ | H |
| 651 | $CONHC_2H_5$ | $OCH_3$ | H |
| 652 | CONH-phenyl | $OCH_3$ | H |
| 653 | $CON(CH_3)_2$ | $OCH_3$ | H |
| 654 | $CON(CH_2CH_3)_2$ | $OCH_3$ | H |
| 655 | $CON(phenyl)_2$ | $OCH_3$ | H |
| 656 | H | Cl | H |
| 657 | F | Cl | H |
| 658 | Cl | Cl | H |
| 659 | Br | Cl | H |
| 660 | OH | Cl | H |
| 661 | SH | Cl | H |
| 662 | $NH_2$ | Cl | H |
| 663 | CN | Cl | H |
| 664 | $NO_2$ | Cl | H |
| 665 | SCN | Cl | H |
| 666 | NH—$NH_2$ | Cl | H |
| 667 | $CH_3$ | Cl | H |
| 668 | $C_2H_5$ | Cl | H |
| 669 | n-$C_3H_7$ | Cl | H |
| 670 | i-$C_3H_7$ | Cl | H |
| 671 | n-$C_4H_9$ | Cl | H |
| 672 | s-$C_4H_9$ | Cl | H |
| 673 | i-$C_4H_9$ | Cl | H |
| 674 | t-$C_4H_9$ | Cl | H |
| 675 | $CH_2Cl$ | Cl | H |
| 676 | $CHCl_2$ | Cl | H |
| 677 | $CCl_3$ | Cl | H |
| 678 | $CH_2F$ | Cl | H |
| 679 | $CHF_2$ | Cl | H |
| 680 | $CF_3$ | Cl | H |
| 681 | $CH_2CF_3$ | Cl | H |
| 682 | $CH_2OCH_3$ | Cl | H |
| 683 | $CH_2OCH_2CH_3$ | Cl | H |
| 684 | $CH_2NH_2$ | Cl | H |
| 685 | $OCH_3$ | Cl | H |
| 686 | $OC_2H_5$ | Cl | H |
| 687 | O-n-$C_3H_7$ | Cl | H |
| 688 | O-i-$C_3H_7$ | Cl | H |
| 689 | O-n-$C_4H_9$ | Cl | H |
| 690 | O-s-$C_4H_9$ | Cl | H |
| 691 | O-i-$C_4H_9$ | Cl | H |
| 692 | O-t-$C_4H_9$ | Cl | H |
| 693 | $OCHF_2$ | Cl | H |
| 694 | $OCF_3$ | Cl | H |
| 695 | $OCH_2CF_3$ | Cl | H |
| 696 | $OCH_2OCH_3$ | Cl | H |
| 697 | $SCH_3$ | Cl | H |
| 698 | $SC_2H_5$ | Cl | H |
| 699 | S-n-$C_3H_7$ | Cl | H |
| 700 | S-i-$C_3H_7$ | Cl | H |
| 701 | S-n-$C_4H_9$ | Cl | H |
| 702 | S-s-$C_4H_9$ | Cl | H |
| 703 | S-i-$C_4H_9$ | Cl | H |
| 704 | S-t-$C_4H_9$ | Cl | H |
| 705 | $SCHF_2$ | Cl | H |
| 706 | $SCF_3$ | Cl | H |
| 707 | $SCH_2CF_3$ | Cl | H |
| 708 | $SCH_2OCH_3$ | Cl | H |
| 709 | $NHCH_3$ | Cl | H |
| 710 | $NHC_2H_5$ | Cl | H |

TABLE A-continued

Particularly preferred combinations of $R^1$, $R^2$ and $R^3$

| | $R^3$ | $R^1$ | $R^2$ |
|---|---|---|---|
| 711 | NHPh | Cl | H |
| 712 | N(CH$_3$)$_2$ | Cl | H |
| 713 | N(CH$_2$CH$_3$)$_2$ | Cl | H |
| 714 | N(phenyl)$_2$ | Cl | H |
| 715 | (CH$_2$)$_2$COCH$_3$ | Cl | H |
| 716 | phenyl | Cl | H |
| 717 | 2-F-phenyl | Cl | H |
| 718 | 3-F-phenyl | Cl | H |
| 719 | 4-F-phenyl | Cl | H |
| 720 | 2-Cl-phenyl | Cl | H |
| 721 | 3-Cl-phenyl | Cl | H |
| 722 | 4-Cl-phenyl | Cl | H |
| 723 | 2-OH-phenyl | Cl | H |
| 724 | 3-OH-phenyl | Cl | H |
| 725 | 4-OH-phenyl | Cl | H |
| 726 | 2-OCH$_3$-phenyl | Cl | H |
| 727 | 3-OCH$_3$-phenyl | Cl | H |
| 728 | 4-OCH$_3$-phenyl | Cl | H |
| 729 | 2-OCF$_3$-phenyl | Cl | H |
| 730 | 3-OCF$_3$-phenyl | Cl | H |
| 731 | 4-OCF$_3$-phenyl | Cl | H |
| 732 | 2-OCHF$_2$-phenyl | Cl | H |
| 733 | 3-OCHF$_2$-phenyl | Cl | H |
| 734 | 4-OCHF$_2$-phenyl | Cl | H |
| 735 | 2-CF$_3$-phenyl | Cl | H |
| 736 | 3-CF$_3$-phenyl | Cl | H |
| 737 | 4-CF$_3$-phenyl | Cl | H |
| 738 | 2-CH$_3$-phenyl | Cl | H |
| 739 | 3-CH$_3$-phenyl | Cl | H |
| 740 | 4-CH$_3$-phenyl | Cl | H |
| 741 | 2-NO$_2$-phenyl | Cl | H |
| 742 | 3-NO$_2$-phenyl | Cl | H |
| 743 | 4-NO$_2$-phenyl | Cl | H |
| 744 | 2-pyridyl | Cl | H |
| 745 | 3-pyridyl | Cl | H |
| 746 | 4-pyridyl | Cl | H |
| 747 | 3'-CH$_3$-2-pyridyl | Cl | H |
| 748 | 4'-CH$_3$-2-pyridyl | Cl | H |
| 749 | 5'-CH$_3$-2-pyridyl | Cl | H |
| 750 | 6'-CH$_3$-2-pyridyl | Cl | H |
| 751 | 2'-CH$_3$-3-pyridyl | Cl | H |
| 752 | 4'-CH$_3$-3-pyridyl | Cl | H |
| 753 | 5'-CH$_3$-3-pyridyl | Cl | H |
| 754 | 6'-CH$_3$-3-pyridyl | Cl | H |
| 755 | 2'-CH$_3$-4-pyridyl | Cl | H |
| 756 | 3'-CH$_3$-4-pyridyl | Cl | H |
| 757 | 3'-Cl-2-pyridyl | Cl | H |
| 758 | 4'-Cl-2-pyridyl | Cl | H |
| 759 | 5'-Cl-2-pyridyl | Cl | H |
| 760 | 6'-Cl-2-pyridyl | Cl | H |
| 761 | 2'-Cl-3-pyridyl | Cl | H |
| 762 | 4'-Cl-3-pyridyl | Cl | H |
| 763 | 5'-Cl-3-pyridyl | Cl | H |
| 764 | 6'-Cl-3-pyridyl | Cl | H |
| 765 | 2'-Cl-4-pyridyl | Cl | H |
| 766 | 3'-Cl-4-pyridyl | Cl | H |
| 767 | cyclohexylamino | Cl | H |
| 768 | cyclopentylamino | Cl | H |
| 769 | morpholino | Cl | H |
| 770 | CO$_2$H | Cl | H |
| 771 | CO$_2$CH$_3$ | Cl | H |
| 772 | CO$_2$C$_2$H$_5$ | Cl | H |
| 773 | CO$_2$-n-C$_3$H$_7$ | Cl | H |
| 774 | CO$_2$-i-C$_3$H$_7$ | Cl | H |
| 775 | CO$_2$-n-C$_4$H$_9$ | Cl | H |
| 776 | CO$_2$-s-C$_4$H$_9$ | Cl | H |
| 777 | CO$_2$-i-C$_4$H$_9$ | Cl | H |
| 778 | CO$_2$-t-C$_4$H$_9$ | Cl | H |
| 779 | CO$_2$-phenyl | Cl | H |
| 780 | CO$_2$-3-pyridyl | Cl | H |
| 781 | CONHCH$_3$ | Cl | H |
| 782 | CONHC$_2$H$_5$ | Cl | H |
| 783 | CONH-phenyl | Cl | H |
| 784 | CON(CH$_3$)$_2$ | Cl | H |
| 785 | CON(CH$_2$CH$_3$)$_2$ | Cl | H |
| 786 | CON(phenyl)$_2$ | Cl | H |
| 787 | 2-fluorophenoxy | CH$_3$ | CH$_3$ |
| 788 | 2-fluorophenoxy | OCH$_3$ | CH$_3$ |
| 789 | 2-fluorophenoxy | Cl | CH$_3$ |
| 790 | 2-fluorophenoxy | CH$_3$ | H |
| 791 | 2-fluorophenoxy | OCH$_3$ | H |
| 792 | 2-fluorophenoxy | Cl | H |
| 793 | phenoxy | CH$_3$ | CH$_3$ |
| 794 | phenoxy | OCH$_3$ | CH$_3$ |
| 795 | phenoxy | Cl | CH$_3$ |
| 796 | phenoxy | CH$_3$ | H |
| 797 | phenoxy | OCH$_3$ | H |
| 798 | phenoxy | Cl | H |
| 799 | 2-methoxyphenoxy | CH$_3$ | CH$_3$ |
| 800 | 2-methoxyphenoxy | OCH$_3$ | CH$_3$ |
| 801 | 2-methoxyphenoxy | Cl | CH$_3$ |
| 802 | 2-methoxyphenoxy | CH$_3$ | H |
| 803 | 2-methoxyphenoxy | OCH$_3$ | H |
| 804 | 2-methoxyphenoxy | Cl | H |
| 805 | cyclopropyl | CH$_3$ | CH$_3$ |
| 806 | cyclopropyl | OCH$_3$ | CH$_3$ |
| 807 | cyclopropyl | Cl | CH$_3$ |
| 808 | cyclopropyl | CH$_3$ | H |
| 809 | cyclopropyl | OCH$_3$ | H |
| 810 | cyclopropyl | Cl | H |

The meanings of the abbreviations given here and below are, for example:

2-F-phenyl=2-fluorophenyl

2-Cl-phenyl=2-chlorophenyl

2-OH-phenyl=2-hydroxyphenyl

2-OCH$_3$-phenyl=2-methoxyphenyl

2-OCF$_3$-phenyl=2-trifluoromethoxyphenyl

2-OCHF$_2$-phenyl=2-difluoromethoxyphenyl

2-NO$_2$-phenyl=2-nitrophenyl

3'-CH$_3$-2-pyridyl=3'-methylpyridin-2-yl

Examples of particularly preferred benzothiazol-5-ylcarbonyl derivatives of pyrazoles according to the invention (compounds I-1=compounds I where X=C—R$^3$ and Y=S) are the compounds listed in Tables 2 to 20.

TABLE 2

Compounds I-1a.1 to I-1a.810

I-1a

Compounds of the formula I-1a where the substituents $R^1$, $R^2$ and $R^3$ for each individual compound correspond in each case to one row of Table A.

TABLE 3

Compounds I-1b.1 to I-1b.810

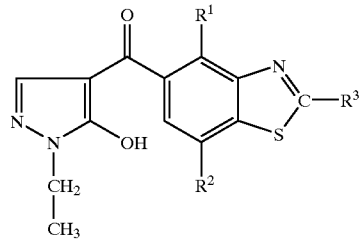
I-1b

Compounds of the formula I-1b where the substituents R¹, R² and R³ for each individual compound correspond in each case to one row of Table A.

TABLE 4

Compounds I-1c.1 to I-1c.810

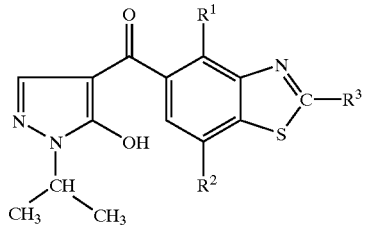
I-1c

Compounds of the formula I-1c where the substituents R¹, R² and R³ for each individual compound correspond in each case to one row of Table A.

TABLE 5

Compounds I-1d.1 to I-1d.810

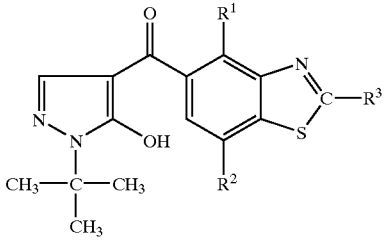
I-1d

Compounds of the formula I-1d where the substituents R¹, R² and R³ for each individual compound correspond in each case to one row of Table A.

TABLE 6

Compounds I-1e.1 to I-1e.810

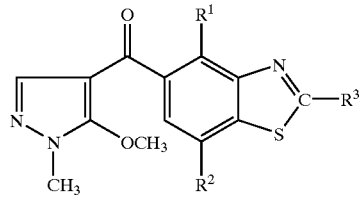
I-1e

Compounds of the formula I-1e where the substituents R¹, R² and R³ for each individual compound correspond in each case to one row of Table A.

TABLE 7

Compounds I-1f.1 to I-1f.810

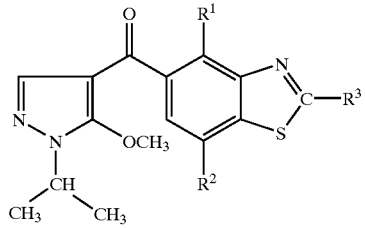
I-1f

Compounds of the formula I-1f where the substituents R¹, R² and R³ for each individual compound correspond in each case to one row of Table A.

TABLE 8

Compounds I-1g.1 to I-1g.810

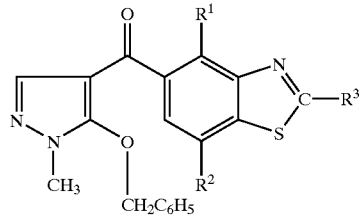
I-1g

Compounds of the formula I-1g where the substituents R¹, R² and R³ for each individual compound correspond in each case to one row of Table A.

TABLE 9

Compounds I-1h.1 to I-1h.810

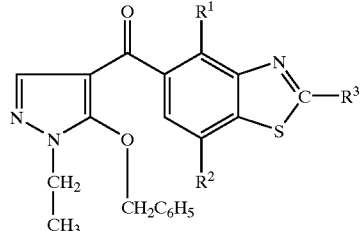
I-1h

Compounds of the formula I-1h where the substituents $R^1$, $R^2$ and $R^3$ for each individual compound correspond in each case to one row of Table A.

TABLE 10

Compounds I-1i.1 to I-1i.810

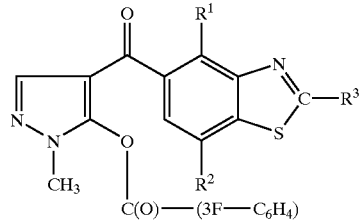

I-1i

Compounds of the formula I-1i where the substituents $R^1$, $R^2$ and $R^3$ for each individual compound correspond in each case to one row of Table A.

TABLE 11

Compounds I-1k.1 to I-1k.810

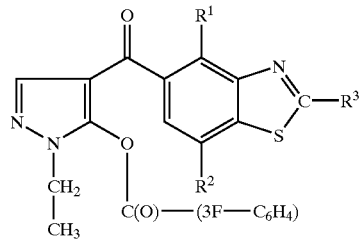

I-1k

Compounds of the formula I-1k where the substituents $R^1$, $R^2$ and $R^3$ for each individual compound correspond in each case to one row of Table A.

TABLE 12

Compounds I-1l.1 to I-1l.810

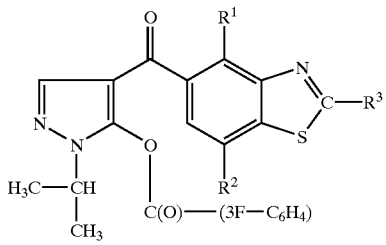

I-1l

Compounds of the formula I-1l where the substituents $R^1$, $R^2$ and $R^3$ for each individual compound correspond in each case to one row of Table A.

TABLE 13

Compounds I-1m.1 to I-1m.810

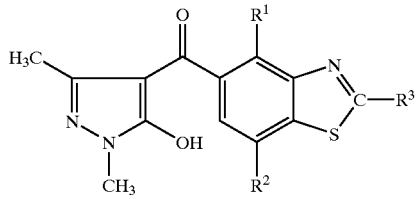

I-1m

Compounds of the formula I-1m where the substituents $R^1$, $R^2$ and $R^3$ for each individual compound correspond in each case to one row of Table A.

TABLE 14

Compounds I-1n.1 to I-1n.810

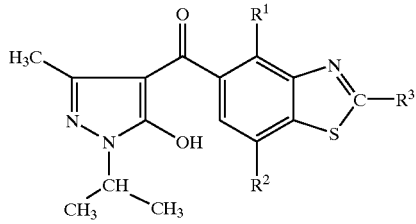

I-1n

Compounds of the formula I-1n where the substituents $R^1$, $R^2$ and $R^3$ for each individual compound correspond in each case to one row of Table A.

TABLE 15

Compounds I-1o.1 to I-1o.810

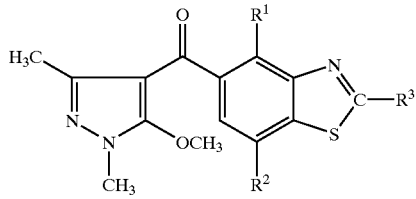

I-1o

Compounds of the formula I-1o where the substituents $R^1$, $R^2$ and $R^3$ for each individual compound correspond in each case to one row of Table A.

TABLE 16

Compounds I-1p.1 to I-1p.810

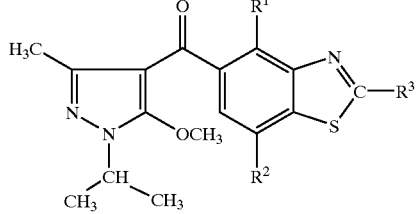

I-1p

Compounds of the formula I-1p where the substituents $R^1$, $R^2$ and $R^3$ for each individual compound correspond in each case to one row of Table A.

TABLE 17

Compounds I-1q.1 to I-1q.810

[Structure I-1q: pyrazole-benzothiazole compound with substituents $R^1$, $R^2$, $R^3$, $CH_3$ on pyrazole N, and $CH_2C_6H_5$ on $R^2$ position]

Compounds of the formula I-1q where the substituents $R^1$, $R^2$ and $R^3$ for each individual compound correspond in each case to one row of Table A.

TABLE 18

Compounds I-1r.1 to I-1r.810

[Structure I-1r: pyrazole-benzothiazole compound with $H_3C-CH(CH_3)$ on pyrazole N, and $CH_2C_6H_5$ on $R^2$ position]

Compounds of the formula I-1r where the substituents $R^1$, $R^2$ and $R^3$ for each individual compound correspond in each case to one row of Table A.

TABLE 19

Compounds I-1s.1 to I-1s.810

[Structure I-1s: pyrazole-benzothiazole compound with $CH_3$ on pyrazole N, and $C(O)-(3F-C_6H_4)$ on $R^2$ position]

Compounds of the formula I-1s where the substituents $R^1$, $R^2$ and $R^3$ for each individual compound correspond in each case to one row of Table A.

TABLE 20

Compounds I-1t.1 to I-1t.810

[Structure I-1t: pyrazole-benzothiazole compound with $H_3C-CH(CH_3)$ on pyrazole N, and $C(O)-(3F-C_6H_4)$ on $R^2$ position]

Compounds of the formula I-1t where the substituents $R^1$, $R^2$ and $R^3$ for each individual compound correspond in each case to one row of Table A.

TABLE 20a

Compounds I-1u.1 to I-1u.810

[Structure I-1u: pyrazole-benzothiazole compound with $CH_3$ on pyrazole N, and $C(O)C_6H_5$ on $R^2$ position]

Compounds of the formula I-1u where the substituents $R^1$, $R^2$ and $R^3$ for each individual compound correspond in each case to one row of Table A.

TABLE 20b

Compounds I-1v.1 to I-1v.810

[Structure I-1v: pyrazole-benzothiazole compound with $CH_3$ on pyrazole N, and $C(O)$cyclopropyl on $R^2$ position]

Compounds of the formula I-1v where the substituents $R^1$, $R^2$ and $R^3$ for each individual compound correspond in each case to one row of Table A.

TABLE 20c

Compounds I-1w.1 to I-1w.810

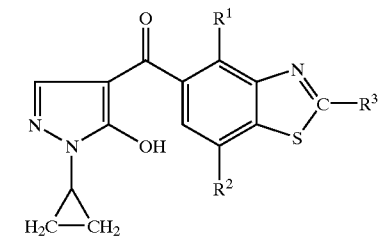

I-1w

Compounds of the formula I-1w where the substituents $R^1$, $R^2$ and $R^3$ for each individual compound correspond in each case to one row of Table A.

Examples of particularly preferred pyrazolyl derivatives according to the invention are the benzothiazole S-dioxide compounds 1-1'a.1 to 1-1'a.810, 1-1'b.1 to 1-1'b.810, . . . 1-1'w.1 to 1-1'w.810 (compounds I-1', =compounds I where X=C—$R_3$ and Y=SO$_2$). They differ from the benzothiazole compounds 1-1a.1 to 1-1a.810, 1-1b.1 to 1-1b.810, . . . 1-1w.1 to 1-1w.810 listed in Tables 1 to 20 in that the heterocyclic sulfur atom is present as an SO$_2$ group.

Examples of particularly preferred pyrazolyl derivatives of benzoxazole 5-carbonyl compounds according to the invention (compounds I-2=compounds I where X=C—$R^3$ and Y=O) are the compounds mentioned in Tables 21 to 39.

TABLE 21

Compounds I-2a.1 to I-2a.810

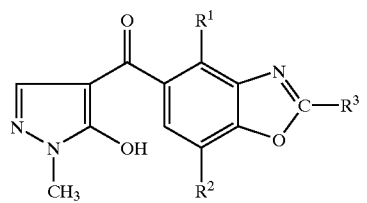

I-2a

Compounds of the formula I-2a where the substituents $R^1$, $R^2$ and $R^3$ for each individual compound correspond in each case to one row of Table A.

TABLE 22

Compounds I-2b.1 to I-2b.810

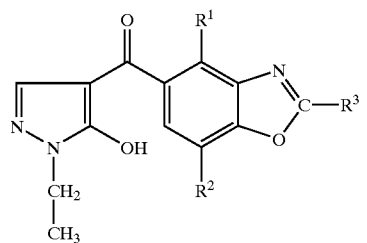

I-2b

Compounds of the formula I-2b where the substituents $R^1$, $R^2$ and $R^3$ for each individual compound correspond in each case to one row of Table A.

TABLE 23

Compounds I-2c.1 to I-2c.810

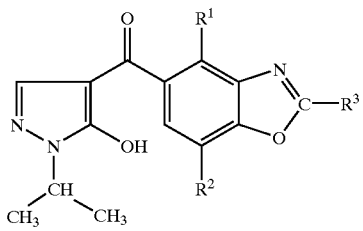

I-2c

Compounds of the formula I-2c where the substituents $R^1$, $R^2$ and $R^3$ for each individual compound correspond in each case to one row of Table A.

TABLE 24

Compounds I-2d.1 to I-2d.810

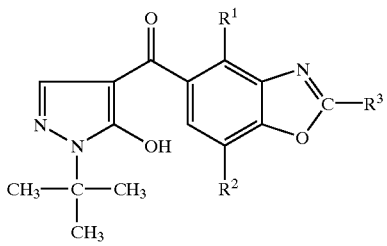

I-2d

Compounds of the formula I-2d where the substituents $R^1$, $R^2$ and $R^3$ for each individual compound correspond in each case to one row of Table A.

TABLE 25

Compounds I-2e.1 to I-2e.810

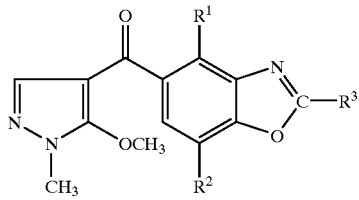

I-2e

Compounds of the formula I-2e where the substituents $R^1$, $R^2$ and $R^3$ for each individual compound correspond in each case to one row of Table A.

TABLE 26

Compounds I-2f.1 to I-2f.810

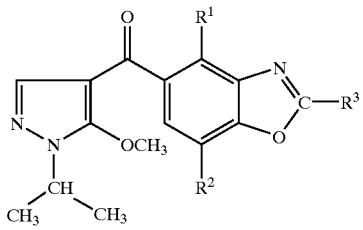

I-2f

Compounds of the formula I-2f where the substituents R¹, R² and R³ for each individual compound correspond in each case to one row of Table A.

TABLE 27

Compounds I-2g.1 to I-2g.810

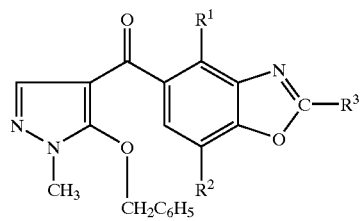

I-2g

Compounds of the formula I-2g where the substituents R¹, R² and R³ for each individual compound correspond in each case to one row of Table A.

TABLE 28

Compounds I-2h.1 to I-2h.810

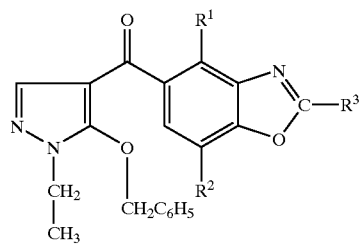

I-2h

Compounds of the formula I-2h where the substituents R¹, R² and R³ for each individual compound correspond in each case to one row of Table A.

TABLE 29

Compounds I-2i.1 to I-2i.810

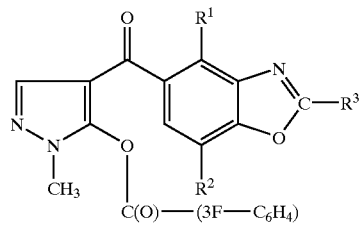

I-2i

Compounds of the formula I-2i where the substituents R¹, R² and R³ for each individual compound correspond in each case to one row of Table A.

TABLE 30

Compounds I-2k.1 to I-2k.810

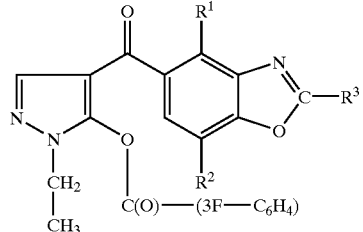

I-2k

Compounds of the formula I-2k where the substituents R¹, R² and R³ for each individual compound correspond in each case to one row of Table A.

TABLE 31

Compounds I-2l.1 to I-2l.810

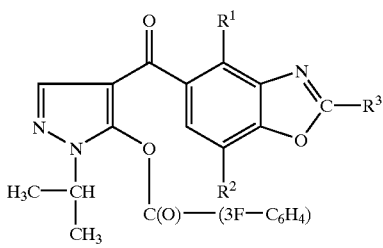

I-2l

Compounds of the formula I-2l where the substituents R¹, R² and R³ for each individual compound correspond in each case to one row of Table A.

TABLE 32

Compounds I-2m.1 to I-2m.810

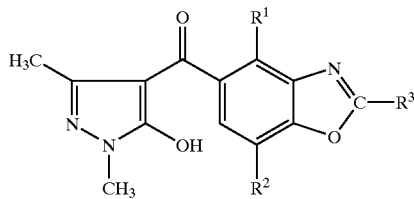

I-2m

Compounds of the formula I-2m where the substituents R¹, R² and R³ for each individual compound correspond in each case to one row of Table A.

TABLE 33

Compounds I-2n.1 to I-2n.810

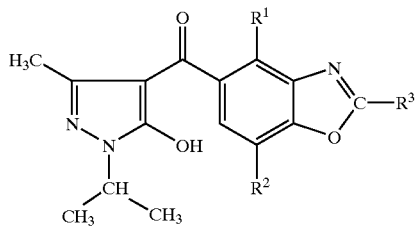

I-2n

Compounds of the formula I-2n where the substituents $R^1$, $R^2$ and $R^3$ for each individual compound correspond in each case to one row of Table A.

TABLE 34

Compounds I-2o.1 to I-2o.810

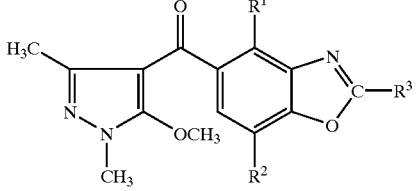

I-2o

Compounds of the formula I-2o where the substituents $R^1$, $R^2$ and $R^3$ for each individual compound correspond in each case to one row of Table A.

TABLE 35

Compounds I-2p.1 to I-2p.810

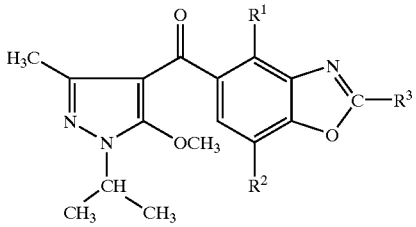

I-2p

Compounds of the formula I-2p where the substituents $R^1$, $R^2$ and $R^3$ for each individual compound correspond in each case to one row of Table A.

TABLE 36

Compounds I-2q.1 to I-2q.810

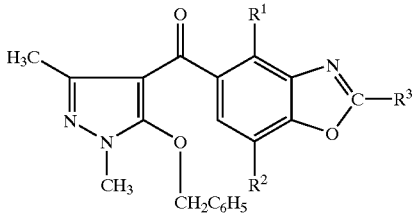

I-2q

Compounds of the formula I-2q where the substituents $R^1$, $R^2$ and $R^3$ for each individual compound correspond in each case to one row of Table A.

TABLE 37

Compounds I-2r.1 to I-2r.810

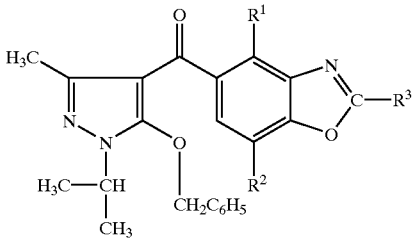

I-2r

Compounds of the formula I-2r where the substituents $R^1$, $R^2$ and $R^3$ for each individual compound correspond in each case to one row of Table A.

TABLE 38

Compounds I-2s.1 to I-2s.810

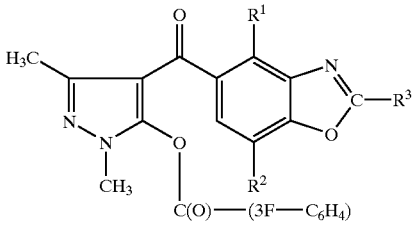

I-2s

Compounds of the formula I-2s where the substituents $R^1$, $R^2$ and $R^3$ for each individual compound correspond in each case to one row of Table A.

TABLE 39

Compounds I-2t.1 to I-2t.810

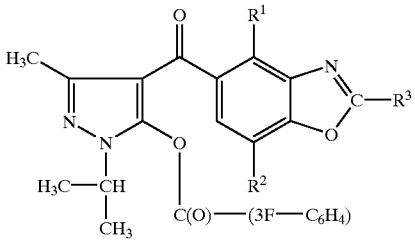

I-2t

Compounds of the formula I-2t where the substituents $R^1$, $R^2$ and $R^3$ for each individual compound correspond in each case to one row of Table A.

TABLE 39a

Compounds I-2u.1 to I-2u.810

I-2u: structure with O, R¹, pyrazole with N-CH₃, benzoxazole with C-R³, R², C(O)C₆H₅

Compounds of the formula I-2u where the substituents R¹, R² and R³ for each individual compound correspond in each case to one row of Table A.

TABLE 39b

Compounds I-2v.1 to I-2v.810

I-2v: structure with O, R¹, pyrazole with N-CH₃, benzoxazole with C-R³, R², C(O)cyclopropyl Compounds of the formula I-2v where the substituents R¹, R² and R³ for each individual compound correspond in each case to one row of Table A.

TABLE 39c

Compounds I-2w.1 to I-2w.810

I-2w: structure with O, R¹, pyrazole with N-CH(H₂C—CH₂), OH, benzoxazole with C-R³, R²

Compounds of the formula I-2w where the substituents R¹, R² and R³ for each individual compound correspond in each case to one row of Table A.

Particularly preferred combinations of R¹, R², R³ and R⁴ for pyrazole derivatives of the formula I according to the invention which are derived from benzimidazole-5-carboxylic acids are listed in Table B below.

TABLE B

|    | $R^3$ | $R^1$ | $R^2$ | $R^4$ |
|----|-------|-------|-------|-------|
| 1  | $CH_3$ | $CH_3$ | $CH_3$ | H |
| 2  | $C_2H_5$ | $CH_3$ | $CH_3$ | H |
| 3  | $n-C_3H_7$ | $CH_3$ | $CH_3$ | H |
| 4  | $i-C_3H_7$ | $CH_3$ | $CH_3$ | H |
| 5  | $n-C_4C_9$ | $CH_3$ | $CH_3$ | H |
| 6  | $s-C_4C_9$ | $CH_3$ | $CH_3$ | H |
| 7  | $i-C_4C_9$ | $CH_3$ | $CH_3$ | H |
| 8  | $t-C_4C_9$ | $CH_3$ | $CH_3$ | H |
| 9  | $CH_2Cl$ | $CH_3$ | $CH_3$ | H |
| 10 | $CHCl_2$ | $CH_3$ | $CH_3$ | H |
| 11 | $CCl_3$ | $CH_3$ | $CH_3$ | H |
| 12 | $CH_2F$ | $CH_3$ | $CH_3$ | H |
| 13 | $CHF_2$ | $CH_3$ | $CH_3$ | H |
| 14 | $CF_3$ | $CH_3$ | $CH_3$ | H |
| 15 | $CH_2CF_3$ | $CH_3$ | $CH_3$ | H |
| 16 | $CH_2OCH_3$ | $CH_3$ | $CH_3$ | H |
| 17 | $CH_2OCH_2CH_3$ | $CH_3$ | $CH_3$ | H |
| 18 | $CH_2NH_2$ | $CH_3$ | $CH_3$ | H |
| 19 | $(CH_2)_2COCH_3$ | $CH_3$ | $CH_3$ | H |
| 20 | phenyl | $CH_3$ | $CH_3$ | H |
| 21 | 2-F-phenyl | $CH_3$ | $CH_3$ | H |
| 22 | 3-F-phenyl | $CH_3$ | $CH_3$ | H |
| 23 | 4-F-phenyl | $CH_3$ | $CH_3$ | H |
| 24 | 2-Cl-phenyl | $CH_3$ | $CH_3$ | H |
| 25 | 3-Cl-phenyl | $CH_3$ | $CH_3$ | H |
| 26 | 4-Cl-phenyl | $CH_3$ | $CH_3$ | H |
| 27 | 2-OH-phenyl | $CH_3$ | $CH_3$ | H |
| 28 | 3-OH-phenyl | $CH_3$ | $CH_3$ | H |
| 29 | 4-OH-phenyl | $CH_3$ | $CH_3$ | H |
| 30 | 2-$OCH_3$-phenyl | $CH_3$ | $CH_3$ | H |
| 31 | 3-$OCH_3$-phenyl | $CH_3$ | $CH_3$ | H |
| 32 | 4-$OCH_3$-phenyl | $CH_3$ | $CH_3$ | H |
| 33 | 2-$OCF_3$-phenyl | $CH_3$ | $CH_3$ | H |
| 34 | 3-$OCF_3$-phenyl | $CH_3$ | $CH_3$ | H |
| 35 | 4-$OCF_3$-phenyl | $CH_3$ | $CH_3$ | H |
| 36 | 2-$OCHF_2$-phenyl | $CH_3$ | $CH_3$ | H |
| 37 | 3-$OCHF_2$-phenyl | $CH_3$ | $CH_3$ | H |
| 38 | 4-$OCHF_2$-phenyl | $CH_3$ | $CH_3$ | H |
| 39 | 2-$CF_3$-phenyl | $CH_3$ | $CH_3$ | H |
| 40 | 3-$CF_3$-phenyl | $CH_3$ | $CH_3$ | H |
| 41 | 4-$CF_3$-phenyl | $CH_3$ | $CH_3$ | H |
| 42 | 2-$CH_3$-phenyl | $CH_3$ | $CH_3$ | H |
| 43 | 3-$CH_3$-phenyl | $CH_3$ | $CH_3$ | H |
| 44 | 4-$CH_3$-phenyl | $CH_3$ | $CH_3$ | H |
| 45 | 2-$NO_2$-phenyl | $CH_3$ | $CH_3$ | H |
| 46 | 3-$NO_2$-phenyl | $CH_3$ | $CH_3$ | H |
| 47 | 4-$NO_2$-phenyl | $CH_3$ | $CH_3$ | H |
| 48 | 2-pyridyl | $CH_3$ | $CH_3$ | H |
| 49 | 3-pyridyl | $CH_3$ | $CH_3$ | H |
| 50 | 4-pyridyl | $CH_3$ | $CH_3$ | H |
| 51 | cyclohexylamino | $CH_3$ | $CH_3$ | H |
| 52 | cyclopentylamino | $CH_3$ | $CH_3$ | H |
| 53 | H | $OCH_3$ | $CH_3$ | H |
| 54 | $CH_3$ | $OCH_3$ | $CH_3$ | H |
| 55 | $C_2H_5$ | $OCH_3$ | $CH_3$ | H |
| 56 | $n-C_3H_7$ | $OCH_3$ | $CH_3$ | H |
| 57 | $i-C_3H_7$ | $OCH_3$ | $CH_3$ | H |
| 58 | $n-C_4C_9$ | $OCH_3$ | $CH_3$ | H |
| 59 | $s-C_4C_9$ | $OCH_3$ | $CH_3$ | H |
| 60 | $i-C_4C_9$ | $OCH_3$ | $CH_3$ | H |
| 61 | $t-C_4C_9$ | $OCH_3$ | $CH_3$ | H |
| 62 | $CH_2Cl$ | $OCH_3$ | $CH_3$ | H |
| 63 | $CHCl_2$ | $OCH_3$ | $CH_3$ | H |
| 64 | $CCl_3$ | $OCH_3$ | $CH_3$ | H |
| 65 | $CH_2F$ | $OCH_3$ | $CH_3$ | H |
| 66 | $CHF_2$ | $OCH_3$ | $CH_3$ | H |
| 67 | $CF_3$ | $OCH_3$ | $CH_3$ | H |
| 68 | $CH_2CF_3$ | $OCH_3$ | $CH_3$ | H |
| 69 | $CH_2OCH_3$ | $OCH_3$ | $CH_3$ | H |
| 70 | $CH_2OCH_2CH_3$ | $OCH_3$ | $CH_3$ | H |
| 71 | $CH_2NH_2$ | $OCH_3$ | $CH_3$ | H |
| 72 | $(CH_2)_2COCH_3$ | $OCH_3$ | $CH_3$ | H |
| 73 | phenyl | $OCH_3$ | $CH_3$ | H |
| 74 | 2-F-phenyl | $OCH_3$ | $CH_3$ | H |
| 75 | 3-F-phenyl | $OCH_3$ | $CH_3$ | H |
| 76 | 4-F-phenyl | $OCH_3$ | $CH_3$ | H |
| 77 | 2-Cl-phenyl | $OCH_3$ | $CH_3$ | H |
| 78 | 3-Cl-phenyl | $OCH_3$ | $CH_3$ | H |
| 79 | 4-Cl-phenyl | $OCH_3$ | $CH_3$ | H |
| 80 | 2-OH-phenyl | $OCH_3$ | $CH_3$ | H |
| 81 | 3-OH-phenyl | $OCH_3$ | $CH_3$ | H |
| 82 | 4-OH-phenyl | $OCH_3$ | $CH_3$ | H |
| 83 | 2-$OCH_3$-phenyl | $OCH_3$ | $CH_3$ | H |
| 84 | 3-$OCH_3$-phenyl | $OCH_3$ | $CH_3$ | H |

TABLE B-continued

| | R³ | R¹ | R² | R⁴ |
|---|---|---|---|---|
| 85 | 4-OCH₃-phenyl | OCH₃ | CH₃ | H |
| 86 | 2-OCF₃-phenyl | OCH₃ | CH₃ | H |
| 87 | 3-OCF₃-phenyl | OCH₃ | CH₃ | H |
| 88 | 4-OCF₃-phenyl | OCH₃ | CH₃ | H |
| 89 | 2-OCHF₂-phenyl | OCH₃ | CH₃ | H |
| 90 | 3-OCHF₂-phenyl | OCH₃ | CH₃ | H |
| 91 | 4-OCHF₂-phenyl | OCH₃ | CH₃ | H |
| 92 | 2-CF₃-phenyl | OCH₃ | CH₃ | H |
| 93 | 3-CF₃-phenyl | OCH₃ | CH₃ | H |
| 94 | 4-CF₃-phenyl | OCH₃ | CH₃ | H |
| 25 | 2-CH₃-phenyl | OCH₃ | CH₃ | H |
| 96 | 3-CH₃-phenyl | OCH₃ | CH₃ | H |
| 97 | 4-CH₃-phenyl | OCH₃ | CH₃ | H |
| 98 | 2-NO₂-phenyl | OCH₃ | CH₃ | H |
| 99 | 3-NO₂-phenyl | OCH₃ | CH₃ | H |
| 100 | 4-NO₂-phenyl | OCH₃ | CH₃ | H |
| 101 | 2-pyridyl | OCH₃ | CH₃ | H |
| 102 | 3-pyridyl | OCH₃ | CH₃ | H |
| 103 | 4-pyridyl | OCH₃ | CH₃ | H |
| 104 | cyclohexylamino | OCH₃ | CH₃ | H |
| 105 | cyclopentylamino | OCH₃ | CH₃ | H |
| 106 | H | Cl | CH₃ | H |
| 107 | CH₃ | Cl | CH₃ | H |
| 108 | C₂H₅ | Cl | CH₃ | H |
| 109 | n-C₃H₇ | Cl | CH₃ | H |
| 110 | i-C₃H₇ | Cl | CH₃ | H |
| 111 | n-C₄C₉ | Cl | CH₃ | H |
| 112 | s-C₄C₉ | Cl | CH₃ | H |
| 113 | i-C₄C₉ | Cl | CH₃ | H |
| 114 | t-C₄C₉ | Cl | CH₃ | H |
| 115 | CH₂Cl | Cl | CH₃ | H |
| 116 | CHCl₂ | Cl | CH₃ | H |
| 117 | CCl₃ | Cl | CH₃ | H |
| 118 | CH₂F | Cl | CH₃ | H |
| 119 | CHF₂ | Cl | CH₃ | H |
| 120 | CF₃ | Cl | CH₃ | H |
| 121 | CH₂CF₃ | Cl | CH₃ | H |
| 122 | CH₂OCH₃ | Cl | CH₃ | H |
| 123 | CH₂OCH₂CH₃ | Cl | CH₃ | H |
| 124 | CH₂NH₂ | Cl | CH₃ | H |
| 125 | (CH₂)₂COCH₃ | Cl | CH₃ | H |
| 126 | phenyl | Cl | CH₃ | H |
| 127 | 2-F-phenyl | Cl | CH₃ | H |
| 128 | 3-F-phenyl | Cl | CH₃ | H |
| 129 | 4-F-phenyl | Cl | CH₃ | H |
| 130 | 2-Cl-phenyl | Cl | CH₃ | H |
| 131 | 3-Cl-phenyl | Cl | CH₃ | H |
| 132 | 4-Cl-phenyl | Cl | CH₃ | H |
| 133 | 2-OH-phenyl | Cl | CH₃ | H |
| 134 | 3-OH-phenyl | Cl | CH₃ | H |
| 135 | 4-OH-phenyl | Cl | CH₃ | H |
| 136 | 2-OCH₃-phenyl | Cl | CH₃ | H |
| 137 | 3-OCH₃-phenyl | Cl | CH₃ | H |
| 138 | 4-OCH₃-phenyl | Cl | CH₃ | H |
| 139 | 2-OCF₃-phenyl | Cl | CH₃ | H |
| 140 | 3-OCF₃-phenyl | Cl | CH₃ | H |
| 141 | 4-OCF₃-phenyl | Cl | CH₃ | H |
| 142 | 2-OCHF₂-phenyl | Cl | CH₃ | H |
| 143 | 3-OCHF₂-phenyl | Cl | CH₃ | H |
| 144 | 4-OCHF₂-phenyl | Cl | CH₃ | H |
| 145 | 2-CF₃-phenyl | Cl | CH₃ | H |
| 146 | 3-CF₃-phenyl | Cl | CH₃ | H |
| 147 | 4-CF₃-phenyl | Cl | CH₃ | H |
| 148 | 2-CH₃-phenyl | Cl | CH₃ | H |
| 149 | 3-CH₃-phenyl | Cl | CH₃ | H |
| 150 | 4-CH₃-phenyl | Cl | CH₃ | H |
| 151 | 2-NO₂-phenyl | Cl | CH₃ | H |
| 152 | 3-NO₂-phenyl | Cl | CH₃ | H |
| 153 | 4-NO₂-phenyl | Cl | CH₃ | H |
| 154 | 2-pyridyl | Cl | CH₃ | H |
| 155 | 3-pyridyl | Cl | CH₃ | H |
| 156 | 4-pyridyl | Cl | CH₃ | H |
| 157 | cyclohexylamino | Cl | CH₃ | H |
| 158 | cyclopentylamino | Cl | CH₃ | H |
| 159 | CH₃ | CH₃ | H | H |
| 160 | C₂H₅ | CH₃ | H | H |
| 161 | n-C₃H₇ | CH₃ | H | H |
| 162 | i-C₃H₇ | CH₃ | H | H |
| 163 | n-C₄C₉ | CH₃ | H | H |
| 164 | s-C₄C₉ | CH₃ | H | H |
| 165 | i-C₄C₉ | CH₃ | H | H |
| 166 | t-C₄C₉ | CH₃ | H | H |
| 167 | CH₂Cl | CH₃ | H | H |
| 168 | CHCl₂ | CH₃ | H | H |
| 169 | CCl₃ | CH₃ | H | H |
| 170 | CH₂F | CH₃ | H | H |
| 171 | CHF₂ | CH₃ | H | H |
| 172 | CF₃ | CH₃ | H | H |
| 173 | CH₂CF₃ | CH₃ | H | H |
| 174 | CH₂OCH₃ | CH₃ | H | H |
| 175 | CH₂OCH₂CH₃ | CH₃ | H | H |
| 176 | CH₂NH₂ | CH₃ | H | H |
| 177 | (CH₂)₂COCH₃ | CH₃ | H | H |
| 178 | phenyl | CH₃ | H | H |
| 179 | 2-F-phenyl | CH₃ | H | H |
| 180 | 3-F-phenyl | CH₃ | H | H |
| 181 | 4-F-phenyl | CH₃ | H | H |
| 182 | 2-Cl-phenyl | CH₃ | H | H |
| 183 | 3-Cl-phenyl | CH₃ | H | H |
| 184 | 4-Cl-phenyl | CH₃ | H | H |
| 185 | 2-OH-phenyl | CH₃ | H | H |
| 186 | 3-OH-phenyl | CH₃ | H | H |
| 187 | 4-OH-phenyl | CH₃ | H | H |
| 188 | 2-OCH₃-phenyl | CH₃ | H | H |
| 189 | 3-OCH₃-phenyl | CH₃ | H | H |
| 190 | 4-OCH₃-phenyl | CH₃ | H | H |
| 191 | 2-OCF₃-phenyl | CH₃ | H | H |
| 192 | 3-OCF₃-phenyl | CH₃ | H | H |
| 193 | 4-OCF₃-phenyl | CH₃ | H | H |
| 194 | 2-OCHF₂-phenyl | CH₃ | H | H |
| 195 | 3-OCHF₂-phenyl | CH₃ | H | H |
| 196 | 4-OCHF₂-phenyl | CH₃ | H | H |
| 197 | 2-CF₃-phenyl | CH₃ | H | H |
| 198 | 3-CF₃-phenyl | CH₃ | H | H |
| 199 | 4-CF₃-phenyl | CH₃ | H | H |
| 200 | 2-CH₃-phenyl | CH₃ | H | H |
| 201 | 3-CH₃-phenyl | CH₃ | H | H |
| 202 | 4-CH₃-phenyl | CH₃ | H | H |
| 203 | 2-NO₂-phenyl | CH₃ | H | H |
| 204 | 3-NO₂-phenyl | CH₃ | H | H |
| 205 | 4-NO₂-phenyl | CH₃ | H | H |
| 206 | 2-pyridyl | CH₃ | H | H |
| 207 | 3-pyridyl | CH₃ | H | H |
| 208 | 4-pyridyl | CH₃ | H | H |
| 209 | cyclohexylamino | CH₃ | H | H |
| 210 | cyclopentylamino | CH₃ | H | H |
| 211 | H | OCH₃ | H | H |
| 212 | CH₃ | OCH₃ | H | H |
| 213 | C₂H₅ | OCH₃ | H | H |
| 214 | n-C₃H₇ | OCH₃ | H | H |
| 215 | i-C₃H₇ | OCH₃ | H | H |
| 216 | n-C₄C₉ | OCH₃ | H | H |
| 217 | s-C₄C₉ | OCH₃ | H | H |
| 218 | i-C₄C₉ | OCH₃ | H | H |
| 219 | t-C₄C₉ | OCH₃ | H | H |
| 220 | CH₂Cl | OCH₃ | H | H |
| 221 | CHCl₂ | OCH₃ | H | H |
| 222 | CCl₃ | OCH₃ | H | H |
| 223 | CH₂F | OCH₃ | H | H |
| 224 | CHF₂ | OCH₃ | H | H |
| 225 | CF₃ | OCH₃ | H | H |
| 226 | CH₂CF₃ | OCH₃ | H | H |
| 227 | CH₂OCH₃ | OCH₃ | H | H |
| 228 | CH₂OCH₂CH₃ | OCH₃ | H | H |
| 229 | CH₂NH₂ | OCH₃ | H | H |
| 230 | (CH₂)₂COCH₃ | OCH₃ | H | H |
| 231 | phenyl | OCH₃ | H | H |
| 232 | 2-F-phenyl | OCH₃ | H | H |
| 233 | 3-F-phenyl | OCH₃ | H | H |
| 234 | 4-F-phenyl | OCH₃ | H | H |
| 235 | 2-Cl-phenyl | OCH₃ | H | H |
| 236 | 3-Cl-phenyl | OCH₃ | H | H |
| 237 | 4-Cl-phenyl | OCH₃ | H | H |
| 238 | 2-OH-phenyl | OCH₃ | H | H |

TABLE B-continued

|  | R³ | R¹ | R² | R⁴ |
|---|---|---|---|---|
| 239 | 3-OH-phenyl | OCH₃ | H | H |
| 240 | 4-OH-phenyl | OCH₃ | H | H |
| 241 | 2-OCH₃-phenyl | OCH₃ | H | H |
| 242 | 3-OCH₃-phenyl | OCH₃ | H | H |
| 243 | 4-OCH₃-phenyl | OCH₃ | H | H |
| 244 | 2-OCF₃-phenyl | OCH₃ | H | H |
| 245 | 3-OCF₃-phenyl | OCH₃ | H | H |
| 246 | 4-OCF₃-phenyl | OCH₃ | H | H |
| 247 | 2-OCHF₂-phenyl | OCH₃ | H | H |
| 248 | 3-OCHF₂-phenyl | OCH₃ | H | H |
| 249 | 4-OCHF₂-phenyl | OCH₃ | H | H |
| 250 | 2-CF₃-phenyl | OCH₃ | H | H |
| 251 | 3-CF₃-phenyl | OCH₃ | H | H |
| 252 | 4-CF₃-phenyl | OCH₃ | H | H |
| 253 | 2-CH₃-phenyl | OCH₃ | H | H |
| 254 | 3-CH₃-phenyl | OCH₃ | H | H |
| 255 | 4-CH₃-phenyl | OCH₃ | H | H |
| 256 | 2-NO₂-phenyl | OCH₃ | H | H |
| 257 | 3-NO₂-phenyl | OCH₃ | H | H |
| 258 | 4-NO₂-phenyl | OCH₃ | H | H |
| 259 | 2-pyridyl | OCH₃ | H | H |
| 260 | 3-pyridyl | OCH₃ | H | H |
| 261 | 4-pyridyl | OCH₃ | H | H |
| 262 | cyclohexylamino | OCH₃ | H | H |
| 263 | cyclopentylamino | OCH₃ | H | H |
| 264 | H | Cl | H | H |
| 265 | CH₃ | Cl | H | H |
| 266 | C₂H₅ | Cl | H | H |
| 267 | n-C₃H₇ | Cl | H | H |
| 268 | i-C₃H₇ | Cl | H | H |
| 269 | n-C₄C₉ | Cl | H | H |
| 270 | s-C₄C₉ | Cl | H | H |
| 271 | i-C₄C₉ | Cl | H | H |
| 272 | t-C₄C₉ | Cl | H | H |
| 273 | CH₂Cl | Cl | H | H |
| 274 | CHCl₂ | Cl | H | H |
| 275 | CCl₃ | Cl | H | H |
| 276 | CH₂F | Cl | H | H |
| 277 | CHF₂ | Cl | H | H |
| 278 | CF₃ | Cl | H | H |
| 279 | CH₂CF₃ | Cl | H | H |
| 280 | CH₂OCH₃ | Cl | H | H |
| 281 | CH₂OCH₂CH₃ | Cl | H | H |
| 282 | CH₂NH₂ | Cl | H | H |
| 283 | (CH₂)₂COCH₃ | Cl | H | H |
| 284 | phenyl | Cl | H | H |
| 285 | 2-F-phenyl | Cl | H | H |
| 286 | 3-F-phenyl | Cl | H | H |
| 287 | 4-F-phenyl | Cl | H | H |
| 288 | 2-Cl-phenyl | Cl | H | H |
| 289 | 3-Cl-phenyl | Cl | H | H |
| 290 | 4-Cl-phenyl | Cl | H | H |
| 291 | 2-OH-phenyl | Cl | H | H |
| 292 | 3-OH-phenyl | Cl | H | H |
| 293 | 4-OH-phenyl | Cl | H | H |
| 294 | 2-OCH₃-phenyl | Cl | H | H |
| 295 | 3-OCH₃-phenyl | Cl | H | H |
| 296 | 4-OCH₃-phenyl | Cl | H | H |
| 297 | 2-OCF₃-phenyl | Cl | H | H |
| 298 | 3-OCF₃-phenyl | Cl | H | H |
| 299 | 4-OCF₃-phenyl | Cl | H | H |
| 300 | 2-OCHF₂-phenyl | Cl | H | H |
| 301 | 3-OCHF₂-phenyl | Cl | H | H |
| 302 | 4-OCHF₂-phenyl | Cl | H | H |
| 303 | 2-CF₃-phenyl | Cl | H | H |
| 304 | 3-CF₃-phenyl | Cl | H | H |
| 305 | 4-CF₃-phenyl | Cl | H | H |
| 306 | 2-CH₃-phenyl | Cl | H | H |
| 307 | 3-CH₃-phenyl | Cl | H | H |
| 308 | 4-CH₃-phenyl | Cl | H | H |
| 309 | 2-NO₂-phenyl | Cl | H | H |
| 310 | 3-NO₂-phenyl | Cl | H | H |
| 311 | 4-NO₂-phenyl | Cl | H | H |
| 312 | 2-pyridyl | Cl | H | H |
| 313 | 3-pyridyl | Cl | H | H |
| 314 | 4-pyridyl | Cl | H | H |
| 315 | cyclohexylamino | Cl | H | H |
| 316 | cyclopentylamino | Cl | H | H |
| 317 | CH₃ | CH₃ | CH₃ | CH₃ |
| 318 | C₂H₅ | CH₃ | CH₃ | CH₃ |
| 319 | n-C₃H₇ | CH₃ | CH₃ | CH₃ |
| 320 | i-C₃H₇ | CH₃ | CH₃ | CH₃ |
| 321 | n-C₄C₉ | CH₃ | CH₃ | CH₃ |
| 322 | s-C₄C₉ | CH₃ | CH₃ | CH₃ |
| 323 | i-C₄C₉ | CH₃ | CH₃ | CH₃ |
| 324 | t-C₄C₉ | CH₃ | CH₃ | CH₃ |
| 325 | CH₂Cl | CH₃ | CH₃ | CH₃ |
| 326 | CHCl₂ | CH₃ | CH₃ | CH₃ |
| 327 | CCl₃ | CH₃ | CH₃ | CH₃ |
| 328 | CH₂F | CH₃ | CH₃ | CH₃ |
| 329 | CHF₂ | CH₃ | CH₃ | CH₃ |
| 330 | CF₃ | CH₃ | CH₃ | CH₃ |
| 331 | CH₂CF₃ | CH₃ | CH₃ | CH₃ |
| 332 | CH₂OCH₃ | CH₃ | CH₃ | CH₃ |
| 333 | CH₂OCH₂CH₃ | CH₃ | CH₃ | CH₃ |
| 334 | CH₂NH₂ | CH₃ | CH₃ | CH₃ |
| 335 | (CH₂)₂COCH₃ | CH₃ | CH₃ | CH₃ |
| 336 | phenyl | CH₃ | CH₃ | CH₃ |
| 337 | 2-F-phenyl | CH₃ | CH₃ | CH₃ |
| 338 | 3-F-phenyl | CH₃ | CH₃ | CH₃ |
| 339 | 4-F-phenyl | CH₃ | CH₃ | CH₃ |
| 340 | 2-Cl-phenyl | CH₃ | CH₃ | CH₃ |
| 341 | 3-Cl-phenyl | CH₃ | CH₃ | CH₃ |
| 342 | 4-Cl-phenyl | CH₃ | CH₃ | CH₃ |
| 343 | 2-OH-phenyl | CH₃ | CH₃ | CH₃ |
| 344 | 3-OH-phenyl | CH₃ | CH₃ | CH₃ |
| 345 | 4-OH-phenyl | CH₃ | CH₃ | CH₃ |
| 346 | 2-OCH₃-phenyl | CH₃ | CH₃ | CH₃ |
| 347 | 3-OCH₃-phenyl | CH₃ | CH₃ | CH₃ |
| 348 | 4-OCH₃-phenyl | CH₃ | CH₃ | CH₃ |
| 349 | 2-OCF₃-phenyl | CH₃ | CH₃ | CH₃ |
| 350 | 3-OCF₃-phenyl | CH₃ | CH₃ | CH₃ |
| 351 | 4-OCF₃-phenyl | CH₃ | CH₃ | CH₃ |
| 352 | 2-OCHF₂-phenyl | CH₃ | CH₃ | CH₃ |
| 353 | 3-OCHF₂-phenyl | CH₃ | CH₃ | CH₃ |
| 354 | 4-OCHF₂-phenyl | CH₃ | CH₃ | CH₃ |
| 355 | 2-CF₃-phenyl | CH₃ | CH₃ | CH₃ |
| 356 | 3-CF₃-phenyl | CH₃ | CH₃ | CH₃ |
| 357 | 4-CF₃-phenyl | CH₃ | CH₃ | CH₃ |
| 358 | 2-CH₃-phenyl | CH₃ | CH₃ | CH₃ |
| 359 | 3-CH₃-phenyl | CH₃ | CH₃ | CH₃ |
| 360 | 4-CH₃-phenyl | CH₃ | CH₃ | CH₃ |
| 361 | 2-NO₂-phenyl | CH₃ | CH₃ | CH₃ |
| 362 | 3-NO₂-phenyl | CH₃ | CH₃ | CH₃ |
| 363 | 4-NO₂-phenyl | CH₃ | CH₃ | CH₃ |
| 364 | 2-pyridyl | CH₃ | CH₃ | CH₃ |
| 365 | 3-pyridyl | CH₃ | CH₃ | CH₃ |
| 366 | 4-pyridyl | CH₃ | CH₃ | CH₃ |
| 367 | cyclohexylamino | CH₃ | CH₃ | CH₃ |
| 368 | cyclopentylamino | CH₃ | CH₃ | CH₃ |
| 369 | H | OCH₃ | CH₃ | CH₃ |
| 370 | CH₃ | OCH₃ | CH₃ | CH₃ |
| 371 | C₂H₅ | OCH₃ | CH₃ | CH₃ |
| 372 | n-C₃H₇ | OCH₃ | CH₃ | CH₃ |
| 373 | i-C₃H₇ | OCH₃ | CH₃ | CH₃ |
| 374 | n-C₄C₉ | OCH₃ | CH₃ | CH₃ |
| 375 | s-C₄C₉ | OCH₃ | CH₃ | CH₃ |
| 376 | i-C₄C₉ | OCH₃ | CH₃ | CH₃ |
| 377 | t-C₄C₉ | OCH₃ | CH₃ | CH₃ |
| 378 | CH₂Cl | OCH₃ | CH₃ | CH₃ |
| 379 | CHCl₂ | OCH₃ | CH₃ | CH₃ |
| 380 | CCl₃ | OCH₃ | CH₃ | CH₃ |
| 381 | CH₂F | OCH₃ | CH₃ | CH₃ |
| 382 | CHF₂ | OCH₃ | CH₃ | CH₃ |
| 383 | CF₃ | OCH₃ | CH₃ | CH₃ |
| 384 | CH₂CF₃ | OCH₃ | CH₃ | CH₃ |
| 385 | CH₂OCH₃ | OCH₃ | CH₃ | CH₃ |
| 386 | CH₂OCH₂CH₃ | OCH₃ | CH₃ | CH₃ |
| 387 | CH₂NH₂ | OCH₃ | CH₃ | CH₃ |
| 388 | (CH₂)₂COCH₃ | OCH₃ | CH₃ | CH₃ |
| 389 | phenyl | OCH₃ | CH₃ | CH₃ |
| 390 | 2-F-phenyl | OCH₃ | CH₃ | CH₃ |
| 391 | 3-F-phenyl | OCH₃ | CH₃ | CH₃ |
| 392 | 4-F-phenyl | OCH₃ | CH₃ | CH₃ |

TABLE B-continued

| | R³ | R¹ | R² | R⁴ |
|---|---|---|---|---|
| 393 | 2-Cl-phenyl | OCH₃ | CH₃ | CH₃ |
| 394 | 3-Cl-phenyl | OCH₃ | CH₃ | CH₃ |
| 395 | 4-Cl-phenyl | OCH₃ | CH₃ | CH₃ |
| 396 | 2-OH-phenyl | OCH₃ | CH₃ | CH₃ |
| 397 | 3-OH-phenyl | OCH₃ | CH₃ | CH₃ |
| 398 | 4-OH-phenyl | OCH₃ | CH₃ | CH₃ |
| 399 | 2-OCH₃-phenyl | OCH₃ | CH₃ | CH₃ |
| 400 | 3-OCH₃-phenyl | OCH₃ | CH₃ | CH₃ |
| 401 | 4-OCH₃-phenyl | OCH₃ | CH₃ | CH₃ |
| 402 | 2-OCF₃-phenyl | OCH₃ | CH₃ | CH₃ |
| 403 | 3-OCF₃-phenyl | OCH₃ | CH₃ | CH₃ |
| 404 | 4-OCF₃-phenyl | OCH₃ | CH₃ | CH₃ |
| 405 | 2-OCHF₂-phenyl | OCH₃ | CH₃ | CH₃ |
| 406 | 3-OCHF₂-phenyl | OCH₃ | CH₃ | CH₃ |
| 407 | 4-OCHF₂-phenyl | OCH₃ | CH₃ | CH₃ |
| 408 | 2-CF₃-phenyl | OCH₃ | CH₃ | CH₃ |
| 409 | 3-CF₃-phenyl | OCH₃ | CH₃ | CH₃ |
| 410 | 4-CF₃-phenyl | OCH₃ | CH₃ | CH₃ |
| 411 | 2-CH₃-phenyl | OCH₃ | CH₃ | CH₃ |
| 412 | 3-CH₃-phenyl | OCH₃ | CH₃ | CH₃ |
| 413 | 4-CH₃-phenyl | OCH₃ | CH₃ | CH₃ |
| 414 | 2-NO₂-phenyl | OCH₃ | CH₃ | CH₃ |
| 415 | 3-NO₂-phenyl | OCH₃ | CH₃ | CH₃ |
| 416 | 4-NO₂-phenyl | OCH₃ | CH₃ | CH₃ |
| 417 | 2-pyridyl | OCH₃ | CH₃ | CH₃ |
| 418 | 3-pyridyl | OCH₃ | CH₃ | CH₃ |
| 419 | 4-pyridyl | OCH₃ | CH₃ | CH₃ |
| 420 | cyclohexylamino | OCH₃ | CH₃ | CH₃ |
| 421 | cyclopentylamino | OCH₃ | CH₃ | CH₃ |
| 422 | H | Cl | CH₃ | CH₃ |
| 423 | CH₃ | Cl | CH₃ | CH₃ |
| 424 | C₂H₅ | Cl | CH₃ | CH₃ |
| 425 | n-C₃H₇ | Cl | CH₃ | CH₃ |
| 426 | i-C₃H₇ | Cl | CH₃ | CH₃ |
| 427 | n-C₄C₉ | Cl | CH₃ | CH₃ |
| 428 | s-C₄C₉ | Cl | CH₃ | CH₃ |
| 429 | i-C₄C₉ | Cl | CH₃ | CH₃ |
| 430 | t-C₄C₉ | Cl | CH₃ | CH₃ |
| 431 | CH₂Cl | Cl | CH₃ | CH₃ |
| 432 | CHCl₂ | Cl | CH₃ | CH₃ |
| 433 | CCl₃ | Cl | CH₃ | CH₃ |
| 434 | CH₂F | Cl | CH₃ | CH₃ |
| 435 | CHF₂ | Cl | CH₃ | CH₃ |
| 436 | CF₃ | Cl | CH₃ | CH₃ |
| 437 | CH₂CF₃ | Cl | CH₃ | CH₃ |
| 438 | CH₂OCH₃ | Cl | CH₃ | CH₃ |
| 439 | CH₂OCH₂CH₃ | Cl | CH₃ | CH₃ |
| 440 | CH₂NH₂ | Cl | CH₃ | CH₃ |
| 441 | (CH₂)₂COCH₃ | Cl | CH₃ | CH₃ |
| 442 | phenyl | Cl | CH₃ | CH₃ |
| 443 | 2-F-phenyl | Cl | CH₃ | CH₃ |
| 444 | 3-F-phenyl | Cl | CH₃ | CH₃ |
| 445 | 4-F-phenyl | Cl | CH₃ | CH₃ |
| 446 | 2-Cl-phenyl | Cl | CH₃ | CH₃ |
| 447 | 3-Cl-phenyl | Cl | CH₃ | CH₃ |
| 448 | 4-Cl-phenyl | Cl | CH₃ | CH₃ |
| 449 | 2-OH-phenyl | Cl | CH₃ | CH₃ |
| 450 | 3-OH-phenyl | Cl | CH₃ | CH₃ |
| 451 | 4-OH-phenyl | Cl | CH₃ | CH₃ |
| 452 | 2-OCH₃-phenyl | Cl | CH₃ | CH₃ |
| 453 | 3-OCH₃-phenyl | Cl | CH₃ | CH₃ |
| 454 | 4-OCH₃-phenyl | Cl | CH₃ | CH₃ |
| 455 | 2-OCF₃-phenyl | Cl | CH₃ | CH₃ |
| 456 | 3-OCF₃-phenyl | Cl | CH₃ | CH₃ |
| 457 | 4-OCF₃-phenyl | Cl | CH₃ | CH₃ |
| 458 | 2-OCHF₂-phenyl | Cl | CH₃ | CH₃ |
| 459 | 3-OCHF₂-phenyl | Cl | CH₃ | CH₃ |
| 460 | 4-OCHF₂-phenyl | Cl | CH₃ | CH₃ |
| 461 | 2-CF₃-phenyl | Cl | CH₃ | CH₃ |
| 462 | 3-CF₃-phenyl | Cl | CH₃ | CH₃ |
| 463 | 4-CF₃-phenyl | Cl | CH₃ | CH₃ |
| 464 | 2-CH₃-phenyl | Cl | CH₃ | CH₃ |
| 465 | 3-CH₃-phenyl | Cl | CH₃ | CH₃ |
| 466 | 4-CH₃-phenyl | Cl | CH₃ | CH₃ |
| 467 | 2-NO₂-phenyl | Cl | CH₃ | CH₃ |
| 468 | 3-NO₂-phenyl | Cl | CH₃ | CH₃ |
| 469 | 4-NO₂-phenyl | Cl | CH₃ | CH₃ |
| 470 | 2-pyridyl | Cl | CH₃ | CH₃ |
| 471 | 3-pyridyl | Cl | CH₃ | CH₃ |
| 472 | 4-pyridyl | Cl | CH₃ | CH₃ |
| 473 | cyclohexylamino | Cl | CH₃ | CH₃ |
| 474 | cyclopentylamino | Cl | CH₃ | CH₃ |
| 475 | CH₃ | CH₃ | H | CH₃ |
| 476 | C₂H₅ | CH₃ | H | CH₃ |
| 477 | n-C₃H₇ | CH₃ | H | CH₃ |
| 478 | i-C₃H₇ | CH₃ | H | CH₃ |
| 479 | n-C₄C₉ | CH₃ | H | CH₃ |
| 480 | s-C₄C₉ | CH₃ | H | CH₃ |
| 481 | i-C₄C₉ | CH₃ | H | CH₃ |
| 482 | t-C₄C₉ | CH₃ | H | CH₃ |
| 483 | CH₂Cl | CH₃ | H | CH₃ |
| 484 | CHCl₂ | CH₃ | H | CH₃ |
| 485 | CCl₃ | CH₃ | H | CH₃ |
| 486 | CH₂F | CH₃ | H | CH₃ |
| 487 | CHF₂ | CH₃ | H | CH₃ |
| 488 | CF₃ | CH₃ | H | CH₃ |
| 489 | CH₂CF₃ | CH₃ | H | CH₃ |
| 490 | CH₂OCH₃ | CH₃ | H | CH₃ |
| 491 | CH₂OCH₂CH₃ | CH₃ | H | CH₃ |
| 492 | CH₂NH₂ | CH₃ | H | CH₃ |
| 493 | (CH₂)₂COCH₃ | CH₃ | H | CH₃ |
| 494 | phenyl | CH₃ | H | CH₃ |
| 495 | 2-F-phenyl | CH₃ | H | CH₃ |
| 496 | 3-F-phenyl | CH₃ | H | CH₃ |
| 497 | 4-F-phenyl | CH₃ | H | CH₃ |
| 498 | 2-Cl-phenyl | CH₃ | H | CH₃ |
| 499 | 3-Cl-phenyl | CH₃ | H | CH₃ |
| 500 | 4-Cl-phenyl | CH₃ | H | CH₃ |
| 501 | 2-OH-phenyl | CH₃ | H | CH₃ |
| 502 | 3-OH-phenyl | CH₃ | H | CH₃ |
| 503 | 4-OH-phenyl | CH₃ | H | CH₃ |
| 504 | 2-OCH₃-phenyl | CH₃ | H | CH₃ |
| 505 | 3-OCH₃-phenyl | CH₃ | H | CH₃ |
| 506 | 4-OCH₃-phenyl | CH₃ | H | CH₃ |
| 507 | 2-OCF₃-phenyl | CH₃ | H | CH₃ |
| 508 | 3-OCF₃-phenyl | CH₃ | H | CH₃ |
| 509 | 4-OCF₃-phenyl | CH₃ | H | CH₃ |
| 510 | 2-OCHF₂-phenyl | CH₃ | H | CH₃ |
| 511 | 3-OCHF₂-phenyl | CH₃ | H | CH₃ |
| 512 | 4-OCHF₂-phenyl | CH₃ | H | CH₃ |
| 513 | 2-CF₃-phenyl | CH₃ | H | CH₃ |
| 514 | 3-CF₃-phenyl | CH₃ | H | CH₃ |
| 515 | 4-CF₃-phenyl | CH₃ | H | CH₃ |
| 516 | 2-CH₃-phenyl | CH₃ | H | CH₃ |
| 517 | 3-CH₃-phenyl | CH₃ | H | CH₃ |
| 518 | 4-CH₃-phenyl | CH₃ | H | CH₃ |
| 519 | 2-NO₂-phenyl | CH₃ | H | CH₃ |
| 520 | 3-NO₂-phenyl | CH₃ | H | CH₃ |
| 521 | 4-NO₂-phenyl | CH₃ | H | CH₃ |
| 522 | 2-pyridyl | CH₃ | H | CH₃ |
| 523 | 3-pyridyl | CH₃ | H | CH₃ |
| 524 | 4-pyridyl | CH₃ | H | CH₃ |
| 525 | cyclohexylamino | CH₃ | H | CH₃ |
| 526 | cyclopentylamino | CH₃ | H | CH₃ |
| 527 | H | OCH₃ | H | CH₃ |
| 528 | CH₃ | OCH₃ | H | CH₃ |
| 529 | C₂H₅ | OCH₃ | H | CH₃ |
| 530 | n-C₃H₇ | OCH₃ | H | CH₃ |
| 531 | i-C₃H₇ | OCH₃ | H | CH₃ |
| 532 | n-C₄C₉ | OCH₃ | H | CH₃ |
| 533 | s-C₄C₉ | OCH₃ | H | CH₃ |
| 534 | i-C₄C₉ | OCH₃ | H | CH₃ |
| 535 | t-C₄C₉ | OCH₃ | H | CH₃ |
| 536 | CH₂Cl | OCH₃ | H | CH₃ |
| 537 | CHCl₂ | OCH₃ | H | CH₃ |
| 538 | CCl₃ | OCH₃ | H | CH₃ |
| 539 | CH₂F | OCH₃ | H | CH₃ |
| 540 | CHF₂ | OCH₃ | H | CH₃ |
| 541 | CF₃ | OCH₃ | H | CH₃ |
| 542 | CH₂CF₃ | OCH₃ | H | CH₃ |
| 543 | CH₂OCH₃ | OCH₃ | H | CH₃ |
| 544 | CH₂OCH₂CH₃ | OCH₃ | H | CH₃ |
| 545 | CH₂NH₂ | OCH₃ | H | CH₃ |
| 546 | (CH₂)₂COCH₃ | OCH₃ | H | CH₃ |

TABLE B-continued

| | R³ | R¹ | R² | R⁴ |
|---|---|---|---|---|
| 547 | phenyl | OCH₃ | H | CH₃ |
| 548 | 2-F-phenyl | OCH₃ | H | CH₃ |
| 549 | 3-F-phenyl | OCH₃ | H | CH₃ |
| 550 | 4-F-phenyl | OCH₃ | H | CH₃ |
| 551 | 2-Cl-phenyl | OCH₃ | H | CH₃ |
| 552 | 3-Cl-phenyl | OCH₃ | H | CH₃ |
| 553 | 4-Cl-phenyl | OCH₃ | H | CH₃ |
| 554 | 2-OH-phenyl | OCH₃ | H | CH₃ |
| 555 | 3-OH-phenyl | OCH₃ | H | CH₃ |
| 556 | 4-OH-phenyl | OCH₃ | H | CH₃ |
| 557 | 2-OCH₃-phenyl | OCH₃ | H | CH₃ |
| 558 | 3-OCH₃-phenyl | OCH₃ | H | CH₃ |
| 559 | 4-OCH₃-phenyl | OCH₃ | H | CH₃ |
| 560 | 2-OCF₃-phenyl | OCH₃ | H | CH₃ |
| 561 | 3-OCF₃-phenyl | OCH₃ | H | CH₃ |
| 562 | 4-OCF₃-phenyl | OCH₃ | H | CH₃ |
| 563 | 2-OCHF₂-phenyl | OCH₃ | H | CH₃ |
| 564 | 3-OCHF₂-phenyl | OCH₃ | H | CH₃ |
| 565 | 4-OCHF₂-phenyl | OCH₃ | H | CH₃ |
| 566 | 2-CF₃-phenyl | OCH₃ | H | CH₃ |
| 567 | 3-CF₃-phenyl | OCH₃ | H | CH₃ |
| 568 | 4-CF₃-phenyl | OCH₃ | H | CH₃ |
| 569 | 2-CH₃-phenyl | OCH₃ | H | CH₃ |
| 570 | 3-CH₃-phenyl | OCH₃ | H | CH₃ |
| 571 | 4-CH₃-phenyl | OCH₃ | H | CH₃ |
| 572 | 2-NO₂-phenyl | OCH₃ | H | CH₃ |
| 573 | 3-NO₂-phenyl | OCH₃ | H | CH₃ |
| 574 | 4-NO₂-phenyl | OCH₃ | H | CH₃ |
| 575 | 2-pyridyl | OCH₃ | H | CH₃ |
| 576 | 3-pyridyl | OCH₃ | H | CH₃ |
| 577 | 4-pyridyl | OCH₃ | H | CH₃ |
| 578 | cyclohexylamino | OCH₃ | H | CH₃ |
| 579 | cyclopentylamino | OCH₃ | H | CH₃ |
| 580 | H | Cl | H | CH₃ |
| 581 | CH₃ | Cl | H | CH₃ |
| 582 | C₂H₅ | Cl | H | CH₃ |
| 583 | n-C₃H₇ | Cl | H | CH₃ |
| 584 | i-C₃H₇ | Cl | H | CH₃ |
| 585 | n-C₄C₉ | Cl | H | CH₃ |
| 586 | s-C₄C₉ | Cl | H | CH₃ |
| 587 | i-C₄C₉ | Cl | H | CH₃ |
| 588 | t-C₄C₉ | Cl | H | CH₃ |
| 589 | CH₂Cl | Cl | H | CH₃ |
| 590 | CHCl₂ | Cl | H | CH₃ |
| 591 | CCl₃ | Cl | H | CH₃ |
| 592 | CH₂F | Cl | H | CH₃ |
| 593 | CHF₂ | Cl | H | CH₃ |
| 594 | CF₃ | Cl | H | CH₃ |
| 595 | CH₂CF₃ | Cl | H | CH₃ |
| 596 | CH₂OCH₃ | Cl | H | CH₃ |
| 597 | CH₂OCH₂CH₃ | Cl | H | CH₃ |
| 598 | CH₂NH₂ | Cl | H | CH₃ |
| 599 | (CH₂)₂COCH₃ | Cl | H | CH₃ |
| 600 | phenyl | Cl | H | CH₃ |
| 701 | 2-F-phenyl | Cl | H | CH₃ |
| 702 | 3-F-phenyl | Cl | H | CH₃ |
| 703 | 4-F-phenyl | Cl | H | CH₃ |
| 704 | 2-Cl-phenyl | Cl | H | CH₃ |
| 705 | 3-Cl-phenyl | Cl | H | CH₃ |
| 706 | 4-Cl-phenyl | Cl | H | CH₃ |
| 707 | 2-OH-phenyl | Cl | H | CH₃ |
| 708 | 3-OH-phenyl | Cl | H | CH₃ |
| 709 | 4-OH-phenyl | Cl | H | CH₃ |
| 710 | 2-OCH₃-phenyl | Cl | H | CH₃ |
| 711 | 3-OCH₃-phenyl | Cl | H | CH₃ |
| 712 | 4-OCH₃-phenyl | Cl | H | CH₃ |
| 713 | 2-OCF₃-phenyl | Cl | H | CH₃ |
| 714 | 3-OCF₃-phenyl | Cl | H | CH₃ |
| 715 | 4-OCF₃-phenyl | Cl | H | CH₃ |
| 716 | 2-OCHF₂-phenyl | Cl | H | CH₃ |
| 717 | 3-OCHF₂-phenyl | Cl | H | CH₃ |
| 718 | 4-OCHF₂-phenyl | Cl | H | CH₃ |
| 719 | 2-CF₃-phenyl | Cl | H | CH₃ |
| 720 | 3-CF₃-phenyl | Cl | H | CH₃ |
| 721 | 4-CF₃-phenyl | Cl | H | CH₃ |
| 722 | 2-CH₃-phenyl | Cl | H | CH₃ |
| 723 | 3-CH₃-phenyl | Cl | H | CH₃ |
| 724 | 4-CH₃-phenyl | Cl | H | CH₃ |
| 725 | 2-NO₂-phenyl | Cl | H | CH₃ |
| 726 | 3-NO₂-phenyl | Cl | H | CH₃ |
| 727 | 4-NO₂-phenyl | Cl | H | CH₃ |
| 728 | 2-pyridyl | Cl | H | CH₃ |
| 729 | 3-pyridyl | Cl | H | CH₃ |
| 730 | 4-pyridyl | Cl | H | CH₃ |
| 731 | cyclohexylamino | Cl | H | CH₃ |
| 732 | cyclopentylamino | Cl | H | CH₃ |
| 733 | CH₃ | CH₃ | CH₃ | C₂H₅ |
| 734 | C₂H₅ | CH₃ | CH₃ | C₂H₅ |
| 735 | n-C₃H₇ | CH₃ | CH₃ | C₂H₅ |
| 736 | i-C₃H₇ | CH₃ | CH₃ | C₂H₅ |
| 737 | n-C₄C₉ | CH₃ | CH₃ | C₂H₅ |
| 738 | s-C₄C₉ | CH₃ | CH₃ | C₂H₅ |
| 739 | i-C₄C₉ | CH₃ | CH₃ | C₂H₅ |
| 740 | t-C₄C₉ | CH₃ | CH₃ | C₂H₅ |
| 741 | CH₂Cl | CH₃ | CH₃ | C₂H₅ |
| 742 | CHCl₂ | CH₃ | CH₃ | C₂H₅ |
| 743 | CCl₃ | CH₃ | CH₃ | C₂H₅ |
| 744 | CH₂F | CH₃ | CH₃ | C₂H₅ |
| 745 | CHF₂ | CH₃ | CH₃ | C₂H₅ |
| 746 | CF₃ | CH₃ | CH₃ | C₂H₅ |
| 747 | CH₂CF₃ | CH₃ | CH₃ | C₂H₅ |
| 748 | CH₂OCH₃ | CH₃ | CH₃ | C₂H₅ |
| 749 | CH₂OCH₂CH₃ | CH₃ | CH₃ | C₂H₅ |
| 750 | CH₂NH₂ | CH₃ | CH₃ | C₂H₅ |
| 751 | (CH₂)₂COCH₃ | CH₃ | CH₃ | C₂H₅ |
| 752 | phenyl | CH₃ | CH₃ | C₂H₅ |
| 753 | 2-F-phenyl | CH₃ | CH₃ | C₂H₅ |
| 754 | 3-F-phenyl | CH₃ | CH₃ | C₂H₅ |
| 755 | 4-F-phenyl | CH₃ | CH₃ | C₂H₅ |
| 756 | 2-Cl-phenyl | CH₃ | CH₃ | C₂H₅ |
| 757 | 3-Cl-phenyl | CH₃ | CH₃ | C₂H₅ |
| 758 | 4-Cl-phenyl | CH₃ | CH₃ | C₂H₅ |
| 759 | 2-OH-phenyl | CH₃ | CH₃ | C₂H₅ |
| 760 | 3-OH-phenyl | CH₃ | CH₃ | C₂H₅ |
| 761 | 4-OH-phenyl | CH₃ | CH₃ | C₂H₅ |
| 762 | 2-OCH₃-phenyl | CH₃ | CH₃ | C₂H₅ |
| 763 | 3-OCH₃-phenyl | CH₃ | CH₃ | C₂H₅ |
| 764 | 4-OCH₃-phenyl | CH₃ | CH₃ | C₂H₅ |
| 765 | 2-OCF₃-phenyl | CH₃ | CH₃ | C₂H₅ |
| 766 | 3-OCF₃-phenyl | CH₃ | CH₃ | C₂H₅ |
| 767 | 4-OCF₃-phenyl | CH₃ | CH₃ | C₂H₅ |
| 768 | 2-OCHF₂-phenyl | CH₃ | CH₃ | C₂H₅ |
| 769 | 3-OCHF₂-phenyl | CH₃ | CH₃ | C₂H₅ |
| 770 | 4-OCHF₂-phenyl | CH₃ | CH₃ | C₂H₅ |
| 771 | 2-CF₃-phenyl | CH₃ | CH₃ | C₂H₅ |
| 772 | 3-CF₃-phenyl | CH₃ | CH₃ | C₂H₅ |
| 773 | 4-CF₃-phenyl | CH₃ | CH₃ | C₂H₅ |
| 774 | 2-CH₃-phenyl | CH₃ | CH₃ | C₂H₅ |
| 775 | 3-CH₃-phenyl | CH₃ | CH₃ | C₂H₅ |
| 776 | 4-CH₃-phenyl | CH₃ | CH₃ | C₂H₅ |
| 777 | 2-NO₂-phenyl | CH₃ | CH₃ | C₂H₅ |
| 778 | 3-NO₂-phenyl | CH₃ | CH₃ | C₂H₅ |
| 779 | 4-NO₂-phenyl | CH₃ | CH₃ | C₂H₅ |
| 780 | 2-pyridyl | CH₃ | CH₃ | C₂H₅ |
| 781 | 3-pyridyl | CH₃ | CH₃ | C₂H₅ |
| 782 | 4-pyridyl | CH₃ | CH₃ | C₂H₅ |
| 783 | cyclohexylamino | CH₃ | CH₃ | C₂H₅ |
| 784 | cyclopentylamino | CH₃ | CH₃ | C₂H₅ |
| 785 | H | OCH₃ | CH₃ | C₂H₅ |
| 786 | CH₃ | OCH₃ | CH₃ | C₂H₅ |
| 787 | C₂H₅ | OCH₃ | CH₃ | C₂H₅ |
| 788 | n-C₃H₇ | OCH₃ | CH₃ | C₂H₅ |
| 789 | i-C₃H₇ | OCH₃ | CH₃ | C₂H₅ |
| 790 | n-C₄C₉ | OCH₃ | CH₃ | C₂H₅ |
| 791 | s-C₄C₉ | OCH₃ | CH₃ | C₂H₅ |
| 792 | i-C₄C₉ | OCH₃ | CH₃ | C₂H₅ |
| 793 | t-C₄C₉ | OCH₃ | CH₃ | C₂H₅ |
| 794 | CH₂Cl | OCH₃ | CH₃ | C₂H₅ |
| 795 | CHCl₂ | OCH₃ | CH₃ | C₂H₅ |
| 796 | CCl₃ | OCH₃ | CH₃ | C₂H₅ |
| 797 | CH₂F | OCH₃ | CH₃ | C₂H₅ |
| 798 | CHF₂ | OCH₃ | CH₃ | C₂H₅ |
| 799 | CF₃ | OCH₃ | CH₃ | C₂H₅ |
| 800 | CH₂CF₃ | OCH₃ | CH₃ | C₂H₅ |

TABLE B-continued

|  | R³ | R¹ | R² | R⁴ |
|---|---|---|---|---|
| 801 | CH₂OCH₃ | OCH₃ | CH₃ | C₂H₅ |
| 802 | CH₂OCH₂CH₃ | OCH₃ | CH₃ | C₂H₅ |
| 803 | CH₂NH₂ | OCH₃ | CH₃ | C₂H₅ |
| 804 | (CH₂)₂COCH₃ | OCH₃ | CH₃ | C₂H₅ |
| 805 | phenyl | OCH₃ | CH₃ | C₂H₅ |
| 806 | 2-F-phenyl | OCH₃ | CH₃ | C₂H₅ |
| 807 | 3-F-phenyl | OCH₃ | CH₃ | C₂H₅ |
| 808 | 4-F-phenyl | OCH₃ | CH₃ | C₂H₅ |
| 809 | 2-Cl-phenyl | OCH₃ | CH₃ | C₂H₅ |
| 810 | 3-Cl-phenyl | OCH₃ | CH₃ | C₂H₅ |
| 811 | 4-Cl-phenyl | OCH₃ | CH₃ | C₂H₅ |
| 812 | 2-OH-phenyl | OCH₃ | CH₃ | C₂H₅ |
| 813 | 3-OH-phenyl | OCH₃ | CH₃ | C₂H₅ |
| 814 | 4-OH-phenyl | OCH₃ | CH₃ | C₂H₅ |
| 815 | 2-OCH₃-phenyl | OCH₃ | CH₃ | C₂H₅ |
| 816 | 3-OCH₃-phenyl | OCH₃ | CH₃ | C₂H₅ |
| 817 | 4-OCH₃-phenyl | OCH₃ | CH₃ | C₂H₅ |
| 818 | 2-OCF₃-phenyl | OCH₃ | CH₃ | C₂H₅ |
| 819 | 3-OCF₃-phenyl | OCH₃ | CH₃ | C₂H₅ |
| 820 | 4-OCF₃-phenyl | OCH₃ | CH₃ | C₂H₅ |
| 821 | 2-OCHF₂-phenyl | OCH₃ | CH₃ | C₂H₅ |
| 822 | 3-OCHF₂-phenyl | OCH₃ | CH₃ | C₂H₅ |
| 823 | 4-OCHF₂-phenyl | OCH₃ | CH₃ | C₂H₅ |
| 824 | 2-CF₃-phenyl | OCH₃ | CH₃ | C₂H₅ |
| 825 | 3-CF₃-phenyl | OCH₃ | CH₃ | C₂H₅ |
| 826 | 4-CF₃-phenyl | OCH₃ | CH₃ | C₂H₅ |
| 827 | 2-CH₃-phenyl | OCH₃ | CH₃ | C₂H₅ |
| 828 | 3-CH₃-phenyl | OCH₃ | CH₃ | C₂H₅ |
| 829 | 4-CH₃-phenyl | OCH₃ | CH₃ | C₂H₅ |
| 830 | 2-NO₂-phenyl | OCH₃ | CH₃ | C₂H₅ |
| 831 | 3-NO₂-phenyl | OCH₃ | CH₃ | C₂H₅ |
| 832 | 4-NO₂-phenyl | OCH₃ | CH₃ | C₂H₅ |
| 833 | 2-pyridyl | OCH₃ | CH₃ | C₂H₅ |
| 834 | 3-pyridyl | OCH₃ | CH₃ | C₂H₅ |
| 835 | 4-pyridyl | OCH₃ | CH₃ | C₂H₅ |
| 836 | cyclohexylamino | OCH₃ | CH₃ | C₂H₅ |
| 837 | cyclopentylamino | OCH₃ | CH₃ | C₂H₅ |
| 838 | H | Cl | CH₃ | C₂H₅ |
| 839 | CH₃ | Cl | CH₃ | C₂H₅ |
| 840 | C₂H₅ | Cl | CH₃ | C₂H₅ |
| 841 | n-C₃H₇ | Cl | CH₃ | C₂H₅ |
| 842 | i-C₃H₇ | Cl | CH₃ | C₂H₅ |
| 843 | n-C₄C₉ | Cl | CH₃ | C₂H₅ |
| 844 | s-C₄C₉ | Cl | CH₃ | C₂H₅ |
| 845 | i-C₄C₉ | Cl | CH₃ | C₂H₅ |
| 846 | t-C₄C₉ | Cl | CH₃ | C₂H₅ |
| 847 | CH₂Cl | Cl | CH₃ | C₂H₅ |
| 848 | CHCl₂ | Cl | CH₃ | C₂H₅ |
| 849 | CCl₃ | Cl | CH₃ | C₂H₅ |
| 850 | CH₂F | Cl | CH₃ | C₂H₅ |
| 851 | CHF₂ | Cl | CH₃ | C₂H₅ |
| 852 | CF₃ | Cl | CH₃ | C₂H₅ |
| 853 | CH₂CF₃ | Cl | CH₃ | C₂H₅ |
| 854 | CH₂OCH₃ | Cl | CH₃ | C₂H₅ |
| 855 | CH₂OCH₂CH₃ | Cl | CH₃ | C₂H₅ |
| 856 | CH₂NH₂ | Cl | CH₃ | C₂H₅ |
| 857 | (CH₂)₂COCH₃ | Cl | CH₃ | C₂H₅ |
| 858 | phenyl | Cl | CH₃ | C₂H₅ |
| 859 | 2-F-phenyl | Cl | CH₃ | C₂H₅ |
| 860 | 3-F-phenyl | Cl | CH₃ | C₂H₅ |
| 861 | 4-F-phenyl | Cl | CH₃ | C₂H₅ |
| 862 | 2-Cl-phenyl | Cl | CH₃ | C₂H₅ |
| 863 | 3-Cl-phenyl | Cl | CH₃ | C₂H₅ |
| 864 | 4-Cl-phenyl | Cl | CH₃ | C₂H₅ |
| 865 | 2-OH-phenyl | Cl | CH₃ | C₂H₅ |
| 866 | 3-OH-phenyl | Cl | CH₃ | C₂H₅ |
| 867 | 4-OH-phenyl | Cl | CH₃ | C₂H₅ |
| 868 | 2-OCH₃-phenyl | Cl | CH₃ | C₂H₅ |
| 869 | 3-OCH₃-phenyl | Cl | CH₃ | C₂H₅ |
| 870 | 4-OCH₃-phenyl | Cl | CH₃ | C₂H₅ |
| 871 | 2-OCF₃-phenyl | Cl | CH₃ | C₂H₅ |
| 872 | 3-OCF₃-phenyl | Cl | CH₃ | C₂H₅ |
| 873 | 4-OCF₃-phenyl | Cl | CH₃ | C₂H₅ |
| 874 | 2-OCHF₂-phenyl | Cl | CH₃ | C₂H₅ |
| 875 | 3-OCHF₂-phenyl | Cl | CH₃ | C₂H₅ |
| 876 | 4-OCHF₂-phenyl | Cl | CH₃ | C₂H₅ |
| 877 | 2-CF₃-phenyl | Cl | CH₃ | C₂H₅ |
| 878 | 3-CF₃-phenyl | Cl | CH₃ | C₂H₅ |
| 879 | 4-CF₃-phenyl | Cl | CH₃ | C₂H₅ |
| 880 | 2-CH₃-phenyl | Cl | CH₃ | C₂H₅ |
| 881 | 3-CH₃-phenyl | Cl | CH₃ | C₂H₅ |
| 882 | 4-CH₃-phenyl | Cl | CH₃ | C₂H₅ |
| 883 | 2-NO₂-phenyl | Cl | CH₃ | C₂H₅ |
| 884 | 3-NO₂-phenyl | Cl | CH₃ | C₂H₅ |
| 885 | 4-NO₂-phenyl | Cl | CH₃ | C₂H₅ |
| 886 | 2-pyridyl | Cl | CH₃ | C₂H₅ |
| 887 | 3-pyridyl | Cl | CH₃ | C₂H₅ |
| 888 | 4-pyridyl | Cl | CH₃ | C₂H₅ |
| 889 | cyclohexylamino | Cl | CH₃ | C₂H₅ |
| 890 | cyclopentylamino | Cl | CH₃ | C₂H₅ |
| 891 | CH₃ | CH₃ | H | C₂H₅ |
| 892 | C₂H₅ | CH₃ | H | C₂H₅ |
| 893 | n-C₃H₇ | CH₃ | H | C₂H₅ |
| 894 | i-C₃H₇ | CH₃ | H | C₂H₅ |
| 895 | n-C₄C₉ | CH₃ | H | C₂H₅ |
| 896 | s-C₄C₉ | CH₃ | H | C₂H₅ |
| 897 | i-C₄C₉ | CH₃ | H | C₂H₅ |
| 898 | t-C₄C₉ | CH₃ | H | C₂H₅ |
| 899 | CH₂Cl | CH₃ | H | C₂H₅ |
| 900 | CHCl₂ | CH₃ | H | C₂H₅ |
| 901 | CCl₃ | CH₃ | H | C₂H₅ |
| 902 | CH₂F | CH₃ | H | C₂H₅ |
| 903 | CHF₂ | CH₃ | H | C₂H₅ |
| 904 | CF₃ | CH₃ | H | C₂H₅ |
| 905 | CH₂CF₃ | CH₃ | H | C₂H₅ |
| 906 | CH₂OCH₃ | CH₃ | H | C₂H₅ |
| 907 | CH₂OCH₂CH₃ | CH₃ | H | C₂H₅ |
| 908 | CH₂NH₂ | CH₃ | H | C₂H₅ |
| 909 | (CH₂)₂COCH₃ | CH₃ | H | C₂H₅ |
| 910 | phenyl | CH₃ | H | C₂H₅ |
| 911 | 2-F-phenyl | CH₃ | H | C₂H₅ |
| 912 | 3-F-phenyl | CH₃ | H | C₂H₅ |
| 913 | 4-F-phenyl | CH₃ | H | C₂H₅ |
| 914 | 2-Cl-phenyl | CH₃ | H | C₂H₅ |
| 915 | 3-Cl-phenyl | CH₃ | H | C₂H₅ |
| 916 | 4-Cl-phenyl | CH₃ | H | C₂H₅ |
| 917 | 2-OH-phenyl | CH₃ | H | C₂H₅ |
| 918 | 3-OH-phenyl | CH₃ | H | C₂H₅ |
| 919 | 4-OH-phenyl | CH₃ | H | C₂H₅ |
| 920 | 2-OCH₃-phenyl | CH₃ | H | C₂H₅ |
| 921 | 3-OCH₃-phenyl | CH₃ | H | C₂H₅ |
| 922 | 4-OCH₃-phenyl | CH₃ | H | C₂H₅ |
| 923 | 2-OCF₃-phenyl | CH₃ | H | C₂H₅ |
| 924 | 3-OCF₃-phenyl | CH₃ | H | C₂H₅ |
| 925 | 4-OCF₃-phenyl | CH₃ | H | C₂H₅ |
| 926 | 2-OCHF₂-phenyl | CH₃ | H | C₂H₅ |
| 927 | 3-OCHF₂-phenyl | CH₃ | H | C₂H₅ |
| 928 | 4-OCHF₂-phenyl | CH₃ | H | C₂H₅ |
| 929 | 2-CF₃-phenyl | CH₃ | H | C₂H₅ |
| 930 | 3-CF₃-phenyl | CH₃ | H | C₂H₅ |
| 931 | 4-CF₃-phenyl | CH₃ | H | C₂H₅ |
| 932 | 2-CH₃-phenyl | CH₃ | H | C₂H₅ |
| 933 | 3-CH₃-phenyl | CH₃ | H | C₂H₅ |
| 934 | 4-CH₃-phenyl | CH₃ | H | C₂H₅ |
| 935 | 2-NO₂-phenyl | CH₃ | H | C₂H₅ |
| 936 | 3-NO₂-phenyl | CH₃ | H | C₂H₅ |
| 937 | 4-NO₂-phenyl | CH₃ | H | C₂H₅ |
| 938 | 2-pyridyl | CH₃ | H | C₂H₅ |
| 939 | 3-pyridyl | CH₃ | H | C₂H₅ |
| 940 | 4-pyridyl | CH₃ | H | C₂H₅ |
| 941 | cyclohexylamino | CH₃ | H | C₂H₅ |
| 942 | cyclopentylamino | CH₃ | H | C₂H₅ |
| 943 | H | OCH₃ | H | C₂H₅ |
| 944 | CH₃ | OCH₃ | H | C₂H₅ |
| 945 | C₂H₅ | OCH₃ | H | C₂H₅ |
| 946 | n-C₃H₇ | OCH₃ | H | C₂H₅ |
| 947 | i-C₃H₇ | OCH₃ | H | C₂H₅ |
| 948 | n-C₄C₉ | OCH₃ | H | C₂H₅ |
| 949 | s-C₄C₉ | OCH₃ | H | C₂H₅ |
| 950 | i-C₄C₉ | OCH₃ | H | C₂H₅ |
| 951 | t-C₄C₉ | OCH₃ | H | C₂H₅ |
| 952 | CH₂Cl | OCH₃ | H | C₂H₅ |
| 953 | CHCl₂ | OCH₃ | H | C₂H₅ |
| 954 | CCl₃ | OCH₃ | H | C₂H₅ |

TABLE B-continued

| | R³ | R¹ | R² | R⁴ |
|---|---|---|---|---|
| 955 | CH₂F | OCH₃ | H | C₂H₅ |
| 956 | CHF₂ | OCH₃ | H | C₂H₅ |
| 957 | CF₃ | OCH₃ | H | C₂H₅ |
| 958 | CH₂CF₃ | OCH₃ | H | C₂H₅ |
| 959 | CH₂OCH₃ | OCH₃ | H | C₂H₅ |
| 960 | CH₂OCH₂CH₃ | OCH₃ | H | C₂H₅ |
| 961 | CH₂NH₂ | OCH₃ | H | C₂H₅ |
| 962 | (CH₂)₂COCH₃ | OCH₃ | H | C₂H₅ |
| 963 | phenyl | OCH₃ | H | C₂H₅ |
| 964 | 2-F-phenyl | OCH₃ | H | C₂H₅ |
| 965 | 3-F-phenyl | OCH₃ | H | C₂H₅ |
| 966 | 4-F-phenyl | OCH₃ | H | C₂H₅ |
| 967 | 2-Cl-phenyl | OCH₃ | H | C₂H₅ |
| 968 | 3-Cl-phenyl | OCH₃ | H | C₂H₅ |
| 969 | 4-Cl-phenyl | OCH₃ | H | C₂H₅ |
| 970 | 2-OH-phenyl | OCH₃ | H | C₂H₅ |
| 971 | 3-OH-phenyl | OCH₃ | H | C₂H₅ |
| 972 | 4-OH-phenyl | OCH₃ | H | C₂H₅ |
| 973 | 2-OCH₃-phenyl | OCH₃ | H | C₂H₅ |
| 974 | 3-OCH₃-phenyl | OCH₃ | H | C₂H₅ |
| 975 | 4-OCH₃-phenyl | OCH₃ | H | C₂H₅ |
| 976 | 2-OCF₃-phenyl | OCH₃ | H | C₂H₅ |
| 977 | 3-OCF₃-phenyl | OCH₃ | H | C₂H₅ |
| 978 | 4-OCF₃-phenyl | OCH₃ | H | C₂H₅ |
| 979 | 2-OCHF₂-phenyl | OCH₃ | H | C₂H₅ |
| 980 | 3-OCHF₂-phenyl | OCH₃ | H | C₂H₅ |
| 981 | 4-OCHF₂-phenyl | OCH₃ | H | C₂H₅ |
| 982 | 2-CF₃-phenyl | OCH₃ | H | C₂H₅ |
| 983 | 3-CF₃-phenyl | OCH₃ | H | C₂H₅ |
| 984 | 4-CF₃-phenyl | OCH₃ | H | C₂H₅ |
| 985 | 2-CH₃-phenyl | OCH₃ | H | C₂H₅ |
| 986 | 3-CH₃-phenyl | OCH₃ | H | C₂H₅ |
| 987 | 4-CH₃-phenyl | OCH₃ | H | C₂H₅ |
| 988 | 2-NO₂-phenyl | OCH₃ | H | C₂H₅ |
| 989 | 3-NO₂-phenyl | OCH₃ | H | C₂H₅ |
| 990 | 4-NO₂-phenyl | OCH₃ | H | C₂H₅ |
| 991 | 2-pyridyl | OCH₃ | H | C₂H₅ |
| 992 | 3-pyridyl | OCH₃ | H | C₂H₅ |
| 993 | 4-pyridyl | OCH₃ | H | C₂H₅ |
| 994 | cyclohexylamino | OCH₃ | H | C₂H₅ |
| 995 | cyclopentylamino | OCH₃ | H | C₂H₅ |
| 996 | H | Cl | H | C₂H₅ |
| 997 | CH₃ | Cl | H | C₂H₅ |
| 998 | C₂H₅ | Cl | H | C₂H₅ |
| 999 | n-C₃H₇ | Cl | H | C₂H₅ |
| 999 | i-C₃H₇ | Cl | H | C₂H₅ |
| 1000 | n-C₄C₉ | Cl | H | C₂H₅ |
| 1001 | s-C₄C₉ | Cl | H | C₂H₅ |
| 1002 | i-C₄C₉ | Cl | H | C₂H₅ |
| 1003 | t-C₄C₉ | Cl | H | C₂H₅ |
| 1004 | CH₂Cl | Cl | H | C₂H₅ |
| 1005 | CHCl₂ | Cl | H | C₂H₅ |
| 1006 | CCl₃ | Cl | H | C₂H₅ |
| 1007 | CH₂F | Cl | H | C₂H₅ |
| 1008 | CHF₂ | Cl | H | C₂H₅ |
| 1009 | CF₃ | Cl | H | C₂H₅ |
| 1010 | CH₂CF₃ | Cl | H | C₂H₅ |
| 1011 | CH₂OCH₃ | Cl | H | C₂H₅ |
| 1012 | CH₂OCH₂CH₃ | Cl | H | C₂H₅ |
| 1013 | CH₂NH₂ | Cl | H | C₂H₅ |
| 1014 | (CH₂)₂COCH₃ | Cl | H | C₂H₅ |
| 1015 | phenyl | Cl | H | C₂H₅ |
| 1016 | 2-F-phenyl | Cl | H | C₂H₅ |
| 1017 | 3-F-phenyl | Cl | H | C₂H₅ |
| 1018 | 4-F-phenyl | Cl | H | C₂H₅ |
| 1019 | 2-Cl-phenyl | Cl | H | C₂H₅ |
| 1020 | 3-Cl-phenyl | Cl | H | C₂H₅ |
| 1021 | 4-Cl-phenyl | Cl | H | C₂H₅ |
| 1022 | 2-OH-phenyl | Cl | H | C₂H₅ |
| 1023 | 3-OH-phenyl | Cl | H | C₂H₅ |
| 1024 | 4-OH-phenyl | Cl | H | C₂H₅ |
| 1025 | 2-OCH₃-phenyl | Cl | H | C₂H₅ |
| 1026 | 3-OCH₃-phenyl | Cl | H | C₂H₅ |
| 1027 | 4-OCH₃-phenyl | Cl | H | C₂H₅ |
| 1028 | 2-OCF₃-phenyl | Cl | H | C₂H₅ |
| 1029 | 3-OCF₃-phenyl | Cl | H | C₂H₅ |
| 1030 | 4-OCF₃-phenyl | Cl | H | C₂H₅ |
| 1031 | 2-OCHF₂-phenyl | Cl | H | C₂H₅ |
| 1032 | 3-OCHF₂-phenyl | Cl | H | C₂H₅ |
| 1033 | 4-OCHF₂-phenyl | Cl | H | C₂H₅ |
| 1034 | 2-CF₃-phenyl | Cl | H | C₂H₅ |
| 1035 | 3-CF₃-phenyl | Cl | H | C₂H₅ |
| 1036 | 4-CF₃-phenyl | Cl | H | C₂H₅ |
| 1037 | 2-CH₃-phenyl | Cl | H | C₂H₅ |
| 1038 | 3-CH₃-phenyl | Cl | H | C₂H₅ |
| 1039 | 4-CH₃-phenyl | Cl | H | C₂H₅ |
| 1040 | 2-NO₂-phenyl | Cl | H | C₂H₅ |
| 1041 | 3-NO₂-phenyl | Cl | H | C₂H₅ |
| 1042 | 4-NO₂-phenyl | Cl | H | C₂H₅ |
| 1043 | 2-pyridyl | Cl | H | C₂H₅ |
| 1044 | 3-pyridyl | Cl | H | C₂H₅ |
| 1045 | 4-pyridyl | Cl | H | C₂H₅ |
| 1046 | cyclohexylamino | Cl | H | C₂H₅ |
| 1047 | cyclopentylamino | Cl | H | C₂H₅ |
| 1048 | CH₃ | CH₃ | CH₃ | i-C₃H₇ |
| 1049 | C₂H₅ | CH₃ | CH₃ | i-C₃H₇ |
| 1050 | n-C₃H₇ | CH₃ | CH₃ | i-C₃H₇ |
| 1051 | i-C₃H₇ | CH₃ | CH₃ | i-C₃H₇ |
| 1052 | n-C₄H₉ | CH₃ | CH₃ | i-C₃H₇ |
| 1053 | s-C₄H₉ | CH₃ | CH₃ | i-C₃H₇ |
| 1054 | i-C₄H₉ | CH₃ | CH₃ | i-C₃H₇ |
| 1055 | t-C₄H₉ | CH₃ | CH₃ | i-C₃H₇ |
| 1056 | CH₂Cl | CH₃ | CH₃ | i-C₃H₇ |
| 1057 | CHCl₂ | CH₃ | CH₃ | i-C₃H₇ |
| 1058 | CCl₃ | CH₃ | CH₃ | i-C₃H₇ |
| 1059 | CH₂F | CH₃ | CH₃ | i-C₃H₇ |
| 1060 | CHF₂ | CH₃ | CH₃ | i-C₃H₇ |
| 1061 | CF₃ | CH₃ | CH₃ | i-C₃H₇ |
| 1062 | CH₂CF₃ | CH₃ | CH₃ | i-C₃H₇ |
| 1063 | CH₂OCH₃ | CH₃ | CH₃ | i-C₃H₇ |
| 1064 | CH₂OCH₂CH₃ | CH₃ | CH₃ | i-C₃H₇ |
| 1065 | CH₂NH₂ | CH₃ | CH₃ | i-C₃H₇ |
| 1066 | (CH₂)₂COCH₃ | CH₃ | CH₃ | i-C₃H₇ |
| 1067 | phenyl | CH₃ | CH₃ | i-C₃H₇ |
| 1068 | 2-F-phenyl | CH₃ | CH₃ | i-C₃H₇ |
| 1069 | 3-F-phenyl | CH₃ | CH₃ | i-C₃H₇ |
| 1070 | 4-F-phenyl | CH₃ | CH₃ | i-C₃H₇ |
| 1071 | 2-Cl-phenyl | CH₃ | CH₃ | i-C₃H₇ |
| 1072 | 3-Cl-phenyl | CH₃ | CH₃ | i-C₃H₇ |
| 1073 | 4-Cl-phenyl | CH₃ | CH₃ | i-C₃H₇ |
| 1074 | 2-OH-phenyl | CH₃ | CH₃ | i-C₃H₇ |
| 1075 | 3-OH-phenyl | CH₃ | CH₃ | i-C₃H₇ |
| 1076 | 4-OH-phenyl | CH₃ | CH₃ | i-C₃H₇ |
| 1077 | 2-OCH₃-phenyl | CH₃ | CH₃ | i-C₃H₇ |
| 1078 | 3-OCH₃-phenyl | CH₃ | CH₃ | i-C₃H₇ |
| 1079 | 4-OCH₃-phenyl | CH₃ | CH₃ | i-C₃H₇ |
| 1080 | 2-OCF₃-phenyl | CH₃ | CH₃ | i-C₃H₇ |
| 1081 | 3-OCF₃-phenyl | CH₃ | CH₃ | i-C₃H₇ |
| 1082 | 4-OCF₃-phenyl | CH₃ | CH₃ | i-C₃H₇ |
| 1083 | 2-OCHF₂-phenyl | CH₃ | CH₃ | i-C₃H₇ |
| 1084 | 3-OCHF₂-phenyl | CH₃ | CH₃ | i-C₃H₇ |
| 1085 | 4-OCHF₂-phenyl | CH₃ | CH₃ | i-C₃H₇ |
| 1086 | 2-CF₃-phenyl | CH₃ | CH₃ | i-C₃H₇ |
| 1087 | 3-CF₃-phenyl | CH₃ | CH₃ | i-C₃H₇ |
| 1088 | 4-CF₃-phenyl | CH₃ | CH₃ | i-C₃H₇ |
| 1089 | 2-CH₃-phenyl | CH₃ | CH₃ | i-C₃H₇ |
| 1090 | 3-CH₃-phenyl | CH₃ | CH₃ | i-C₃H₇ |
| 1091 | 4-CH₃-phenyl | CH₃ | CH₃ | i-C₃H₇ |
| 1092 | 2-NO₂-phenyl | CH₃ | CH₃ | i-C₃H₇ |
| 1093 | 3-NO₂-phenyl | CH₃ | CH₃ | i-C₃H₇ |
| 1094 | 4-NO₂-phenyl | CH₃ | CH₃ | i-C₃H₇ |
| 1095 | 2-pyridyl | CH₃ | CH₃ | i-C₃H₇ |
| 1096 | 3-pyridyl | CH₃ | CH₃ | i-C₃H₇ |
| 1097 | 4-pyridyl | CH₃ | CH₃ | i-C₃H₇ |
| 1098 | cyclohexylamino | CH₃ | CH₃ | i-C₃H₇ |
| 1099 | cyclopentylamino | CH₃ | CH₃ | i-C₃H₇ |
| 1100 | H | OCH₃ | CH₃ | i-C₃H₇ |
| 1101 | CH₃ | OCH₃ | CH₃ | i-C₃H₇ |
| 1102 | C₂H₅ | OCH₃ | CH₃ | i-C₃H₇ |
| 1103 | n-C₃H₇ | OCH₃ | CH₃ | i-C₃H₇ |
| 1104 | i-C₃H₇ | OCH₃ | CH₃ | i-C₃H₇ |
| 1105 | n-C₄C₉ | OCH₃ | CH₃ | i-C₃H₇ |
| 1106 | s-C₄C₉ | OCH₃ | CH₃ | i-C₃H₇ |
| 1107 | i-C₄C₉ | OCH₃ | CH₃ | i-C₃H₇ |

TABLE B-continued

| | R³ | R¹ | R² | R⁴ |
|---|---|---|---|---|
| 1108 | t-C₄C₉ | OCH₃ | CH₃ | i-C₃H₇ |
| 1109 | CH₂Cl | OCH₃ | CH₃ | i-C₃H₇ |
| 1110 | CHCl₂ | OCH₃ | CH₃ | i-C₃H₇ |
| 1111 | CCl₃ | OCH₃ | CH₃ | i-C₃H₇ |
| 1112 | CH₂F | OCH₃ | CH₃ | i-C₃H₇ |
| 1113 | CHF₂ | OCH₃ | CH₃ | i-C₃H₇ |
| 1114 | CF₃ | OCH₃ | CH₃ | i-C₃H₇ |
| 1115 | CH₂CF₃ | OCH₃ | CH₃ | i-C₃H₇ |
| 1116 | CH₂OCH₃ | OCH₃ | CH₃ | i-C₃H₇ |
| 1117 | CH₂OCH₂CH₃ | OCH₃ | CH₃ | i-C₃H₇ |
| 1118 | CH₂NH₂ | OCH₃ | CH₃ | i-C₃H₇ |
| 1119 | (CH₂)₂COCH₃ | OCH₃ | CH₃ | i-C₃H₇ |
| 1120 | phenyl | OCH₃ | CH₃ | i-C₃H₇ |
| 1121 | 2-F-phenyl | OCH₃ | CH₃ | i-C₃H₇ |
| 1122 | 3-F-phenyl | OCH₃ | CH₃ | i-C₃H₇ |
| 1123 | 4-F-phenyl | OCH₃ | CH₃ | i-C₃H₇ |
| 1124 | 2-Cl-phenyl | OCH₃ | CH₃ | i-C₃H₇ |
| 1125 | 3-Cl-phenyl | OCH₃ | CH₃ | i-C₃H₇ |
| 1126 | 4-Cl-phenyl | OCH₃ | CH₃ | i-C₃H₇ |
| 1127 | 2-OH-phenyl | OCH₃ | CH₃ | i-C₃H₇ |
| 1128 | 3-OH-phenyl | OCH₃ | CH₃ | i-C₃H₇ |
| 1129 | 4-OH-phenyl | OCH₃ | CH₃ | i-C₃H₇ |
| 1130 | 2-OCH₃-phenyl | OCH₃ | CH₃ | i-C₃H₇ |
| 1131 | 3-OCH₃-phenyl | OCH₃ | CH₃ | i-C₃H₇ |
| 1132 | 4-OCH₃-phenyl | OCH₃ | CH₃ | i-C₃H₇ |
| 1133 | 2-OCF₃-phenyl | OCH₃ | CH₃ | i-C₃H₇ |
| 1134 | 3-OCF₃-phenyl | OCH₃ | CH₃ | i-C₃H₇ |
| 1135 | 4-OCF₃-phenyl | OCH₃ | CH₃ | i-C₃H₇ |
| 1136 | 2-OCHF₂-phenyl | OCH₃ | CH₃ | i-C₃H₇ |
| 1137 | 3-OCHF₂-phenyl | OCH₃ | CH₃ | i-C₃H₇ |
| 1138 | 4-OCHF₂-phenyl | OCH₃ | CH₃ | i-C₃H₇ |
| 1139 | 2-CF₃-phenyl | OCH₃ | CH₃ | i-C₃H₇ |
| 1140 | 3-CF₃-phenyl | OCH₃ | CH₃ | i-C₃H₇ |
| 1141 | 4-CF₃-phenyl | OCH₃ | CH₃ | i-C₃H₇ |
| 1142 | 2-CH₃-phenyl | OCH₃ | CH₃ | i-C₃H₇ |
| 1143 | 3-CH₃-phenyl | OCH₃ | CH₃ | i-C₃H₇ |
| 1144 | 4-CH₃-phenyl | OCH₃ | CH₃ | i-C₃H₇ |
| 1145 | 2-NO₂-phenyl | OCH₃ | CH₃ | i-C₃H₇ |
| 1146 | 3-NO₂-phenyl | OCH₃ | CH₃ | i-C₃H₇ |
| 1147 | 4-NO₂-phenyl | OCH₃ | CH₃ | i-C₃H₇ |
| 1148 | 2-pyridyl | OCH₃ | CH₃ | i-C₃H₇ |
| 1149 | 3-pyridyl | OCH₃ | CH₃ | i-C₃H₇ |
| 1150 | 4-pyridyl | OCH₃ | CH₃ | i-C₃H₇ |
| 1151 | cyclohexylamino | OCH₃ | CH₃ | i-C₃H₇ |
| 1152 | cyclopentylamino | OCH₃ | CH₃ | i-C₃H₇ |
| 1153 | H | Cl | CH₃ | i-C₃H₇ |
| 1154 | CH₃ | Cl | CH₃ | i-C₃H₇ |
| 1155 | C₂H₅ | Cl | CH₃ | i-C₃H₇ |
| 1156 | n-C₃H₇ | Cl | CH₃ | i-C₃H₇ |
| 1157 | i-C₃H₇ | Cl | CH₃ | i-C₃H₇ |
| 1158 | n-C₄C₉ | Cl | CH₃ | i-C₃H₇ |
| 1159 | s-C₄C₉ | Cl | CH₃ | i-C₃H₇ |
| 1160 | i-C₄C₉ | Cl | CH₃ | i-C₃H₇ |
| 1161 | t-C₄C₉ | Cl | CH₃ | i-C₃H₇ |
| 1162 | CH₂Cl | Cl | CH₃ | i-C₃H₇ |
| 1163 | CHCl₂ | Cl | CH₃ | i-C₃H₇ |
| 1164 | CCl₃ | Cl | CH₃ | i-C₃H₇ |
| 1165 | CH₂F | Cl | CH₃ | i-C₃H₇ |
| 1166 | CHF₂ | Cl | CH₃ | i-C₃H₇ |
| 1167 | CF₃ | Cl | CH₃ | i-C₃H₇ |
| 1168 | CH₂CF₃ | Cl | CH₃ | i-C₃H₇ |
| 1169 | CH₂OCH₃ | Cl | CH₃ | i-C₃H₇ |
| 1170 | CH₂OCH₂CH₃ | Cl | CH₃ | i-C₃H₇ |
| 1171 | CH₂NH₂ | Cl | CH₃ | i-C₃H₇ |
| 1172 | (CH₂)₂COCH₃ | Cl | CH₃ | i-C₃H₇ |
| 1173 | phenyl | Cl | CH₃ | i-C₃H₇ |
| 1174 | 2-F-phenyl | Cl | CH₃ | i-C₃H₇ |
| 1175 | 3-F-phenyl | Cl | CH₃ | i-C₃H₇ |
| 1176 | 4-F-phenyl | Cl | CH₃ | i-C₃H₇ |
| 1177 | 2-Cl-phenyl | Cl | CH₃ | i-C₃H₇ |
| 1178 | 3-Cl-phenyl | Cl | CH₃ | i-C₃H₇ |
| 1179 | 4-Cl-phenyl | Cl | CH₃ | i-C₃H₇ |
| 1180 | 2-OH-phenyl | Cl | CH₃ | i-C₃H₇ |
| 1181 | 3-OH-phenyl | Cl | CH₃ | i-C₃H₇ |
| 1182 | 4-OH-phenyl | Cl | CH₃ | i-C₃H₇ |
| 1183 | 2-OCH₃-phenyl | Cl | CH₃ | i-C₃H₇ |
| 1184 | 3-OCH₃-phenyl | Cl | CH₃ | i-C₃H₇ |
| 1185 | 4-OCH₃-phenyl | Cl | CH₃ | i-C₃H₇ |
| 1186 | 2-OCF₃-phenyl | Cl | CH₃ | i-C₃H₇ |
| 1187 | 3-OCF₃-phenyl | Cl | CH₃ | i-C₃H₇ |
| 1188 | 4-OCF₃-phenyl | Cl | CH₃ | i-C₃H₇ |
| 1189 | 2-OCHF₂-phenyl | Cl | CH₃ | i-C₃H₇ |
| 1190 | 3-OCHF₂-phenyl | Cl | CH₃ | i-C₃H₇ |
| 1191 | 4-OCHF₂-phenyl | Cl | CH₃ | i-C₃H₇ |
| 1192 | 2-CF₃-phenyl | Cl | CH₃ | i-C₃H₇ |
| 1193 | 3-CF₃-phenyl | Cl | CH₃ | i-C₃H₇ |
| 1194 | 4-CF₃-phenyl | Cl | CH₃ | i-C₃H₇ |
| 1195 | 2-CH₃-phenyl | Cl | CH₃ | i-C₃H₇ |
| 1196 | 3-CH₃-phenyl | Cl | CH₃ | i-C₃H₇ |
| 1197 | 4-CH₃-phenyl | Cl | CH₃ | i-C₃H₇ |
| 1198 | 2-NO₂-phenyl | Cl | CH₃ | i-C₃H₇ |
| 1199 | 3-NO₂-phenyl | Cl | CH₃ | i-C₃H₇ |
| 1200 | 4-NO₂-phenyl | Cl | CH₃ | i-C₃H₇ |
| 1201 | 2-pyridyl | Cl | CH₃ | i-C₃H₇ |
| 1202 | 3-pyridyl | Cl | CH₃ | i-C₃H₇ |
| 1203 | 4-pyridyl | Cl | CH₃ | i-C₃H₇ |
| 1204 | cyclohexylamino | Cl | CH₃ | i-C₃H₇ |
| 1205 | cyclopentylamino | Cl | CH₃ | i-C₃H₇ |
| 1206 | CH₃ | CH₃ | H | i-C₃H₇ |
| 1207 | C₂H₅ | CH₃ | H | i-C₃H₇ |
| 1208 | n-C₃H₇ | CH₃ | H | i-C₃H₇ |
| 1209 | i-C₃H₇ | CH₃ | H | i-C₃H₇ |
| 1210 | n-C₄C₉ | CH₃ | H | i-C₃H₇ |
| 1211 | s-C₄C₉ | CH₃ | H | i-C₃H₇ |
| 1212 | i-C₄C₉ | CH₃ | H | i-C₃H₇ |
| 1213 | t-C₄C₉ | CH₃ | H | i-C₃H₇ |
| 1214 | CH₂Cl | CH₃ | H | i-C₃H₇ |
| 1215 | CHCl₂ | CH₃ | H | i-C₃H₇ |
| 1116 | CCl₃ | CH₃ | H | i-C₃H₇ |
| 1217 | CH₂F | CH₃ | H | i-C₃H₇ |
| 1218 | CHF₂ | CH₃ | H | i-C₃H₇ |
| 1219 | CF₃ | CH₃ | H | i-C₃H₇ |
| 1220 | CH₂CF₃ | CH₃ | H | i-C₃H₇ |
| 1221 | CH₂OCH₃ | CH₃ | H | i-C₃H₇ |
| 1222 | CH₂OCH₂CH₃ | CH₃ | H | i-C₃H₇ |
| 1223 | CH₂NH₂ | CH₃ | H | i-C₃H₇ |
| 1224 | (CH₂)₂COCH₃ | CH₃ | H | i-C₃H₇ |
| 1225 | phenyl | CH₃ | H | i-C₃H₇ |
| 1226 | 2-F-phenyl | CH₃ | H | i-C₃H₇ |
| 1227 | 3-F-phenyl | CH₃ | H | i-C₃H₇ |
| 1228 | 4-F-phenyl | CH₃ | H | i-C₃H₇ |
| 1229 | 2-Cl-phenyl | CH₃ | H | i-C₃H₇ |
| 1230 | 3-Cl-phenyl | CH₃ | H | i-C₃H₇ |
| 1231 | 4-Cl-phenyl | CH₃ | H | i-C₃H₇ |
| 1232 | 2-OH-phenyl | CH₃ | H | i-C₃H₇ |
| 1233 | 3-OH-phenyl | CH₃ | H | i-C₃H₇ |
| 1234 | 4-OH-phenyl | CH₃ | H | i-C₃H₇ |
| 1235 | 2-OCH₃-phenyl | CH₃ | H | i-C₃H₇ |
| 1236 | 3-OCH₃-phenyl | CH₃ | H | i-C₃H₇ |
| 1237 | 4-OCH₃-phenyl | CH₃ | H | i-C₃H₇ |
| 1238 | 2-OCF₃-phenyl | CH₃ | H | i-C₃H₇ |
| 1239 | 3-OCF₃-phenyl | CH₃ | H | i-C₃H₇ |
| 1240 | 4-OCF₃-phenyl | CH₃ | H | i-C₃H₇ |
| 1241 | 2-OCHF₂-phenyl | CH₃ | H | i-C₃H₇ |
| 1242 | 3-OCHF₂-phenyl | CH₃ | H | i-C₃H₇ |
| 1243 | 4-OCHF₂-phenyl | CH₃ | H | i-C₃H₇ |
| 1244 | 2-CF₃-phenyl | CH₃ | H | i-C₃H₇ |
| 1245 | 3-CF₃-phenyl | CH₃ | H | i-C₃H₇ |
| 1246 | 4-CF₃-phenyl | CH₃ | H | i-C₃H₇ |
| 1247 | 2-CH₃-phenyl | CH₃ | H | i-C₃H₇ |
| 1248 | 3-CH₃-phenyl | CH₃ | H | i-C₃H₇ |
| 1249 | 4-CH₃-phenyl | CH₃ | H | i-C₃H₇ |
| 1250 | 2-NO₂-phenyl | CH₃ | H | i-C₃H₇ |
| 1251 | 3-NO₂-phenyl | CH₃ | H | i-C₃H₇ |
| 1252 | 4-NO₂-phenyl | CH₃ | H | i-C₃H₇ |
| 1253 | 2-pyridyl | CH₃ | H | i-C₃H₇ |
| 1254 | 3-pyridyl | CH₃ | H | i-C₃H₇ |
| 1255 | 4-pyridyl | CH₃ | H | i-C₃H₇ |
| 1256 | cyclohexylamino | CH₃ | H | i-C₃H₇ |
| 1257 | cyclopentylamino | CH₃ | H | i-C₃H₇ |
| 1258 | H | OCH₃ | H | i-C₃H₇ |
| 1259 | CH₃ | OCH₃ | H | i-C₃H₇ |
| 1260 | C₂H₅ | OCH₃ | H | i-C₃H₇ |
| 1261 | n-C₃H₇ | OCH₃ | H | i-C₃H₇ |

TABLE B-continued

| | $R^3$ | $R^1$ | $R^2$ | $R^4$ |
|---|---|---|---|---|
| 1262 | i-$C_3H_7$ | $OCH_3$ | H | i-$C_3H_7$ |
| 1263 | n-$C_4C_9$ | $OCH_3$ | H | i-$C_3H_7$ |
| 1264 | s-$C_4C_9$ | $OCH_3$ | H | i-$C_3H_7$ |
| 1265 | i-$C_4C_9$ | $OCH_3$ | H | i-$C_3H_7$ |
| 1266 | t-$C_4C_9$ | $OCH_3$ | H | i-$C_3H_7$ |
| 1267 | $CH_2Cl$ | $OCH_3$ | H | i-$C_3H_7$ |
| 1268 | $CHCl_2$ | $OCH_3$ | H | i-$C_3H_7$ |
| 1269 | $CCl_3$ | $OCH_3$ | H | i-$C_3H_7$ |
| 1270 | $CH_2F$ | $OCH_3$ | H | i-$C_3H_7$ |
| 1271 | $CHF_2$ | $OCH_3$ | H | i-$C_3H_7$ |
| 1272 | $CF_3$ | $OCH_3$ | H | i-$C_3H_7$ |
| 1273 | $CH_2CF_3$ | $OCH_3$ | H | i-$C_3H_7$ |
| 1274 | $CH_2OCH_3$ | $OCH_3$ | H | i-$C_3H_7$ |
| 1275 | $CH_2OCH_2CH_3$ | $OCH_3$ | H | i-$C_3H_7$ |
| 1276 | $CH_2NH_2$ | $OCH_3$ | H | i-$C_3H_7$ |
| 1277 | $(CH_2)_2COCH_3$ | $OCH_3$ | H | i-$C_3H_7$ |
| 1278 | phenyl | $OCH_3$ | H | i-$C_3H_7$ |
| 1279 | 2-F-phenyl | $OCH_3$ | H | i-$C_3H_7$ |
| 1280 | 3-F-phenyl | $OCH_3$ | H | i-$C_3H_7$ |
| 1281 | 4-F-phenyl | $OCH_3$ | H | i-$C_3H_7$ |
| 1282 | 2-Cl-phenyl | $OCH_3$ | H | i-$C_3H_7$ |
| 1283 | 3-Cl-phenyl | $OCH_3$ | H | i-$C_3H_7$ |
| 1284 | 4-Cl-phenyl | $OCH_3$ | H | i-$C_3H_7$ |
| 1285 | 2-OH-phenyl | $OCH_3$ | H | i-$C_3H_7$ |
| 1286 | 3-OH-phenyl | $OCH_3$ | H | i-$C_3H_7$ |
| 1287 | 4-OH-phenyl | $OCH_3$ | H | i-$C_3H_7$ |
| 1288 | 2-$OCH_3$-phenyl | $OCH_3$ | H | i-$C_3H_7$ |
| 1289 | 3-$OCH_3$-phenyl | $OCH_3$ | H | i-$C_3H_7$ |
| 1290 | 4-$OCH_3$-phenyl | $OCH_3$ | H | i-$C_3H_7$ |
| 1291 | 2-$OCF_3$-phenyl | $OCH_3$ | H | i-$C_3H_7$ |
| 1292 | 3-$OCF_3$-phenyl | $OCH_3$ | H | i-$C_3H_7$ |
| 1293 | 4-$OCF_3$-phenyl | $OCH_3$ | H | i-$C_3H_7$ |
| 1294 | 2-$OCHF_2$-phenyl | $OCH_3$ | H | i-$C_3H_7$ |
| 1295 | 3-$OCHF_2$-phenyl | $OCH_3$ | H | i-$C_3H_7$ |
| 1296 | 4-$OCHF_2$-phenyl | $OCH_3$ | H | i-$C_3H_7$ |
| 1297 | 2-$CF_3$-phenyl | $OCH_3$ | H | i-$C_3H_7$ |
| 1298 | 3-$CF_3$-phenyl | $OCH_3$ | H | i-$C_3H_7$ |
| 1299 | 4-$CF_3$-phenyl | $OCH_3$ | H | i-$C_3H_7$ |
| 1300 | 2-$CH_3$-phenyl | $OCH_3$ | H | i-$C_3H_7$ |
| 1301 | 3-$CH_3$-phenyl | $OCH_3$ | H | i-$C_3H_7$ |
| 1302 | 4-$CH_3$-phenyl | $OCH_3$ | H | i-$C_3H_7$ |
| 1303 | 2-$NO_2$-phenyl | $OCH_3$ | H | i-$C_3H_7$ |
| 1304 | 3-$NO_2$-phenyl | $OCH_3$ | H | i-$C_3H_7$ |
| 1305 | 4-$NO_2$-phenyl | $OCH_3$ | H | i-$C_3H_7$ |
| 1306 | 2-pyridyl | $OCH_3$ | H | i-$C_3H_7$ |
| 1307 | 3-pyridyl | $OCH_3$ | H | i-$C_3H_7$ |
| 1308 | 4-pyridyl | $OCH_3$ | H | i-$C_3H_7$ |
| 1309 | cyclohexylamino | $OCH_3$ | H | i-$C_3H_7$ |
| 1310 | cyclopentylamino | $OCH_3$ | H | i-$C_3H_7$ |
| 1311 | H | Cl | H | i-$C_3H_7$ |
| 1312 | $CH_3$ | Cl | H | i-$C_3H_7$ |
| 1313 | $C_2H_5$ | Cl | H | i-$C_3H_7$ |
| 1314 | n-$C_3H_7$ | Cl | H | i-$C_3H_7$ |
| 1315 | i-$C_3H_7$ | Cl | H | i-$C_3H_7$ |
| 1316 | n-$C_4C_9$ | Cl | H | i-$C_3H_7$ |
| 1317 | s-$C_4C_9$ | Cl | H | i-$C_3H_7$ |
| 1318 | i-$C_4C_9$ | Cl | H | i-$C_3H_7$ |
| 1319 | t-$C_4C_9$ | Cl | H | i-$C_3H_7$ |
| 1320 | $CH_2Cl$ | Cl | H | i-$C_3H_7$ |
| 1321 | $CHCl_2$ | Cl | H | i-$C_3H_7$ |
| 1322 | $CH_3$ | Cl | H | i-$C_3H_7$ |
| 1323 | $CH_2F$ | Cl | H | i-$C_3H_7$ |
| 1324 | $CHF_2$ | Cl | H | i-$C_3H_7$ |
| 1325 | $CF_3$ | Cl | H | i-$C_3H_7$ |
| 1326 | $CH_2CF_3$ | Cl | H | i-$C_3H_7$ |
| 1327 | $CH_2OCH_3$ | Cl | H | i-$C_3H_7$ |
| 1328 | $CH_2OCH_2CH_3$ | Cl | H | i-$C_3H_7$ |
| 1329 | $CH_2NH_2$ | Cl | H | i-$C_3H_7$ |
| 1330 | $(CH_2)_2COCH_3$ | Cl | H | i-$C_3H_7$ |
| 1331 | phenyl | Cl | H | i-$C_3H_7$ |
| 1332 | 2-F-phenyl | Cl | H | i-$C_3H_7$ |
| 1333 | 3-F-phenyl | Cl | H | i-$C_3H_7$ |
| 1334 | 4-F-phenyl | Cl | H | i-$C_3H_7$ |
| 1335 | 2-Cl-phenyl | Cl | H | i-$C_3H_7$ |
| 1336 | 3-Cl-phenyl | Cl | H | i-$C_3H_7$ |
| 1337 | 4-Cl-phenyl | Cl | H | i-$C_3H_7$ |
| 1338 | 2-OH-phenyl | Cl | H | i-$C_3H_7$ |
| 1339 | 3-OH-phenyl | Cl | H | i-$C_3H_7$ |
| 1340 | 4-OH-phenyl | Cl | H | i-$C_3H_7$ |
| 1341 | 2-$OCH_3$-phenyl | Cl | H | i-$C_3H_7$ |
| 1342 | 3-$OCH_3$-phenyl | Cl | H | i-$C_3H_7$ |
| 1343 | 4-$OCH_3$-phenyl | Cl | H | i-$C_3H_7$ |
| 1344 | 2-$OCF_3$-phenyl | Cl | H | i-$C_3H_7$ |
| 1345 | 3-$OCF_3$-phenyl | $OCH_3$ | H | i-$C_3H_7$ |
| 1346 | 4-$OCF_3$-phenyl | $OCH_3$ | H | i-$C_3H_7$ |
| 1347 | 2-$OCHF_2$-phenyl | $OCH_3$ | H | i-$C_3H_7$ |
| 1348 | 3-$OCHF_2$-phenyl | $OCH_3$ | H | i-$C_3H_7$ |
| 1349 | 4-$OCHF_2$-phenyl | $OCH_3$ | H | i-$C_3H_7$ |
| 1350 | 2-$CF_3$-phenyl | $OCH_3$ | H | i-$C_3H_7$ |
| 1351 | 3-$CF_3$-phenyl | $OCH_3$ | H | i-$C_3H_7$ |
| 1352 | 4-$CF_3$-phenyl | $OCH_3$ | H | i-$C_3H_7$ |
| 1353 | 2-$CH_3$-phenyl | $OCH_3$ | H | i-$C_3H_7$ |
| 1353 | 3-$CH_3$-phenyl | $OCH_3$ | H | i-$C_3H_7$ |
| 1354 | 4-$CH_3$-phenyl | $OCH_3$ | H | i-$C_3H_7$ |
| 1355 | H | $CH_3$ | H | H |
| 1356 | 3-$NO_2$-phenyl | $OCH_3$ | H | i-$C_3H_7$ |
| 1357 | H | $CH_3$ | $CH_3$ | $CH_3$ |
| 1358 | 2-pyridyl | $OCH_3$ | H | i-$C_3H_7$ |
| 1359 | H | $CH_3$ | $CH_3$ | $C_2H_5$ |
| 1360 | H | $CH_3$ | H | $C_2H_5$ |
| 1361 | H | $CH_3$ | $CH_3$ | i-$C_3H_7$ |
| 1362 | H | $CH_3$ | H | i-$C_3H_7$ |
| 1363 | H | $CH_3$ | H | $CH_3$ |

Examples of benzimidazol-5-ylcarbonyl derivatives of pyrazoles (compounds I-3=compounds I where X=C—$R^3$ and Y=N—$R^4$) which are particularly preferred according to the invention are the compounds listed in Tables 40 to 58.

TABLE 40

Compounds I-3a.1 to I-3a.1363

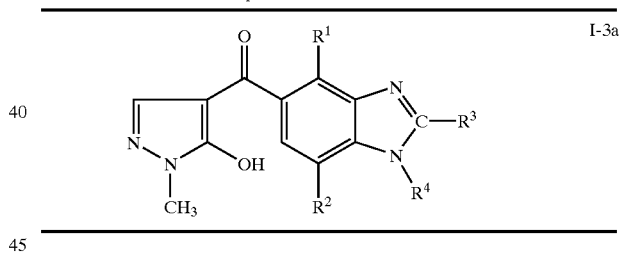

I-3a

Compounds of the formula I-3a, in which the substituents $R^1$, $R^2$, $R^3$ and $R^4$ for each individual compound correspond in each case to one row of Table B.

TABLE 41

Compounds I-3b.1 to I-3b.1363

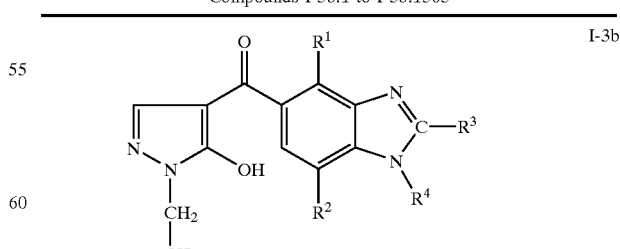

I-3b

Compounds of the formula I-3b, in which the substituents $R^1$, $R^2$, $R^3$ and $R^4$ for each individual compound correspond in each case to one row of Table B.

TABLE 42

Compounds I-3c.1 to I-3c.1363

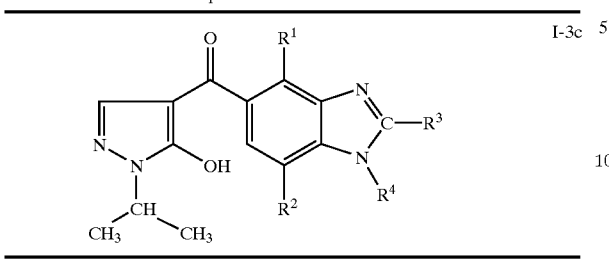

I-3c

Compounds of the formula I-3c, in which the substituents $R^1$, $R^2$, $R^3$ and $R^4$ for each individual compound correspond in each case to one row of Table B.

TABLE 43

Compounds I-3d.1 to I-3d.1363

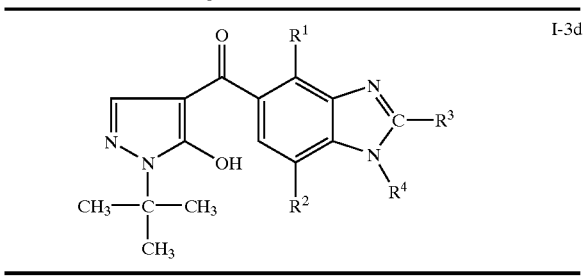

I-3d

Compounds of the formula I-3d, in which the substituents $R^1$, $R^2$, $R^3$ and $R^4$ for each individual compound correspond in each case to one row of Table B.

TABLE 44

Compounds I-3e.1 to I-3e.1363

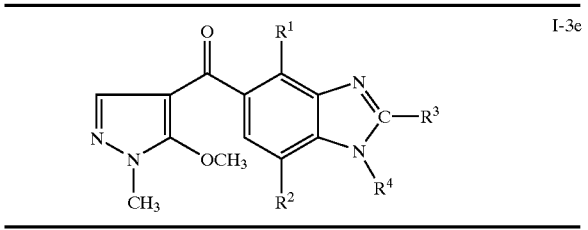

I-3e

Compounds of the formula I-3e, in which the substituents $R^1$, $R^2$, $R^3$ and $R^4$ for each individual compound correspond in each case to one row of Table B.

TABLE 45

Compounds I-3f.1 to I-3f.1363

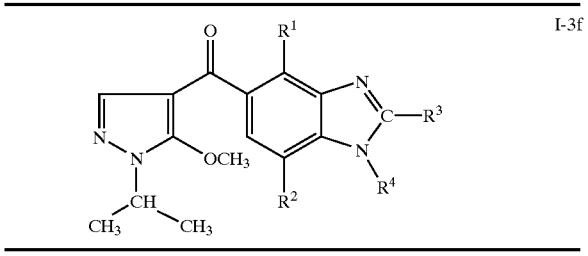

I-3f

Compounds of the formula I-3f, in which the substituents $R^1$, $R^2$, $R^3$ and $R^4$ for each individual compound correspond in each case to one row of Table B.

TABLE 46

Compounds I-3g.1 to I-3g.1363

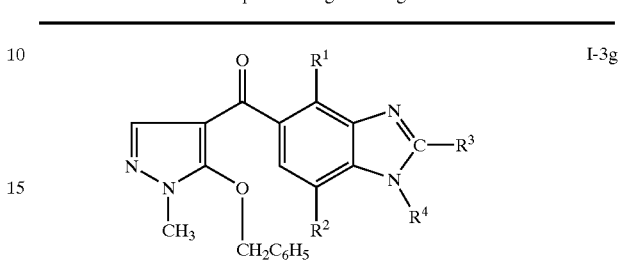

I-3g

Compounds of the formula I-3g, in which the substituents $R^1$, $R^2$, $R^3$ and $R^4$ for each individual compound correspond in each case to one row of Table B.

TABLE 47

Compounds I-3h.1 to I-3h.1363

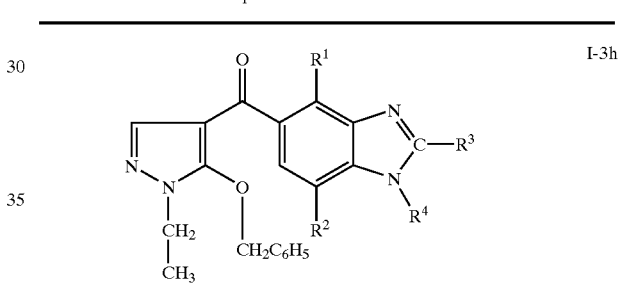

I-3h

Compounds of the formula I-3h, in which the substituents $R^1$, $R^2$, $R^3$ and $R^4$ for each individual compound correspond in each case to one row of Table B.

TABLE 48

Compounds I-3i.1 to I-3i.1363

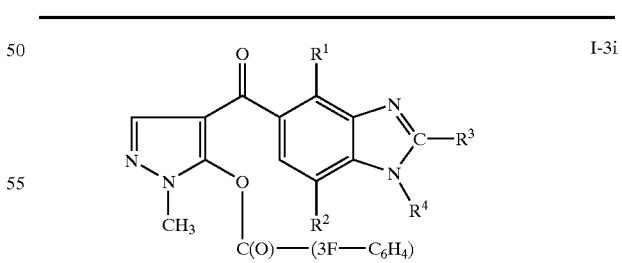

I-3i

Compounds of the formula I-3i, in which the substituents $R^1$, $R^2$, $R^3$ and $R^4$ for each individual compound correspond in each case to one row of Table B.

TABLE 49

Compounds I-3k.1 to I-3k.1363

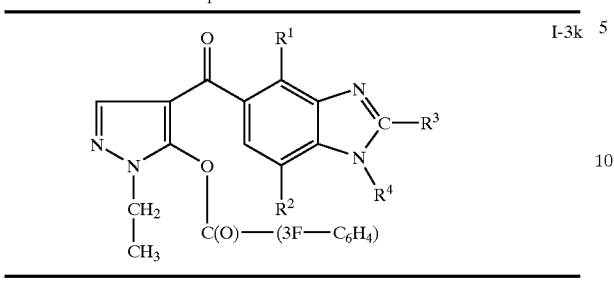

I-3k

Compounds of the formula I-3k, in which the substituents $R^1$, $R^2$, $R^3$ and $R^4$ for each individual compound correspond in each case to one row of Table B.

TABLE 50

Compounds I-3l.1 to I-3l.1363

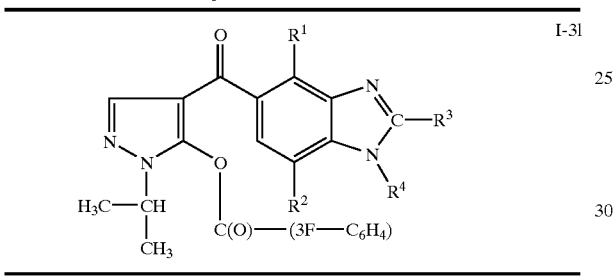

I-3l

Compounds of the formula I-3l, in which the substituents $R^1$, $R^2$, $R^3$ and $R^4$ for each individual compound correspond in each case to one row of Table B.

TABLE 51

Compounds I-3m.1 to I-3m.1363

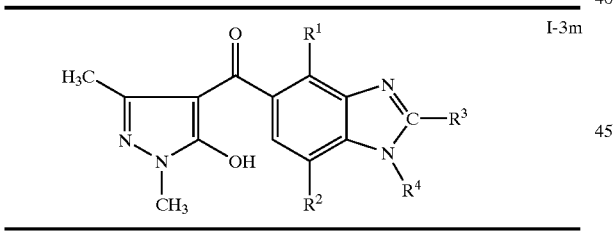

I-3m

Compounds of the formula I-3m, in which the substituents $R^1$, $R^2$, $R^3$ and $R^4$ for each individual compound correspond in each case to one row of Table B.

TABLE 52

Compounds I-3n.1 to I-3n.1363

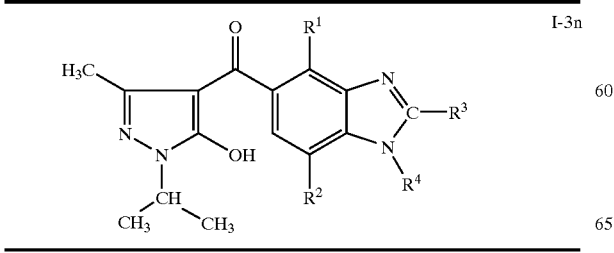

I-3n

Compounds of the formula I-3n, in which the substituents $R^1$, $R^2$, $R^3$ and $R^4$ for each individual compound correspond in each case to one row of Table B.

TABLE 53

Compounds I-3o.1 to I-3o.1363

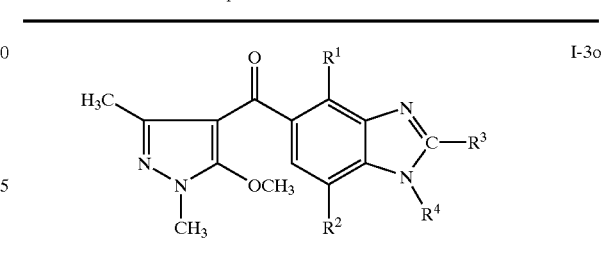

I-3o

Compounds of the formula I-3o, in which the substituents $R^1$, $R^2$, $R^3$ and $R^4$ for each individual compound correspond in each case to one row of Table B.

TABLE 54

Compounds I-3p.1 to I-3p.1363

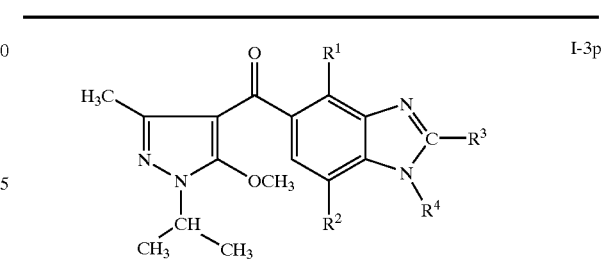

I-3p

Compounds of the formula I-3p, in which the substituents $R^1$, $R^2$, $R^3$ and $R^4$ for each individual compound correspond in each case to one row of Table B.

TABLE 55

Compounds I-3q.1 to I-3q.1363

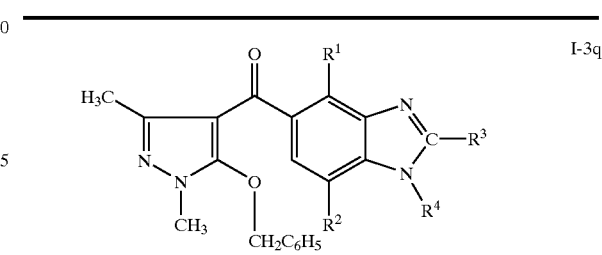

I-3q

Compounds of the formula I-3q, in which the substituents $R^1$, $R^2$, $R^3$ and $R^4$ for each individual compound correspond in each case to one row of Table B.

TABLE 56

Compounds I-3r.1 to I-3r.1363

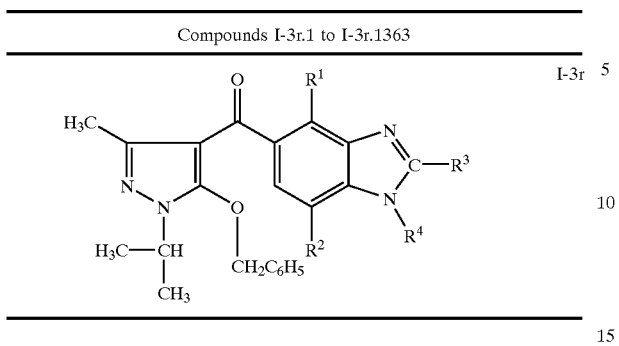

I-3r

Compounds of the formula I-3r, in which the substituents $R^1$, $R^2$, $R^3$ and $R^4$ for each individual compound correspond in each case to one row of Table B.

TABLE 57

Compounds I-3s.1 to I-3s.1363

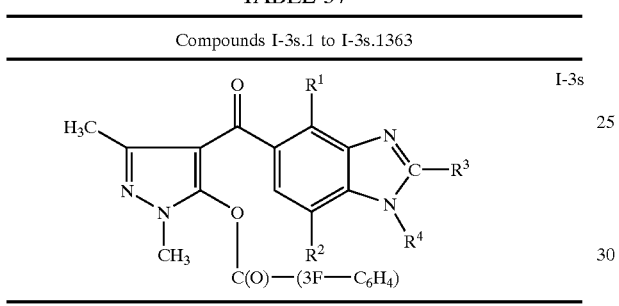

I-3s

Compounds of the formula I-3s, in which the substituents $R^1$, $R^2$, $R^3$ and $R^4$ for each individual compound correspond in each case to one row of Table B.

TABLE 58

Compounds I-3t.1 to I-3t.1363

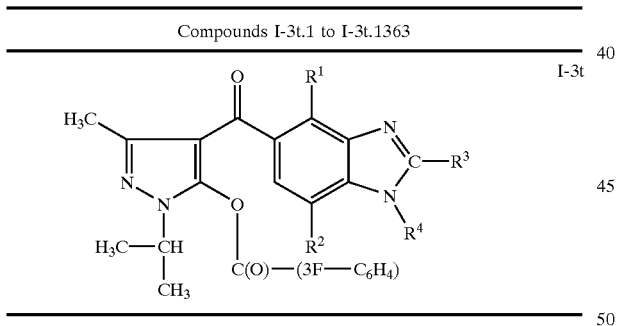

I-3t

Compounds of the formula I-3t, in which the substituents $R^1$, $R^2$, $R^3$ and $R^4$ for each individual compound correspond in each case to one row of Table B.

TABLE C

| | $R^1$ | $R^2$ | X | Y |
|---|---|---|---|---|
| 1 | H | H | N | S |
| 2 | $CH_3$ | H | N | S |
| 3 | Cl | H | N | S |
| 4 | $OCH_3$ | H | N | S |
| 5 | $SCH_3$ | H | N | S |
| 6 | $S(O)_2CH_3$ | H | N | S |
| 7 | H | Cl | N | S |
| 8 | $CH_3$ | Cl | N | S |
| 9 | Cl | Cl | N | S |
| 10 | $OCH_3$ | Cl | N | S |

TABLE C-continued

| | $R^1$ | $R^2$ | X | Y |
|---|---|---|---|---|
| 11 | $SCH_3$ | Cl | N | S |
| 12 | $S(O)_2CH_3$ | Cl | N | S |
| 13 | H | $CH_3$ | N | S |
| 14 | $CH_3$ | $CH_3$ | N | S |
| 15 | Cl | $CH_3$ | N | S |
| 16 | $OCH_3$ | $CH_3$ | N | S |
| 17 | $SCH_3$ | $CH_3$ | N | S |
| 18 | $S(O)_2CH_3$ | $CH_3$ | N | S |
| 19 | H | H | N | NH |
| 20 | $CH_3$ | H | N | NH |
| 21 | Cl | H | N | NH |
| 22 | $OCH_3$ | H | N | NH |
| 23 | $SCH_3$ | H | N | NH |
| 24 | $S(O)_2CH_3$ | H | N | NH |
| 25 | H | Cl | N | NH |
| 26 | $CH_3$ | Cl | N | NH |
| 27 | Cl | Cl | N | NH |
| 28 | $OCH_3$ | Cl | N | NH |
| 29 | $SCH_3$ | Cl | N | NH |
| 30 | $S(O)_2CH_3$ | Cl | N | NH |
| 31 | H | $CH_3$ | N | NH |
| 32 | $CH_3$ | $CH_3$ | N | NH |
| 33 | Cl | $CH_3$ | N | NH |
| 34 | $OCH_3$ | $CH_3$ | N | NH |
| 35 | $SCH_3$ | $CH_3$ | N | NH |
| 36 | $S(O)_2CH_3$ | $CH_3$ | N | NH |
| 37 | H | H | N | $NCH_3$ |
| 38 | $CH_3$ | H | N | $NCH_3$ |
| 39 | Cl | H | N | $NCH_3$ |
| 40 | $OCH_3$ | H | N | $NCH_3$ |
| 41 | $SCH_3$ | H | N | $NCH_3$ |
| 42 | $S(O)_2CH_3$ | H | N | $NCH_3$ |
| 43 | H | Cl | N | $NCH_3$ |
| 44 | $CH_3$ | Cl | N | $NCH_3$ |
| 45 | Cl | Cl | N | $NCH_3$ |
| 46 | $OCH_3$ | Cl | N | $NCH_3$ |
| 47 | $SCH_3$ | Cl | N | $NCH_3$ |
| 48 | $S(O)_2CH_3$ | Cl | N | $NCH_3$ |
| 49 | H | $CH_3$ | N | $NCH_3$ |
| 50 | $CH_3$ | $CH_3$ | N | $NCH_3$ |
| 51 | Cl | $CH_3$ | N | $NCH_3$ |
| 52 | $OCH_3$ | $CH_3$ | N | $NCH_3$ |
| 53 | $SCH_3$ | $CH_3$ | N | $NCH_3$ |
| 54 | $S(O)_2CH_3$ | $CH_3$ | N | $NCH_3$ |
| 55 | H | H | N | $NC_2H_5$ |
| 56 | $CH_3$ | H | N | $NC_2H_5$ |
| 57 | Cl | H | N | $NC_2H_5$ |
| 58 | $OCH_3$ | H | N | $NC_2H_5$ |
| 59 | $SCH_3$ | H | N | $NC_2H_5$ |
| 60 | $S(O)_2CH_3$ | H | N | $NC_2H_5$ |
| 61 | H | Cl | N | $NC_2H_5$ |
| 62 | $CH_3$ | Cl | N | $NC_2H_5$ |
| 63 | Cl | Cl | N | $NC_2H_5$ |
| 64 | $OCH_3$ | Cl | N | $NC_2H_5$ |
| 65 | $SCH_3$ | Cl | N | $NC_2H_5$ |
| 66 | $S(O)_2CH_3$ | Cl | N | $NC_2H_5$ |
| 67 | H | $CH_3$ | N | $NC_2H_5$ |
| 68 | $CH_3$ | $CH_3$ | N | $NC_2H_5$ |
| 69 | Cl | $CH_3$ | N | $NC_2H_5$ |
| 70 | $OCH_3$ | $CH_3$ | N | $NC_2H_5$ |
| 71 | $SCH_3$ | $CH_3$ | N | $NC_2H_5$ |
| 72 | $S(O)_2CH_3$ | $CH_3$ | N | $NC_2H_5$ |
| 73 | H | H | N | $N\text{-}i\text{-}C_3H_7$ |
| 74 | $CH_3$ | H | N | $N\text{-}i\text{-}C_3H_7$ |
| 75 | Cl | H | N | $N\text{-}i\text{-}C_3H_7$ |
| 76 | $OCH_3$ | H | N | $N\text{-}i\text{-}C_3H_7$ |
| 77 | $SCH_3$ | H | N | $N\text{-}i\text{-}C_3H_7$ |
| 78 | $S(O)_2CH_3$ | H | N | $N\text{-}i\text{-}C_3H_7$ |
| 79 | H | Cl | N | $N\text{-}i\text{-}C_3H_7$ |
| 80 | $CH_3$ | Cl | N | $N\text{-}i\text{-}C_3H_7$ |
| 81 | Cl | Cl | N | $N\text{-}i\text{-}C_3H_7$ |
| 82 | $OCH_3$ | Cl | N | $N\text{-}i\text{-}C_3H_7$ |
| 83 | $SCH_3$ | Cl | N | $N\text{-}i\text{-}C_3H_7$ |
| 84 | $S(O)_2CH_3$ | Cl | N | $N\text{-}i\text{-}C_3H_7$ |
| 85 | H | $CH_3$ | N | $N\text{-}i\text{-}C_3H_7$ |
| 86 | $CH_3$ | $CH_3$ | N | $N\text{-}i\text{-}C_3H_7$ |
| 87 | Cl | $CH_3$ | N | $N\text{-}i\text{-}C_3H_7$ |

TABLE C-continued

|  | R¹ | R² | X | Y |
|---|---|---|---|---|
| 88 | OCH₃ | CH₃ | N | N-i-C₃H₇ |
| 89 | SCH₃ | CH₃ | N | N-i-C₃H₇ |
| 90 | S(O)₂CH₃ | CH₃ | N | N-i-C₃H₇ |

Other examples of benzothiadiazol-5-ylcarbonyl derivatives of pyrazoles (X=N, Y=S) and benzotriazol-5-ylcarbonyl derivatives of pyrazoles (X=N, Y=N—R⁴) which are preferred according to the invention are the compounds listed in Tables 59 to 77 (compounds I-4).

TABLE 59

Compounds I-4a.1 to I-4a.90

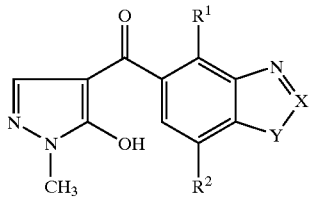

I-4a

Compounds of the formula I-4a, in which the substituents R¹, R², X and Y for each individual compound correspond in each case to one row of Table C.

TABLE 60

Compounds I-4b.1 to I-4b.90

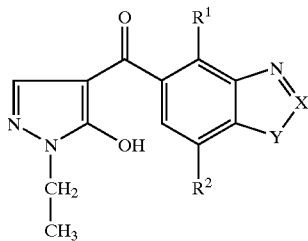

I-4b

Compounds of the formula I-4b, in which the substituents R¹, R², X and Y for each individual compound correspond in each case to one row of Table C.

TABLE 61

Compounds I-4c.1 to I-4c.90

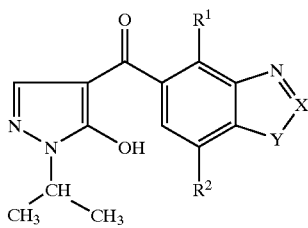

I-4c

Compounds of the formula I-4c, in which the substituents R¹, R², X and Y for each individual compound correspond in each case to one row of Table C.

TABLE 62

Compounds I-4d.1 to I-4d.90

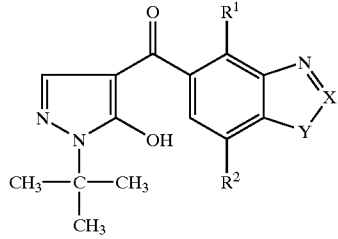

I-4d

Compounds of the formula I-4d, in which the substituents R¹, R², X and Y for each individual compound correspond in each case to one row of Table C.

TABLE 63

Compounds I-4e.1 to I-4e.90

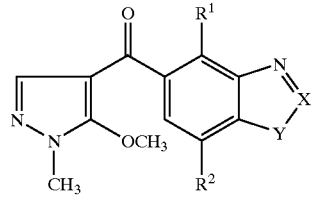

I-4e

Compounds of the formula I-4e, in which the substituents R¹, R², X and Y for each individual compound correspond in each case to one row of Table C.

TABLE 64

Compounds I-4f.1 to I-4f.90

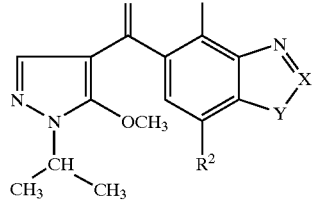

I-4f

Compounds of the formula I-4f, in which the substituents R¹, R², X and Y for each individual compound correspond in each case to one row of Table C.

TABLE 65

Compounds I-4g.1 to I-4g.90

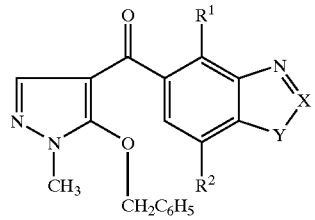

I-4g

Compounds of the formula I-4g, in which the substituents $R^1$, $R^2$, X and Y for each individual compound correspond in each case to one row of Table C.

TABLE 66

Compounds I-4h.1 to I-4h.90

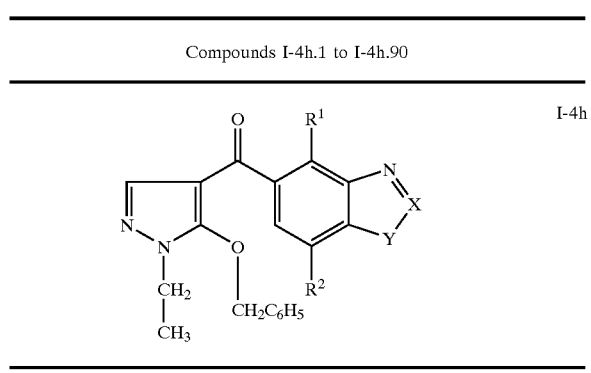
I-4h

Compounds of the formula I-4h, in which the substituents $R^1$, $R^2$, X and Y for each individual compound correspond in each case to one row of Table C.

TABLE 67

Compounds I-4i.1 to I-4i.90

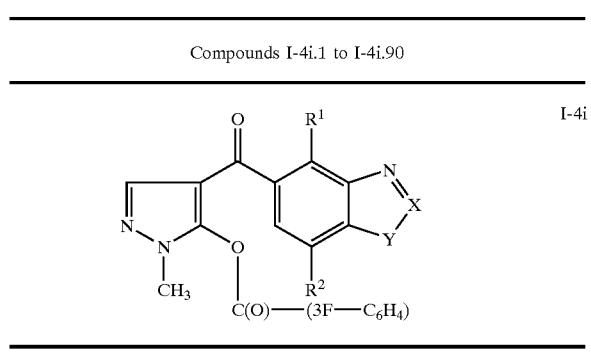
I-4i

Compounds of the formula I-4i, in which the substituents $R^1$, $R^2$, X and Y for each individual compound correspond in each case to one row of Table C.

TABLE 68

Compounds I-4k.1 to I-4k.90

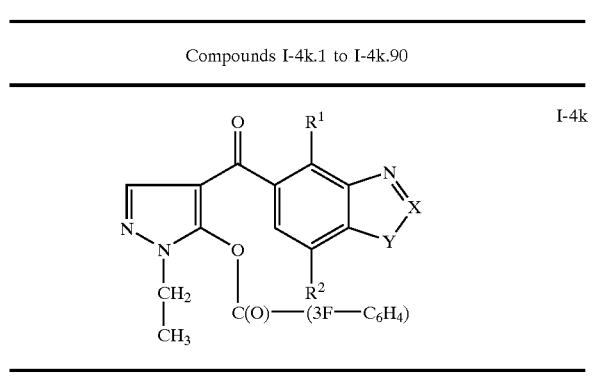
I-4k

Compounds of the formula I-4k, in which the substituents $R^1$, $R^2$, X and Y for each individual compound correspond in each case to one row of Table C.

TABLE 69

Compounds I-4l.1 to I-4l.90

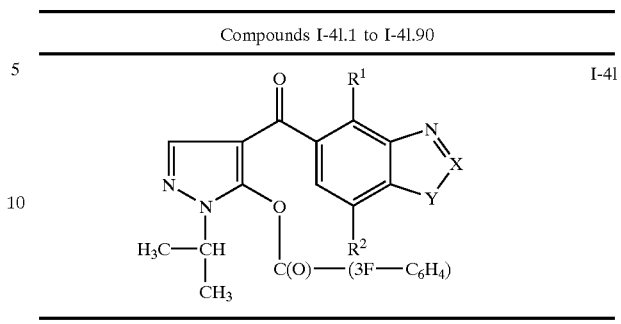
I-4l

Compounds of the formula I-4l, in which the substituents $R^1$, $R^2$, X and Y for each individual compound correspond in each case to one row of Table C.

TABLE 70

Compounds I-4m.1 to I-4m.90

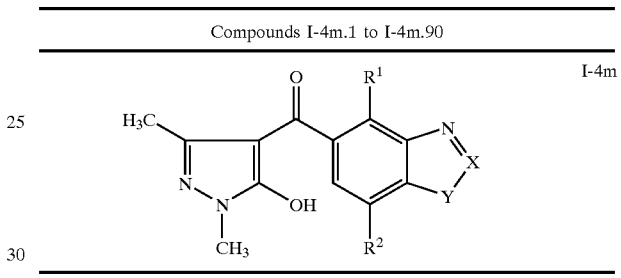
I-4m

Compounds of the formula I-4m, in which the substituents $R^1$, $R^2$, X and Y for each individual compound correspond in each case to one row of Table C.

TABLE 71

Compounds I-4n.1 to I-4n.90

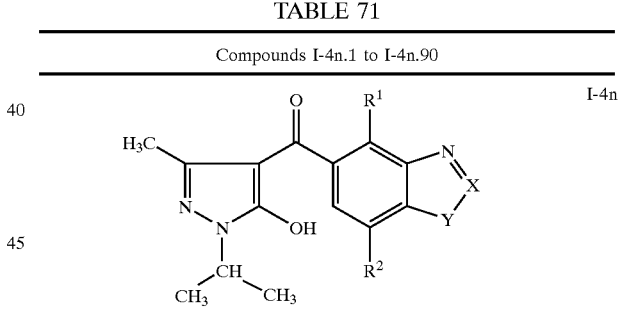
I-4n

Compounds of the formula I-4n, in which the substituents $R^1$, $R^2$, X and Y for each individual compound correspond in each case to one row of Table C.

TABLE 72

Compounds I-4o.1 to I-4o.90

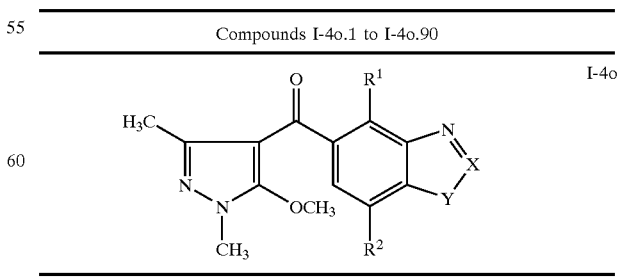
I-4o

Compounds of the formula I-4o, in which the substituents R$^1$, R$^2$, X and Y for each individual compound correspond in each case to one row of Table C.

TABLE 73

Compounds I-4p.1 to I-4p.90

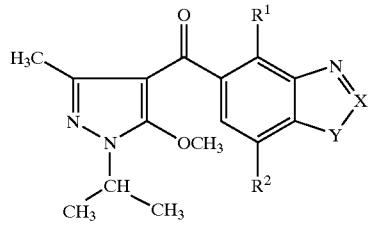
I-4p

Compounds of the formula I-4p, in which the substituents R$^1$, R$^2$, X and Y for each individual compound correspond in each case to one row of Table C.

TABLE 74

Compounds I-4q.1 to I-4q.90

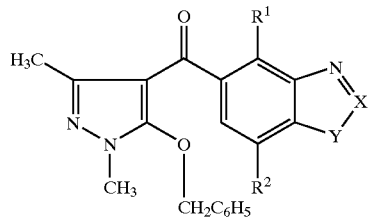
I-4q

Compounds of the formula I-4q, in which the substituents R$^1$, R$^2$, X and Y for each individual compound correspond in each case to one row of Table C.

TABLE 75

Compounds I-4r.1 to I-4r.90

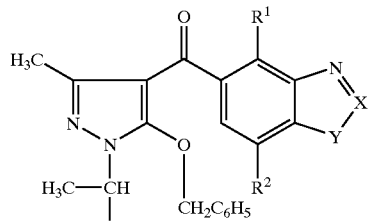
I-4r

Compounds of the formula I-4r, in which the substituents R$^1$, R$^2$, X and Y for each individual compound correspond in each case to one row of Table C.

TABLE 76

Compounds I-4s.1 to I-4s.90

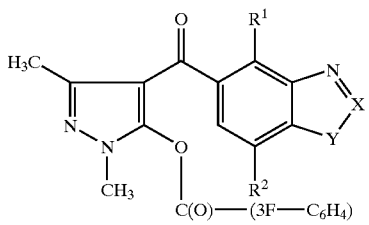
I-4s

Compounds of the formula I-4s, in which the substituents R$^1$, R$^2$, X and Y for each individual compound correspond in each case to one row of Table C.

TABLE 77

Compounds I-4t.1 to I-4t.90

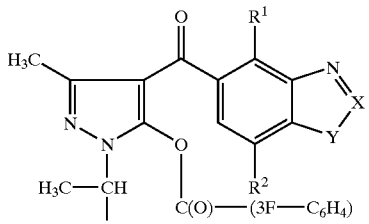
I-4t

Compounds of the formula I-4t, in which the substituents R$^1$, R$^2$, X and Y for each individual compound correspond in each case to one row of Table C.

Compounds of the formula I where R$^8$ is hydroxyl are prepared by reacting an activated carboxylic acid IVb or a carboxylic acid IVa, which is preferably activated in situ, with 5-hydroxypyrazole of the formula III to give the acylation product, followed by rearrangement.

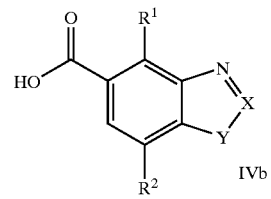
IVb

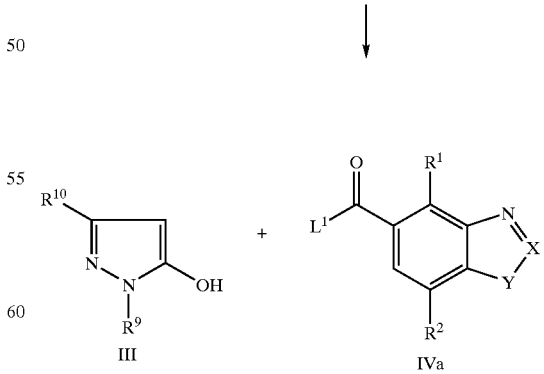
III          IVa

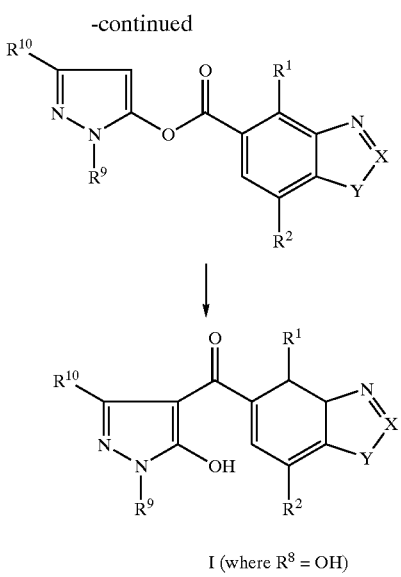

I (where $R^8$ = OH)

$L^1$ is a nucleophilically replaceable leaving group, such as halogen, for example bromine or chlorine, hetaryl, for example imidazolyl or pyridyl, carboxylate, for example acetate or trifluoroacetate, etc.

The activated carboxylic acid IVa can be employed directly, such as in the case of the benzoyl halides, or be generated in situ, for example using a carbodiimide, such as ethyl-(3'-dimethylaminopropyl)carbodiimide, dicyclohexylcarbodiimide, triphenylphosphine/azodicarboxylic ester, 2-pyridine disulfide/triphenylphosphine, carbonyldiimidazole, etc.

If appropriate, it may be advantageous to carry out the acylation reaction in the presence of a base. Here, the reactants and the auxiliary base are advantageously employed in equimolar amounts. In some cases, it may be advantageous to employ a slight excess of the auxiliary base, for example from 1.2 to 1.5 molar equivalents, based on IVa or IVb.

Suitable auxiliary bases are tertiary alkylamines, pyridine, 4-dimethylaminopyridine or alkali metal carbonates. Suitable solvents are, for example, chlorinated hydrocarbons, such as methylene chloride or 1,2-dichloroethane, aromatic hydrocarbons, such as toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or esters, such as ethyl acetate, or mixtures of these.

If the activated carboxylic acid component used is a halide, it may be advantageous to cool the reaction mixture to 0–10° C. when adding this reactant. The mixture is subsequently stirred at 20–100° C., preferably at 25–50° C., until the reaction has gone to completion. Work-up is carried out in a customary manner, for example by pouring the reaction mixture into water and extracting the product of value. Solvents which are suitable for this purpose are, in particular, methylene chloride, diethyl ether and ethyl acetate. After the organic phase has been dried and the solvent has been removed, the crude ester can be employed for the rearrangement without further purification.

The rearrangement of the esters to give the compounds of the formula I is advantageously carried out at 20–100° C. in a solvent and in the presence of a base and, if appropriate, using a cyano compound as catalyst.

Suitable solvents are, for example, acetonitrile, methylene chloride, 1,2-dichloroethane, dioxane, ethyl acetate, toluene or mixtures of these. Preferred solvents are acetonitrile and dioxane.

Suitable bases are tertiary amines, such as triethylamine, aromatic amines, such as pyridine, or alkali metal carbonates, such as sodium carbonate or potassium carbonate, which are preferably employed in an equimolar amount or an up to 4-fold excess, based on the ester. Preference is given to using triethylamine or alkali metal carbonate, preferably in twice the equimolar amount, based on the ester.

Suitable cyano compounds are inorganic cyanides, such as sodium cyanide or potassium cyanide, and organic cyano compounds, such as acetonecyanohydrin or trimethylsilyl cyanide. They are employed in an amount of 1–50 mol percent, based on the ester. Preference is given to using acetonecyanohydrin or trimethylsilyl cyanide, for example in an amount of 5–15, preferably about 10, mol percent, based on the ester.

Work-up can be carried out in a manner known per se. The reaction mixture is, for example, acidified with dilute mineral acid, such as 5% strength hydrochloric acid or sulfuric acid, and extracted with an organic solvent, for example methylene chloride or ethyl acetate. The organic extract can be extracted with 5–10% strength alkali metal carbonate solution, for example sodium carbonate or potassium carbonate solution. The aqueous phase is acidified and the precipitate that is formed is filtered off with suction and/or extracted with methylene chloride or ethyl acetate, dried and concentrated.

B. Preparation of compounds of the formula I where $R^8$=halogen is carried out by reacting pyrazole derivatives of the formula I (where $R^8$=hydroxyl) with halogenating agents:

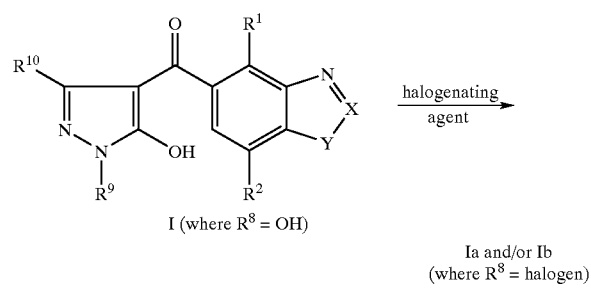

I (where $R^8$ = OH)

Ia and/or Ib
(where $R^8$ = halogen)

Here and below, "compound Ia" is a compound of the formula I where Pz is a pyrazolyl radical of the formula IIa and, correspondingly, compound Ib is a compound of the formula I where Pz is a radical IIb.

Suitable halogenating agents are, for example phosgene, diphosgene, triphosgene, thionyl chloride, oxalyl chloride, phosphorus oxychloride, phosphorus pentachloride, mesyl chloride, chloromethylene-N,N-dimethylammonium chloride, oxalyl bromide, phosphorus oxybromide, etc.

C. Preparation of compounds of the formula I where $R^8$=$OR^{11}$, $OSO_2R^{12}$, $OPOR^{13}R^{14}$ or $OPSR^{13}R^{14}$ by reacting pyrazole derivatives of the formula I (where $R^8$=hydroxyl) with alkylating, sulfonylating or phosphonylating agents Vα, Vβ, Vγ and Vδ, respectively.

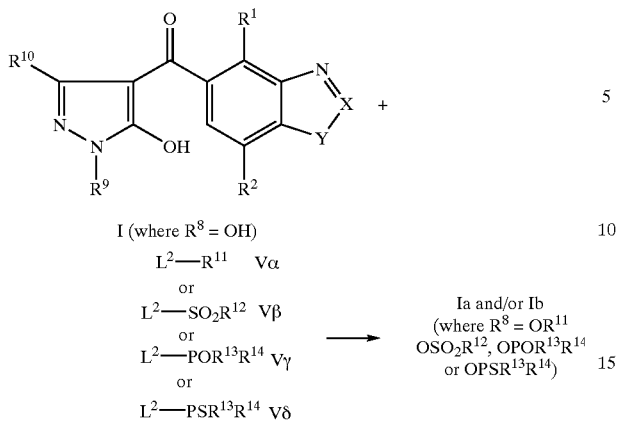

I (where $R^8$ = OH)

$L^2$—$R^{11}$ Vα
or
$L^2$—$SO_2R^{12}$ Vβ
or
$L^2$—$POR^{13}R^{14}$ Vγ
or
$L^2$—$PSR^{13}R^{14}$ Vδ

Ia and/or Ib
(where $R^8$ = $OR^{11}$
$OSO_2R^{12}$, $OPOR^{13}R^{14}$
or $OPSR^{13}R^{14}$)

$L^2$ is a nucleophilically replaceable leaving group, such as halogen, for example chlorine or bromine, hetaryl, for example imidazolyl, carboxylate, for example acetate, or sulfonate, for example mesylate or triflate, etc.

When preparing compounds of the formula I where $R^8$=$OR^{11}$ from compounds of the formula I where $R^8$=OH, the reaction is preferably carried out in the presence of a base.

Reactants and base are expediently employed in equimolar amounts. In certain cases, a slight excess of base, for example 1.1–1.5 molar equivalents, based on I, may be advantageous.

Suitable bases are tertiary amines, pyridines, alkali metal carbonates or alkali metal hydrides. Suitable solvents are, for example, chlorinated hydrocarbons such as methylene chloride or 1,2-dichloroethane, aromatic hydrocarbons such as toluene, xylene or chlorobenzene, ethers such as diethyl ether, methyl tert-butyl ether, tetrahydrofuran, dioxane or dimethoxyethane, polar aprotic solvents such as acetonitrile, dimethylformamide or dimethyl sulfoxide or esters such as ethyl acetate and mixtures thereof.

If, instead of the alcohol I ($R^8$=OH), halides ($R^8$=halogen) or activated alcohols such as mesylate or tosylate ($R^8$=$OSO_2CH_3$ or $OSO_2$-tolyl) are employed for the derivatization, it may be expedient to cool the reaction mixture to from 0 to 10° C. when adding the reaction partner. Subsequently, the mixture is stirred at 20–100° C., preferably at 20–75° C., until the reaction has gone to completion.

Work-up is carried out in a customary manner, for example by pouring the reaction mixture into water and extracting the product of value. Solvents suitable for this purpose are, in particular, solvents such as methylene chloride, ethyl acetate, methyl tert-butyl ether or diethyl ether. After drying of the organic phase and removal of the solvent, the crude product can, if desired, be purified by silica gel column chromatography. Suitable mobile phases are solvents such as methylene chloride, ethyl acetate, cyclohexane, petroleum ether, methanol, acetone or chloroform and mixtures thereof.

Compounds of the formula Vα, Vβ, Vγ or Vδ can be employed directly, such as in the case of the carbonyl halides, or be generated in situ, for example activated carboxylic acids (using carboxylic acid and dicyclohexylcarbodiimide, etc.).

D. Compounds of the formula I where $R^8$=$OR^{11}$, $SR^{11}$, $POR^{13}R^{14}$, $NR^{15}R^{16}$, $ONR^{15}R^{16}$ or N-bonded heterocyclyl are prepared by reacting compounds of the formula I where $R^8$=halogen, $OSO_2R^{12}$ with compounds of the formula VIα, VIβ, VIγ, VIδ, VIε or VIη, if appropriate in the presence of a base or with prior formation of salt.

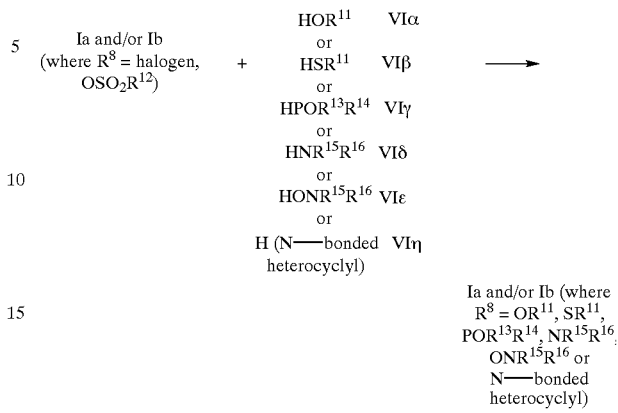

E. Compounds of the formula I where $R^8$=$SOR^{12}$, $SO_2R^{12}$ are prepared, for example, by reacting compounds of the formula I where $R^8$=$SR^{12}$ with an oxidizing agent.

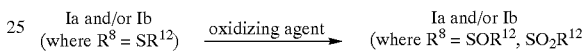

Suitable oxidizing agents are, for example, m-chloroperbenzoic acid, peroxyacetic acid, trifluoroperoxyacetic acid, hydrogen peroxide, if appropriate in the presence of a catalyst, such as tungstate.

For the reactions mentioned under points B to E, the following conditions apply:

The starting materials are generally employed in equimolar amounts. However, it may also be advantageous to employ an excess of one or the other component.

If appropriate, it may be advantageous to carry out the reactions in the presence of a base. Reactants and base are advantageously employed in equimolar amounts.

With respect to the processes C and D, it may, in certain cases, be advantageous to employ an excess of base, for example 1.5 to 3 molar equivalents, in each case based on the starting material.

Suitable bases are tertiary alkylamines, such as triethylamine, aromatic amines, such as pyridine, alkali metal carbonates, for example sodium carbonate or potassium carbonate, alkali metal bicarbonates, such as sodium bicarbonate and potassium bicarbonate, alkali metal alkoxides, such as sodium methoxide, sodium ethoxide, potassium tert-butoxide, or alkali metal hydrides, for example sodium hydride. Preference is given to using triethylamine or pyridine.

Suitable solvents are, for example, chlorinated hydrocarbons, such as methylene chloride or 1,2-dichloroethane, aromatic hydrocarbons, for example toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or esters, such as ethyl acetate, or mixtures of these.

In general, the reaction temperature is in the range from 0° C. to the boiling point of the reaction mixture.

Work-up can be carried out in a manner known per se to give the product.

Depending on the reaction conditions, in the processes B to D the compounds Ia, Ib, or mixtures of these can be formed. The latter can be separated by classic separation methods, for example crystallization, chromatography, etc.

F. The preparation of compounds of the formula I where Pz is a group of the formula IIa can also be carried out by reacting a metallated pyrazole derivative of the formula VII with a carboxylic acid derivative of the formula IVa:

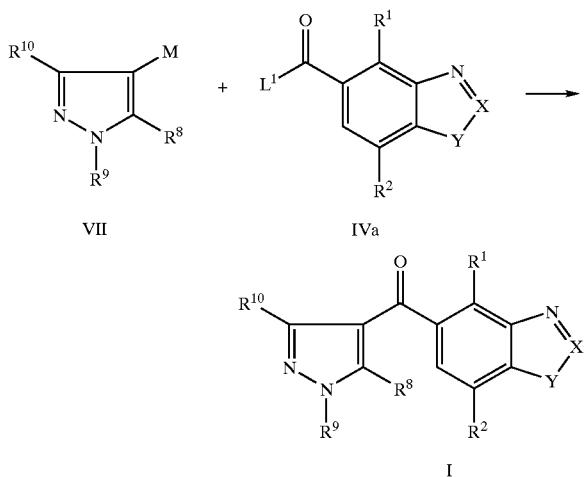

Here, M is a metal, in particular an alkali metal, such as lithium or sodium, an alkaline earth metal, such as magnesium, or a transition metal, such as palladium, nickel, etc., and $L^1$ is a nucleophilically replaceable leaving group, such as halogen, for example chlorine or bromine, alkylsulfonate, such as mesylate, haloalkylsulfonate, such as triflate or cyanide. Preferably, $R^8$ does not have any acidic hydrogen atoms.

The reaction is generally carried out at temperatures from −100° C. to the reflux temperature of the reaction mixture. Suitable solvents are. inert aprotic solvents, such as ethers, for example diethyl ether, tetrahydrofuran. The compounds of the formula IVa are generally employed in excess; however, it may also be advantageous to employ them in equimolar amounts or in excess. Work-up is carried out to afford the product.

The metallated pyrazole derivatives of the formula VII can be formed in a manner known per se by reacting pyrazoles which are halogenated in the 4 position with metals such as lithium, sodium, magnesium, etc., or with organometallic compounds, for example butyllithium. However, it is also possible to metallate pyrazoles which are linked in the 4 position to hydrogen directly, for example using the abovementioned metals or organometallic compounds. The reactions are generally carried out in an inert aprotic solvent, preferably in ethers, such as diethyl ether, tetrahydrofuran, etc. The reaction temperature is in the range from −100° C. to the boiling point of the reaction mixture. The compounds of the formula VII are preferably generated in situ and reacted directly.

The 5-hydroxypyrazoles of the formula III used as starting materials are known or can be prepared by processes known per se as described, for example, in EP-A 240 001, in J. Chem. Soc. 315, (1997), p. 383, J. Prakt. Chem. 315, (1973), p. 382 (see also the reviews in Advances Heterocycle. Chem. 48, (1990), pp. 223–299 and Katritzky, Rees (Eds.), Comprehensive Heterocyclic Chem. Vol. 5, Pergamon Press 1984, Oxford, pp. 167–343 and literature cited therein). Furthermore, 1,3-dimethyl-5-hydroxypyrazole is a compound which is commercially available.

The alkylating agents Vα, sulfonylating agents Vβ, phosphonylating agents Vγ and Vδ, and the compounds VIα, VIβ, VIγ, VIδ and VIε are likewise known, or they can be prepared by known processes.

The carboxylic acids of the formula IVa and their activated derivatives IVb are either known from the literature, or they can be prepared analogously to known processes.

Scheme 1 shows a customary route to benzothiazol-5-carboxylic acids (compounds IV-1).

Scheme 1

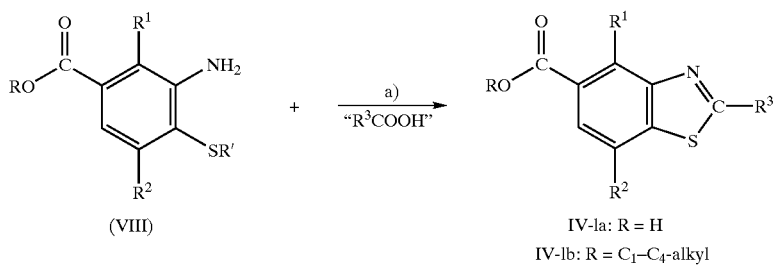

IV-la: R = H
IV-lb: R = $C_1$–$C_4$-alkyl

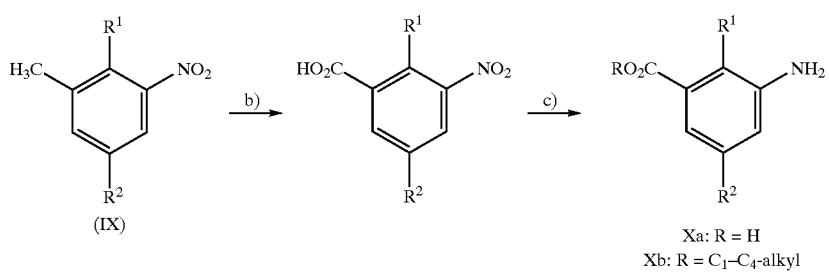

Xa: R = H
Xb: R = $C_1$–$C_4$-alkyl

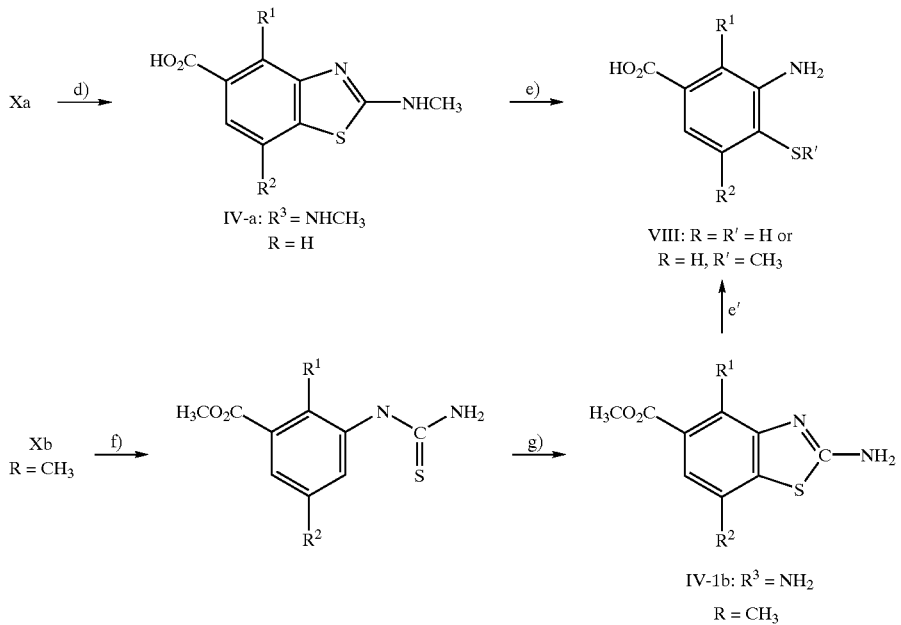

In the formula IV-1, R is hydrogen (compound IV-1a) or a hydrocarbon radical which can be hydrolyzed, for example methyl (compound IV-1b). Compounds of the formula IV-1 can be prepared, for example, according to reaction step a) by condensation of ortho-aminothiophenols of the formula VIII (R'=H) or of ortho-aminothioethers of the formula VIII (R'=$C_1$–$C_4$-alkyl, for example methyl), using a carboxylic acid equivalent "$R^3$—$CO_2H$" i.e. a carboxylic acid $R^3CO_2H$ or activated derivatives $R^3COL^1$, $R^3C(L^3)_3$ thereof where $L^1$ is a reactive leaving group and $L^3$ is a $C_1$–$C_4$-alkoxy group. Examples of $L^1$ are chlorine, bromine, carboxylate, such as acetate, trifluoroacetate, N-heterocyclyl, such as imidazolyl, pyridyl etc. Examples of $R^3COL^1$ and $R^3C(L^3)_3$ are acyl halides, carboxylic esters and carboxylic anhydrides, and the ortho esters of the carboxylic acids $R^3CO_2H$.

The condensation reaction a) is preferably carried out under neutral to acidic reaction conditions, preferably in the presence of an inorganic or organic acid, for example hydrochloric acid, sulfuric acid, p-toluenesulfonic acid and pyridinium p-toluenesulfonate, in an organic solvent at 0–150° C., preferably in the range from 20 to 120° C. Suitable solvents are, in particular, saturated hydrocarbons, halogenated hydrocarbons, aromatic hydrocarbons, such as benzene, aliphatic ethers, such as diethyl ether and tert-butyl methyl ether, or pyridine. For the preparation of benzothiazoles from o-aminothiophenols or corresponding thiomethyl ethers, see also Houben-Weyl, Methoden der Organischen Chemie, Vol. E 8b, pp.869–871.

Step a) can also be carried out in two steps, by initially converting the amino function in VIII with a carboxylic acid $R^9$—COOH or a derivative thereof into the carboxamide, which is subsequently cyclized to give the benzothiazole of the formula IV-1.

The conversion into the amide is carried out under the conditions which are customary for amide formation, for example by reacting an acid in the presence of a water-binding agent. Cyclization succeeds with Lewis acids or phosgene. In this case, the cyclization is preferably carried out in an inert organic solvent, for example an aliphatic or aromatic hydrocarbon, or in a halogenated hydrocarbon.

According to Scheme 1, ortho-aminothiophenols of the formula VIII (R'=H) can be prepared starting with 3-nitrotoluenes of the formula IX. Their methyl group can be oxidized in a known manner, catalytically or stoichiometrically, to give the carboxylic acid (step b). Suitable oxidizing agents are, for example, metal oxides of transition metals, for example manganese dioxide, chromium trioxide and their anionic complex salts, for example sodium dichromate or chromyl chloride, pyridinium chromate, furthermore oxidizing acids, for example $HNO_3$, oxidizing gases, such as oxygen or chlorine, if appropriate in the presence of transition metals (or salts thereof, for example oxides or chlorides) as catalysts. Depending on the solubility of the compound to be oxidized and depending on the oxidizing agent used, the reaction is preferably carried out in aqueous solutions, monophasic systems of water and water-miscible organic solvents or in multiphasic systems of water and organic solvents with phase-transfer catalysis. Depending on the chosen oxidizing agent, the oxidation is generally carried out in the range from –15 to +150° C., preferably in the range from 0 to 100° C. For the oxidation of aromatic methyl groups to benzoic acids, see, for example, Houben-Weyl: "Methoden der organischen Chemie", Vol. V, IV/1a, 1981; Vol. VIII 1952; E. Bengtsson, Acta Chem. Scand. 7 (1953), 774; Singer et al., Org. Synth. Coll. Vol III, 1955, 740; B. A. S. Hay et al., Can. J. Chem. 43 (1965), 1306).

The resulting 3-nitrobenzoic acid derivatives are subsequently, in step c), reduced to the 3-aminobenzoic acids. The selective reduction of aromatic nitro groups in the presence of carboxylic acid groups is known in principle. Suitable reducing agents are, for example, hydrazines, metal hydrides, such as aluminum hydride, and complex compounds derived therefrom, such as lithium aluminium hydride, diisobutylaluminum hydride or boranes. The preferred reducing agent is hydrogen in the presence of catalytic amounts of transition metals, for example Ni, Pd, Pt, Ru or Rh, which may be employed in supported form, for example on active carbon, in the form of activated metals, for example Raney nickel, or in the form of soluble complex compounds. Suitable solvents for the reduction are, depending on the solubility of the substrate to be hydrogenated and the chosen reducing agent, $C_1$–$C_4$-alkohols, such as methanol, ethanol, n-propanol, isopropanol or n-butanol, halogenated $C_1$–$C_6$-hydrocarbons, such as dichloromethane, trichloromethane, trichloroethane, trichloroethylene, aromatic hydrocarbons, such as benzene, toluene, xylenes, chlorobenzene, aqueous solutions of inorganic or organic acids, such as aqueous hydrochloric acid. The reduction is usually carried out in the range from −15 to +100° C., preferably in the range from 0 to 40° C. The reduction with hydrogen is usually carried out at a hydrogen pressure in the range from 1 to 50 bar, preferably in the range from 1 to 10 bar. For the catalytic hydrogenation of aromatic nitro groups, see, for example, Rylander in "Catalytic Hydrogenation over Platinum Metals", Academic press, New York, 1967, 168–202; Furst et al., Chem. Rev. 65 (1965), 52; Tepko et al., J. Org. Chem. 45 (1980), 4992.

The resulting m-aminobenzoic acids of the formula Xa (R=H) are then, in a further reaction step d), reacted with an organic isothiocyanate (in scheme 1 methyl isothiocyanate) to give a substituted thiourea derivative which, without further isolation, is cyclized oxidatively to give the benzothiazole-5-carboxylic acid of the formula IX-1a (in scheme 1 with $R^3$=NH—$CH_3$).

The first reaction step in step d), i.e. the conversion of the m-aminobenzoic acid of the formula Xa into the substituted urea is carried out by reaction with a $C_1$–$C_6$-alkyl isothiocyanate or an unsubstituted or substituted phenyl isothiocyanate in an anhydrous organic solvent at from −15° C. to 150° C., preferably in the range from −15° C. to 100° C. Suitable solvents are, for example, aliphatic or cycloaliphatic hydrocarbons, such as n-hexane or cyclohexane, halogenated hydrocarbons, such as dichloromethane, trichloromethane, trichloroethane, trichloroethylene, aromatic hydrocarbons, such as benzene or anisole, dialkyl ethers or cyclic ethers, such as diethyl ether, methyl tert-butyl ether, tetrahydrofuran or dioxane, anhydrous carboxylic acids, such as glacial acetic acid, or pyridine. For the preparation of substituted thioureas see, for example: F. Kurzer, Org. Synth. 31 (1951), 21; R. R. Gupta et al., Synth. Commun. 17(2) (1987), 229–240; Rathke, Ber. Dtsch. Chem. Ges. 18 (1885), 3102; Schiff, Justus Liebigs Ann. Chem. 148 (1868), 338; R. L. Frank, P. V. Smith, Org. Synth. III (1955), 735, N. B. Ambati et al., Synth. Commun. 27 (9). (1997), 1487–1493; W. O. Foye, J. Pharm. Sci. 66 (7) (1977), 923–926.

The resulting substituted thiourea derivative is then, in a second reaction step d), cyclized using a halogen-containing oxidizing agent, such as bromine, sulfuryl chloride or chlorine in an inert organic solvent, to give the substituted 2-aminobenzothiazole-5-carboxylic acid of the general formula IV-1a (in scheme 1, $R^3$ is NH—$CH_3$). The cyclization is generally carried out in the range from −15 to +150° C., preferably in the range from 0 to 120° C. Suitable solvents are, in particular, the abovementioned aliphatic or cycloaliphatic hydrocarbons, the abovementioned aromatic hydrocarbons, the abovementioned anhydrous carboxylic acids, and furthermore $C_1$–$C_4$-alkanols, for example methanol, ethanol or isopropanol, dialkyl ethers, cyclic ethers and mixtures of the abovementioned solvents. For the oxidative cyclization of substituted thioureas to benzothiazoles see, for example, Houben-Weyl: "Methoden der organischen Chemie" V, Vol. E8B, 1994, p.865 f.

The substituted 2-aminobenzothiazole-5-carboxylic acid of the formula IV-1a can either be reacted directly in the abovementioned manner with a hydroxypyrazole of the formula III or an activated derivative thereof to give the compound I according to the invention (where Y=S and X=C—NH—R'", where R" is $C_1$–$C_6$-alkyl or unsubstituted or substituted phenyl).

If $R^3$ in the formula IV-1a is NH—$CH_3$, it is also possible to prepare the o-aminothiobenzoic acids of the formula VIII (where R=R'=H) by hydrolysis according to step e). The hydrolysis is generally followed by the methylation to give the methyl thioether VIII (R=H, R'=$CH_3$). The hydrolysis in step e) is carried out, for example, by reacting the compound IV-1a (where $R^3$=NH—$CH_3$) with an alkali metal hydroxide, for example lithium hydroxide, sodium hydroxide or potassium hydroxide, an alkaline earth metal hydroxide or an alkali metal iodide, such as sodium iodide, in a suitable solvent at elevated temperature, the reaction preferably being carried out in the absence of oxygen. Customary reaction temperatures are in the range from 0 to 200° C,. in particular in the range from 20 to 180° C. Suitable solvents are, in addition to the abovementioned aliphatic or cycloaliphatic hydrocarbons, the halogenated hydrocarbons, the aromatic hydrocarbons, the abovementioned ethers and alcohols, in particular aqueous monophasic systems and pyridine.

For the hydrolysis of the substituted 2-aminobenzothiazole-5-carboxylic acids see, for example: Organikum, 16th edition 1986, p. 415; Mc Murry, Org. React. 24 (1976), 187; Taschner et al., Rocz. Chem. 30 (1956), 323; Houben-Weyl: "Methoden der organischen Chemie", Volume E8b, 1994; p. 1010 f.; J. Chem. Soc. Perkin Trans., Part 1, No. 12, (1976), 1291–1296, in particular A. R. Katritzky et al., J. Heterocycl. Chem. 30 (1) (1993), 135–139. The conversion into the methyl thioether VIII where R=H and R'=$CH_3$ succeeds in a simple manner by reacting with methyl iodide or dimethyl sulfate.

In a similar manner, it is possible to obtain compounds of the formula VIII where R=H by initially esterifying the 3-aminobenzoic acid of the formula Xa with a $C_1$–$C_4$-alkanol, for example with methanol, in a known manner. The resulting ester of the formula Xb (R=$C_1$–$C_4$-alkyl, in particular methyl) is then, in step f), reacted with isothiocyanic acid or a suitable salt of isothiocyanic acid, for example sodium isothiocyanate, in the presence of a concentrated mineral acid, to give the thiourea derivative. The reaction conditions correspond to the reaction conditions mentioned under step d) for the urea derivatives. The thiourea derivative is subsequently, in step g), cyclized under the abovementioned conditions to give the 2-aminobenzothiazole-5-carboxylic ester of the formula IV-1b ($R^3$=$NH_2$). The resulting compound of the formula IV-1b where $R^3$=$NH_2$ can be hydrolyzed in step e' to give the compound VIII, which is subsequently, if appropriate, methylated (VIII: R=H, R'=$CH_3$).

It is also possible to convert the compound IV-1b in the manner described above into the compound,I according to the invention (where X=C—$NH_2$ and Y=S). Moreover, it is possible to initially diazotize the 2-amino group of the compound IV-1b and to introduce further functionalities into the 2-position of the benzothiazole skeleton in this way. The conversion of $R^3$=$NH_2$ into $R^3$=halogen is carried out in a known manner under Sandmeyer conditions. The conversion of $R^3$=$NH_2$ into $R^3$=H is carried out in a known manner by successive reaction of the 2-aminobenzothiazole-5-carboxylic ester with nitrite under acid conditions and then with a reducing agent, such as hypophosphoric acid, sodium borohydride, trialkylsilanes, trialkylstannanes, $SnCl_2$, NO, Wilkinson catalysts; see also J. Am. Chem. Soc. 71 (1949), p. 2137; J. Am. Chem. Soc. 72 (1950), p. 3013; 76 (1954) Vol. 76, p. 290.

A further route to the compounds of the formula VIII is shown in scheme 2.

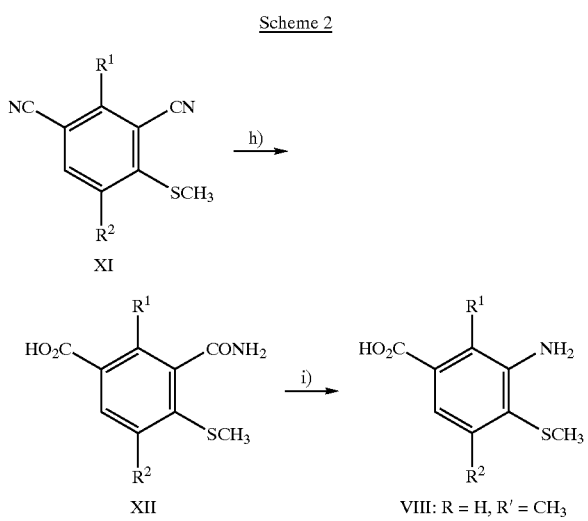

Starting from 2,4-dicyanothioanisoles of the formula XI, in step h) the amide of the formula XII is prepared by selected hydrolysis. Owing to the different reactivity of the two methyl groups, the preparation succeeds under customary alkaline hydrolysis conditions, but the progress of the reaction is preferably monitored. Methods for the alkaline hydrolysis of nitriles are known, for example, from Org. Synth. Coll. Vol. 1, 1941, p. 321. In a further step i), the amide function in the compounds of the formula XII is then converted into an amino function by Hofmann degradation. This gives compounds of the formula VIII where R=H and R'=$CH_3$. Typical conditions for the Hofmann degradation are: aqueous alkaline chlorine or hypochloride solutions, temperatures in the range from 0 to 150° C., preferably in the range from 20 to 120° C. (see also Organikum, 16th edition 1986, p. 572).

A further route to benzothiazole-5-carboxylic acids is shown in scheme 3. This route utilizes the conversion of benzothiazoles of the formula XIV into the corresponding carboxylic acids, as shown in reaction step o).

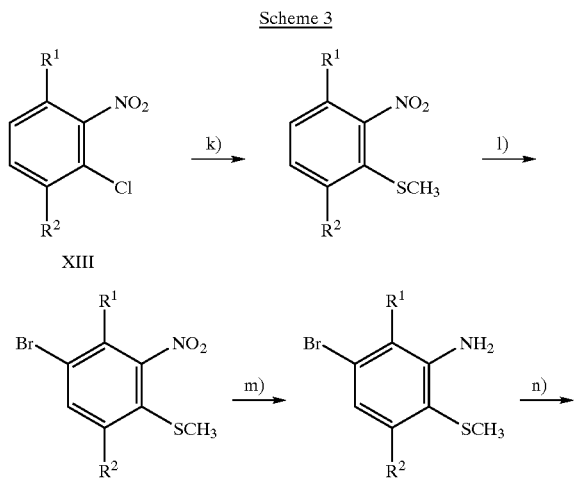

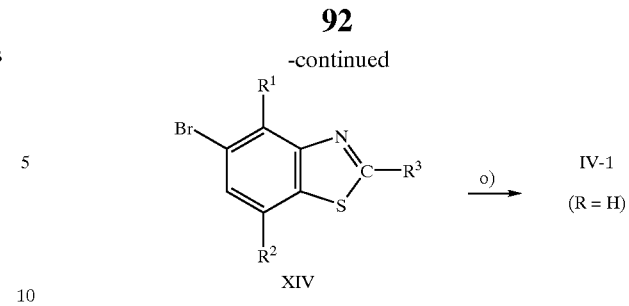

The conversion of the bromobenzothiazole of the formula XIV into Fit the carboxylic acid of the formula IV-1 (R=H) is carried out, for example, by successive reaction of XIV with magnesium to give the corresponding Grignard compound and subsequent reaction of the Grignard compound with carbon dioxide. Alternatively, the compound XIV can be converted into the compound IV-1 by halogen-metal exchange using an alkali metal alkyl, for example a lithium alkyl, such as methyllithium, n-butyllithium or tert-butyllithium, and subsequent reaction of the reaction product with $CO_2$.

Reaction step o) in scheme 3 can also be realized by reacting the 5-bromobenzothiazole of the formula XIV with carbon monoxide, a base and water, under elevated pressure in the presence of a Pd, Ni, Co or Rh catalyst.

The catalysts nickel, cobalt, rhodium and in particular palladium can be present in metallic form or in the form of customary salts, such as in the form of halogen compounds, for example $PdCl_2$, $RhCl_3 \cdot H_2O$, acetates, for example $Pd(OAc)_2$, cyanides, etc., in the known valence states. Metal complexes with tertiary phosphines, metal alkylcarbonyls, metal carbonyls, e.g. $CO_2(CO)_8$, $Ni(CO)_4$, metal carbonyl complexes with tertiary phosphines, e.g. $(PPh_3)_2Ni(CO)_2$, or transition metal salts complexed with tertiary phosphines can also be present. The last-mentioned embodiment is preferred, in particular when the catalyst used is palladium. Here, the type of phosphine ligands is widely variable. They can be represented, for example, by the following formulae:

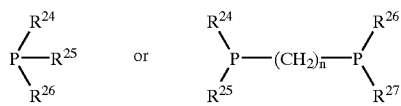

where n is the numbers 1, 2, 3 or 4 and the radicals $R^{24}$ to $R^{26}$ are low-molecular-weight alkyl, for example $C_1-C_6$-alkyl, aryl, $C_1-C_4$-alkylaryl, for example benzyl or phenethyl, or aryloxy. Aryl is, for example, naphthyl, anthryl and preferably unsubstituted or substituted phenyl, where, with respect to the substituents, attention has to be paid only to their inertness to the carboxylation reaction, otherwise they can be widely varied and include all inert organocarbon radicals, such as $C_1-C_6$-alkyl radicals, for example methyl, carboxyl radicals, such as COOH, COOM (M is, for example, an alkali metal, alkaline earth metal or ammonium salt), or organocarbon radicals attached via oxygen, such as $C_1-C_6$-alkoxy radicals.

The phosphine complexes can be prepared in a manner known per se, for example as described in the documents mentioned at the outset. For example, customary commercially available metal salts such as $PdCl_2$ or $Pd(OCOCH_3)_2$ are used as starting materials and the phosphine, for example $P(C_6H_5)_3$, $P(n-C_4H_9)_3$, $PCH_3(C_6H_5)_2$, 1,2-bis(diphenylphosphino)ethane, is added.

The amount of phosphine, based on the transition metal, is usually from 0 to 20, in particular from 0.1 to 10, molar equivalents, particularly preferably from 1 to 5 molar equivalents.

The amount of transition metal is not critical. Of course, for reasons of cost, preference is given to using a relatively small amount, for example from 0.1 to 10 mol %, in particular from 1 to mol %, based on the starting material IV.

For preparing the benzothiazole-5-carboxylic acids IV-1 (R=OH), the reaction is carried out with carbon monoxide and at least equimolar amounts of water, based on the starting materials XIV. The reaction component water can simultaneously also serve as solvent, i.e. the maximum amount is not critical.

However, depending on the nature of the starting materials and the catalysts used, it may also be advantageous for the solvent used to be, instead of the reaction component, another inert solvent or the base which is used for the carboxylation.

Suitable inert solvents for carboxylation reactions are customary solvents such as hydrocarbons, for example toluene, xylene, hexane, pentane, cyclohexane, ethers, for example methyl tert-butyl ether, tetrahydrofuran, dioxane, dimethoxyethane, substituted amides, such as dimethylformamide, persubstituted ureas, such as tetra-$C_1$–$C_4$-alkylureas, or nitrites, such as benzonitrile or acetonitrile.

In a preferred embodiment of the process, one of the reaction components, in particular the base, is used in an excess, so that no additional solvent is necessary.

Bases which are suitable for the process are all inert bases which are able to bind hydrogen iodide or hydrogen bromide liberated during the reaction. Examples which may be mentioned here are tertiary amines, such as tert-alkylamines, trialkylamines, such as triethylamine, cyclic amines, such as N-methylpiperidine or N,N'-dimethylpiperazine, pyridine, alkali metal carbonates or bicarbonates, or tetraalkyl-substituted urea derivatives, such as tetra-$C_1$–$C_4$-alkylurea, for example tetramethylurea.

The amount of base is not critical, customarily from 1 to 10, in particular from 1 tb 5, mol are used. When the base is simultaneously used as solvent, the amount is generally such that the reaction components are dissolved, unnecessarily high excesses being avoided for reasons of practicability in order to save costs, to be able to employ small reaction vessels and to ensure that the reaction components have maximum contact.

During the reaction, the carbon monoxide pressure is adjusted such that an excess of CO, based on XIV, is always present. At room temperature, the carbon monoxide pressure is preferably from 1 to 250 bar, in particular from 5 to 150 bar, of CO.

The carbonylation is generally carried out continuously or batchwise at from 20 to 250° C., in particular from 30 to 150° C. In the case of batchwise operation, carbon monoxide is advantageously continuously injected onto the reaction mixture to maintain a constant pressure.

The 5-bromobenzothiazoles XIV used as starting materials are known or can easily be prepared by suitable combination of known syntheses and according to the reaction sequence described in scheme 3.

According to scheme 3, it is possible, for example, to convert o-chloronitrobenzenes of the formula XIII into the corresponding o-nitrothioethers using alkali metal salts of alkylmercaptans (step k). The resulting thioether can be brominated selectively in the 3-position with respect to the nitro group (step 1). Brominating reagents which are customarily used for this purpose are, in addition to bromine—if appropriate in combination with a Lewis acid such as $FeBr_3$—, also N-bromosuccinimide, N-bromohydantoin and pyridinium perbromide. The bromination is preferably carried out in an organic solvent, for example an aliphatic or cycloaliphatic hydrocarbon, halogenated hydrocarbon or anhydrous organic acids, at temperatures in the range from –15 to 150° C., preferably in the range from –15 to 100° C. (see, for example, Organikum, 16th edition, 1985, p. 315). Subsequently, in step m), the nitro group is reduced to the amino group. The conditions for step m) correspond to the conditions given for step c) in scheme 1. The o-aminothioether from step m) is subsequently, in step n), cyclized to the 5-bromobenzothiazole XIV. The reaction conditions required for this step correspond to the conditions given for step a) in scheme 1.

For preparing the benzothiazole S-dioxide compounds of the formula I (Y=$SO_2$), for example, the benzothiazole-5-carboxylic acids IV-1a or IV-1b or the 5-bromobenzothiazole-5-carboxylic acids XIV are reacted with an oxidizing agent giving the corresponding S-dioxide, which is then processed further as described to give the target compound of the formula I where Y=$SO_2$. However, preference is given to initially oxidizing the thiomethyl ether of the formula VIII (scheme 1, formula VIII where R=H and R'=$CH_3$) to give the S-dioxide VIIIc, which is subsequently cyclized to give the benzothiazole S-dioxide 5-carboxylic acid of the formula IV-1c.

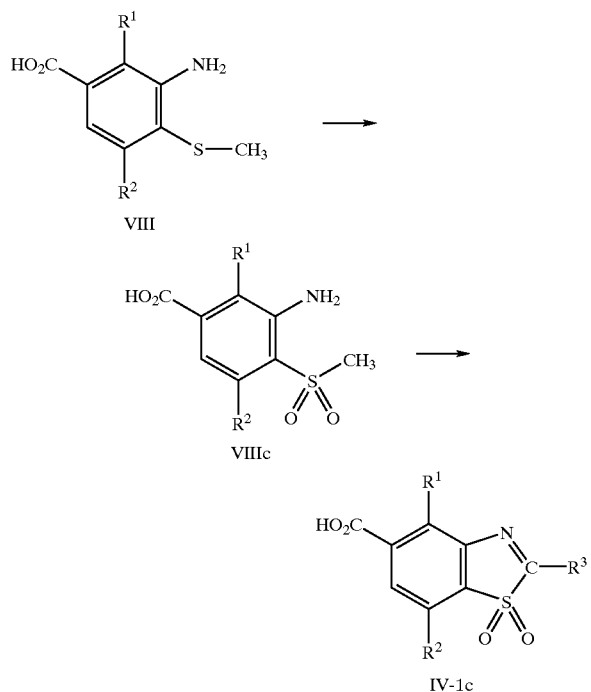

Scheme 1a

The oxidation of VIII to the S-dioxide is carried out using oxidizing agents, such as peroxy acids, for example m-chloroperbenzoic acid, peroxyacetic acid, trifluoroperoxyacetic acid, or using hydrogen peroxide, which is preferably employed together with a transition metal catalyst, for example sodium tungstate (VI). The cyclization of o-methylsulfonylaminobenzenes of formula VIIIc is carried out analogously to the method described in Chem. Heterocycl. Comp. Vol.3, 1967, p.197 ff.

A synthesis of benzoxazole-5-carboxylic ester derivatives of the formula IV-2 (X=C—$R^3$, Y=O) is described in scheme 4. Here, starting from 3-nitrotoluenes of the formula IX, a 3-aminobenzoic ester of the formula Xb (R=$C_1$–$C_4$-alkyl) is initially prepared in the manner described for scheme 1. In step p), the amino group in Xb is first diazotized in a known manner, and the product is subsequently reacted with alkali metal azides to give the corresponding 3-azidobenzoic acids of the formula XV. The azide XV is then, in reaction step q), reacted with an alkanecarboxylic acid, which may also be halogenated, for example formic acid, acetic acid, trifluoroacetic acid or propionic acid, to give the benzoxazole-5-carboxylic ester of the formula IV-2a ($R^3=C_1-C_4$-alkyl). The compound IV-2a can either be reacted directly to give the pyrazolyl derivative of the formula I according to the invention where $X=CR^3$ and $Y=O$ or, alternatively, be hydrolyzed in reaction step r) to give the o-aminophenol of the formula XVI. Like the o-aminothiophenols of the formula VIII, the compounds XVI can then be converted into benzoxazole-5-carboxylic esters of the formula IV-2.

chlorobenzene. The reaction temperature is generally in the range from 0 to 150° C. and preferably in the range from 50 to 145° C. (See also B. Decroix et al., Bull. Soc. Chim. Fr. 1976, 621; S. Chaudhury et al., Can. J. Chem. 60 (1982), 1122). The hydrolysis of the benzoxazole-5-carboxylic ester obtained in step q) to give the 3-amino-4-hydroxybenzoic ester of the formula XVI is carried out, for example, under the conditions given for reaction step e) in scheme 1. The condensation of compound XVI to the benzoxazole-5-carboxylic ester in step 8) is carried out, for examples under the reaction conditions given for step a) in scheme 1. (For step s), see also Houben-Weyl, "Methoden der organischen Chemie", Vol. E8a, 1993, p. 1020 f.)

Another route to the benzoxazole-5-carboxylic acids of the formula IV ($X=C-R^3$, $Y=O$) is shown in scheme 5.

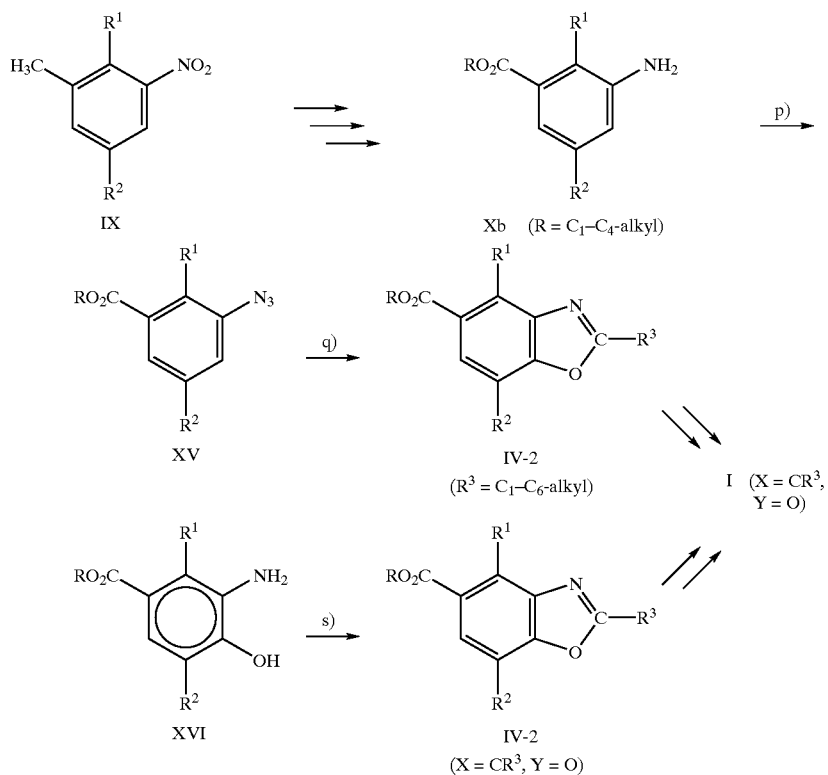

In reaction step p), initially an aromatic diazonium compound is prepared from the amine of the formula Xb, in aqueous acidic solution or in an anhydrous acid, such as formic acid, acetic acid or trifluoroacetic acid, using an inorganic nitrite, such as sodium nitrite, or an organic nitrite, such as isoamyl nitrite. An alkali metal azide, for example sodium azide, is then added to the solution or suspension of the diazonium compound, giving the 3-azidobenzoic ester according to scheme 4. The reaction temperature for the reaction is generally in the range from −15 to +50° C., preferably in the range from 0 to 20° C. See also K. G. Pinney et al., J. Org. Chem. [JOCEAH] 56 (9) (1991), 3125–3133.

Reaction step q) is preferably carried out in the anhydrous acid HOOC—$R^3$ which is desired for the condensation, in an aromatic hydrocarbon, such as benzene, toluene, xylene or

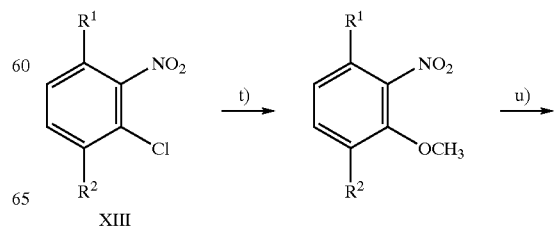

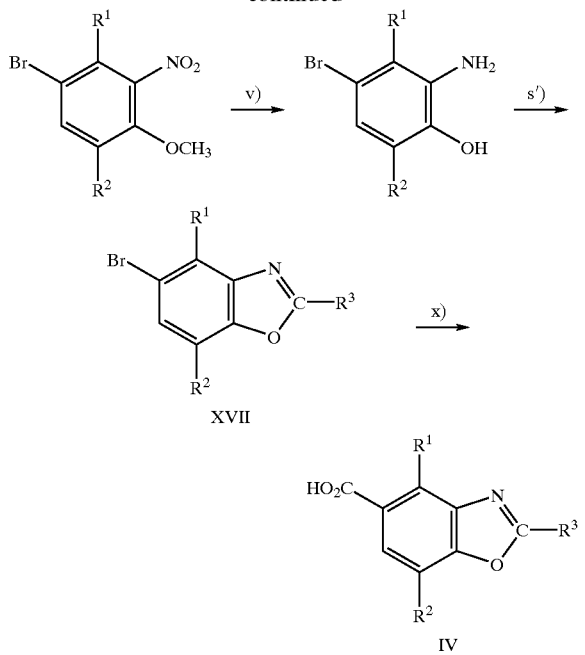

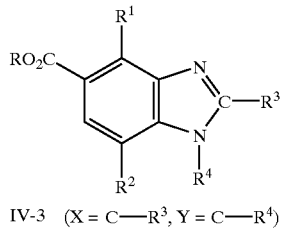

IV-3 (X = C—R³, Y = C—R⁴)

Once more, 3-nitrotoluenes are used as starting materials here, and they are converted in the manner described above into 3-aminobenzoic esters of the formula Xb. The compounds Xb are then, in reaction step y), reacted with a carboxylic acid of the formula $R^3$—$CO_2H$ or a reactive carboxylic acid equivaent $RCOL^1$, where $L^1$ is as defined above, to give a carboxamide of the formula XVIII. Here, $R^3$ has one of the meanings given above. XVIII is then converted under acidic conditions, for example with phosgene or phosphoryl chloride, into a nitrilium ion, which is quenched with an amine of the formula $R^4$—$NH_2$ or ammonia, resulting in an imino amide of the formula XIX. The compound XIX can then be converted under oxidizing conditions, as described, for example, for reaction step b) or g) in scheme 1, into the benzimidazole-5-carboxylic esters, which for its part can be hydrolyzed with the carboxylic acid.

Step y) is generally carried out under the customary reaction conditions for forming amides from carboxylic acids or carboxylic acid derivatives and aromatic amines. The reaction temperature is generally in the range from −15 to 200° C., preferably in the range from 20 to 150° C.

For preparing the imino amide of the formula XIX, the amide of the formula XVIII is initially dissolved under exclusion of water in an organic solvent, for example one of the abovementioned cycloaliphatic or aromatic hydrocarbons or an ether, and converted into the nitrilium ion using an inorganic acid, for example hydrochloric acid, or sulfuric acid, a Lewis acid, such as titanium tetrachloride, or an acid chloride, such as sulfonyl chloride, sulfuryl chloride, phosphoryl chloride or phosgene. The required temperatures are generally in the range from −15 to 150° C. and preferably in the range from 20 to 140° C. The nitrilium ion is then quenched with ammonia or an amine of the formula $R^4$—$NH_2$.

The cyclization of the compound XIX to the benzimidazole-5-carboxylic ester of the formula IV (X=C—$R^3$, Y=C-$R^4$) is generally carried out using an oxidizing agent, such as lead tetraacetate, thallium(III) nitrite, sulfuryl chloride or sodium hypochlorite, under anhydrous conditions. Suitable solvents are, for example, aliphatic or cycloaliphatic hydrocarbons, aromatic hydrocarbons or ethers. The reaction is generally carried out at temperatures in the range from −15 to +150° C. and preferably in the range from 0 to 140° C. For the preparation of benzimidazoles from iminoamides see also (Can. J. Chem. 60 (1982), p.1122).

Benzoisothiodiazoles of the formula IV-4 (X—Y=S=N) are prepared, for example, starting from benzimidazole-5-carboxylic acids or their esters, in the manner described in scheme 7.

Here, an o-chloronitrobenzene of the formula XIII is initially converted by nucleophilic exchange of halogen for methoxy into an o-nitroanisole (step t)). This is then brominated under the reaction conditions given for step 1) in scheme 3, the bromine atom being introduced selectively into the p position to the methoxy group. The brominated nitroanisole is then initially reduced selectively to give the amino compound, and the hydroxyl function is subsequently released by ether cleavage. This gives 2-amino-4-bromophenols. These are then cyclized to the 5-bromobenzoxazole of the formula XVII under the reaction conditions given for step s). Compound XVII is then reacted under the reaction conditions described for step o) in scheme 3 to give the benzoxazole-5-carboyxlic acid of the formula IV (X=C—$R^3$ and Y=O).

A process for preparing benzimidazole-5-carboxylic esters is shown in scheme 6.

Scheme 6

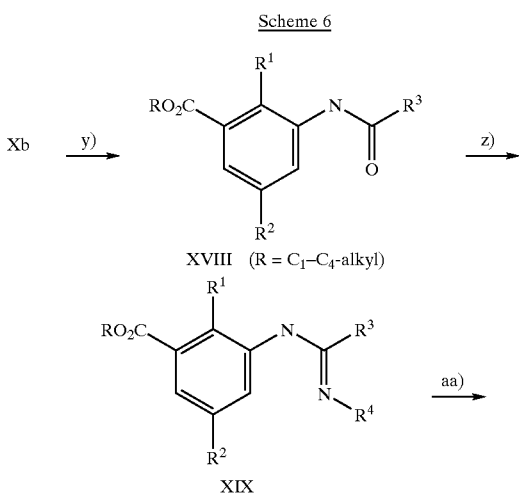

Scheme 7

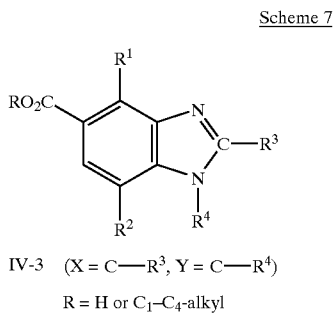

IV-3 (X = C—R³, Y = C—R⁴)

R = H or $C_1$–$C_4$-alkyl

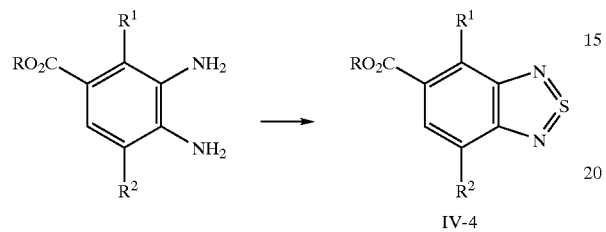

In this case a benzimidazolecarboxylic ester or the free carboxylic acid is initially hydrolyzed to 3,4-diaminobenzoic acid. This is subsequently cyclized with sulfurous acid or its derivatives, for example $SO_2$ or $SO_2Cl_2$, to give the benzoisothiadiazole-5-carboxylic acid of the formula IV-4. The cyclization is usually carried out at from 0 to 200° C. and preferably at from 50 to 150° C., for example in a solvent or in the melt (see also: Chem. Ber. 100 (1967), 2164).

Scheme 8

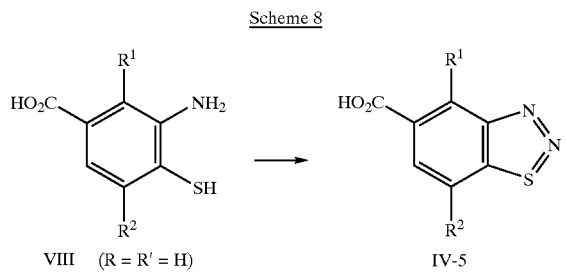

VIII (R = R' = H)      IV-5

Benzothiadiazole-5-carboxylic acids of the formula IV-5 (X=N, Y=S) can be prepared starting from 2-aminothiophenol-5-carboxylic acids of the formula VIII (R=R'=H). To this end, the compounds of the formula VIII are initially diazotized, for example by reaction with organic or inorganic nitrite in an aqueous neutral reaction medium at temperatures in the range from −15 to +20° C. The aqueous solution or suspension of the diazonium salt is subsequently acidified, whereupon the compound of the formula IV-5 forms. This can then be obtained in a conventional manner from the reaction mixture, for example by extraction with an organic solvent. The preparation of the starting materials III is described in scheme 1. The benzothiadiazolecarboxylic acids IV-5 (X=N, Y=S) can be prepared, for example analogously to the process described in U.S. Pat. No. 5,770,758.

EXAMPLES

4-[4'-Methylbenzothiazol-5'-ylcarbonyl]-5-hydroxy-1-methylpyrazole (Example 1)

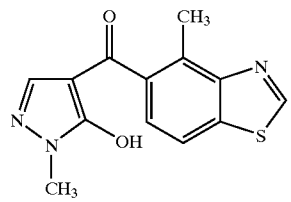

1.1 2-Methyl-4-thiocyanoisophthalonitrile

With heating, 189 g (1 mol) of 2-methyl-3-cyano-4-thiocyanoaniline were dissolved in 1 kg of glacial acetic acid, and 400 g (4 mol) of conc. HCl and, after 15 min of stirring, 400 ml of water were then added such that a finely divided suspension of the hydrochloride was formed. After brief stirring (15 to 30 min), a solution of 69 g (1 mol) of sodium nitrite in 140 ml of water was slowly added dropwise at from −5 to 0° C. In a separate stirred flask, 245 g (5 mol) of NaCN were dissolved in a mixture of.1.5 l of water and 136 g (2 mol) of a 25 percent solution of ammonia and water, and 250 g (1 mol) of $CuSO_4.5H_2O$ were then added. At 25° C., a diazonium solution, which had been prepared beforehand and was kept at 0° C., was then rapidly added dropwise to the Cu complex, the temperature not exceeding 40° C. After the evolution of gas had ceased, stirring was continued for 30 min. The precipitated solid was filtered off with suction and washed three times with water. The filtrate was extracted with 2 l of methylene chloride. The solid was then added to a stirred vessel and admixed with 1 l of conc. HCl. The methylene chloride extract was subsequently added, and the mixture was stirred for 15 min. The organic phase was separated off, undissolved fractions were filtered off and the organic phase was then washed three times with water and, after drying over sodium sulfate, concentrated. To remove undesirable components, the crude product was dissolved in ethyl acetate, undissolved particles were filtered off and the solution was then concentrated.

Yield: 170 g (85%). M.p.: 95–107° C.

1.2 3-Methyl-2,4-dicyanothiophenol

At 25–35° C., a solution of 110.5 g (0.85 mol) of 60 percent pure sodium sulfide in 425 ml of water was added dropwise to a solution of 170 g (0.85 mol) of 2-methyl-4-thiocyanoisophthalonitrile in 850 ml of methanol, and the mixture was stirred at room temperature for 3 hours. The mixture was then admixed with 1000 ml of water and extracted with methyl tert-butyl ether. The aqueous phase was acidified to pH 1 using HCl, and the thiophenol was extracted with methylene chloride. The extract was washed three times with water, and the organic phase was then separated off, dried over sodium sulfate and concentrated. Yield: 150 g (99%).

M.p.: 172–179° C.

1.3 3-Methyl-2,4-dicyanothioanisole 50 g (0.29 mol) of 3-methyl-2,4-dicyanothiophenol were added to a solution of 23 g (0.58 mol) of NaOH in 400 ml of water, and 73 g (0.58 mol) of dimethyl sulfate were then added dropwise at 25–35° C. The mixture was stirred at 25°

C. for 16 h, after which a solid had precipitated out, which was filtered off with suction, washed twice with water and then recrystallized from glacial acetic acid/water. Yield: 43 g (80%).

M.p.: 176–181° C.

1.4 2-Methyl-3-aminocarbonyl-4-methylsulfanylbenzoic Acid 34 g (0.181 mol) of 3-methyl-2,4-dicyanothioanisole were suspended in a solution of 21.7 g (0.54 mol) of NaOH in 200 ml of water, and the mixture was heated at the boil for 8 h. After cooling, some of the product precipitated out and was isolated by filtration with suction and washing with water. The still alkaline filtrate was extracted with MTBE, and the extract was discarded. The aqueous phase was acidified with conc. HCl (pH 1) and extracted with ethyl acetate. Yield: 29 g (71%).

M.p.: 230–240° C.

1.5 3-Amino-2-methyl-4-methylsulfanylbenzoic Acid a) From 2-Methyl-3-aminocarbonyl-4-methylsulfanylbenzoic Acid At, 0° C., 2.9 g of bromine (0.018 mol) were added dropwise to a solution of 3.64 g (0.09 mol) of NaOH in 40 ml of water. 4.1 g (0.018 mol) of 2-methyl-3-aminocarbonyl-4-methylsulfanylbenzoic acid were then added a little at a time at 0° C. The mixture was stirred at 0° C. for 1 h and then warmed to 20° C. The reaction mixture was subsequently acidified using 10% strength HCl and extracted with ethyl acetate. The resulting precipitate was repeatedly suspended in ethyl acetate and dried. Yield: 0.95 g (27%).

b) From Methyl 2-Amino-4-methylbenzothiazole-5-carboxylate 10 g of methyl 2-amino-4-methylbenzothiazole-5-carboxylate (0.045 mol.) were dissolved in a mixture of 120 ml of water, 120 ml of ethylene glycol and 50 g of NaOH, and the mixture was stirred at 130° C. for 20 h. The mixture was then diluted with 50 g of ice, 3 drops of (n-Bu)$_4$N+ OH— solution were added and finally, at 20° C., 6.25 ml of dimethyl sulfate (0.05 mol) in 15 ml of toluene were added dropwise. After 30 min, the mixture was acidified with conc. HCl and the precipitate was filtered off with suction, washed with water and dried.

Yield: 7 g (71%). M.p.: 225° C. (decomp.)

1.6 Methyl 3-Amino-2-methyl-4-methylsulfanylbenzoate 2 g of 3-amino-2-methyl-4-methylsulfanylbenzoic acid (0.01 mol) were dissolved in 20 ml of methanol and admixed with 2.0 g of conc. sulfuric acid, and the mixture was heated at 60° C. for 2 h. After cooling, the reaction mixture was poured into water, neutralized and extracted with ethyl acetate. After washing and drying, the solvent was removed.

Yield: 1.3 g (62%). M.p.: 98–103° C.

1.7 Methyl 3-Formamidyl-2-methyl-4-methylsulfanylbenzoate

At 40° C., 4.75 g of methyl 3-amino-2-methyl-4-methylsulfanylbenzoate (0.05 mol) were added a little at a time to a mixture of 30 ml of acetic anhydride and 2.2 g of formic acid (0.05 mol). After 5 h, the solution was allowed to cool and poured into ice-water, and the mixture was extracted exhaustively with methylene chloride. The organic phases were washed and dried, and the solvent was subsequently removed. Yield: 4.7 g (0.044 mol).

M.p.: 170–176° C.

1.8 Methyl 4-Methylbenzothiazole-5-carboxylate a) From Methyl 3-Formamidyl-2-methyl-4-methylsulfanylbenzoate 2.4 g of methyl 3-formamidyl-2-methyl-4-methylsulfanylbenzoate (0.01 mol) were dissolved in methylene chloride. The mixture was saturated with phosgene gas, and excess phosgene was subsequently flushed out with nitrogen. 1.5 g of triethylamine were then added dropwise. After removal of the solvent under reduced pressure, the residue was taken up in ethyl acetate, the salt was filtered off and the organic phase was reconcentrated. The residue was purified by silica gel column chromatography. Yield: 1.6 g (77%).

b) From Methyl 2-Amino-4-methylbenzothiazole-5-carboxylate 15 g of methyl 2-amino-4-methylbenzothiazole-5-carboxylate (0.07 mol) were initially charged in 450 ml of phosphoric acid, and the mixture was cooled to -8° C. 27.9 g of NaNO$_2$ (0.4 mol) in 30 ml of water were then added dropwise such that the temperature did not exceed -4° C. The diazonium salt was then added dropwise, at 5–10° C., to 169 ml of hypophosphoric acid, and the mixture was stirred at 20° C. overnight. The reaction solution was then neutralized and extracted exhaustively with ethyl acetate. The organic phases Age were washed and dried and the solvent was then removed.

Yield: 6.84 g (49%). M.p.: 90–92° C.

1.9 4-Methylbenzothiazole-5-carboxylic Acid 16.6 g of methyl 4-methylbenzothiazole-5-carboxylate (0.08 mol) were dissolved in 280 ml of 5% strength aqueous potassium hydroxide solution and heated at reflux for 2.5 h. After cooling, the mixture was acidified using phosphoric acid. The product was filtered off and subsequently dried.

Yield: 14.34 g (93%). M.p.: 260–265° C.

1.10 1-Methylpyrazol-5-yl 4-Methylbenzothiazole-5-carboxylate

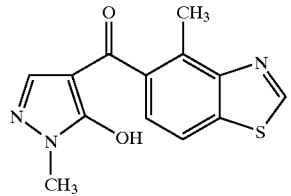

0.65 g of 4-methylbenzothiazole-5-carboxylic acid (0.004 mol) and 0.33 g of 1-methyl-5-hydroxypyrazole (0.004 mol) were dissolved in 30 ml of abs. acetonitrile and admixed with 0.65 g of EDC (0.004 mol), 0.5 ml of triethylamine and a catalytical amount of DMAP. After the reaction had ended, the solution was poured into water and extracted with ethyl acetate. The organic phase was washed and dried, and the product was then purified by silica gel column chromatography. Yield: 0.42 g (41%).

$^1$H NMR (CDCl$_3$, TMS): δ=3.18 (s, 3H); 3.83 (s, 3H); 6.24 (d, 1H); 7.49 (d, 1H); 7.94 (d, 1H); 8.21 (d, 1H); 9.08 (s, 1H); ppm. EDC=ethyl-(3'-dimethylaminopropyl) carbodiimide DMAP=4-dimethylaminopyridine

1.11 4-(4'-Methylbenzothiazol-5'-ylcarbonyl)-5-hydroxy-1-methylpyrazole 0.38 g of 1-methylpyrazol-5-yl 4-methylbenzothiazole-5-carboxylate (1.39 mmol) was dissolved in 25 ml of dioxane, and the mixture was admixed with 0.28 g of $K_2CO_3$ (2 mmol). The mixture was refluxed until the reaction had gone to completion, the solvent was removed under reduced pressure and the residue was taken up in water. The aqueous phase was extracted with methylene chloride, adjusted to pH 2 and extracted with ethyl acetate. The solvent was removed and the product was then purified by trituration. Yield: 0.25 g (66%).

M.p.: 149–150° C.

4-(2'-Chloro-4'-methylbenzothiazol-5'-ylcarbonyl)-5-hydroxy-1-methylpyrazole (Example 2)

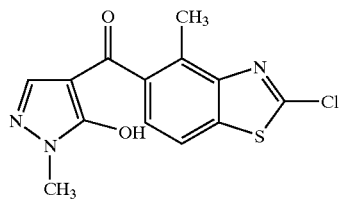

2.1 Methyl 3-Amino-2-methylbenzoate 210 g of methyl 2-methyl-3-nitrobenzoate (1.08 mol) were dissolved in 4 l of methanol, 21 g of Pd/C were added and the mixture was subsequently hydrogenated at ambient pressure. After the reaction had ended, the catalyst was filtered off and the solvent was removed. Yield: 178 g (quant.).

$^1$H NMR (CDCl$_3$, TMS): δ=2.34 (s, 3H); 3.60 (s, brd, 2H, NH$_2$); 3.84 (s, 3H); 6.80 (d, 1H); 7.04 (dd, 1H); 7.21 (d, 1H) ppm.

2.2 N-(2-Methyl-3-methoxycarbonylphenyl)thiourea 90.7 g of methyl 3-amino-2-methylbenzoate (0.55 mol) were dissolved in 510 ml of chlorobenzene and, at –5° C., admixed with 14 ml of conc. sulfuric acid and 49 g of sodium thiocyanate (0.6 mol). 2 ml of 15-crown-5 were then added, and the reaction mixture was heated at 100° C. for 13 h. After cooling, the solid was filtered off with suction, washed with water and dried. Yield: 104.8 g (85%).

M.p.: 198° C.

2.3 Methyl 2-Amino-4-methylbenzothiazole-5-carboxylate 56 g of N-(2-methyl-3-methoxycarbonylphenyl)thiourea (0.25 mol) were dissolved in 2 l of chlorobenzene, and the mixture was cooled to 0° C. 40 g of bromine (0.25 mol) in 100 ml of chlorobenzene were then added dropwise. The reaction mixture was heated at 90° C. for 3 h, and the precipitate was filtered off with suction and washed with methylene chloride. The precipitate was then dissolved in ethyl acetate and extracted with sodium bicarbonate solution. After washing and drying, the product was obtained by stripping off the solvent. Yield: 43 g (80%).

M.p.: 220° C.

2.4 Methyl 2-chloro-4-methylbenzothiazole-5-carboxylate

At –8° C., a solution of 9.3 g of NaNO$_2$ (0.14 mol) in 10 ml of water was added dropwise to a solution of 5 g of methyl 2-amino-4-methylbenzothiazole-5-carboxylate (0.02 mol) in 150 ml of phosphoric acid. At 5° C., a solution of 3 g of CuCl and 12 ml of conc. HCl was then added dropwise. The reaction mixture was heated to 100° C. After cooling, the residue was filtered off with suction, washed with water and dried. The product was purified by silica gel column chromatography.

Yield: 3 g (55%). $^1$H NMR (CDCl$_3$, TMS) δ=2.98 (s, 3H); 3.95 (s, 3H); 7.67 (d, 1H); 7.95 (d, 1H) ppm.

2.5 2-Chloro-4-methylbenzothiazole-5-carboxylic Acid 3 g of methyl 2-chloro-4-methylbenzothiazole-5-carboxylate (0.012 mol). were dissolved in 50 ml of THF, and the mixture was cooled to 0° C. and admixed with a solution of 0.6 g of LiOH in 20 ml of water. After 1 h, the mixture was allowed to warm to 20° C., and stirring was continued for another 20 h. The solvent was then removed under reduced pressure, and the aqueous phase was acidified with phosphoric acid and extracted with ethyl acetate. The extract was washed and dried and the solvent was stripped off to give the product.

Yield: 2.6 g (92%). M.p.: >250° C. $^1$H NMR (D$_6$-DMSO, TMS) δ=2.85 (s, 3H); 7.90 (d, 1H); 8.02 (d, 1H) ppm.

2.6 1-Methylpyrazol-5-yl 3-Chloro-4-methylbenzothiazole-5-carboxylate

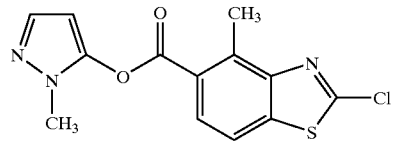

1 g of 3-chloro-4-methylbenzothiazol-5-carboxylic acid (4.4 mol) and 0.46 g of 1-methyl-5-hydroxypyrazole (4.7 mol) were dissolved in 50 ml of abs. acetonitrile and admixed with 1 g of EDC, 0.7 ml of triethylamine and a catalytic amount of DMAP. After the reaction had ended, the solution was poured into water and the product was extracted with ethyl acetate. The organic phase was washed and dried and the product was purified by crystallization/column chromatography. Yield: 0.22 g (16%).

$^1$H NMR (CDCl$_3$, TMS) δ=3.08 (s, 3H); 3.80 (s, 3H); 6.25 (s, 1H); 7.46 (s, 1H); 7.77 (d, 1H); 8.17 (d, 1H) ppm.

2.7 4-(3'-Chloro-4'-methylbenzothiazol-5'-ylcarbonyl)-5-hydroxy-1-methylpyrazole 0.22 g of 1-methylpyrazole-5-yl 3-chloro-4-methylbenzothiazole-5-carboxylate (0.7 mol) was dissolved in 35 ml of dioxane and admixed with 0.5 g of K$_2$CO$_3$. The mixture was refluxed until the reaction had gone to completion, the solvent was removed under reduced pressure and the residue was taken up in water. The aqueous phase was extracted with methylene chloride, adjusted to pH 2 and extracted with ethyl acetate. The solvent was removed and the product was then purified by trituration. Yield: 0.19 g (86%).

$^1$H NMR (CDCl$_3$, TMS) δ=2.82 (s, 3H); 3.76 (s, 3H); 7.40 (s, 1H); 7.52 (d, 1H); 7.73 (d, 1H) ppm.

4-(4'-Methylbenzothiadiazol-5'-ylcarbonyl)-5-hydroxy-1-methylpyrazole (Example 3)

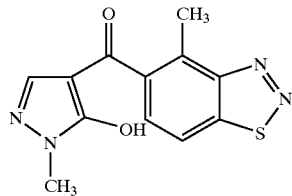

3.1 4-Methylbenzothiadiazole-5-carboxylic Acid 5 g of methyl 2-amino-4-methylbenzothiazole-5-carboxylate (0.02 mol) in 28.6 g of 50% strength KOH were stirred at 120° C. for 4 h. The mixture was then neutralized with 10% strength HCl and admixed with an excess of 40% strength $NaNO_2$ solution at 0–10° C. The reaction mixture was acidified and extracted with ethyl acetate. The extract was washed and dried, and the product was obtained by stripping off the solvent. Yield: 1.3 g (28%).

3.2 4-(4'-Methylbenzothiadiazol-5'-ylcarbonyl)-5-hydroxy-1-methylpyrazole 1.3 g of 4-methylbenzothiadiazole-5-carboxylic acid (6.3 mmol) and 0.65 g of 1-methyl-5-hydroxypyrazole (6.6 mmol) were dissolved in 50 ml of abs. acetonitrile and admixed with 1.4 g of EDC (7.5 mmol), 1 ml of triethylamine and a catalytic amount of DMAP. After the reaction had ended, the solution was poured into water and the product was extracted with ethyl acetate. The organic phase was washed and dried, and the product was then purified by silica gel column chromatography. Yield: 0.7 g (39%).

M.p.: 152–153° C.

3.3 4-(4'-Methylbenzothiadiazol-5'-ylcarbonyl)-5-hydroxy-1-methylpyrazole 0,7 g of 1-methylpyrazol-5-yl 4-methylbenzothiadiazole-5-carboxylate (2.4 mmol) was dissolved in 40 ml of dioxane and admixed with 0.5 g of $K_2CO_3$. The mixture was refluxed until the reaction had gone to completion, the solvent was removed under reduced pressure and the residue was taken up in water. The aqueous phase was extracted with methylene chloride, adjusted to pH 2 and extracted with ethyl acetate. The solvent was removed and the product was then purified by trituration. Yield: 0.65 g (93%).

M.p.: 207–209° C.

4-(2'-Methylamino-4'-methylbenzothiazole-5'-ylcarbonyl)-5-hydroxy-1-methylpyrazole (Example 4)

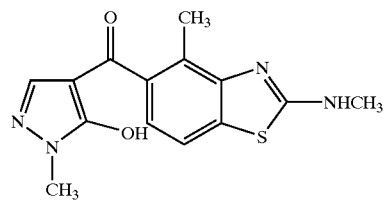

4.1 2-Methylamino-4-methylbenzothiazole-5-carboxylic Acid 99 g of 3-amino-2-methylbenzoic acid (0.655 mol) were initially charged in 500 ml of acetic acid and, at 80° C,. admixed with 51 g of methyl isothiocyanate (7 mol) in 100 ml of acetic acid. After 2 h, 106 g of bromine (0.66 mol) in 20 ml of acetic acid were added dropwise at 50° C. The mixture was subsequently heated at about 100° C. for 2 h and, after the reaction had ended, allowed to cool. The precipitate was filtered off, the filtrate was concentrated to about 50 ml and the remaining filtrate and the precipitate were added to water. The aqueous phase was adjusted to pH 5 and the precipitate was filtered off at 8° C. It was subsequently washed with water and dried. Yield: 66 g (42%).

$^1$H NMR ($D_6$-DMSO, TMS) δ=2.72 (s, 3H); 2.95 (d, 3H); 7.46 (d, 1H); 7.57 (d, 1H); 8.04 (q, 1H, NH) ppm.

4.2 1-Methylpyrazol-5-yl 2-Methylamino-4-methylbenzothiazole-5-carboxylate

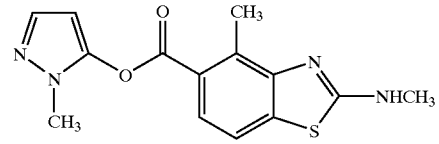

3.1 g of 2-methylamino-4-methylbenzothiazole-5-carboxylic acid (0.014 mol) and 1.4 g of 1-methyl-5-hydroxypyrazole (0.015 mol) were dissolved in 110 ml of abs. acetonitrile and admixed with 2.67 g of EDC (0.014 mol), 1,2 ml of triethylamine and a catalytic amount of DMAP. After the reaction had ended, the solution was poured into water and the mixture was extracted with ethyl acetate. The organic phase was washed and dried, and the product was then purified by crystallization. Yield: 2.2 g (52%).

$^1$H NMR ($D_6$-DMSO): δ=2.80 (s, 3H); 3.00 (d, 3H); 3.73 (s, 3H); 6.22 (d, 1H); 7.43 (d, 1H); 7.72 (d, 1H); 7.84 (d, 1H); 8.20 (s, brd, 1H) ppm.

4-(1'-Methylbenzotriazol-5'-ylcarbonyl)-5-hydroxy-1-methylpyrazole (Example 5)

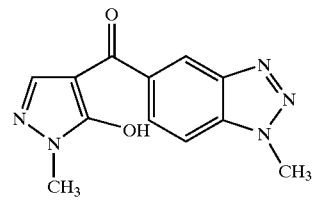

5.1 1-Methylpyrazol-5-yl 1-Methylbenzotriazole-5-carboxylate

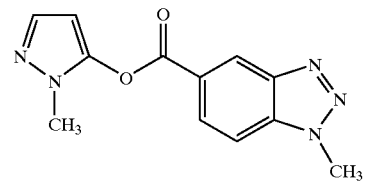

1.5 g of 1-methylbenzotriazole-5-carboxylic acid (8.5 mmol) and 0.87 g of 1-methyl-5-hydroxypyrazole (8.9 mmol) were dissolved in 70 ml of abs. acetonitrile and admixed with 1.62 g of EDC (8.5 mmol), 2 ml of triethylamine and a catalytic amount of DMAP. After the reaction had ended, the solution was poured into water and the mixture was extracted with ethyl acetate. The organic phase was washed and dried, and the product was then purified by crystallization. Yield: 0.77 g (35%).

$^1$H NMR (CDCl$_3$, TMS): δ=3.82 (s, 3H); 4.40 (s, 3H); 6.28 (d, 1H); 7.48 (d, 1H); 7.67 (d, 1H); 8.36 (d, 1H); 8.98 (s, 1H) ppm.

5.2 4-(1'-Methylbenzotriazol-5-ylcarbonyl)-5-hydroxy-1-methylpyrazole 0.53 g of 1-methylpyrazol-5-yl 1-methylbenzotriazole-5-carboxylate (2 mmol) was dissolved in 30 ml of dioxane and admixed with 0.43 g of K$_2$CO$_3$ (3 mmol). The mixture was refluxed until the reaction had gone to completion, the solvent was removed under reduced pressure and the residue was taken up in water. The aqueous phase was extracted with methylene chloride, adjusted to pH 2 and extracted with ethyl acetate. The solvent was removed and the product was then purified by trituration. Yield: 0.31 g (58%).

$^1$H NMR (CDCl$_3$, TMS): δ=3.78 (s, 3H); 4.39 (s, 3H); 4.75 (s, brd, 1H); 7.63 (d, 1H); 7.86 (s, 1H); 8.08 (d, 1H); 8.56 (s, 1H) ppm.

6. 4-(4'-Methylbenzothiazol-5'-ylcarbonyl)-5-methoxy-1-methylpyrazole (Example 6)

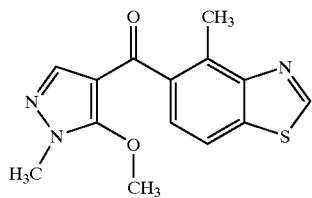

At room temperature, 0.26 g of iodomethane was added dropwise to a mixture of 0.3 g of 4-(4'-methylbenzothiazol-5'-yl-carbonyl)-5-hydroxy-1-methylpyrazole from Example 1 and 0.18 g of potassium carbonate in 15 ml of dimethylformamide. The mixture was stirred at 50° C. for 75 min and at room temperature overnight. For work-up, the reaction mixture was poured into water and extracted with methyl tert-butyl ether. Washing and drying of the combined organic phases and removal of the solvent gave the compound I-1e.394 in the form of whitish-yellow crystals. Yield: 0.15 g (48%).

M.p.: 138–141° C.

In an analogous manner, the compound of Example 13 (I-1g.394) was prepared by reacting the compound I-1a.394 from Example 1 with benzyl bromide, and the compounds I-1i.394 (Example 16), I-1u.394 (Example 15) and I-1v.394 (Example 18) were prepared by reaction with the respective acid chloride.

The compounds of Example 7 to 12, 14, 17 and 19 to 52 were prepared analogously to the sequence described in Example 1, steps 1.10 and 1.11, by reacting the respective carboxylic acid IVb with the appropriate 5-hydroxypyrazole III.

| Ex. | Structure/Compound No. | M.p. [° C.] or $^1$H-NMR [ppm] |
|---|---|---|
| 1 | I-1a.394 | 149–150° C. |
| 2 | I-1a.396 | 135–137° C. |
| 3 |  | 207–209° C. |

| Ex. | Structure/Compound No. | M.p. [° C.] or <br> ¹H-NMR [ppm] |
|---|---|---|
| 4 | 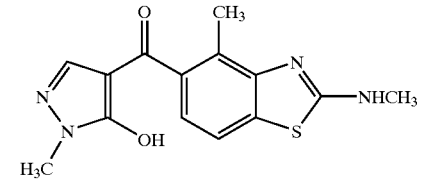 <br> I-4a.2 <br> 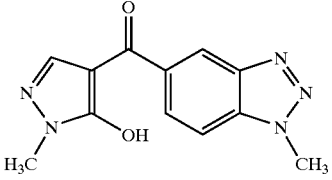 <br> I-1a.447 | |
| 5 | 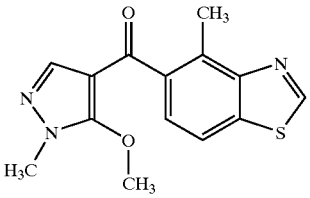 <br> I-4a.38 | CDCl₃, TMS: 3.78(s, 3H), 4.39(s, 3H), 4.75(OH), 7.63(d, 1H), 7.86(s, 1H), 8.08(d, 1H), 8.56(s, 1H) ppm. |
| 6 | 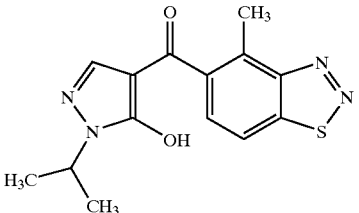 <br> I-1e.394 | 138–141° C. |
| 7 | 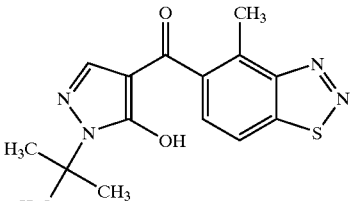 <br> I-4c.2 | 141–143° C. |
| 8 | 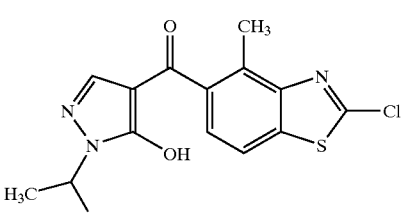 <br> I-4d.2 | 122–125° C. |
| 9 |  <br> I-1c.396 | 118–122° C. |

-continued
| Ex. | Structure/Compound No. | M.p. [° C.] or ¹H-NMR [ppm] |
|---|---|---|
| 10 | 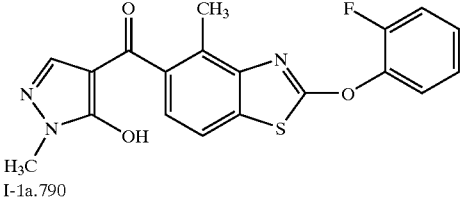 I-1a.790 | CDCl₃, TMS: 2.6(s, 3H), 3.78(s, 3H), 5.5(OH), 7.2–7.38(m, 3H), 7.4–7.55 (m, 3H), 7.6(d, 1H) ppm. |
| 11 | 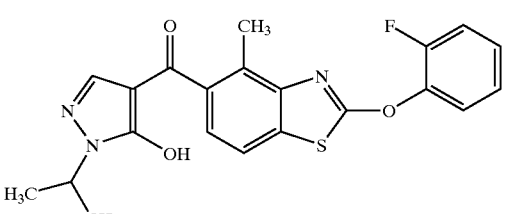 I-1c.790 | CDCl₃, TMS: 1.55(d,6H), 2.62(s, 3H), 4.6(m, 1H) 5,5(OH), 7.2–7.38(m, 3H), 7.4–7.55(m, 3H), 7.6(d, 1H) ppm. |
| 12 | 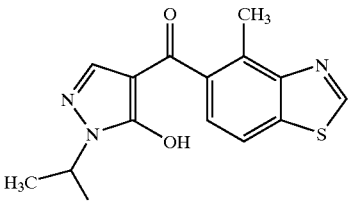 I-1c.394 | 135–137° C. |
| 13 | 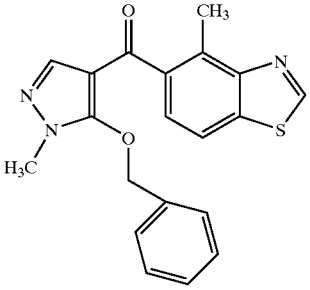 I-1g.394 | CDCl₃, TMS: 2.81(s, 3H), 3.79(s, 3H), 5.2(s, 2H) 7.08(d, 1H), 7.2–7.45(m, 6H), 7.65(d, 1H), 9.1(s, 1H) ppm. |
| 14 | 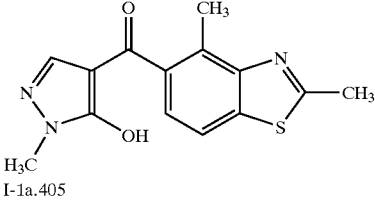 I-1a.405 | 148–152° C. |
| 15 | 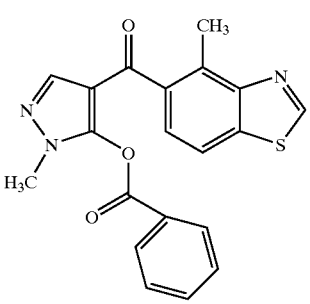 | CDCl₃, TMS: 2.78(s, 3H), 3.78(s, 3H), 7.25–7.55(m, 4H), 7.65(d, 1H), 7.8–7.9(m, 3H), 8.9(s, 1H) ppm. |

-continued
| Ex. | Structure/Compound No. | M.p. [° C.] or ¹H-NMR [ppm] |
|---|---|---|
| | I-1u.394 | |
| 16 | 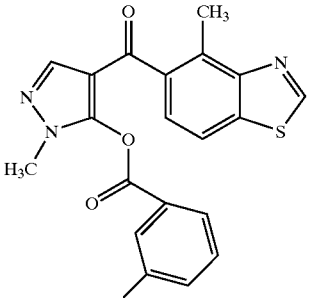 I-1i.394 | CDCl₃, TMS: 2.78(s, 3H), 3.78(s, 3H), 7.2–7.38(m, 3H), 7.58(d, 1H), 7.67–7.78(m, 2H), 7.82(s, 1H), 8.99(s, 1H) ppm. |
| 17 | 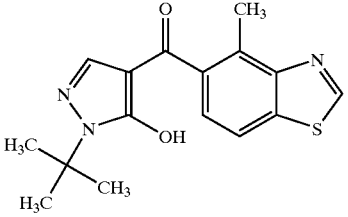 I-1d.394 | 98–101° C. |
| 18 | 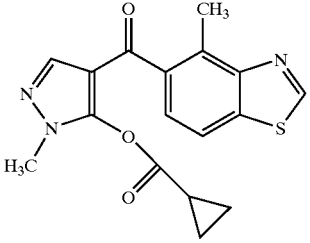 I-1v.394 | CDCl₃, TMS: 0.8(m, 2H), 1.05(m, 2H), 1.66(m, 1H), 2.8(s, 3H), 3.75(s, 3H), 5,6(OH), 7.45(d, 1H), 7.8(s, 1H), 7.82(d, 1H), 9.03(s, 1H) ppm. |
| 19 | 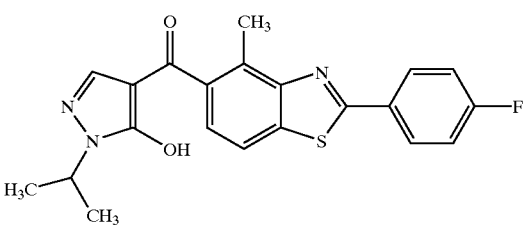 I-1c.412 | 145–148° C. |
| 20 |  I-1c.457 | CDCl₃, TMS: 1.58(d, 6H), 2.90(s, 3H), 4.62(m, 1H), 7.2(m, 2H), 7.48(s, 1H), 7.54(d, 1H), 7.8(d, 1H), 8.14(m, 2H) ppm. |

-continued
| Ex. | Structure/Compound No. | M.p. [° C.] or ¹H-NMR [ppm] |
|---|---|---|
| 21 | 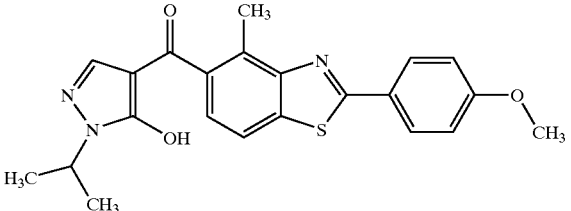<br>I-1c.466 | CDCl₃, TMS: 1.56(d, 6H), 2.92(s, 3H), 3.9(s, 3H), 4.62(m, 1H), 7.02(d, 2H), 7.46(s, 1H), 7.5(d, 1H), 7.80(d, 1H), 8.08(d, 2H) ppm. |
| 22 | 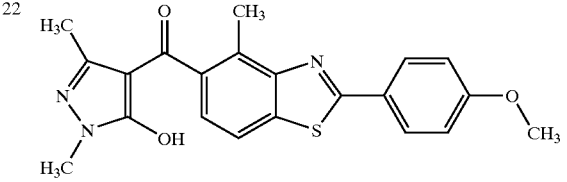<br>I-1m.466 | CDCl₃, TMS: 1.72(s, 3H), 2.88(s, 3H), 3.64(s, 3H), 3.88(s, 3H), 7.0(m, 2H), 7.22(d, 1H), 7.78(d, 1H), 8.06(d, 2H) ppm. |
| 23 | 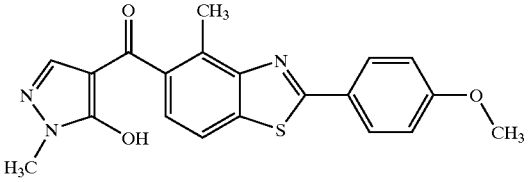<br>I-1a.466 | 204–205° C. |
| 24 | 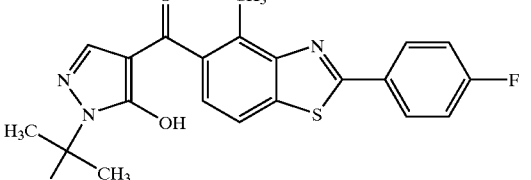<br>I-1d.457 | CDCl₃, TMS: 1.64(s, 9H), 2.92(s, 3H), 7.20(m, 2H), 7.48(s, 1H), 7.62(d, 1H), 7.82(d, 1H), 8.16(m, 2H) ppm. |
| 25 | 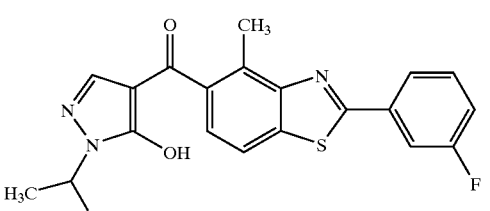<br>I-1c.456 | 127–128° C. |
| 26 | 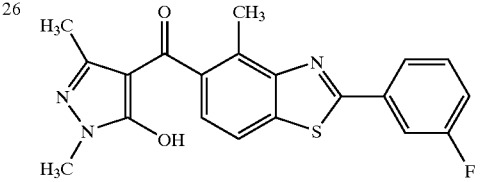<br>I-1m.456 | 123–127° C. |

| Ex. | Structure/Compound No. | M.p. [° C.] or ¹H-NMR [ppm] |
|---|---|---|
| 27 | 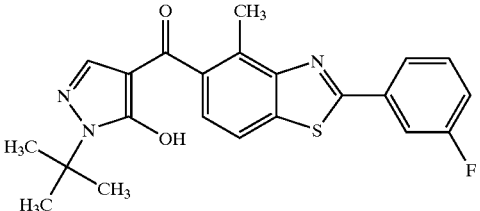<br>I-1d.456 | 153–154° C. |
| 28 | 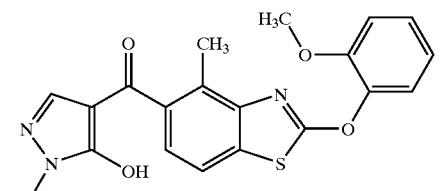<br>I-1a.802 | CDCl₃, TMS: 2.78(s, 3H), 3.78(s, 3H), 3.88(s, 3H), 7.0–7.12(m, 2H), 7.2–7.4(m, 4H), 7.46(d, 1H), 8.85(OH) ppm. |
| 29 | 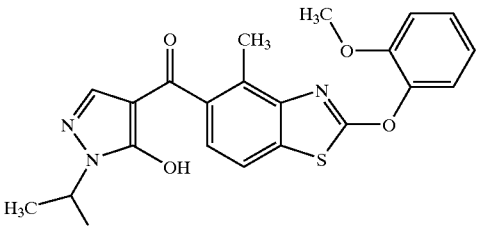<br>I-1c.802 | CDCl₃, TMS: 1.61(d, 6H), 2.80(s, 3H), 3.90(s, 3H), 4.63(m, 1H), 7.0–7.12(m, 2H), 7.25–7.48(m, 4H), 7.55(d, 1H), 8.95(OH) ppm. |
| 30 | 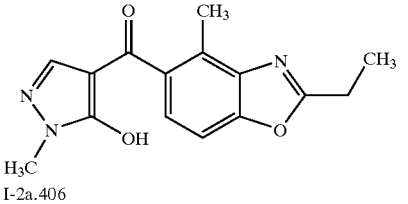<br>I-2a.406 | 134–137° C. |
| 31 | 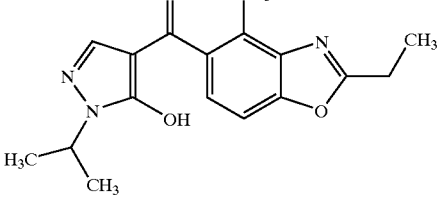<br>I-2c.406 | CDCl₃, TMS: 1.53(t, 3H), 1.55(d, 6H), 2.78(s, 3H), 3.03(q, 2H), 4.62(m, 1H), 738(d, 1H), 7.42(s, 1H), 7.53(d, 1H) ppm. |
| 32 | 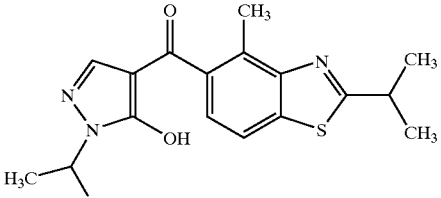<br>I-1c.408 | 102–105° C. |

-continued
| Ex. | Structure/Compound No. | M.p. [° C.] or $^1$H-NMR [ppm] |
|---|---|---|
| 33 | 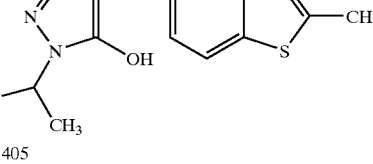<br>I-1c.405 | 107–110° C. |
| 34 | 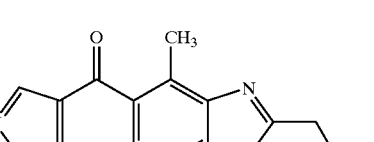<br>I-1a.420 | CDCl$_3$, TMS: 2.82(s, 3H), 3.58(s, 3H), 3.70(s, 3H), 4.88(s, 2H); 742(s, 1H), 7.52(d, 1H), 7.82(d, 1H), 7.90(OH) ppm. |
| 35 | 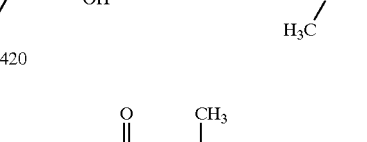<br>I-1d.475 | 197–200° C. |
| 36 | 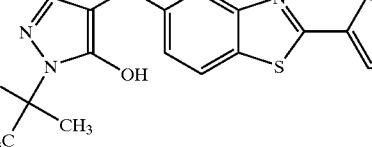<br>I-1c.420 | 100–104° C. |
| 37 | 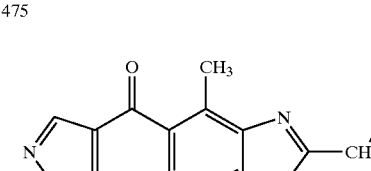<br>I-1a.418 | 108–112° C. |
| 38 | 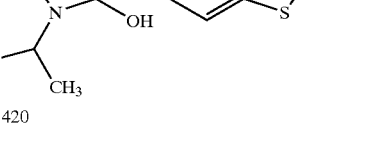<br>I-1c.418 | 84–87° C. |

-continued
| Ex. | Structure/Compound No. | M.p. [° C.] or $^1$H-NMR [ppm] |
|---|---|---|
| 39 | 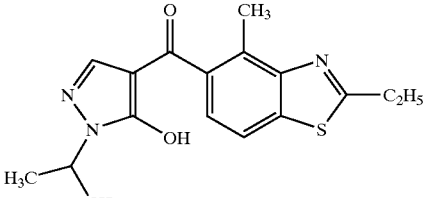 I-1c.406 | 105–107° C. |
| 40 | 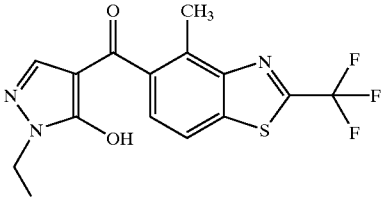 I-1b.418 | 81–85° C. |
| 41 | 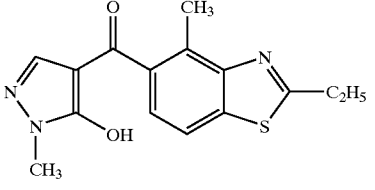 I-1a.406 | 125–128° C. |
| 42 | 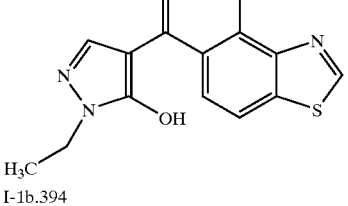 I-1b.394 | 105–110° C. |
| 43 | 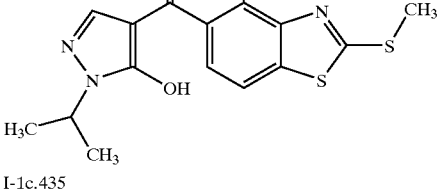 I-1c.435 | 139–143° C. |
| 44 | 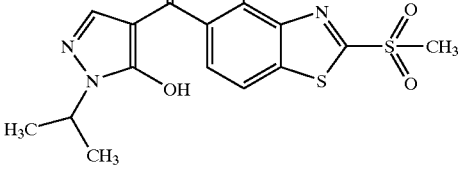 I-1c.435a | 172–177° C. |

-continued
| Ex. | Structure/Compound No. | M.p. [° C.] or $^1$H-NMR [ppm] |
|---|---|---|
| 45 | 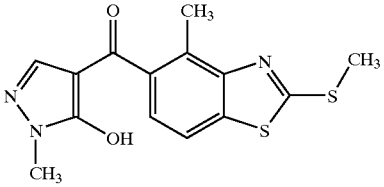<br>I-1a.435 | 138–144° C. |
| 46 | 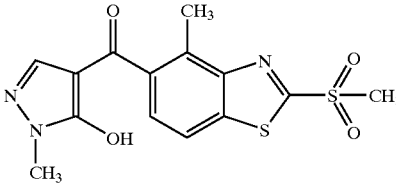<br>I-1a.435a | 208–210° C. |
| 47 | 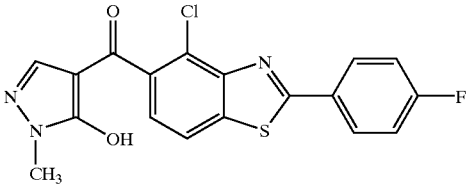<br>I-1a.457 | 235–236° C. |
| 48 | 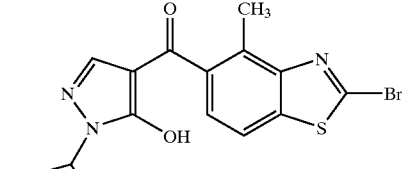<br>I-1c.397 | CDCl$_3$, TMS: 1.55(d, 6H), 2.82(s, 3H), 4.61(m, 1H), 7.39(s, 1H), 7.56(d, 1H), 7.77(d, 1H) ppm. |
| 49 | 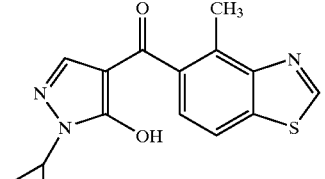<br>I-1w.394 | CDCl$_3$, TMS: 1.08(m, 2H), 1.22(m, 2H), 2.90(s, 3H), 3.40(m, 1H), 7.38(s, 1H), 7.56(d, 1H), 7.90(d, 1H), 8.95(OH), 9.03(s, 1H) ppm. |
| 50 | 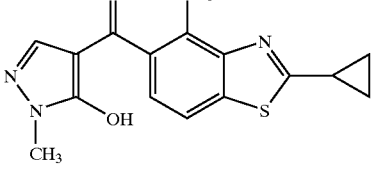<br>I-1a.808 | 69–71° C. |

-continued

| Ex. | Structure/Compound No. | M.p. [° C.] or $^1$H-NMR [ppm] |
|---|---|---|
| 51 | 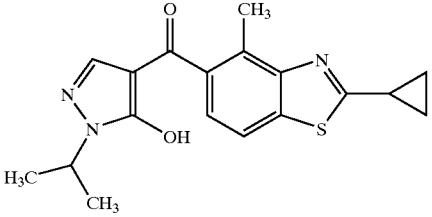<br>I-1c.808 | 115–118° C. |
| 52 | 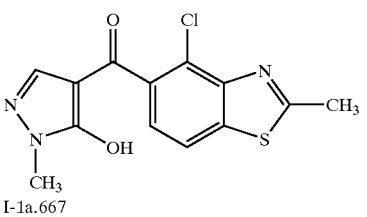<br>I-1a.667 | 141–144° C. |

The compounds of the formula I and their agriculturally useful salts are suitable, both as isomer mixtures and in the form of the pure isomers, for use as herbicides. The herbicidal compositions comprising compounds of the formula I effect very good control of vegetation on non-crop areas, especially at high application rates. In crops such as wheat, rice, maize, soybeans and cotton, they act against broad-leaved weeds and grass weeds without causing any significant damage to the crop plants. This effect is observed in particular at low application rates.

Depending on the application method in question, the compounds of the formula I or the herbicidal compositions comprising them can additionally be employed in a further number of crop plants for eliminating undesirable plants. Suitable crops are, for example, the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea-canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N.rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, vitis vinifera* and *Zea mays.*

In addition, the compounds of the formula I can also be used in crops which tolerate the action of herbicides due to breeding, including genetic engineering methods.

The compounds of the formula I, or the compositions comprising them, can be applied, for example, in the form of directly sprayable aqueous solutions, powders, suspensions, including highly-concentrated aqueous, oily or other suspensions or dispersions, emulsions, oil dispersions, pastes, dusts, materials for broadcasting or granules, by means of spraying, atomizing, dusting, broadcasting or pouring. The use forms depend on the intended purposes; in each case, they should ensure the finest possible distribution of the active ingredients according to the invention.

The herbicidal compositions comprise a herbicidally effective amount of at least one compound of the formula I or an agriculturally useful salt of I and usually the auxiliaries which are customarily used for formulating crop protection agents.

Suitable inert auxiliaries are essentially: Mineral oil fractions of medium to high boiling point, such as kerosene and diesel oil, furthermore coal tar oils and oils of vegetable or animal origin, aliphatic, cyclic and aromatic hydrocarbons, for example paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, for example amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the compounds of the formula I, as such or dissolved in an oil or solvent, can be homogenized in water by means of wetting agent, tackifier, dispersant or emulsifier. Alternatively, it is possible to prepare concentrates from active substance, wetting agent, tackifier, dispersant or emulsifier and, if desired, solvent or oil, and these concentrates are suitable for dilution with water.

Suitable surfactants are the alkali metal salts, alkaline earth metal salts and ammonium salts of aromatic sulfonic acids, for example ligno-, phenol-, naphthalene- and dibutylnaphthalenesulfonic acid, and of fatty acids, of alkyl- and alkylarylsulfonates, of alkyl sulfates, lauryl ether sulfates and fatty alcohol sulfates, and the salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or concomitant grinding of the active substances with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders, or other solid carriers.

The concentrations of the compounds of the formula I in the ready-to-use products can be varied within wide ranges. In general, the formulations comprise approximately from 0.001 to 98% by weight, preferably 0.01 to 95% by weight, of at least one active ingredient. The active ingredients are employed in a purity of from 90% to 100%, preferably 95% to 100% (according to NMR spectrum).

The formulation examples which follow illustrate the preparation of such products:

I. 20 parts by weight of the compound of the formula I in question are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

II. 20 parts by weight of the compound of the formula I in question are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

III. 20 parts by weight of the compound of the formula I in question are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

IV. 20 parts by weight of the compound of the formula I in question are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

V. 3 parts by weight of the compound of the formula I in question are mixed with 97 parts by weight of finely divided kaolin. This gives a dust which comprises 3% by weight of the active ingredient.

VI. 20 parts by weight of the compound of the formula I in question are mixed intimately with 2 parts by weight of calcium dodecylbenzenesulfonate, 8 parts by weight of fatty alcohol polyglylcol ether, 2 parts by weight of the sodium salt of a phenol/urea/formaldehyde condensate and 68 parts by weight of a paraffinic mineral oil. This gives a stable oily dispersion.

VII. 1 part by weight of the compound of the formula I in question is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound of the formula I in question is dissolved in a mixture composed of 80 parts by weight of cyclohexanone and 20 parts by weight of Wettol$^R$ EM 31 (=non-ionic emulsifier based on ethoxylated castor oil). This gives a stable emulsion concentrate.

The compounds of the formula I, or the herbicidal compositions, can be applied pre- or post-emergence. If the active ingredients are less well tolerated by certain crop plants, it is possible to use application techniques in which the herbicidal compositions are sprayed, with the aid of the spraying equipment, in such a way that they come into as little contact as possible, if any, with the leaves of the sensitive crop plants while the active ingredients reach the leaves of undesirable plants which grow underneath, or the bare soil surface (post-directed, lay-by).

Depending on the intended aim, the season, the target plants and the growth stage, the rates of application of the compound of the formula I are from 0.001 to 3.0, preferably 0.01 to 1.0, kg of active substance (a.s.)/ha.

To widen the spectrum of action and to achieve synergistic effects, the compounds of the formula I according to the invention may be mixed, and applied jointly, with a large number of representatives of other groups of herbicidally or growth-regulating active ingredients. Suitable examples of components in mixtures are 1,2,4-thiadiazoles, 1,3,4-thiadiazoles, amides, aminophosphoric acid and its derivatives, aminotriazoles, anilides, aryloxy/hetaryloxyalkanoic acids and their derivatives, benzoic acid and its derivatives, benzothiadiazinones, 2-aroyl-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, cyclohexanone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Moreover, it may be advantageous to apply the compounds of the formula I, alone or in combination with other herbicides, even in the form of a mixture together with further crop protection agents, for example with pesticides or agents for controlling phytopathogenic fungi or bacteria. Also of interest is the miscibility with mineral salt solutions which are employed for treating nutritional and trace element deficiencies. Nonphytotoxic oils and oil concentrates may also be added.

Use Examples

The herbicidal activity of the compounds of the formula I according to the invention was demonstrated by the following greenhouse experiments:

The culture containers used were plastic flowerpots containing loamy sand with approximately 3.0% of humus as substrate. The seeds of the test plants were sown separately for each species.

For the pre-emergence treatment, the active ingredients, suspended or emulsified in water, were applied directly after sowing by means of finely distributing nozzles. The containers were irrigated gently to promote germination and growth and subsequently covered with translucent plastic hoods until the plants had rooted. This cover caused uniform germination of the test plants unless this was adversely affected by the active ingredients.

For the post-emergence treatment, the test plants were first grown to a plant height of from 3 to 15 cm, depending on the plant habit, and only then treated with the active ingredients which had been suspended or emulsified in water. To this end, the test plants were either sown directly and grown in the same containers, or they were first grown separately as seedlings and transplanted into the test containers a few days prior to treatment. The rate of application for the post-emergence treatment was 0.5 or 0.25 kg of a.s. (active. substance)/ha.

Depending on the species, the plants were kept at from 10 to 25° C., or 20–35° C., respectively. The test period extended over 2 to 4 weeks. During this time, the plants were tended, and their response to the individual treatments was evaluated.

Evaluation was carried out using a scale of from 0 to 100. 100 means no emergence of the plants, or complete destruction of at least the aerial parts, and 0 means no damage, or normal course of growth.

The plants used in the greenhouse experiments belonged to the following species:

| Bayer-code | Common name |
| --- | --- |
| AMARE | redroot pigweed |
| AVEFA | wild oats |
| CHEAL | lambsquarters (goosefoot) |
| CAPBP | shepherd's purse |
| DIGSA | fingergrass, hairy |
| ECHCG | barnyard grass |
| EPHHL | spurge |
| GASPA | smallflower |
| GALAP | catchweed bedstraw |
| LAMAM | henbit |
| MYOAR | forget-me-not |
| PAPRH | corn poppy |
| POLPE | ladysthumb |
| SETIT | foxtail |
| STEME | common chickweed |
| SOLNI | black nightshade |
| THLAR | fanweed |
| TRZAS | spring wheat |

At application rates of 0.5 and 0.25 kg/ha (a.s.), the compound 4-(4'-methylbenzothiazol-5'-ylcarbonyl)-5-hydroxy-1-methylpyrazole (Example 1) showed very good herbicidal action against the harmful plants AVEFA, CHEAL, POLPE, SOLNI and GALAP, when applied by the post-emergence method.

At application rates of 0.125 and 0.0625 kg/ha, the compound 4-(2',4'-dimethylbenzothiazol-5'-ylcarbonyl)-5-hydroxy-1-methylpyrazole (Example 14) shows very good herbicidal action against GASPA, LAMAM, STEME, THLAR, when applied by the post-emergence method.

At application rates of 0.125 and 0.0625 kg/ha, the compound 4-(4'-methylbenzothiazol-5'-ylcarbonyl)-5-benzyloxy-1-methylpyrazole (Example 13) shows very good herbicidal action against CHEAL, EPHHL, MYOAR, PAPRH, SOLNI, and selectivity in wheat when applied by the post-emergence method.

At application rates of 0.25 and 0.125 kg/ha, the compound 4-(2'-ethyl-4'-methylbenzoxazol-5'-ylcarbonyl)-5-hydroxy-1-isopropylpyrazole (Example 31) shows very good herbicidal action against AMARE, CHEAL, LAMAM, PAPRH, POLPE, THLAR, when applied by the post-emergence method.

At application rates of 0.25 and 0.125 kg/ha, the compound 4-(2',4'-dimethylbenzothiazol-5'-ylcarbonyl)-5-hydroxy-1-isopropylpyrazole (Example 33) shows very good herbicidal action against AMARE, CHEAL, LAMAM, MYOAR, PAPRH, THLAR, when applied by the post-emergence method.

At application rates of 0.25 and 0.125 kg/ha, the compound 4-(2'-methoxymethyl-4'-methylbenzothiazol-5'-ylcarbonyl)-5-hydroxy-1-methylpyrazole (Example 34) shows very good herbicidal action against CHEAL, LAMAM, PAPRH, STEME, THLAR, when applied by the post-emergence method.

At application rates of 0.25 and 0.125 kg/ha, the compound 4-(2'-ethyl-4'-methylbenzoxazol-5'-ylcarbonyl)-5-hydroxy-1-methylpyrazole (Example 30) shows very good herbicidal action against CHEAL, LAMAM, PAPRH, POLPE, THLAR, when applied by the post-emergence method.

At application rates of 0.25 and 0.125 kg/ha, the compound 4-(2'-methoxymethyl-4'-methylbenzothiazol-5'-ylcarbonyl)-5-hydroxy-1-isopropylpyrazole (Example 36) show very good herbicidal action against CHEAL, EPHHL, MYOAR, PAPRH, SOLNI, STEME, when applied by the post-emergence method.

At application rates of 0.25 and 0.125 kg/ha, the compound 4-(4'-methylbenzothiazol-5'-ylcarbonyl)-5-hydroxy-1-isopropylpyrazole (Example 12) shows very good herbicidal action against CHEAL, LAMAM, PAPRH, STEME, THLAR, when applied by the post-emergence method.

At application rates of 0.5 and 0.25 kg/ha, the compound 4-(4'-methylbenzothiazol-5'-ylcarbonyl)-5-(3"-fluorobenzoyl)oxy-1-methylpyrazole (Example 16) shows very good herbicidal action against AMARE, ECHCG, CHEAL, GALAP, POLPE, when applied by the post-emergence method.

At application rates of 0.25 and 0.125 kg/ha, the compound 4-(4'-methylbenzothiazol-5'-ylcarbonyl)-5-benzoyloxy-1-methylpyrazole (Example 15) shows very good herbicidal action against AVEFA, AMARE, ECHCG, CHEAL, POLPE, when applied by the post-emergence method.

At application rates of 0.25 and 0.125 kg/ha, the compound 4-(4'-methylbenzothiazol-5'-ylcarbonyl)-5-cyclopropylcarbonyloxy-1-methylpyrazole (Example 18) shows very good herbicidal action against AVEFA, AMARE, ECHCG, CHEAL, POLPE, when applied by the post-emergence method.

We claim:

1. A pyrazolyl derivative of benzo-fused unsaturated 5-membered nitrogen heterocycles of the formula I,

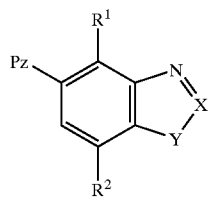

where

X is N or a group C—$R^3$;

Y is O, S, SO, $SO_2$ or $NR^4$ or

X—Y is S=N, and X is sulfur;

$R^1$ is hydrogen, nitro, halo, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_{1-6}$-haloalkylsulfonyl, aminosulfonyl, $C_1$–$C_6$-alkoxy-$C_1$–$C_6$-alkyl, $C_1$–$C_6$-alkylthio-$C_1$–$C_6$-alkyl, $C_1$–$C_6$-alkylsulfinyl-$C_1$–$C_6$-alkyl, $C_1$–$C_6$-alkylsulfonyl-$C_1$–$C_6$-alkyl, $C_1$–$C_6$-alkylamino-$C_1$–$C_6$-alkyl, or di($C_1$–$C_6$-alkyl)amino-$C_1$–$C_6$-alkyl;

$R^2$ is hydrogen, halogen or $C_1$–$C_6$-alkyl;

$R^3$ is hydrogen, halogen, nitro, cyano, hydroxyl, amino, mercapto, thiocyanato, hydrazide, $C_1$–$C_6$-alkyl, $C_1$–$C_6$-haloalkyl, $C_1$–$C_6$-hydroxyalkyl, $C_1$–$C_6$-aminoalkyl, $C_1$–$C_6$-alkoxy-$C_1$–$C_6$-alkyl, $C_1$–$C_6$-alkylcarbonyl-$C_1$–$C_6$-alkyl, $C_1$–$C_6$-alkoxy, $C_1$–$C_6$-haloalkoxy, $C_1$–$C_6$-hydroxyalkoxy, $C_1$–$C_6$-alkoxy-$C_1$–$C_6$-alkoxy, $C_3$–$C_6$-cycloalkyl, is $C_1$–$C_6$-alkylamino, di-$C_1$–$C_6$-alkylamino, $C_3$–$C_6$-cycloalkylamino, where the alkyl and cycloalkyl groups of the three last-mentioned radicals may be partially or fully halogenated and/or may carry one to three substituents selected from the group consisting of $C_1$–$C_4$-alkoxy and hydroxyl, is $C_1$–$C_6$-alkylthio, $C_1$–$C_6$-haloalkylthio, $C_1$–$C_6$-hydroxyalkylthio, $C_1$–$C_6$-alkoxy-$C_1$–$C_6$-alkylthio, $C_1$–$C_6$-alkylsulfonyl, $C_1$–$C_6$-alkylsulfinyl, is phenyl, naphthyl, heterocyclyl, phenylamino, phenoxy, diphenylamino, where the phenyl and heterocyclyl groups of the six last-mentioned radicals for their part may be partially or fully halogenated and/or may carry one, two or three substituents selected from the group consisting of nitro, cyano, hydroxyl, $C_1$–$C_4$-alkyl, $C_1$–$C_4$-haloalkyl, $C_1$–$C_4$-alkoxy and $C_1$–$C_4$-haloalkoxy, is C(O)$OR^5$, or C(O)N($R^6$)$R^1$; and $R^4$ is hydrogen, $C_1$–$C_6$-alkyl, $C_1$–$C_6$-haloalkyl, $C_1$–$C_6$-hydroxyalkyl, $C_1$–$C_6$-alkoxy-$C_1$–$C_6$-alkyl, is phenyl, naphthyl, where the two last-mentioned radicals for their part may be partially or fully halogenated and/or may carry one, two or three substituents selected from the group consisting of nitro, cyano, hydroxyl, $C_1$–$C_4$-alkyl, $C_1$–$C_4$-haloalkyl, $C_1$–$C_4$-alkoxy and $C_1$–$C_4$-haloalkoxy; where $R^5$ is hydrogen, $C_1$–$C_6$-alkyl, $C_1$–$C_6$-haloalkyl, $C_1$–$C_6$-hydroxyalkyl, $C_1$–$C_6$-alkoxy-$C_1$–$C_6$-alkyl, is phenyl, naphthyl or heterocyclyl, where the three last-mentioned radicals for their part may be partially or fully halogenated and/or may carry one, two or three substituents selected from the group consisting of nitro cyano, hydroxyl, $C_1$–$C_4$-alkyl, $C_1$–$C_4$-haloalkyl, $C_1$–$C_4$-alkoxy and $C_1$–$C_4$-haloalkoxy;

$R^6$, $R^7$ independently of one another are hydrogen, $C_1$–$C_6$-alkyl, $C_1$–$C_6$-haloalkyl, $C_1$–$C_6$-hydroxyalkyl, $C_1$–$C_6$-alkoxy-$C_1$–$C_6$-alkyl, are phenyl or naphthyl, where the two last-mentioned radicals for their part may be partially or fully halogenated and/or may carry one, two or three substituents selected from the group consisting of nitro, cyano, hydroxyl, $C_1$–$C_4$-alkyl, $C_1$–$C_4$-haloalkyl, $C_1$–$C_4$-alkoxy and $C_1$–$C_4$-haloalkoxy;

and Pz is a radical of the formula IIa or IIb,

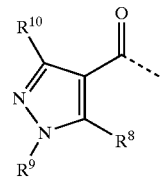

IIa

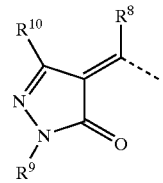

IIb where the variables $R^8$, $R^9$ and $R^{10}$ are as defined below:

$R^8$ is hydroxyl, mercapto, halogen, $OR^{11}$, $SR^{11}$, $SOR^{12}$, $SO_2R^{12}$, $OSO_2R^{12}$, $P(O)R^{13}R^{14}$, $OP(O)R^{13}R^{14}$, $P(S)R^{13}R^{14}$, $OP(S)R^{13}R^{14}$, $NR^{15}R^{16}$, $ONR^{15}R^{16}$ or N-bonded heterocyclyl, which may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^9$ is hydrogen, $C_1$–$C_6$-alkyl, $C_1$–$C_6$-haloalkyl, $C_3$–$C_6$-cycloalkyl, hydroxyl, $C_1$–$C_6$-alkoxy or $C_1$–$C_6$-haloalkoxy;

$R^{10}$ is hydrogen, halogen, $C_1$–$C_6$-alkyl, $C_1$–$C_6$-haloalkyl, hydroxyl, $C_1$–$C_6$-alkoxy, $C_1$–$C_6$-haloalkoxy, $C_1$–$C_6$-alkylthio or $C_1$–$C_6$-haloalkylthio; where $R^{11}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkylcarbonyl, $C_2$–$C_6$-alkenylcarbonyl, $C_2$–$C_6$-alkynylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl)aminocarbonyl, N—($C_3$–$C_6$-alkenyl)—N—($C_1$–$C_6$-alkyl)aminocarbonyl, N—($C_3$–$C_6$-alkynyl)—N—($C_1$–$C_6$-alkyl)aminocarbonyl, N—($C_1$–$C_6$-alkoxy)—N—($C_1$–$C_6$-alkyl)aminocarbonyl, N—($C_3$–$C_6$-alkenyl)—N—($C_1$–$C_6$-alkoxy)aminocarbonyl, N—($C_3$–$C_6$-alkynyl)—N—($C_1$–$C_6$-alkoxy)aminocarbonyl, di($C_1$–$C_6$-alkyl)aminothiocarbonyl or $C_1$–$C_6$-alkoxyimino-$C_1$–$C_6$-alkyl, where the alkyl, cycloalkyl and alkoxy radicals mentioned may be partially or fully halogenated and/or may carry one to three of the following groups: cyano, $C_1$–$C_4$-alkoxy, $C_1$–$C_4$-alkylthio, di($C_1$–$C_4$-alkyl)amino, $C_1$–$C_4$- alkylcarbonyl, $C_1$–$C_4$-alkoxycarbonyl, $C_1$–$C_4$-alkoxy-$C_1$–$C_4$-alkoxycarbonyl, $C_1$–$C_4$-alkylaminocarbonyl, di($C_1$–$C_4$-alkyl)aminocarbonyl, aminocarbonyl, $C_1$–$C_4$-alkylcarbonyloxy or $C_3$–$C_6$-cycloalkyl;

is phenyl, phenyl-$C_1$–$C_6$-alkyl, phenylcarbonyl-$C_1$–$C_6$-alkyl, phenylcarbonyl, phenoxycarbonyl, phenyloxythiocarbonyl, phenylaminocarbonyl, N—($C_1$–$C_6$-alkyl)—N—(phenyl)aminocarbonyl, phenyl-$C_2$–$C_6$-alkenylcarbonyl, heterocyclyl, heterocyclyl-$C_1$–$C_6$-alkyl, heterocyclylcarbonyl-$C_1$–$C_6$-alkyl, heterocyclylcarbonyl, heterocyclyloxycarbonyl, heterocyclyloxythiocarbonyl, heterocyclylaminocarbonyl, N—($C_1$–$C_6$-alkyl)—N—(heterocyclyl)aminocarbonyl, or heterocyclyl-$C_2$–$C_6$-alkenylcarbonyl, where the phenyl and the heterocyclyl radical of the 18 last-mentioned substituents may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{12}$ is $C_1$–$C_6$-alkyl, $C_3$–$C_6$-alkenyl, $C_3$–$C_6$-alkynyl or $C_3$–$C_6$-cycloalkyl, where the four radicals mentioned may be partially or fully halogenated and/or may carry one, two or three of the following groups: cyano, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylcarbonyl, $C_1$–$C_4$-alkoxycarbonyl or $C_1$–$C_4$-haloalkoxycarbonyl;

is phenyl, phenyl-$C_1$–$C_6$-alkyl, heterocyclyl or heterocyclyl-$C_1$–$C_6$-alkyl, where the phenyl and the heterocyclyl radical of the last-mentioned substituents may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{13}$ $R^{14}$ independently of one another are hydrogen, hydroxyl, $C_1$–$C_6$-alkyl, $C_1$–$C_6$-alkoxy, $C_1$–$C_6$-alkylthio, phenyl, phenyl-$C_1$–$C_4$-alkyl or phenoxy, where the three last-mentioned substituents may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{15}$ is hydrogen, $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkylcarbonyl, hydroxyl, $C_1$–$C_6$-alkoxy, $C_3$–$C_6$-alkenyloxy, $C_3$–$C_6$-alkynyloxy, amino, $C_1$–$C_6$-alkylamino, di($C_1$–$C_6$-alkyl)amino or $C_1$–$C_6$-alkylcarbonylamino, where the alkyl, cycloalkyl and alkoxy radicals mentioned may be partially or fully halogenated and/or may carry one, two or three of the following radicals: cyano, $C_1$–$C_4$-alkoxycarbonyl, $C_1$–$C_4$-alkylaminocarbonyl, di($C_1$–$C_4$-alkyl)aminocarbonyl or $C_3$–$C_6$cycloalkyl;

is phenyl, phenyl-$C_1$–$C_4$-alkyl, phenylcarbonyl, heterocyclyl, heterocyclyl-$C_1$–$C_4$-alkyl or heterocyclylcarbonyl, where the phenyl or heterocyclyl radical of the six last-mentioned substituents may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy or $C_1$–$C_4$-haloalkoxy; and $R^{16}$ is hydrogen, $C_1$–$C_6$-alkyl or $C_3$–$C_6$-alkenyl, $C_3$–$C_6$-alkynyl;

and its agriculturally useful salts.

2. A pyrazole derivative as claimed in claim 1 where X in the formula I is C—$R^3$, where $R^3$ is hydrogen, halogen, cyano, thiocyanato, $C_1$–$C_6$-alkyl, $C_1$–$C_6$-haloalkyl, $C_1$–$C_6$-alkoxy, $C_1$–$C_6$-alkoxy-$C_1$–$C_6$-alkyl, $C_3$–$C_6$-cycloalkyl, $C_1$–$C_6$-haloalkoxy, $C_1$–$C_6$-alkylthio, $C_1$–$C_6$-haloalkylthio, is phenyl, phenoxy or pyridyl, where the three last-mentioned radicals may be partially or fully halogenated and/or may carry one of the following radicals: $C_1$–$C_4$-alkoxy, $C_1$–$C_4$-haloalkyl, and $C_1$–$C_4$-haloalkoxy; or is COOR$^5$ where R$^5$ is as defined in claim 1.

3. A pyrazole derivative as claimed in claim 1 where X in the formula I is C—$R^3$ and Y is selected from the group consisting of S, SO and $SO_2$.

4. A pyrazole derivative as claimed in claim 1, where Y in the formula I is N—$R^4$, where $R^4$ is as defined in claim 1, and X is C—$R^3$, where $R^3$ is as defined in claim 1.

5. A pyrazole derivative as claimed in claim 1 where X is N and Y is selected from the group consisting of S, SO, $SO_2$ and N—$R^4$.

6. A pyrazole derivative as claimed in claim 1 where Pz in the formula I is a radical of the formula IIa, where $R^8$ is selected from the group consisting of hydroxyl, OR$^{11}$ and $OSO_2R^{12}$, where $R^{11}$ and $R^{12}$ are as defined in claim 1, $R^9$ and $R^{10}$ being as defined in claim 1.

7. A pyrazole derivative as claimed in claim 6, where in the formula IIa $R^8$ is hydroxyl, $C_1$–$C_4$-alkyloxy, O—$CH_2$-phenyl, phenylcarbonyloxy, 2-, 3- or 4-fluorophenylcarbonyloxy, cyclopropylcarbonyloxy, $C_1$–$C_4$-sulfonyloxy, phenylsulfonyloxy and 2-, 3- or 4-methylphenylsulfonyloxy;

$R^9$ is $C_1$–$C_4$-alkyl or cyclopropyl and $R^{10}$ is hydrogen or $C_1$–$C_4$-alkyl.

8. A process for preparing compounds of the formula I where $R^8$=hydroxyl, as claimed in claim 1, which comprises acylating a 5-hydroxypyrazole of the formula III,

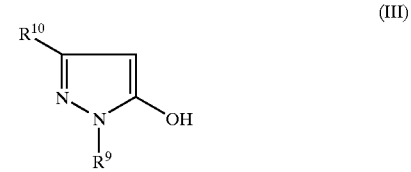

(III)

where the variables $R^9$ and $R^{10}$ are as defined in claim 1 with an activated carboxylic acid IVa or a carboxylic acid IVb

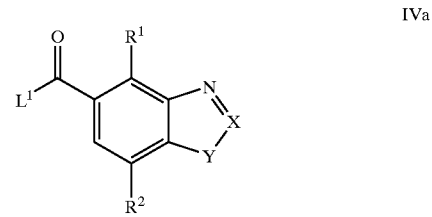

IVa

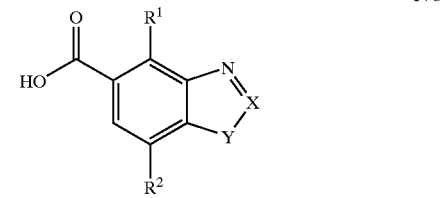

IVb where the variables X, Y, $R^1$ and $R^2$ are as defined in claim 1 and $L^1$ is nucleophilically replaceable leaving group, and rearranging the acylation product, if appropriate in the presence of a catalyst, to give the compounds I where $R^8$=hydroxyl.

9. A process for preparing compounds of the formula I as claimed in claim 1 where $R^8$=halogen, which comprises reacting a pyrazole derivative of the formula I where $R^8$=hydroxyl with a halogenating agent.

10. A process for preparing compounds of the formula I as claimed in claim 1 where $R^8$=$OR^{11}$, $OSO_2R^{12}$, $OP(O)R^{13}R^{14}$ or $OP(S)R^{13}R^{14}$, which comprises reacting a pyrazole derivative of the formula I where $R^8$=hydroxyl with an alkylating agent Vα, sulfonylating agent Vβ or phosphonylating agent Vγ or Vδ,

| $L^2$-$R^{11}$ | $L^2$-$SO_2R^{12}$ | $L^2$-$P(O)R^{13}R^{14}$ | $L^2$-$P(S)R^{13}R^{14}$ |
|---|---|---|---|
| IVα | IVβ | IVγ | IVδ | where the variables $R^{11}$ to $R^{14}$ are as defined in claim 1 and $L^2$ is a nucleophilically replaceable leaving group.

11. A process for preparing compounds of the formula I as claimed in claim 1 where $R^8$=$OR^{11}$, $SR^{11}$, $P(O)R^{13}R^{14}$, $NR^{15}R^{16}$, $ONR^{15}R^{16}$ or N-bonded heterocyclyl, which comprises reacting a pyrazole derivative of the formula I where $R^8$=halogen or $OSO_2R^{12}$ with a compound of the formula VIα, VIβ, VIγ, VIδ, VIε or VIη

| $HOR^{11}$ | $HSR^{11}$ | $HPOR^{13}R^{14}$ | $HNR^{15}R^{16}$ | $HONR^{15}R^{16}$ |
|---|---|---|---|---|
| VIα | VIβ | VIγ | VIδ | VIε | if appropriate in the presence of a base.

12. A process for preparing compounds of the formula I where $P_z$=IIa as claimed in claim 1, which comprises reacting a metallated pyrazole derivative of the formula VII, where M is a metal and $R^8$ to $R^{10}$ are as defined in claim 1 with a carboxylic acid derivative of the formula IVa, where $R^1$, $R^2$, X and Y are as defined in claim 1 and $L^1$ is a nucleophilically replaceable leaving group.

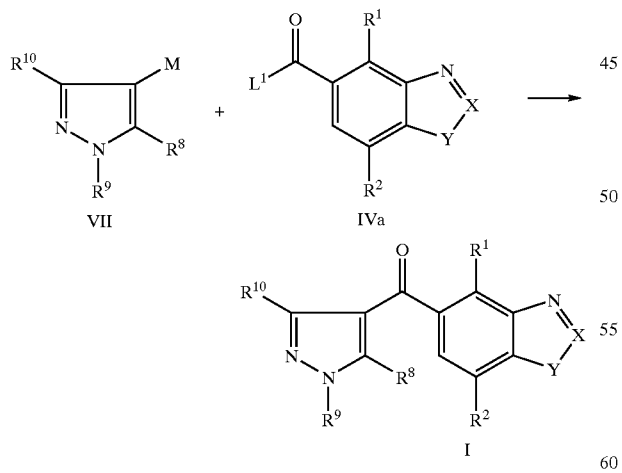

13. A herbicidal composition, comprising a herbicidally effective amount of at least one pyrazole derivative of the formula I or an agriculturally useful salt of I as defined in claim 1, and customary auxiliaries.

14. A method for controlling undesirable vegetation, which comprises allowing a herbicidally effective amount of at least one pyrazole derivative of the formula I or an agriculturally useful salt of I as claimed in claim 1 to act on plants, their habitat and/or on seed.

15. A pyrazolyl derivative of benzo-fused unsaturated 5-membered nitrogen heterocycles of the formula I,

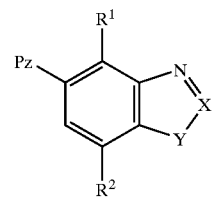

where
  X is a group C—$R^3$;
  Y is O;
  $R^1$ is hydrogen, nitro, halo, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, $C_1$–$C_6$-alkoxy-$C_1$–$C_6$-alkyl, $C_1$–$C_6$-alkylthio-$C_1$–$C_6$-alkyl, $C_1$–$C_6$-alkylsulfinyl-$C_1$–$C_6$-alkyl, $C_1$–$C_6$-alkylsulfonyl-$C_1$–$C_6$-alkyl, $C_1$–$C_6$-alkylamino-$C_1$–$C_6$-alkyl, or di($C_1$–$C_6$-alkyl)amino-$C_1$–$C_6$-alkyl;
  $R^2$ is hydrogen, halogen or $C_1$–$C_6$-alkyl;
  $R^3$ is hydrogen, halogen, nitro, cyano, hydroxyl, amino, mercapto, thiocyanato, hydrazide, $C_1$–$C_6$-alkyl, $C_1$–$C_6$-haloalkyl, $C_1$–$C_6$-hydroxyalkyl, $C_1$–$C_6$-aminoalkyl, $C_1$–$C_6$-alkoxy-$C_1$–$C_6$-alkyl, $C_1$–$C_6$-alkylcarbonyl-$C_1$–$C_6$-alkyl, $C_1$–$C_6$-alkoxy, $C_1$–$C_6$-haloalkoxy, $C_1$–$C_6$-hydroxyalkoxy, $C_1$–$C_6$-alkoxy-$C_1$–$C_6$-alkoxy, $C_3$–$C_6$-cycloalkyl, or
    is $C_1$–$C_6$-alkylamino, di-$C_1$–$C_6$-alkylamino, $C_3$–$C_6$-cycloalkylamino, where the alkyl and cycloalkyl groups of the three last-mentioned radicals may be partially or fully halogenated and/or may carry one to three substituents selected from the group consisting of $C_1$–$C_4$-alkoxy and hydroxyl, or
    is $C_1$–$C_6$-alkylthio, $C_1$–$C_6$-haloalkylthio, $C_1$–$C_6$-hydroxyalkylthio, $C_1$–$C_6$-alkoxy-$C_1$–$C_6$-alkylthio, $C_1$–$C_6$-alkylsulfonyl, $C_1$–$C_6$-alkylsulfinyl, or
    is phenyl, naphthyl, phenylamino, phenoxy, diphenylamino, where the phenyl groups of the five last-mentioned radicals for their part may be partially or fully halogenated and/or may carry one, two or three substituents selected from the group consisting of nitro, cyano, hydroxyl, $C_1$–$C_4$-alkyl, $C_1$–$C_4$-haloalkyl, $C_1$–$C_4$-alkoxy and $C_1$–$C_4$-haloalkoxy, or
    is $C(O)OR^5$, or $C(O)N(R^6)R^7$; and
  $R^4$ is hydrogen, $C_1$–$C_6$-alkyl, $C_1$–$C_6$-haloalkyl, $C_1$–$C_6$-hydroxyalkyl, $C_1$–$C_6$-alkoxy-$C_1$–$C_6$-alkyl, or
    is phenyl, naphthyl, where the two last-mentioned radicals for their part may be partially or fully halogenated and/or may carry one, two or three substituents selected from the group consisting of nitro, cyano, hydroxyl, $C_1$–$C_4$-alkyl, $C_1$–$C_4$-haloalkyl, $C_1$–$C_4$-alkoxy and $C_1$–$C_4$-haloalkoxy;
  $R^5$ is hydrogen, $C_1$–$C_6$-alkyl, $C_1$–$C_6$-haloalkyl, $C_1$–$C_6$-hydroxyalkyl, $C_1$–$C_6$-alkoxy-$C_1$–$C_6$-alkyl, or
    is phenyl or naphthyl, where the two last-mentioned radicals for their part may be partially or fully halogenated and/or may carry one, two or three substituents selected from the group consisting of nitro, cyano, hydroxyl, $C_1$–$C_4$-alkyl, $C_1$–$C_4$-haloalkyl, $C_1$–$C_4$-alkoxy and $C_1$–$C_4$-haloalkoxy;

$R^6$, $R^7$ independently of one another are hydrogen, $C_1$–$C_6$-alkyl, $C_1$–$C_6$-haloalkyl, $C_1$–$C_6$-hydroxyalkyl, $C_1$–$C_6$-alkoxy-$C_1$–$C_6$-alkyl, or are phenyl or naphthyl, where the two last-mentioned radicals for their part may be partially or fully halogenated and/or may carry one, two or three substituents selected from the group consisting of nitro, cyano, hydroxyl, $C_1$–$C_4$-alkyl, $C_1$–$C_4$-haloalkyl, $C_1$–$C_4$-alkoxy and $C_1$–$C_4$-haloalkoxy;

and Pz is a radical of the formula IIa or IIb,

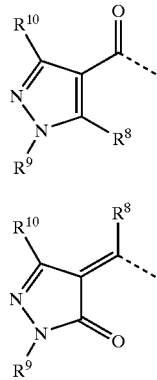

IIa

IIb where the variables $R^8$, $R^9$ and $R^{10}$ are as defined below:

$R^8$ is hydroxyl, mercapto, halogen, $OR^{11}$, $SR^{11}$, $SOR^{12}$, $SO_2R^{12}$, $OSO_2R^{12}$, $P(O)R^{13}R^{14}$, $OP(O)R^{13}R^{14}$, $P(S)R^{13}R^{14}$, $OP(S)R^{13}R^{14}$, $NR^{15}R^{16}$, $ONR^{15}R^{16}$ or N-bonded heterocyclyl, which may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^9$ is hydrogen, $C_1$–$C_6$-alkyl, $C_1$–$C_6$-haloalkyl, $C_3$–$C_6$-cycloalkyl, hydroxyl, $C_1$–$C_6$-alkoxy or $C_1$–$C_6$-haloalkoxy;

$R^{10}$ is hydrogen, halogen, $C_1$–$C_6$-alkyl, $C_1$–$C_6$-haloalkyl, hydroxyl, $C_1$–$C_6$-alkoxy, $C_1$–$C_6$-haloalkoxy, $C_1$–$C_6$-alkylthio or $C_1$–$C_6$-haloalkylthio;

$R^{11}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkylcarbonyl, $C_2$–$C_6$-alkenylcarbonyl, $C_2$–$C_6$-alkynylcarbonyl, $C_3$–$C_6$-cycloalkylcarbonyl, $C_3$–$C_6$-alkoxycarbonyl, $C_3$–$C_6$-alkenyloxycarbonyl, $C_3$–$C_6$-alkynyloxycarbonyl, $C_3$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl)aminocarbonyl, N—($C_3$–$C_6$-alkenyl)—N—($C_1$–$C_6$-alkyl)aminocarbonyl, N—($C_3$–$C_6$-alkynyl)—N—($C_1$–$C_6$-alkyl)aminocarbonyl, N—($C_1$–$C_6$-alkoxy)—N—($C_1$–$C_6$-alkyl)aminocarbonyl, N—($C_3$–$C_6$-alkenyl)—N—($C_1$–$C_6$-alkoxy)aminocarbonyl, N—($C_3$–$C_6$-alkynyl)—N—($C_1$–$C_6$-alkoxy)aminocarbonyl, di($C_1$–$C_6$-alkyl)aminothiocarbonyl or $C_1$–$C_6$-alkoxyimino-$C_1$–$C_6$-alkyl, where the alkyl, cycloalkyl and alkoxy radicals mentioned may be partially or fully halogenated and/or may carry one to three of the following groups: cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, $C_1$–$C_4$-alkylaminocarbonyl, di($C_1$–$C_4$-alkyl)aminocarbonyl, aminocarbonyl, $C_1$–$C_4$-alkylcarbonyloxy or $C_3$–$C_6$-cycloalkyl; or is phenyl, phenyl-$C_1$–$C_6$-alkyl, phenylcarbonyl-$C_1$–$C_6$-alkyl, phenylcarbonyl, phenoxycarbonyl, phenyloxythiocarbonyl, phenylaminocarbonyl, N—($C_1$–$C_6$-alkyl)—N—(phenyl)aminocarbonyl, or phenyl-$C_2$–$C_6$-alkenylcarbonyl, where the phenyl radical of the 9 last-mentioned substituents may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{12}$ is $C_1$–$C_6$-alkyl, $C_3$–$C_6$-alkenyl, $C_3$–$C_6$-alkynyl or $C_3$–$C_6$-cycloalkyl, where the four radicals mentioned may be partially or fully halogenated and/or may carry one, two or three of the following groups: cyano, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylcarbonyl, $C_1$–$C_4$-alkoxycarbonyl or $C_1$–$C_4$-haloalkoxycarbonyl; or is phenyl or phenyl-$C_1$–$C_6$-alkyl, where the phenyl radical of the last-mentioned substituents may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{13}$, $R^{14}$ independently of one another are hydrogen, hydroxyl, $C_1$–$C_6$-alkyl, $C_1$–$C_6$-alkoxy, $C_1$–$C_6$-alkylthio, phenyl, phenyl-$C_1$–$C_4$-alkyl or phenoxy, where the three last-mentioned substituents may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{15}$ is hydrogen, $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkylcarbonyl, hydroxyl, $C_1$–$C_6$-alkoxy, $C_3$–$C_6$-alkenyloxy, $C_3$–$C_6$-alkynyloxy, amino, $C_1$–$C_6$-alkylamino, di($C_1$–$C_6$-alkyl)amino or $C_1$–$C_6$-alkylcarbonylamino, where the alkyl, cycloalkyl and alkoxy radicals mentioned may be partially or fully halogenated and/or may carry one, two or three of the following radicals: cyano, $C_1$–$C_4$-alkoxycarbonyl, $C_1$–$C_4$-alkylaminocarbonyl, di($C_1$–$C_4$-alkyl)aminocarbonyl or $C_3$–$C_6$-cycloalkyl; or is phenyl, phenyl-$C_1$–$C_4$-alkyl or phenylcarbonyl, where the phenyl radical of the three last-mentioned substituents may be partially or fully halogenated and/or may carry one, two or three of the following radicals: nitro, cyano, $C_1$–$C_4$-alkyl, $C_1$–$C_4$-haloalkyl, $C_1$–$C_4$-alkoxy or $C_1$–$C_4$-haloalkoxy; and $R^{16}$ is hydrogen, $C_1$–$C_6$-alkyl or $C_3$–$C_6$-alkenyl, $C_3$–$C_6$-alkynyl;

and its agriculturally useful salts.

16. A pyrazole derivative as claimed in claim 15 where $R^3$ is hydrogen, halogen, cyano, thiocyanato, $C_1$–$C_6$-alkyl, $C_1$–$C_6$-haloalkyl, $C_1$–$C_6$-alkoxy, $C_1$–$C_6$-alkoxy-$C_1$–$C_6$-alkyl, $C_3$–$C_6$-cycloalkyl, $C_1$–$C_6$-haloalkoxy, $C_1$–$C_6$-alkylthio, $C_1$–$C_6$-haloalkylthio, or is phenyl, phenoxy or pyridyl, where the three last-mentioned radicals may be partially or fully halogenated and/or may carry one of the following radicals: $C_1$–$C_4$-alkoxy, $C_1$–$C_4$-haloalkyl, and $C_1$–$C_4$-haloalkoxy; or is $COOR^5$ where $R^5$ is as defined in claim 15.

* * * * *